(12) United States Patent
Xiao et al.

(10) Patent No.: US 12,043,654 B2
(45) Date of Patent: Jul. 23, 2024

(54) ANTI-GCC ANTIBODY AND CAR THEREOF FOR TREATING DIGESTIVE SYSTEM CANCER

(71) Applicants: Innovative Cellular Therapeutics Holdings, Ltd., Grand Cayman (KY); Innovative Cellular Therapeutics, Inc., Rockville, MD (US)

(72) Inventors: Lei Xiao, Rockville, MD (US); Xiaogang Shen, Shanghai (CN); Wensheng Wang, Shanghai (CN); Dongqi Chen, Shanghai (CN); Beibei Jia, Shanghai (CN); Chengfei Pu, Shanghai (CN); Le Tian, Rockville, MD (US)

(73) Assignees: Innovative Cellular Therapeutics Holdings, Ltd., George Town, KY (US); Innovative Cellular Therapeutics, Inc., Rockville, MD (US)

( * ) Notice: Subject to any disclaimer, the term of this patent is extended or adjusted under 35 U.S.C. 154(b) by 388 days.

(21) Appl. No.: 17/331,289

(22) Filed: May 26, 2021

(65) Prior Publication Data
US 2021/0371492 A1    Dec. 2, 2021

Related U.S. Application Data

(63) Continuation-in-part of application No. 16/999,357, filed on Aug. 21, 2020.

(60) Provisional application No. 63/142,181, filed on Jan. 27, 2021, provisional application No. 63/033,611, filed on Jun. 2, 2020.

(51) Int. Cl.
| | |
|---|---|
| *C07K 16/40* | (2006.01) |
| *A61K 35/17* | (2015.01) |
| *A61P 35/00* | (2006.01) |
| *C07K 14/725* | (2006.01) |
| *A61K 38/00* | (2006.01) |

(52) U.S. Cl.
CPC .......... *C07K 14/7051* (2013.01); *A61K 35/17* (2013.01); *A61P 35/00* (2018.01); *C07K 16/40* (2013.01); *A61K 38/00* (2013.01); *C12Y 406/01002* (2013.01)

(58) Field of Classification Search
CPC ..... C07K 14/7051; C07K 16/40; A61P 35/00; A61K 35/17; A61K 38/00; C12Y 406/01002
See application file for complete search history.

(56) References Cited

U.S. PATENT DOCUMENTS

| | | |
|---|---|---|
| 9,388,237 B2 | 7/2016 | Govindan |
| 9,572,837 B2 | 2/2017 | Wu |
| 9,932,405 B2 | 4/2018 | Xiao et al. |
| 10,561,686 B2 | 2/2020 | Xiao et al. |
| 10,869,888 B2 | 12/2020 | Xiao et al. |
| 2002/0052027 A1 | 5/2002 | Chen et al. |
| 2002/0192183 A1 | 12/2002 | Jensen |
| 2005/0079170 A1 | 4/2005 | Le Gall et al. |
| 2011/0110936 A1* | 5/2011 | Nam et al. ............. C07K 16/40 |
| 2013/0108609 A1 | 5/2013 | Vihko |
| 2013/0287748 A1 | 10/2013 | June et al. |
| 2014/0050708 A1 | 2/2014 | Powell et al. |
| 2014/0227237 A1 | 8/2014 | June et al. |
| 2014/0271635 A1 | 9/2014 | Brogdon et al. |
| 2015/0037356 A1 | 2/2015 | Elvin et al. |
| 2015/0038684 A1 | 2/2015 | Jensen |
| 2016/0024175 A1 | 1/2016 | Chow et al. |
| 2016/0250258 A1 | 9/2016 | Delaney et al. |
| 2016/0256488 A1 | 9/2016 | Wu |
| 2016/0362472 A1 | 12/2016 | Bitter et al. |
| 2017/0015746 A1 | 1/2017 | Jensen |
| 2017/0096638 A1 | 4/2017 | Wu |
| 2017/0136063 A1 | 5/2017 | Perez et al. |
| 2017/0137783 A1 | 5/2017 | Bedoya et al. |
| 2017/0145094 A1 | 5/2017 | Galetto |
| 2017/0145108 A1 | 5/2017 | Schreiber et al. |
| 2017/0209492 A1 | 7/2017 | June et al. |
| 2017/0218337 A1 | 8/2017 | Friedman |
| 2017/0224798 A1 | 8/2017 | Cooper et al. |
| 2017/0319638 A1 | 11/2017 | Conner et al. |

(Continued)

FOREIGN PATENT DOCUMENTS

| | | |
|---|---|---|
| EP | 2508176 A1 | 10/2012 |
| JP | 2016500659 A1 | 1/2016 |

(Continued)

OTHER PUBLICATIONS

Rizzardi, et al., "Evaluation of Protein Biomarkers of Prostate Cancer Aggressiveness," Dec. 2014. BMC Cancer, 14(1): 14 pgs.
European Office Action mailed Mar. 17, 2022 for European Patent Application No. 19700326.2, a foreign counterpart to U.S. Pat. No. 10,561,686, 7 pages.
Partial European Search Report mailed May 4, 2022 for European Patent Application No. 19854895.0, 13 pages.
Brischwein et al. "Strictly target cell-dependent activation of T cells by bispecific single-chain antibody constructs of the BiTE class" Nov. 2007, J Immunother, vol. 30, pp. 798-807.

(Continued)

*Primary Examiner* — Daniel E Kolker
*Assistant Examiner* — Estella M. Gustilo
(74) *Attorney, Agent, or Firm* — Lee & Hayes, P.C.; Sally Teng

(57) ABSTRACT

The present disclosure relates to compositions and methods of treating a subject having digestive tract cancer, the method comprising: administering an effective amount of a composition to the subject, the composition comprising a first population of cells comprising a first CAR binding a first antigen, and a second population of cells comprising a second CAR binding GCC, wherein the first antigen comprises a cell surface molecule of a white blood cell (WBC).

21 Claims, 22 Drawing Sheets

Specification includes a Sequence Listing.

(56) References Cited

U.S. PATENT DOCUMENTS

| | | |
|---|---|---|
| 2017/0335281 A1 | 11/2017 | Loew et al. |
| 2017/0362325 A1 | 12/2017 | Jung et al. |
| 2017/0368098 A1 | 12/2017 | Chen et al. |
| 2018/0028631 A1 | 2/2018 | Chen |
| 2018/0153977 A1 | 6/2018 | Wu et al. |
| 2018/0179289 A1 | 6/2018 | Xiao et al. |
| 2018/0222995 A1 | 8/2018 | Xiao et al. |
| 2018/0223255 A1 | 8/2018 | Wu et al. |
| 2018/0243340 A1 | 8/2018 | Varadarajan et al. |
| 2018/0334490 A1 | 11/2018 | Brogdon et al. |
| 2018/0346876 A1 | 12/2018 | Xiao et al. |
| 2019/0000878 A1 | 1/2019 | Xiao et al. |
| 2019/0185817 A1 | 6/2019 | Melton et al. |
| 2019/0216851 A1 | 7/2019 | Xiao et al. |
| 2019/0314410 A1 | 10/2019 | Rossi et al. |
| 2019/0314411 A1 | 10/2019 | Xiao et al. |
| 2020/0155598 A1 | 5/2020 | Xiao et al. |
| 2021/0060069 A1 | 3/2021 | Xiao et al. |
| 2021/0077532 A1 | 3/2021 | Xiao et al. |
| 2021/0100841 A1 | 4/2021 | Xiao et al. |
| 2021/0137983 A1 | 5/2021 | Xiao et al. |
| 2021/0161961 A1 | 6/2021 | Xiao et al. |
| 2021/0230308 A1 | 7/2021 | Xiao et al. |
| 2021/0252059 A1 | 8/2021 | Pu et al. |
| 2021/0379149 A1 | 12/2021 | Pu et al. |
| 2022/0000921 A1 | 1/2022 | Xiao et al. |
| 2022/0096546 A1 | 3/2022 | Xiao et al. |
| 2022/0105134 A1 | 4/2022 | Cao et al. |
| 2022/0339193 A1 | 10/2022 | Xiao et al. |
| 2022/0348682 A1 | 11/2022 | Xiao et al. |

FOREIGN PATENT DOCUMENTS

| | | |
|---|---|---|
| JP | 2018508539 A | 3/2018 |
| JP | 2018518939 A | 7/2018 |
| JP | 2018528774 A | 10/2018 |
| JP | 2021510540 A | 4/2021 |
| JP | 2022507830 A | 1/2022 |
| NO | 168969 B | 1/1992 |
| WO | WO8303679 A1 | 10/1983 |
| WO | WO2008131445 A1 | 10/2008 |
| WO | WO2010081738 A1 | 7/2010 |
| WO | WO2010126766 A1 | 11/2010 |
| WO | WO2012050374 A1 | 4/2012 |
| WO | WO2012066495 A2 | 5/2012 |
| WO | WO2012079000 A1 | 6/2012 |
| WO | WO2013123061 A1 | 8/2013 |
| WO | WO2014011984 A1 | 1/2014 |
| WO | WO2014011988 A2 | 1/2014 |
| WO | WO2015157384 A1 | 10/2015 |
| WO | WO2015157432 A1 | 10/2015 |
| WO | WO2016061574 A1 | 4/2016 |
| WO | WO2016070136 A1 | 5/2016 |
| WO | WO2016090034 A2 | 6/2016 |
| WO | WO2016090190 A1 | 6/2016 |
| WO | WO2016113203 A1 | 7/2016 |
| WO | WO2016164731 A2 | 10/2016 |
| WO | WO2016174652 A1 | 11/2016 |
| WO | WO2016210293 A1 | 12/2016 |
| WO | WO2017011804 A1 | 1/2017 |
| WO | WO2017027291 A1 | 2/2017 |
| WO | WO2017050884 A1 | 3/2017 |
| WO | WO2017075537 A1 | 5/2017 |
| WO | WO2017120525 A1 | 7/2017 |
| WO | WO2017040324 A1 | 9/2017 |
| WO | WO2017149515 A1 | 9/2017 |
| WO | WO2017167217 A1 | 10/2017 |
| WO | WO2017172952 A1 | 10/2017 |
| WO | WO2017172981 | 10/2017 |
| WO | WO2017173403 A1 | 10/2017 |
| WO | WO2017177137 A1 | 10/2017 |
| WO | WO2017210617 A2 | 12/2017 |
| WO | WO2018013918 A1 | 1/2018 |
| WO | WO2018018958 A1 | 2/2018 |
| WO | WO2018023976 A1 | 2/2018 |
| WO | WO2018027155 A1 | 2/2018 |
| WO | WO2018049418 A1 | 3/2018 |
| WO | WO2018067697 A1 | 4/2018 |
| WO | WO2018106732 A1 | 6/2018 |
| WO | WO2018111763 A1 | 6/2018 |
| WO | WO2019091478 A1 | 5/2019 |
| WO | WO2019136305 A1 | 7/2019 |
| WO | WO2019140100 A1 | 7/2019 |
| WO | WO2019178576 A1 | 9/2019 |
| WO | WO2020086742 A1 | 4/2020 |
| WO | WO2020086989 A1 | 4/2020 |
| WO | WO2020106843 A1 | 5/2020 |
| WO | WO2020146743 A1 | 7/2020 |

OTHER PUBLICATIONS

Chmielewski, "Of CARs and TRUCKs: Chimeric antigen receptor (CAR) T Cells Engineered with an Inducible Cytokine to Modulate the Tumor Stroma," Jan. 2014. Imunological Reviews, 257(1): 83-90.

European Search Report mailed Aug. 31, 2021 in European Application No. 21275039.2, a foreign corresponding application of U.S. Appl. No. 16/999,357, 13 pages.

Huang et al., "Interleukin-armed Chimeric Antigen Receptor-modified T Cells for Cancer Immunotherapy," Sep. 2017. Gene Thereapy, 25(3):192-197.

International Preliminary Report on Patentability dated Jul. 22, 2021 in PCT Application No. PCT/US2020/013099, 9 pages.

Internatioanl Search Report & Written Opinion mailed Aug. 13, 2021 from PCT Application No. PCT/2021/028429, 12 pages.

Lee et al., "Use of a Single CAR T Cell and Several Bispecific Adapters Facilitates Eradication of Multiple Antigenically Different Solid Tumors," Nov. 2018. Cancer Research, 79(2): 387-396.

Wong et al. "Blinatumomab induces autologous T-cell killing of chronic lymphocytic leukemia cells," Jun. 2013, Haematologica, 98(12): 1930-1938.

Bork, P., "Powers and Pitfalls in Sequence Analysis: The 70% Hurdle," Genome Research, 2000, 10:398-400.

Bowie et al., "Deciphering the Message in Protein Sequences: Tolerance to Amino Acid Substitutions," Science, Mar. 1990, 247:1306-1310.

Burgess et al., "Possible Dissociation of the Heparin-binding and Mitogenic Activities of Heparin-binding (Acidic Fibroblast) Growth Factor-1 from its Receptor-binding Activities by Site-directed Mutagenesis of a Single Lysine Residue," J. Cell Biol., Nov. 1990, 111:2129-2138.

Duong et al., "Bacteria-cancer Interactions: Bacteria-based Cancer Therapy," Experimental & Molecular Medicine, 2019, 51:152, 15 pages.

Japanese Office Action mailed May 30, 2023 for Japanese Patent Application No. 2020-558861, a foreign counterpart to U.S. Pat. No. 10,561,686, 7 pages.

Lazar et al., "Transforming Growth Factor Alpha: Mutation of Aspartic Acid 47 and Leucine 48 Results in Different Biological Activities," Mol. Cell. Biol., Mar. 1988, 8(3):1247-1252.

Mirzaei et al., "Chimeric Antigen Receptors T Cell Therapy in Solid Tumor: Challenges and Clinical Applications," Frontiers in Immunology, Dec. 2017, 8:1850, 13 pages.

Singapore Office action mailed Feb. 28, 2023, in Singapore Application No. 11202107269X, a corresponding foreign application of U.S. Appl. No. 16/387,166, 12 pages.

Turtle et al., "Immunotherapy of Non-Hodgkin's Lymphoma with a Defined Ratio of CD8+ and CD4+ CD19-specific Chimeric Antigen Receptor-modified T cells," Science Translational Medicine, Sep. 2016, 8:355, 29 pages.

Zhou et al, "The Use of tMUC1 Highly Specific Chimeric Antigen Receptor-redirected T cells for the Eradication of Triple Negative Breast Cancer," J Immunol, May 2017, 198 (1 Supplement): 198.10, 2 pages, Abstract.

Bollino et al., "Chimeric Antigen Receptor-Engineered Natural Killer and Natural Killer T cells for Cancer Immunotherapy," Translational Research, Jun. 2017, 187:32-43.

(56) References Cited

OTHER PUBLICATIONS

Fang et al., "NK Cell-based Immunotherapy for Cancer," Seminars in Immunology, Aug. 2017, 31:37-54.

Sarvaria et al., "B cell Regulation in Cancer and Anti-Tumor Immunity", Cellular and Molecular Immunology, Apr. 2017, 14:662-674.

Ghadially et al., "Differential Regulation of CCL22 Gene Expression in Murine Dendritic Cells and B Cells," The Journal of Immunology, 2005, 174(9):5620-5629.

Kim et al., "Increased IL-12 inhibits B Cells' Differentiation to Germinal Center Cells and Promotes Differentiation to Short-lived Plasmablasts," The Journal of Experimental Medicine, Sep. 2008, 205(10):2437-2448.

Largeot et al., "The B-Side of Cancer Immunity: The Underrated Tune," Cells, May 2019, 8(449), 20 pages.

U.S. Appl. No. 16/146,218, filed Sep. 28, 2018, US-2019-0216851-A1, U.S. Pat. No. 10,561,686, Granted.

U.S. Appl. No. 16/961,418, filed Jul. 10, 2020, Pending.

U.S. Appl. No. 16/445,965, filed Jun. 19, 2019, US-2020-0155598-A1, U.S. Pat. No. 10,918,667, Granted.

U.S. Appl. No. 17/144,800, filed Jan. 8, 2021, US 2021-0161961 A1, Pending.

U.S. Appl. No. 17/295,364, filed May 19, 2021, US 2022-0000921 A1, Pending.

U.S. Appl. No. 17/749,824, filed May 20, 2022, Pending.

U.S. Appl. No. 16/387,166, filed Apr. 17, 2019, US 2019-0314411 A1, U.S. Pat. No. 10,869,888, Granted.

U.S. Appl. No. 17/091,741, filed Nov. 6, 2020, US 2021-0137983 A1, Pending.

U.S. Appl. No. 17/108,076, filed Dec. 1, 2020, US 2021-0077532 A1, Pending.

U.S. Appl. No. 17/420,066, filed Jun. 30, 2021, US 2022/0096546, Pending.

U.S. Appl. No. 17/270,571, filed Feb. 23, 2021, Pending.

U.S. Appl. No. 17/220,387, filed Apr. 1, 2021, US 2021-0230308 A1, U.S. Pat. No. 11,161,913, Granted.

U.S. Appl. No. 17/123,732, filed Dec. 16, 2020, Pending.

U.S. Appl. No. 17/173,504, filed Feb. 11, 2021, US 2021-0252059 A1, Pending.

U.S. Appl. No. 16/996,237, filed Aug. 18, 2020, US 2021-0060069 A1, Pending.

U.S. Appl. No. 17/331,289, filed May 26, 2021, US 2021-0371492 A1, Pending.

U.S. Appl. No. 16/999,357, filed Aug. 21, 2020, US 2021-0100841 A1, Pending.

U.S. Appl. No. 16/961,418, filed Jul. 10, 2020, US 2022-0265708 A1, Pending.

U.S. Appl. No. 17/749,824, filed May 20, 2022, US-2022-0339193-A1, Pending.

U.S. Appl. No. 17/420,066, filed Jun. 30, 2021, US 2022/0096546 A1, Pending.

U.S. Appl. No. 17/270,571, filed Feb. 23, 2021, US 2022-0348682 A1, Pending.

U.S. Appl. No. 17/996,589, filed Oct. 19, 2022, Pending.

Canadian Office Action mailed Sep. 1, 2023 for Canadian Patent Application No. 3,125,646, a foreign counterpart to U.S. Pat. No. 10,869,888, 4 pages.

Cherkassky et al., "Human CAR T Cells with Cell-intrinsic PD-1 Checkpoint Blockade Resist Tumor-mediated Inhibition," Journal of Clinical Investigation, May 2016, 126(8):3130-3144.

Chmielewski et al., "CAR T Cells Releasing IL-18 Convert to T-Bethigh FoxO1low Effectors that Exhibit Augmented Activity Against Solid Tumors," Cell Reports, Dec. 2017, 21:3205-3219.

Eyquem et al., "Targeting a CAR to the TRAC Locus with CRISPR/Cas9 Enhances Tumour Rejection," Nature, Mar. 2017, 543:113-117.

Grada et al., "TanCar: A Novel Bispecific Chimeric Antigen Receptor for Cancer Immunotherapy," Molecular Therapy—Nucleic Acids, Jul. 2013, 2:e105, 11 pages.

Liu et al., "A Chimeric Switch-receptor Targeting PD1 Augments the Efficacy of Second-Generation CAR T Cells in Advanced Solid Tumors," Cancer Research, Mar. 2016, 76(6):1578-1590.

Magee et al., "GUCY2C-directed CAR-T Cells Oppose Colorectal Cancer Metastases Without Autoimmunity," OncoImmunology, Oct. 2016, 5(1):e1227897, 11 pages.

Roybal et al., "Engineering T cells with Customized Therapeutic Response Programs Using Synthetic Notch Receptors," Cell, Oct. 2016, 167:419-432.

Canadian Office Action mailed Oct. 25, 2023 for Canadian Application No. 3,088,161, a foreign counterpart to U.S. Pat. No. 10,561,686, 4 pages.

Japanese Office Action mailed Jan. 16, 2024 for Japanese Application No. 2020-558861, a foreign counterpart to U.S. Pat. No. 10,561,686, 7 pages.

Canadian Office Action for Canadian Patent Appl.: 3,088,161, mailed Sep. 22, 2021, a foreign corresponding application of U.S. Appl. No. 16/999,357, 4 pages.

Altuntas et al., "Autoimmunity to Uroplakin II Causes Cystitis in Mice: A Novel Model of Interstitial Cystitis," Eur Urol, Jan. 2012, 61(1):193-200.

Auerbach et al., "Angiogenesis Assays: Problems and Pitfalls," Cancer and Metastasis Reviews, Jun. 2000, 19:167-172.

Beans, "Targeting Metastasis to Halt Cancer's Spread," PNAS, Dec. 2018, 115(50):12539-12543.

Canadian Office Action mailed Sep. 14, 2023 for Canadian Application No. 3120153, a foreign corresponding application of U.S. Appl. No. 16/445,965, 4 pages.

Canadian Office Action mailed Sep. 19, 2023 for Canadian Application No. 3110096, a foreign corresponding application of U.S. Appl. No. 17/270,571, 3 pages.

Gravanis et al., "The Changing World of Cancer Drug Development: The Regulatory Bodies' Perspective," Chinese Clinical Oncology, May 2014, 3(2):22, 5 pages.

Gura, "Systems for Identifying New Drugs Are Often Faulty," Science, Nov. 1997, 278(5340):1041-1042.

Hait, "Anticancer Drug Development: The Grand Challenges," Nature Reviews/Drug Discovery, Apr. 2010, 9:253-254.

Heppner et al., "Tumor Heterogeneity: Biological Implications and Therapeutic Consequences," Cancer Metastasis Review 1983, 2:5-23.

Hoang et al, "A Newly Developed Uroplakin II Antibody With Increased Sensitivity in Urothelial Carcinoma of the Bladder," Arch Pathol Lab Med, Jul. 2014, 138:943-949.

Jain, "Barriers to Drug Delivery in Solid Tumors," Scientific American, Jul. 1994, 271(1):58-65.

Japanese Office Action mailed Oct. 17, 2023 for Japanese Application No. 2021-527959, a foreign corresponding application of U.S. Appl. No. 16/445,965, 6 pages.

Japanese Office Action mailed Oct. 31, 2023 for Japanese Application No. 2022-154638, aa foreign corresponding application of U.S. Appl. No. 17/270,571, 6 pages.

Liou et al., "Macrophage-secreted Cytokines Drive Pancreatic Acinar-to-ductal Metaplasia Through NF-KB and MMPs," Journal of Cell Biology, 2013, 202(3):563-577.

Mishu et al., "Effects of Recombinant Canine Granulocyte Colony-stimulating Factor on White Blood Cell Production in Clinically Normal and Neutropenic Dogs," J Am Vet Med Assoc., Jun. 1992, 200(12), Abstract, 1 page.

Rahman et al., "Histology, Natural Killer Cells," retrieved from <<https://www.ncbi.nlm.nih.gov/books/NBK565844/>>, StatPearls Publishing, Feb. 2023, 6 pages.

Rohaan et al., "Adoptive Cellular Therapies: The Current Landscape," Virchows Archiv, Nov. 2018, 474:449-461.

Snook et al., "GUCY2C-targeted Cancer Immunotherapy: Past, Present and Future," Immunology Research, Dec. 2011, 51:161-169.

Sporn et al., "Chemoprevention of Cancer", Carcinogenesis, Mar. 2000, 21(3):525-530.

Tigner et al., "Histology, White Blood Cell," retrieved from <<https://www.ncbi.nlm.nih.gov/books/NBK563148/>>, StatPearls Publishing, Nov. 2022, 5 pages.

(56) References Cited

OTHER PUBLICATIONS

Wu et al., "Potentiating Antilymphoma Efficacy of Chemotherapy Using a Liposome for Integration of CD20 Targeting, Ultra-violet Irradiation Polymerizing, and Controlled Drug Delivery", Nanoscale Research Letters, 2014, 9(447), 11 pages.
Yu et al., "CART Cell Therapy for Prostate Cancer: Status and Promise," OncoTargets and Therapy, 2019, 12:391-395.
U.S. Appl. No. 16/146,218, filed Sep. 28, 2018, US-2019-0216851-A1, U.S. Pat. No. 10,561,686, Issued.
U.S. Appl. No. 16/961,418, filed Jul. 10, 2020, Active.
U.S. Appl. No. 16/445,965, filed Jun. 19, 2019, US-2020-0155598-A1, U.S. Pat. No. 10,918,667, Issued.
U.S. Appl. No. 17/144,800, filed Jan. 8, 2021, Active.
U.S. Appl. No. 17/295,364, filed May 19, 2021, Active.
U.S. Appl. No. 16/387,166, filed Apr. 17, 2019, US 2019-0314411 A1, U.S. Pat. No. 10,869,888, Issued.
U.S. Appl. No. 17/091,741, filed Nov. 6, 2020, Active.
U.S. Appl. No. 17/108,076, filed Dec. 1, 2020, US 2021-0077532 A1, Active.
U.S. Appl. No. 17/270,571, filed Feb. 23, 2021, Active.
U.S. Appl. No. 17/220,387, filed Apr. 1, 2021, Active.
U.S. Appl. No. 17/123,732, filed Dec. 16, 2020, Active.
U.S. Appl. No. 17/173,504, filed Feb. 11, 2021, Active.
U.S. Appl. No. 16/996,237, filed Aug. 18, 2020, US 2021-0060069 A1, Active.
U.S. Appl. No. 16/999,357, filed Aug. 21, 2020, Active.
Canadian Office Action mailed Jul. 20, 2022 for Canadian Patent Application No. 3,088,161, a foreign counterpart to U.S. Pat. No. 10,561,686, 4 pages.
Chmielewski, et al., "IL-12 Release by Engineered T Cells Expressing Chimeric Antigen Receptors Can Effectively Muster and Antigen-Independent Macrophage Response on Tumor Cells That Have Shut Down Tumor Antigen Expression", Cancer Research, Jul. 2011, 71(17):5697-5706.
Extended European Search Report mailed Nov. 14, 2022 for European Patent Application No. 19887928.0, a foreign corresponding application of U.S. Appl. No. 16/445,965, 12 pages.
Extended European Search Report mailed Nov. 24, 2022 for European Patent Application No. 20739064.2, a foreign corresponding application of U.S. Appl. No. 16/387,166, 13 pages.
European Search Report mailed Aug. 4, 2022 in European Patent Application No. 19854895.0, a foreign corresponding application of U.S. Appl. No. 17/270,571, 8 pages.
Hoyos, et al., "Engineering CD19-specific T lymphocytes with interleukin-15 and a suicide gene to enhance their anti-lymphoma/leukemia effects and safety", Leukemia, Apr. 2010, 24(6):1160-1170.
Japanese Office Action mailed Sep. 20, 2022 for Japanese Patent Application No. 2020-558861, a foreign counterpart to U.S. Pat. No. 10,561,686, 7 pages.
Klaver, et al., "Plasma IFN-[gamma] and IL-6 levels correlate with peripheral T-cell Nos. but not toxicity in RCC patients treated with CAR T-cells", Clinical Immunology, Jul. 2016, 169:107-113.
Koneru, et al., "IL-12 Secreting tumor-targeted chimeric antigen receptor T cells eradicate ovarian tumors in vivo", Oncoimmunology, Jan. 2015, 4(3):e994446, 11 pages.
Posey et al., "Engineered CAR T Cells Targeting the Cancer-Associated Tn-Glycoform of the Membrane Mucin MUC1 Control Adenocarcinoma", Immunity, Jun. 2016, 44(6):1444-1454.
Leon-Triana, et al., "Dual-Target CAR-Ts with On- and Off-Tumor Activity May Override Immune Suppression in Solid Cancers: A Mathematical Proof of Concept", Cancers, Feb. 2021, 13(4):703, 20 pages.
Trinchieri, "Interleukin-12 and the regulation of innate resistance and adaptive immunity", Nature Reviews Immunology. Feb. 2003, 3(2):133-146.
Ghadially, et al., "Differential Regulation of CCL22 Gene Expression in Murine Dendritic Cells and B Cells", The Journal of Immunology, May 2009, 174(9):5620-5629.
Largeot, et al., "The B-Side of Cancer Immunity: The Underrated Tune", Cells, May 2019, 8(449):1-20.
Japanese office action mailed Apr. 5, 2022 in Japanese Application No. 2021-512204, a foreign correspondeing application of U.S. Appl. No. 17/220,387, 10 pages. Translated.
Marks et al., "By-passing Immunization: Human Antibodies from V-gene Libraries Displayed on Phage" 1991. Journal of Molecular Biology, 222(3): 581-597.
"Anti-ACPP Product Datasheet", Atlas Antibodies, retrieved on Oct. 31, 2019 from https://www.atlasantibodies.com/api/print_datasheet/HPA004335.pdf, Dec. 2012 1 page.
"Anti-UPK2 Product Datasheet", Atlas Antibodies, retrieved on Oct. 31, 2019 from https://www.atlasantibodies.com/api/print_datasheet/HPA061106.pdf, Dec. 2012, 1 page.
Chen, et al., "CAR T-cell intrinsic PD-1 checkpoint blockade: a two-in-one approach for solid tumor immunotherapy," Feb. 2017, OncoImmunology, 6:2, e1273302, DOI: 10.1080/2162402X.2016. 1273302. 4 pages.
Extended European Search Report mailed Nov. 25, 2019 in EP Application No. 19180127.3, Xiao et al., a corresponding foreign application of U.S. Appl. No. 16/146,218, 11 pages.
Fang et al., "Stable antibody expression at therapeutic levels using the 2A peptide," 2005, Nature Biotechnology. 23(5):584-590.
Invitation to Pay Additional Fees mailed on Nov. 13, 2019 for PCT Application PCT/US19/48890, 3 Pages.
Invitation to Pay Fees dtd Mar. 30, 2020 for PCT Application No. PCT/US20/13099, "Modified Cell Expansion and Uses Thereof", 2 pages.
Jernberg-Wiklund, et al., "Recombinant interferon-gamma inhibits the growth of IL-6-dependent human multiple myeloma cell lines in vitro," 1991. Eur J Haematol, 46:231.239.
Lee et al., "T cells expressing CD19 chimeric antigen receptors for acute lymphoblastic leukemia in children and young adults: a phase 1 dose-escalation trial," Oct. 2014. The Lancet, 385(9967): 517-528.
Maude et al., "Chimeric antigen receptor T cells for sustained remissions in leukemia," Oct. 2014. N Engl J Med. 371(16): 1507-1517.
Milone, et al., "Chimeric receptors containing CD137 signal transduction domains mediate enhanced survival of T cells and increased antileukemic efficacy in vivo," Apr. 2009. Molecular Therapy, 17(8): 1453-1464.
Partial European Search Report mailed Nov. 4, 2019 in EP Application No. 19180127.3, Xiao et al., a corresponding foreign application of U.S. Appl. No. 16/146,218, 18 pages.
International Preliminary Report on Patentability mailed Mar. 11, 2021 for PCT Application No. PCT/US19/48890, 8 pages.
International Search Report and Written Opinion mailed on Jun. 17, 2019 for PCT Application No. PCT/US19/13068, 14 pages.
International Search Report and Written Opinion mailed on Feb. 20, 2020 for PCT Application No. PCT/US19/62417, 14 pages.
International Search Report and Written Opinion mailed on Feb. 7, 2020 for PCT Application No. PCT/US19/48890, 15 pages.
International Search Report and Written Opinion mailed on Jun. 4, 2020 for PCT Application No. PCT/US2020/013099, 13 pages.
Qin et al., "Incorporation of a hinge domain improves the expansion of chimeric antigen receptor T cells," 2017, Journal of Hematology & Oncology, 10:68, 11 pages.
Sahm et al, "Expression of IL-15 in NK Cells Results in Rapid Enrichment and Selective Cytotoxicity of Gene-Modified Effectors That Carry a Tumor-Specific Antigen Receptor", Cancer Immunol Immunother, vol. 61, No. 9, Sep. 2012, pp. 1451-1461.
Supplemental European Search Report mailed Jan. 13, 2020 in EP Application No. 19700326, Xiao et al., a corresponding foreign application of U.S. Appl. No. 16/146,218, 7 pages.
Takahashi, et al, "Expression of MUC1 on myeloma cells and induction of HJLA-unrestricted CTL against MUC1 from a multiple myeloma patient," 1994. J Immunol, 153:2102-2109.
Wilkie, et al. "Retargeting of human T cells to tumor-associated MUC1: The evolution of a chimeric antigen receptor," 2008, J. Immunol., 180:4901-4909.
Xiao et al., "Pre-clinical experiments of cart cells identifying tshr as a potential target against metastatic thyroid cancer," May 2018.

(56) References Cited

OTHER PUBLICATIONS

Database EMBASE [Online] Elsevier Science Publishers, Database Accession No. EMB-623339571, 1 page.
You et al., "Phase 1 clinical trial demonstrated that MUC1 positive metastatic seminal vesicle cancer can be effectively eradicated y modified Anti-MUC1 chimeric antigen receptor transduced T cells", Apr. 2016, Science China: Life Sciences, 59(4): 386-397.
Almagro et al., "Progress and challenges in the design and clinical development of antibodies for cancer therapy," Frontiers in Immunology, Jan. 2018, 8:1751, 19 pages.
Breloer et al., "CD83 Regulates Lymphocyte Maturation, Activation and Homeostasis," Trends in Immunology, Mar. 2008, 29(4):186-194.
Brown et al., "Tolerance of Single, But Not Multiple, Amino Acid Replacements in Antibody VH CDR 2: A Means of Minimizing B Cell Wastage from Somatic Hypermutation?" Journal of Immunology, May 1996, 156(9):3285-3291.
Brudno et al., "Toxicities of Chimeric Antigen Receptor T Cells: Recognition and Management," Blood, Jun. 2016, 127(26):3321-3330.
Cho et al., "Triple Costimulation Via CD80, 4-1BB, and CD83 Ligand Elicits the Long-Term Growth of Vγ9Vδ2 T Cells in Low Levels of IL-2," Journal of Leukocyte Biology, Apr. 2016, 99(4):521-529.
Du et al., "Granulocyte Colony-Stimulating Factor Treatment During Radiotherapy Is Associated With Survival Benefit in Patients With Lung Cancer," Technology in Cancer Research & Treatment, Dec. 2018, 17:1-7.
European Office Action mailed Feb. 5, 2024 for European Application No. 19854895.0, a foreign counterpart to U.S. Appl. No. 17/270,571, 6 pages.
Japanese Office Action mailed Jan. 30, 2024 for Japanese Application No. 2021-540137, a foreign counterpart to U.S. Appl. No. 17/420,066, 7 pages.

Konjevic et al., "The Role of Cytokines in the Regulation of NK Cells in the Tumor Environment," Cytokine, May 2019, 117:30-40.
Li et al., "CD83: Activation Marker for Antigen Presenting Cells and Its Therapeutic Potential," Frontiers in Immunology, Jun. 2019, 10:Article 1312, 9 pages.
Ping et al., "T-cell Receptor-engineered T Cells for Cancer Treatment: Current Status and Future Directions," Protein Cell, Mar. 2018, 9(3):254-266.
Priceman et al., "Co-stimulatory Signaling Determines Tumor Antigen Sensitivity and Persistence of CAR T Cells Targeting PSCA+ Metastatic Prostate Cancer," OncoImmunology, Feb. 2018, 7(2):e1380764, 13 pages.
Rabinowich et al., "Response of Human NK Cells to IL-6 Alterations of the Cell Surface Phenotype, Adhesion to Fibronectin and Laminin, and Tumor Necrosis Factor-Alpha/Beta Secretion," Journal of immunology, Jun. 1993, 150(11):4844-4855.
Scheuermann et al., "CD19 Antigen in Leukemia and Lymphoma Diagnosis and Immunotherapy," Leukemia & Lymphoma, 1995, 18(5-6):385-397.
Su et al., "Interleukin-7 Expression and its Effect on Natural Killer Cells in Patients with Multiple Sclerosis," J Neuroimmunol., Nov. 2014, 276(0):180-186.
Zhang et al., "The Emerging World of TCR-T Cell Trials Against Cancer: A Systematic Review," Technology in Cancer Research & Treatment, Jul. 2019, 18:1-13.
Office Action for European Application No. 21275039.2, mailed May 23, 2024, 7 pages.
Office Action for Japanese Application No. 2021-527959, mailed May 7, 2024, 6 pages.
Kim, et al., "High Cleavage Efficiency of a 2A Peptide Derived from Porcine Teschovirus-1 in Human Cell Lines, Zebrafish and Mice", PLoS One, vol. 6, No. 4, Apr. 29, 2011, pp. 1-8.

* cited by examiner

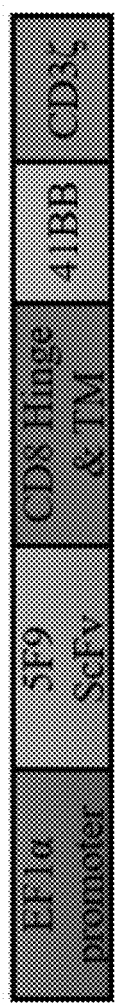
FIG. 10B
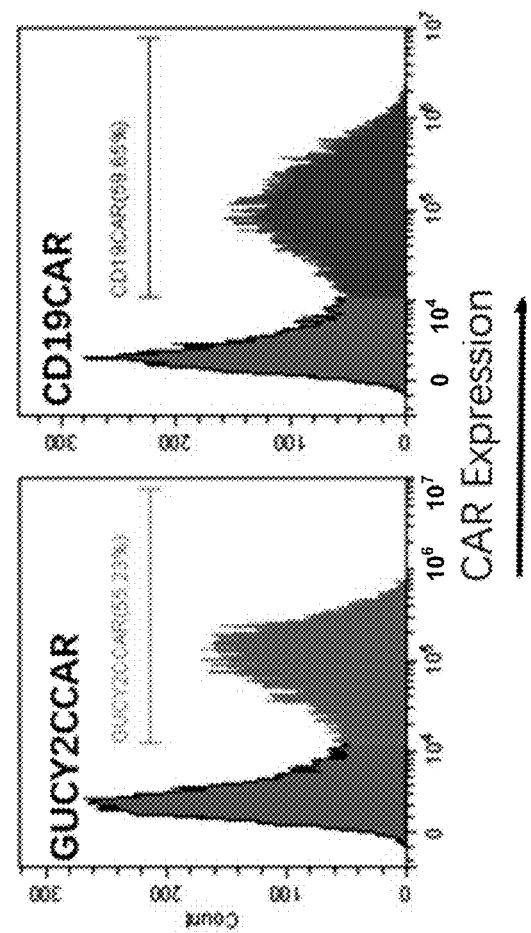
FIG. 10C
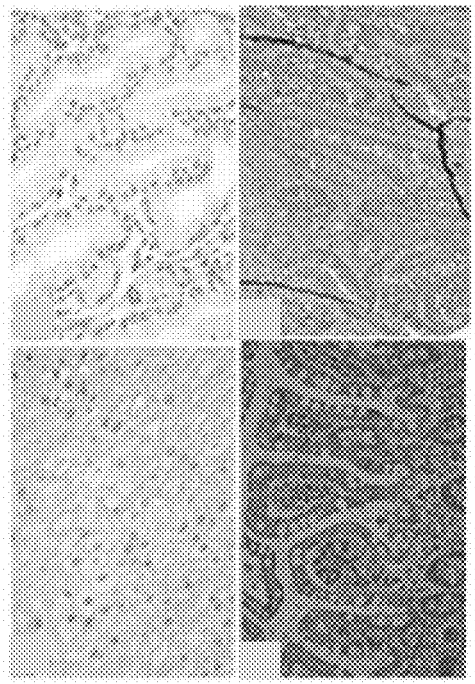
FIG. 10A1 FIG. 10A2
FIG. 10A3 FIG. 10A4

RNA level expression: expressed in colorectal and stomach cancer (FPKM average: 22.3 and 3.7)

Staining result: Stomach tumor staining intensity is Low

Staining result: the intensity of Stomach tumor staining is Medium

SEQUENCE LISTING

<160> NUMBER OF SEQ ID NOS: 64

<210> SEQ ID NO 1
<211> LENGTH: 21
<212> TYPE: PRT
<213> ORGANISM: Artificial Sequence
<220> FEATURE:
<223> OTHER INFORMATION: Synthesized

<400> SEQUENCE: 1

Met Ala Leu Pro Val Thr Ala Leu Leu Leu Pro Leu Ala Leu Leu Leu
1               5                   10                  15

His Ala Ala Arg Pro
            20

<210> SEQ ID NO 2
<211> LENGTH: 69
<212> TYPE: PRT
<213> ORGANISM: Artificial Sequence
<220> FEATURE:
<223> OTHER INFORMATION: Synthesized

<400> SEQUENCE: 2

Ala Lys Pro Thr Thr Thr Pro Ala Pro Arg Pro Pro Thr Pro Ala Pro

```
                1               5                  10                  15
Thr Ile Ala Ser Gln Pro Leu Ser Leu Arg Pro Glu Ala Cys Arg Pro
            20                  25                  30

Ala Ala Gly Gly Ala Val His Thr Arg Gly Leu Asp Phe Ala Cys Asp
        35                  40                  45

Ile Tyr Ile Trp Ala Pro Leu Ala Gly Thr Cys Gly Val Leu Leu Leu
50                  55                  60

Ser Leu Val Ile Thr
65

<210> SEQ ID NO 3
<211> LENGTH: 42
<212> TYPE: PRT
<213> ORGANISM: Artificial Sequence
<220> FEATURE:
<223> OTHER INFORMATION: Synthesized

<400> SEQUENCE: 3

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40

<210> SEQ ID NO 4
<211> LENGTH: 112
<212> TYPE: PRT
<213> ORGANISM: Artificial Sequence
<220> FEATURE:
<223> OTHER INFORMATION: Synthesized

<400> SEQUENCE: 4

Arg Val Lys Phe Ser Arg Ser Ala Asp Ala Pro Ala Tyr Lys Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 5
<211> LENGTH: 242
<212> TYPE: PRT
<213> ORGANISM: Artificial Sequence
<220> FEATURE:
<223> OTHER INFORMATION: Synthesized

<400> SEQUENCE: 5

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Lys Tyr
            20                  25                  30
```

Leu Asn Trp Tyr Gln Gln Lys Pro Gly Lys Ala Pro Lys Leu Leu Ile
            35                  40                  45

Tyr His Thr Ser Arg Leu His Ser Gly Val Pro Ser Arg Phe Ser Gly
         50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Asn Thr Leu Pro Tyr
                 85                  90                  95

Thr Phe Gly Gln Gly Thr Lys Val Glu Ile Lys Gly Gly Gly Gly Ser
                100                 105                 110

Gly Gly Gly Gly Ser Gly Gly Gly Ser Glu Val Gln Leu Val Glu
            115                 120                 125

Ser Gly Gly Gly Leu Val Gln Pro Gly Gly Ser Leu Arg Leu Ser Cys
130                 135                 140

Ala Ala Ser Gly Val Ser Leu Pro Asp Tyr Gly Val Ser Trp Val Arg
145                 150                 155                 160

Gln Ala Pro Gly Lys Gly Leu Glu Trp Val Ser Val Ile Trp Gly Ser
                165                 170                 175

Glu Thr Thr Tyr Tyr Asn Ser Ala Leu Lys Ser Arg Phe Thr Ile Ser
                180                 185                 190

Arg Asp Asn Ala Lys Asn Ser Leu Tyr Leu Gln Met Asn Ser Leu Arg
            195                 200                 205

Ala Glu Asp Thr Ala Val Tyr Tyr Cys Ala Lys His Tyr Tyr Tyr Gly
        210                 215                 220

Gly Ser Tyr Ala Met Asp Tyr Trp Gly Gln Gly Thr Leu Val Thr Val
225                 230                 235                 240

Ser Ser

<210> SEQ ID NO 6
<211> LENGTH: 242
<212> TYPE: PRT
<213> ORGANISM: Artificial Sequence
<220> FEATURE:
<223> OTHER INFORMATION: Synthesized

<400> SEQUENCE: 6

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Lys Pro Asp Gly Thr Val Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Thr Gly Gly Gly Gly Ser
            100                 105                 110

Gly Gly Gly Gly Ser Gly Gly Gly Gly Ser Glu Val Lys Leu Gln Glu
        115                 120                 125

Ser Gly Pro Gly Leu Val Ala Pro Ser Gln Ser Leu Ser Val Thr Cys
130                 135                 140

-continued

Thr Val Ser Gly Val Ser Leu Pro Asp Tyr Gly Val Ser Trp Ile Arg
145                 150                 155                 160

Gln Pro Pro Arg Lys Gly Leu Glu Trp Leu Gly Val Ile Trp Gly Ser
                165                 170                 175

Glu Thr Thr Tyr Tyr Asn Ser Ala Leu Lys Ser Arg Leu Thr Ile Ile
            180                 185                 190

Lys Asp Asn Ser Lys Ser Gln Val Phe Leu Lys Met Asn Ser Leu Gln
        195                 200                 205

Thr Asp Asp Thr Ala Ile Tyr Tyr Cys Ala Lys His Tyr Tyr Tyr Gly
    210                 215                 220

Gly Ser Tyr Ala Met Asp Tyr Trp Gly Gln Gly Thr Ser Val Thr Val
225                 230                 235                 240

Ser Ser

<210> SEQ ID NO 7
<211> LENGTH: 241
<212> TYPE: PRT
<213> ORGANISM: Artificial Sequence
<220> FEATURE:
<223> OTHER INFORMATION: Synthesized

<400> SEQUENCE: 7

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Arg Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Gly Ser Leu Gln Ser
65                  70                  75                  80

Glu Asp Phe Ala Val Tyr Tyr Cys Gln Gln Tyr Lys Thr Trp Pro Arg
                85                  90                  95

Thr Phe Gly Gln Gly Thr Asn Val Glu Ile Lys Gly Gly Gly Gly Ser
            100                 105                 110

Gly Gly Gly Gly Ser Gly Gly Gly Ser Gln Val Gln Leu Gln Gln
        115                 120                 125

Trp Gly Ala Gly Leu Leu Lys Pro Ser Glu Thr Leu Ser Leu Thr Cys
130                 135                 140

Ala Val Phe Gly Gly Ser Phe Ser Gly Tyr Tyr Trp Ser Trp Ile Arg
145                 150                 155                 160

Gln Pro Pro Gly Lys Gly Leu Glu Trp Ile Gly Glu Ile Asn His Arg
                165                 170                 175

Gly Asn Thr Asn Asp Asn Pro Ser Leu Lys Ser Arg Val Thr Ile Ser
            180                 185                 190

Val Asp Thr Ser Lys Asn Gln Phe Ala Leu Lys Leu Ser Ser Val Thr
        195                 200                 205

Ala Ala Asp Thr Ala Val Tyr Tyr Cys Ala Arg Glu Arg Gly Tyr Thr
    210                 215                 220

Tyr Gly Asn Phe Asp His Trp Gly Gln Gly Thr Leu Val Thr Val Ser
225                 230                 235                 240

Ser

<210> SEQ ID NO 8

```
<211> LENGTH: 407
<212> TYPE: PRT
<213> ORGANISM: Homo sapiens

<400> SEQUENCE: 8

Ser Gln Val Ser Gln Asn Cys His Asn Gly Ser Tyr Glu Ile Ser Val
1               5                   10                  15

Leu Met Met Gly Asn Ser Ala Phe Ala Glu Pro Leu Lys Asn Leu Glu
            20                  25                  30

Asp Ala Val Asn Glu Gly Leu Glu Ile Val Arg Gly Arg Leu Gln Asn
        35                  40                  45

Ala Gly Leu Asn Val Thr Val Asn Ala Thr Phe Met Tyr Ser Asp Gly
    50                  55                  60

Leu Ile His Asn Ser Gly Asp Cys Arg Ser Ser Thr Cys Glu Gly Leu
65                  70                  75                  80

Asp Leu Leu Arg Lys Ile Ser Asn Ala Gln Arg Met Gly Cys Val Leu
                85                  90                  95

Ile Gly Pro Ser Cys Thr Tyr Ser Thr Phe Gln Met Tyr Leu Asp Thr
            100                 105                 110

Glu Leu Ser Tyr Pro Met Ile Ser Ala Gly Ser Phe Gly Leu Ser Cys
        115                 120                 125

Asp Tyr Lys Glu Thr Leu Thr Arg Leu Met Ser Pro Ala Arg Lys Leu
    130                 135                 140

Met Tyr Phe Leu Val Asn Phe Trp Lys Thr Asn Asp Leu Pro Phe Lys
145                 150                 155                 160

Thr Tyr Ser Trp Ser Thr Ser Tyr Val Tyr Lys Asn Gly Thr Glu Thr
                165                 170                 175

Glu Asp Cys Phe Trp Tyr Leu Asn Ala Leu Glu Ala Ser Val Ser Tyr
            180                 185                 190

Phe Ser His Glu Leu Gly Phe Lys Val Val Leu Arg Gln Asp Lys Glu
        195                 200                 205

Phe Gln Asp Ile Leu Met Asp His Asn Arg Lys Ser Asn Val Ile Ile
    210                 215                 220

Met Cys Gly Gly Pro Glu Phe Leu Tyr Lys Leu Lys Gly Asp Arg Ala
225                 230                 235                 240

Val Ala Glu Asp Ile Val Ile Leu Val Asp Leu Phe Asn Asp Gln
                245                 250                 255

Tyr Phe Glu Asp Asn Val Thr Ala Pro Asp Tyr Met Lys Asn Val Leu
            260                 265                 270

Val Leu Thr Leu Ser Pro Gly Asn Ser Leu Leu Asn Ser Ser Phe Ser
        275                 280                 285

Arg Asn Leu Ser Pro Thr Lys Arg Asp Phe Ala Leu Ala Tyr Leu Asn
    290                 295                 300

Gly Ile Leu Leu Phe Gly His Met Leu Lys Ile Phe Leu Glu Asn Gly
305                 310                 315                 320

Glu Asn Ile Thr Thr Pro Lys Phe Ala His Ala Phe Arg Asn Leu Thr
                325                 330                 335

Phe Glu Gly Tyr Asp Gly Pro Val Thr Leu Asp Asp Trp Gly Asp Val
            340                 345                 350

Asp Ser Thr Met Val Leu Leu Tyr Thr Ser Val Asp Thr Lys Lys Tyr
        355                 360                 365

Lys Val Leu Leu Thr Tyr Asp Thr His Val Asn Lys Thr Tyr Pro Val
    370                 375                 380

Asp Met Ser Pro Thr Phe Thr Trp Lys Asn Ser Lys Leu Pro Asn Asp
```

```
                385                 390                 395                 400
Ile Thr Gly Arg Gly Pro Gln
                405

<210> SEQ ID NO 9
<211> LENGTH: 7902
<212> TYPE: DNA
<213> ORGANISM: Artificial Sequence
<220> FEATURE:
<223> OTHER INFORMATION: Synthesized

<400> SEQUENCE: 9
gtcgacacta gtaatcaacc tctggattac aaaatttgtg aaagattgac tggtattctt      60
aactatgttg ctcctttac gctatgtgga tacgctgctt taatgccttt gtatcatgct     120
attgcttccc gtatggcttt cattttctcc tccttgtata atcctggtt gctgtctctt      180
tatgaggagt tgtggcccgt tgtcaggcaa cgtggcgtgg tgtgcactgt gtttgctgac     240
gcaaccccca ctggttgggg cattgccacc acctgtcagc tcctttccgg gactttcgct     300
ttcccctcc ctattgccac ggcggaactc atcgccgcct gccttgcccg ctgctggaca      360
ggggctcggc tgttgggcac tgacaattcc gtggtgttgt cggggaagct gacgtccttt     420
ccatggctgc tcgcctgtgt tgccacctgg attctgcgcg gacgtccttt ctgctacgtc     480
ccttcggccc tcaatccagc ggaccttcct cccgcggcc tgctgccggc tctgcggcct      540
cttccgcgtc ttcgccttcg ccctcagacg agtcggatct ccctttgggc cgcctcccg      600
cctgccgcgg aattcgagct cggtaccttt aagaccaatg acttacaagg cagctgtaga     660
tcttagccac tttttaaaag aaaagggggg actggaaggg ctaattcact cccaacgaag     720
acaagatctg cttttttgctt gtactgagtc tctctggtta gaccagatct gagcctggga     780
gctctctggc taactaggga acccactgct taagcctcaa taaagcttgc cttgagtgct     840
tcaagtagtg tgtgcccgtc tgttgtgtga ctctggtaac tagagatccc tcagaccctt     900
ttagtcagtg tggaaaatct ctagcagtag tagttcatgt catcttatta ttcagtattt     960
ataacttgca aagaaatgaa tatcagagag tgagaggaac ttgtttattg cagcttataa    1020
tggttacaaa taaagcaata gcatcacaaa tttcacaaat aaagcatttt tttcactgca    1080
ttctagttgt ggtttgtcca aactcatcaa tgtatcttat catgtctggc tctagctatc    1140
ccgcccctaa ctccgcccat cccgcccta actccgccca gttccgccca ttctccgccc    1200
catggctgac taattttttt tatttatgca gaggccgagg ccgcctcggc ctctgagcta    1260
ttccagaagt agtgaggagg cttttttgga ggcctaggga cgtacccaat cgccctata     1320
gtgagtcgta ttacgcgcgc tcactggccg tcgttttaca acgtcgtgac tgggaaaacc    1380
ctggcgttac ccaacttaat cgccttgcag cacatcccc tttcgccagc tggcgtaata    1440
gcgaagaggc ccgcaccgat cgcccttccc aacagttgcg cagcctgaat ggcgaatggg    1500
acgcgccctg tagcggcgca ttaagcgcgg cgggtgtggt ggttacgcgc agcgtgaccg    1560
ctacacttgc cagcgcccta gcgcccgctc ctttcgcttt cttcccttcc tttctcgcca    1620
cgttcgccgg ctttccccgt caagctctaa atcgggggct ccctttaggg ttccgattta    1680
gtgctttacg gcacctcgac cccaaaaaac ttgattaggg tgatggttca cgtagtgggc    1740
catcgccctg atagacggtt tttcgccctt tgacgttgga gtccacgttc tttaatagtg    1800
gactcttgtt ccaaactgga acaacactca accctatctc ggtctattct tttgatttat    1860
aagggatttt gccgatttcg gcctattggt taaaaaatga gctgatttaa caaaaattta    1920
```

```
acgcgaattt taacaaaata ttaacgctta caatttaggt ggcacttttc ggggaaatgt    1980
gcgcggaacc cctatttgtt tattttctta aatacattca aatatgtatc cgctcatgag    2040
acaataaccc tgataaatgc ttcaataata ttgaaaaagg aagagtatga gtattcaaca    2100
tttccgtgtc gcccttattc ccttttttgc ggcattttgc cttcctgttt ttgctcaccc    2160
agaaacgctg gtgaaagtaa aagatgctga agatcagttg ggtgcacgag tgggttacat    2220
cgaactggat ctcaacagcg gtaagatcct tgagagtttt cgccccgaag aacgttttcc    2280
aatgatgagc acttttaaag ttctgctatg tggcgcggta ttatcccgta ttgacgccgg    2340
gcaagagcaa ctcggtcgcc gcatacacta ttctcagaat gacttggttg agtactcacc    2400
agtcacagaa aagcatctta cggatggcat gacagtaaga gaattatgca gtgctgccat    2460
aaccatgagt gataacactg cggccaactt acttctgaca acgatcggag gaccgaagga    2520
gctaaccgct tttttgcaca acatggggga tcatgtaact cgccttgatc gttgggaacc    2580
ggagctgaat gaagccatac caaacgacga gcgtgacacc acgatgcctg tagcaatggc    2640
aacaacgttg cgcaaactat taactggcga actacttact ctagcttccc ggcaacaatt    2700
aatagactgg atggaggcgg ataaagttgc aggaccactt ctgcgctcgg cccttccggc    2760
tggctggttt attgctgata aatctggagc cggtgagcgt ggctctcgcg gtatcattgc    2820
agcactgggg ccagatggta agccctcccg tatcgtagtt atctacacga cggggagtca    2880
ggcaactatg gatgaacgaa atagacagat cgctgagata ggtgcctcac tgattaagca    2940
ttggtaactg tcagaccaag tttactcata tatactttag attgatttaa aacttcattt    3000
ttaatttaaa aggatctagg tgaagatcct ttttgataat ctcatgacca aaatccctta    3060
acgtgagttt tcgttccact gagcgtcaga ccccgtagaa aagatcaaag gatcttcttg    3120
agatcctttt tttctgcgcg taatctgctg cttgcaaaca aaaaaaccac cgctaccagc    3180
ggtggtttgt ttgccggatc aagagctacc aactcttttt ccgaaggtaa ctggcttcag    3240
cagagcgcag ataccaaata ctgttcttct agtgtagccg tagttaggcc accacttcaa    3300
gaactctgta gcaccgccta catacctcgc tctgctaatc ctgttaccag tggctgctgc    3360
cagtggcgat aagtcgtgtc ttaccgggtt ggactcaaga cgatagttac cggataaggc    3420
gcagcggtcg ggctgaacgg ggggttcgtg cacacagccc agcttggagc gaacgaccta    3480
caccgaactg agatacctac agcgtgagct atgagaaagc gccacgcttc ccgaagggag    3540
aaaggcggac aggtatccgg taagcggcag ggtcggaaca ggagagcgca cgagggagct    3600 tccagggggga aacgcctggt atctttatag tcctgtcggg tttcgccacc tctgacttga    3660
gcgtcgattt ttgtgatgct cgtcaggggg gcggagccta tggaaaaacg ccagcaacgc    3720 ggcctttttta cggttcctgg ccttttgctg gccttttgct cacatgttct ttcctgcgtt    3780
atcccctgat tctgtggata accgtattac cgcctttgag tgagctgata ccgctcgccg    3840
cagccgaacg accgagcgca gcgagtcagt gagcgaggaa gcggaagagc gcccaatacg    3900
caaaccgcct ctccccgcgc gttggccgat tcattaatgc agctggcacg acaggtttcc    3960
cgactggaaa gcgggcagtg agcgcaacgc aattaatgtg agttagctca ctcattaggc    4020
accccaggct ttacacttta tgcttccggc tcgtatgttg tgtggaattg tgagcggata    4080
acaatttcac acaggaaaca gctatgacca tgattacgcc aagcgcgcaa ttaaccctca    4140
ctaaagggaa caaagctgga gctgcaagc ttaatgtagt cttatgcaat actcttgtag    4200
tcttgcaaca tggtaacgat gagttagcaa catgccttac aaggagagaa aaagcaccgt    4260
gcatgccgat tggtggaagt aaggtggtac gatcgtgcct tattaggaag gcaacagacg    4320
```

```
ggtctgacat ggattggacg aaccactgaa ttgccgcatt gcagagatat tgtatttaag    4380
tgcctagctc gatacataaa cggctctctc tggttagacc agatctgagc ctgggagctc    4440
tctggctaac tagggaaccc actgcttaag cctcaataaa gcttgccttg agtgcttcaa    4500
gtagtgtgtg cccgtctgtt gtgtgactct ggtaactaga gatccctcag acccttttag    4560
tcagtgtgga aaatctctag cagtggcgcc cgaacaggga cttgaaagcg aagggaaac     4620 cagaggagct ctctcgacgc aggactcggc ttgctgaagc gcgcacggca agaggcgagg    4680
ggcggcgact ggtgagtacg ccaaaaattt tgactagcgg aggctagaag gagagagatg    4740
ggtgcgagag cgtcagtatt aagcggggga gaattagatc gcgatgggaa aaaattcggt    4800
taaggccagg gggaagaaa aaatataaat taaaacatat agtatgggca agcagggagc     4860
tagaacgatt cgcagttaat cctggcctgt tagaaacatc agaaggctgt agacaaatac    4920
tgggacagct acaaccatcc cttcagacag gatcagaaga acttagatca ttatataata    4980
cagtagcaac cctctattgt gtgcatcaaa ggatagagat aaaagacacc aaggaagctt    5040
tagacaagat agaggaagag caaaacaaaa gtaagaccac cgcacagcaa gcggccgctg    5100
atcttcagac ctggaggagg agatatgagg gacaattgga gaagtgaatt atataaatat    5160
aaagtagtaa aaattgaacc attaggagta gcacccacca aggcaaagag aagagtggtg    5220
cagagagaaa aaagagcagt gggaatagga gctttgttcc ttgggttctt gggagcagca    5280
ggaagcacta tgggcgcagc gtcaatgacg ctgacggtac aggccagaca attattgtct    5340
ggtatagtgc agcagcagaa caatttgctg agggctattg aggcgcaaca gcatctgttg    5400
caactcacag tctggggcat caagcagctc caggcaagaa tcctggctgt ggaaagatac    5460
ctaaaggatc aacagctcct ggggatttgg ggttgctctg gaaaactcat ttgcaccact    5520
gctgtgcctt ggaatgctag ttggagtaat aaatctctgg aacagatttg gaatcacacg    5580
acctggatgg agtgggacag agaaattaac aattacacaa gcttaataca ctccttaatt    5640
gaagaatcgc aaaaccagca agaaaagaat gaacaagaat tattggaatt agataaatgg    5700
gcaagtttgt ggaattggtt taacataaca aattggctgt ggtatataaa attattcata    5760
atgatagtag gaggcttggt aggtttaaga atagttttg ctgtactttc tatagtgaat     5820
agagttaggc agggatattc accattatcg tttcagaccc acctcccaac cccgagggga    5880
cccgacaggc ccgaaggaat agaagaagaa ggtggagaga gagacagaga cagatccatt    5940
cgattagtga acggatctcg acggtatcga tcacgagact agcctcgaca caaatggcag    6000
tattcatcca caatttttaaa agaaaagggg ggattggggg gtacagtgca ggggaaagaa   6060
tagtagacat aatagcaaca gacatacaaa ctaaagaatt acaaaaacaa attacaaaaa    6120
ttcaaaattt tcgggtttat tacagggaca gcagaaatcc actttggctc gagaagcttg    6180
atatcggctc cggtgcccgt cagtgggcag agcgcacatc gcccacagtc cccgagaagt    6240
tggggggagg ggtcggcaat tgaaccggtg cctagaaag gtgcgcgggg gtaaactggg     6300
aaagtgatgt cgtgtactgg ctccgccttt ttcccgaggg tgggggagaa ccgtatataa    6360
gtgcagtagt cgccgtgaac gttcttttc gcaacgggtt tgccgccaga acacaggatc     6420
cgccaccatg gccttaccag tgaccgcctt gctcctgccg ctggcttgc tgctccacgc     6480 cgccaggccg gatatccaga tgacccagag cccgagcagc ctgagcgcga gcgtgggtga    6540
tcgcgtgacc attacctgca gggcaagtca ggacattagt aaatatttaa attggtatca    6600
gcagaaaccg ggtaaagcgc cgaaactgtt aatttatcat acatcaagat tacactcagg    6660
```

```
cgtgccgtcg cgttttagcg gctcgggttc gggcaccgat tttaccctga ccatctcgag    6720
cttgcagccg gaggacttcg ccacctacta ttgccaacag gtaatacgc ttccgtacac     6780 gttcggtcag ggcaccaaag tggagatcaa aggtggcggt ggctcgggcg tggtgggtc     6840 gggtggcggc ggatctgagg tgcagctggt ggagtctggg ggaggcttgg tacagcctgg    6900
ggggtccctg agactctcct gtgcagcctc tggagtgtcc ctgcctgatt atggcgtgtc    6960
ctgggtccgc caggctccag gaaggggct ggagtgggtt tcagtgatct ggggcagcga     7020
gacaacctac tacaacagcg ccctgaagtc ccgattcacc atctccagag acaatgccaa    7080
gaactcactg tatctgcaaa tgaacagcct gagagccgag gacacggctg tgtattactg    7140
tgcgaagcac tactactacg gcggcagcta cgctatggac tactggggcc aaggaaccct    7200
ggtcaccgtg tcctcaacca cgacgccagc gccgcgacca ccaacaccgg cgcccaccat    7260
cgcgtcgcag cccctgtccc tgcgcccaga ggcgtgccgg ccagcggcgg ggggcgcagt    7320
gcacacgagg gggctggact cgcctgtga tatctacatc tgggcgccct tggccgggac      7380 ttgtgggggtc cttctcctgt cactggttat caccctttac tgcaaacggg gcagaaagaa   7440
actcctgtat atattcaaac aaccattttat gagaccagta caaactactc aagaggaaga   7500
tggctgtagc tgccgatttc cagaagaaga agaaggagga tgtgaactga gagtgaagtt    7560
cagcaggagc gcagacgccc ccgcgtacaa gcagggccag aaccagctct ataacgagct    7620
caatctagga cgaagagagg agtacgatgt tttggacaag aggcgtggcc gggaccctga    7680 gatggggga aagccgagaa ggaagaaccc tcaggaaggc ctgtacaatg aactgcagaa     7740
agataagatg gcggaggcct acagtgagat tgggatgaaa ggcgagcgcc ggaggggcaa    7800
ggggcacgat ggcctttacc agggtctcag tacagccacc aaggacacct acgacgccct    7860
tcacatgcag gccctgcccc ctcgctaatc tagaggcgcg cc                       7902
```

<210> SEQ ID NO 10
<211> LENGTH: 244
<212> TYPE: PRT
<213> ORGANISM: Artificial Sequence
<220> FEATURE:
<223> OTHER INFORMATION: Synthesized

<400> SEQUENCE: 10

```
Asp Ile Val Met Thr Gln Ser Pro Ser Ser Leu Thr Val Thr Ala Gly
1               5                   10                  15

Glu Lys Val Thr Met Ile Cys Lys Ser Ser Gln Ser Leu Leu Asn Ser
            20                  25                  30

Gly Asp Gln Lys Asn Tyr Leu Thr Trp Tyr Gln Gln Lys Pro Gly Gln
        35                  40                  45

Pro Pro Lys Leu Leu Ile Phe Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp Tyr Ser Tyr Pro Leu Thr Phe Gly Ala Gly Thr Lys Leu Glu Leu
            100                 105                 110

Lys Gly Gly Gly Gly Ser Gly Gly Gly Gly Ser Gly Gly Gly Gly Ser
        115                 120                 125

Gln Val Gln Leu Gln Gln Ser Asp Ala Glu Leu Val Lys Pro Gly Ser
    130                 135                 140
```

```
Ser Val Lys Ile Ser Cys Lys Ala Ser Gly Tyr Thr Phe Thr Asp His
145                 150                 155                 160

Ala Ile His Trp Val Lys Gln Lys Pro Glu Gln Gly Leu Glu Trp Ile
                165                 170                 175

Gly His Phe Ser Pro Gly Asn Thr Asp Ile Lys Tyr Asn Asp Lys Phe
            180                 185                 190

Lys Gly Lys Ala Thr Leu Thr Val Asp Arg Ser Ser Thr Ala Tyr
        195                 200                 205

Met Gln Leu Asn Ser Leu Thr Ser Glu Asp Ser Ala Val Tyr Phe Cys
    210                 215                 220

Lys Thr Ser Thr Phe Phe Phe Asp Tyr Trp Gly Gln Gly Thr Thr Leu
225                 230                 235                 240

Thr Val Ser Ser
```

<210> SEQ ID NO 11
<211> LENGTH: 97
<212> TYPE: PRT
<213> ORGANISM: Artificial Sequence
<220> FEATURE:
<223> OTHER INFORMATION: Synthesized

<400> SEQUENCE: 11

```
Cys Ser Arg Ala Ala Arg Gly Thr Ile Gly Ala Arg Arg Thr Gly Gln
1               5                   10                  15

Pro Leu Lys Glu Asp Pro Ser Ala Val Pro Val Phe Ser Val Asp Ala
                20                  25                  30

Gly Glu Leu Asp Phe Gln Trp Arg Glu Lys Thr Pro Glu Pro Pro Val
            35                  40                  45

Pro Cys Val Pro Glu Gln Thr Glu Ala Ala Thr Ile Val Phe Pro Ser
    50                  55                  60

Gly Met Gly Thr Ser Ser Pro Ala Arg Arg Gly Ser Ala Asp Gly Pro
65                  70                  75                  80

Arg Ser Ala Gln Pro Leu Arg Pro Glu Asp Gly His Cys Ser Trp Pro
                85                  90                  95

Leu
```

<210> SEQ ID NO 12
<211> LENGTH: 339
<212> TYPE: DNA
<213> ORGANISM: Homo sapiens

<400> SEQUENCE: 12

```
agagtgaagt tcagcaggag cgcagacgcc ccgcgtacc agcagggcca gaaccagctc      60
tataacgagc tcaatctagg acgaagagag gagtacgatg ttttggacaa gaggcgtggc     120
cgggaccctg agatgggggg aaagccgaga aggaagaacc ctcaggaagg cctgtacaat    180
gaactgcaga agataagat ggcggaggcc tacagtgaga ttgggatgaa aggcgagcgc     240 cggagggggca aggggcacga tggcctttac cagggtctca gtacagccac caaggacacc    300
tacgacgccc ttcacatgca ggccctgccc cctcgctaa                           339
```

<210> SEQ ID NO 13
<211> LENGTH: 15
<212> TYPE: PRT
<213> ORGANISM: Artificial Sequence
<220> FEATURE:
<223> OTHER INFORMATION: Synthesized

<400> SEQUENCE: 13

```
Gly Gly Gly Gly Ser Gly Gly Gly Ser Gly Gly Gly Ser
1               5                   10                  15
```

<210> SEQ ID NO 14
<211> LENGTH: 120
<212> TYPE: PRT
<213> ORGANISM: Artificial Sequence
<220> FEATURE:
<223> OTHER INFORMATION: Synthesized

<400> SEQUENCE: 14

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Val Ser Leu Pro Asp Tyr
            20                  25                  30

Gly Val Ser Trp Val Arg Gln Ala Pro Gly Lys Gly Leu Glu Trp Val
        35                  40                  45

Ser Val Ile Trp Gly Ser Glu Thr Thr Tyr Tyr Asn Ser Ala Leu Lys
    50                  55                  60

Ser Arg Phe Thr Ile Ser Arg Asp Asn Ala Lys Asn Ser Leu Tyr Leu
65                  70                  75                  80

Gln Met Asn Ser Leu Arg Ala Glu Asp Thr Ala Val Tyr Tyr Cys Ala
                85                  90                  95

Lys His Tyr Tyr Tyr Gly Gly Ser Tyr Ala Met Asp Tyr Trp Gly Gln
            100                 105                 110

Gly Thr Leu Val Thr Val Ser Ser
        115                 120
```

<210> SEQ ID NO 15
<211> LENGTH: 107
<212> TYPE: PRT
<213> ORGANISM: Artificial Sequence
<220> FEATURE:
<223> OTHER INFORMATION: Synthesized

<400> SEQUENCE: 15

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Lys Tyr
            20                  25                  30

Leu Asn Trp Tyr Gln Gln Lys Pro Gly Lys Ala Pro Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Asn Thr Leu Pro Tyr
                85                  90                  95

Thr Phe Gly Gln Gly Thr Lys Val Glu Ile Lys
            100                 105
```

<210> SEQ ID NO 16
<211> LENGTH: 241
<212> TYPE: PRT
<213> ORGANISM: Artificial Sequence
<220> FEATURE:
<223> OTHER INFORMATION: Synthesized

<400> SEQUENCE: 16

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Arg Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Gly Ser Leu Gln Ser
65                  70                  75                  80

Glu Asp Phe Ala Val Tyr Tyr Cys Gln Gln Tyr Lys Thr Trp Pro Arg
                85                  90                  95

Thr Phe Gly Gln Gly Thr Asn Val Glu Ile Lys Gly Gly Gly Gly Ser
            100                 105                 110

Gly Gly Gly Gly Ser Gly Gly Gly Ser Gln Val Gln Leu Gln Gln
            115                 120                 125

Trp Gly Ala Gly Leu Leu Lys Pro Ser Glu Thr Leu Ser Leu Thr Cys
        130                 135                 140

Ala Val Phe Gly Gly Ser Phe Ser Gly Tyr Tyr Trp Ser Trp Ile Arg
145                 150                 155                 160

Gln Pro Pro Gly Lys Gly Leu Glu Trp Ile Gly Glu Ile Asn His Arg
                165                 170                 175

Gly Asn Thr Asn Asp Asn Pro Ser Leu Lys Ser Arg Val Thr Ile Ser
            180                 185                 190

Val Asp Thr Ser Lys Asn Gln Phe Ala Leu Lys Leu Ser Ser Val Thr
        195                 200                 205

Ala Ala Asp Thr Ala Val Tyr Tyr Cys Ala Arg Glu Arg Gly Tyr Thr
210                 215                 220

Tyr Gly Asn Phe Asp His Trp Gly Gln Gly Thr Leu Val Thr Val Ser
225                 230                 235                 240

Ser

<210> SEQ ID NO 17
<211> LENGTH: 241
<212> TYPE: PRT
<213> ORGANISM: Artificial Sequence
<220> FEATURE:
<223> OTHER INFORMATION: Synthesized

<400> SEQUENCE: 17

Gln Val Gln Leu Gln Gln Trp Gly Ala Gly Leu Leu Lys Pro Ser Glu
1               5                   10                  15

Thr Leu Ser Leu Thr Cys Ala Val Phe Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Arg Gly Asn Thr Asn Asp Asn Pro Ser Leu Lys
    50                  55                  60

Ser Arg Val Thr Ile Ser Val Asp Thr Ser Lys Asn Gln Phe Ala Leu
65                  70                  75                  80

Lys Leu Ser Ser Val Thr Ala Ala Asp Thr Ala Val Tyr Tyr Cys Ala
                85                  90                  95

Arg Glu Arg Gly Tyr Thr Tyr Gly Asn Phe Asp His Trp Gly Gln Gly
            100                 105                 110

Thr Leu Val Thr Val Ser Ser Gly Gly Gly Gly Ser Gly Gly Gly Gly

```
                115                 120                 125
Ser Gly Gly Gly Gly Ser Glu Ile Val Met Thr Gln Ser Pro Ala Thr
    130                 135                 140

Leu Ser Val Ser Pro Gly Glu Arg Ala Thr Leu Ser Cys Arg Ala Ser
145                 150                 155                 160

Gln Ser Val Ser Arg Asn Leu Ala Trp Tyr Gln Gln Lys Pro Gly Gln
                165                 170                 175

Ala Pro Arg Leu Leu Ile Tyr Gly Ala Ser Thr Arg Ala Thr Gly Ile
            180                 185                 190

Pro Ala Arg Phe Ser Gly Ser Gly Ser Gly Thr Glu Phe Thr Leu Thr
        195                 200                 205

Ile Gly Ser Leu Gln Ser Glu Asp Phe Ala Val Tyr Tyr Cys Gln Gln
    210                 215                 220

Tyr Lys Thr Trp Pro Arg Thr Phe Gly Gln Gly Thr Asn Val Glu Ile
225                 230                 235                 240

Lys

<210> SEQ ID NO 18
<211> LENGTH: 9780
<212> TYPE: DNA
<213> ORGANISM: Artificial Sequence
<220> FEATURE:
<223> OTHER INFORMATION: Synthesized

<400> SEQUENCE: 18
cggctccggt gcccgtcagt gggcagagcg cacatcgccc acagtccccg agaagttggg      60
gggaggggtc ggcaattgaa ccggtgccta gagaaggtgg cgcggggtaa actgggaaag     120
tgatgtcgtg tactggctcc gccttttttcc cgagggtggg ggagaaccgt atataagtgc     180
agtagtcgcc gtgaacgttc tttttcgcaa cgggtttgcc gccagaacac aggatccgcc     240
accatggcct accagtgac cgccttgctc ctgccgctgg ccttgctgct ccacgccgcc     300
aggccggata tccagatgac ccagagcccg agcagcctga gcgcgagcgt gggtgatcgc     360
gtgaccatta cctgcagggc aagtcaggac attagtaaat atttaaattg gtatcagcag     420
aaaccgggta aagcgccgaa actgttaatt tatcatacat caagattaca ctcaggcgtg     480
ccgtcgcgtt ttagcggctc gggttcgggc accgattta ccctgaccat ctcgagcttg     540
cagccggagg acttcgccac ctactattgc aacagggta atacgcttcc gtacacgttc     600
ggtcagggca ccaaagtgga gatcaaaggt ggcggtggct cgggcggtgg tgggtcgggt     660
ggcggcggat ctgaggtgca gctggtggag tctggggga gcttggtaca gcctgggggg     720
tccctgagac tctcctgtgc agcctctgga gtgtccctgc ctgattatgg cgtgtcctgg     780
gtccgccagg ctccagggaa ggggctggag tgggtttcag tgatctgggg cagcgagaca     840
acctactaca cagcgccct gaagtcccga ttcaccatct ccagagacaa tgccaagaac     900
tcactgtatc tgcaaatgaa cagcctgaga gccgaggaca cggctgtgta ttactgtgcg     960
aagcactact actacggcgg cagctacgct atggactact ggggccaagg aaccctggtc    1020
accgtgtcct caaccacgac gccagcgccg cgaccaccaa caccggcgcc caccatcgcg    1080
tcgcagcccc tgtccctgcg cccagaggcg tgccggccag cggcggggg gcgcagtgcac    1140 acgagggggc tggacttcgc ctgtgatatc tacatctggg cgcccttggc cgggacttgt    1200
ggggtccttc tcctgtcact ggttatcacc ctttactgca aacggggcag aaagaaactc    1260
ctgtatatat tcaaacaacc atttatgaga ccagtacaaa ctactcaaga ggaagatggc    1320
```

```
tgtagctgcc gatttccaga agaagaagaa ggaggatgtg aactgagagt gaagttcagc    1380
aggagcgcag acgccccgc gtaccagcag ggccagaacc agctctataa cgagctcaat     1440
ctaggacgaa gagaggagta cgatgttttg acaagaggc gtggccggga ccctgagatg     1500
gggggaaagc cgagaaggaa gaaccctcag gaaggcctgt acaatgaact gcagaaagat    1560
aagatggcgg aggcctacag tgagattggg atgaaaggcg agcgccggag gggcaagggg    1620
cacgatggcc tttaccaggg tctcagtaca gccaccaagg acacctacga cgcccttcac    1680
atgcaggccc tgccccctcg ctaagtcgac tctagaacta gtaatcaacc tctggattac    1740
aaaatttgtg aaagattgac tggtattctt aactatgttg ctccttttac gctatgtgga    1800
tacgctgctt taatgccttt gtatcatgct attgcttccc gtatggcttt cattttctcc    1860
tccttgtata aatcctggtt gctgtctctt tatgaggagt tgtggcccgt tgtcaggcaa    1920
cgtggcgtgg tgtgcactgt gtttgctgac gcaaccccca ctggttgggg cattgccacc    1980
acctgtcagc tcctttccgg gactttcgct ttccccctcc ctattgccac ggcggaactc    2040
atcgccgcct gccttgcccg ctgctggaca ggggctcggc tgttgggcac tgacaattcc    2100
gtggtgttgt cggggaagct gacgtccttt ccatggctgc tcgcctgtgt tgccacctgg    2160
attctgcgcg gacgtccttt ctgctacgtc ccttcggccc tcaatccagc ggaccttcct    2220
tcccgcggcc tgctgccggc tctgcggcct cttccgcgtc ttcgccttcg ccctcagacg    2280
agtcggatct cccctttggg cgcctccccg cctgccgcgg aattcgagct cggtaccttt    2340
aagaccaatg acttacaagg cagctgtaga tcttagccac ttttttaaaag aaaagggggg    2400
actgaaggg ctaattcact cccaacgaag acaagatctg cttttgctt gtactgggtc      2460
tctctggtta gaccagatct gagcctggga gctctctggc taactaggga acccactgct    2520
taagcctcaa taaagcttgc cttgagtgct tcaagtagtg tgtgcccgtc tgttgtgtga    2580
ctctggtaac tagagatccc tcagaccctt ttagtcagtg tggaaaatct ctagcagtag    2640
tagttcatgt catcttatta ttcagtattt ataacttgca aagaaatgaa tatcagagag    2700
tgagaggaac ttgtttattg cagcttataa tggttacaaa taaagcaata gcatcacaaa    2760
tttcacaaat aaagcatttt tttcactgca ttctagttgt ggtttgtcca aactcatcaa    2820
tgtatcttat catgtctggc tctagctatc ccgcccctaa ctccgcccat cccgccccta    2880
actccgccca gttccgccca ttctccgccc catggctgac taatttttt tatttatgca    2940
gaggccgagg ccgcctcggc ctctgagcta ttccagaagt agtgaggagg cttttttgga    3000
ggcctaggga cgtacccaat cgccctata gtgagtcgta ttacgcgcgc tcactggccg    3060
tcgttttaca acgtcgtgac tgggaaaacc ctggcgttac ccaacttaat cgccttgcag    3120
cacatccccc tttcgccagc tggcgtaata gcgaagaggc ccgcaccgat cgcccttccc    3180
aacagttgcg cagcctgaat ggcgaatggg acgcgccctg tagcggcgca ttaagcgcgg    3240
cgggtgtggt ggttacgcgc agcgtgaccg ctacacttgc cagcgcccta gcgcccgctc    3300
ctttcgcttt cttcccttcc tttctcgcca cgttcgccgg ctttccccgt caagctctaa    3360
atcgggggct ccctttaggg ttccgattta gtgctttacg gcacctcgac cccaaaaaac    3420
ttgattaggg tgatggttca cgtagtgggc catcgccctg atagacggtt tttcgccctt    3480
tgacgttgga gtccacgttc tttaatagtg gactcttgtt ccaaactgga acaacactca    3540
accctatctc ggtctattct tttgatttat aagggatttt gccgatttcg gcctattggt    3600
taaaaaatga gctgatttaa caaaaattta acgcgaattt aacaaaata ttaacgctta    3660
caatttaggt ggcactttc ggggaaatgt gcgcggaacc cctatttgtt tatttttcta    3720
```

```
aatacattca aatatgtatc cgctcatgag acaataaccc tgataaatgc ttcaataata   3780
ttgaaaaagg aagagtatga gccatattca acgggaaacg tcttgctcta ggccgcgatt   3840
aaattccaac atggatgctg atttatatgg gtataaatgg gctcgcgata atgtcgggca   3900
atcaggtgcg acaatctatc gattgtatgg gaagcccgat gcgccagagt tgtttctgaa   3960
acatggcaaa ggtagcgttg ccaatgatgt tacagatgag atggtcagac taaactggct   4020
gacggaattt atgcctcttc cgaccatcaa gcatttatc cgtactcctg atgatgcatg   4080
gttactcacc actgcgatcc ccgggaaaac agcattccag gtattagaag aatatcctga   4140
ttcaggtgaa aatattgttg atgcgctggc agtgttcctg cgccggttgc attcgattcc   4200
tgtttgtaat tgtcctttta acagcgatcg cgtatttcgt ctggctcagg cgcaatcacg   4260
aatgaataac ggtttggttg atgcgagtga ttttgatgac gagcgtaatg gctggcctgt   4320
tgaacaagtc tggaaagaaa tgcataaact tttgccattc tcaccggatt cagtcgtcac   4380
tcatggtgat ttctcacttg ataaccttat ttttgacgag gggaaattaa taggttgtat   4440
tgatgttgga cgagtcggaa tcgcagaccg ataccaggat cttgccatcc tatggaactg   4500
cctcggtgag ttttctcctt cattacagaa acggcttttt caaaaatatg gtattgataa   4560
tcctgatatg aataaattgc agtttcattt gatgctcgat gagtttttct aactgtcaga   4620
ccaagtttac tcatatatac tttagattga tttaaaactt catttttaat ttaaaaggat   4680
ctaggtgaag atcctttttg ataatctcat gaccaaaatc ccttaacgtg agttttcgtt   4740
ccactgagcg tcagacccg tagaaaagat caaaggatct tcttgagatc cttttttct   4800 gcgcgtaatc tgctgcttgc aaacaaaaaa accaccgcta ccagcggtgg tttgtttgcc   4860
ggatcaagag ctaccaactc tttttccgaa ggtaactggc ttcagcagag cgcagatacc   4920
aaatactgtt cttctagtgt agccgtagtt aggccaccac ttcaagaact ctgtagcacc   4980
gcctacatac ctcgctctgc taatcctgtt accagtggct gctgccagtg gcgataagtc   5040
gtgtcttacc gggttggact caagacgata gttaccggat aaggcgcagc ggtcgggctg   5100
aacggggggt tcgtgcacac agcccagctt ggagcgaacg acctacaccg aactgagata   5160
cctacagcgt gagctatgag aaagcgccac gcttcccgaa gggagaaagg cggacaggta   5220
tccggtaagc ggcagggtcg gaacaggaga gcgcacgagg gagcttccag ggggaaacgc   5280
ctggtatctt tatagtcctg tcgggtttcg ccacctctga cttgagcgtc gatttttgtg   5340
atgctcgtca ggggggcgga gcctatggaa aaacgccagc aacgcggcct ttttacggtt   5400
cctggccttt tgctggcctt ttgctcacat gttctttcct gcgttatccc ctgattctgt   5460
ggataaccgt attaccgcct ttgagtgagc tgataccgct cgccgcagcc gaacgaccga   5520
gcgcagcgag tcagtgagcg aggaagcgga agagcgccca atacgcaaac cgcctctccc   5580
cgcgcgttgg ccgattcatt aatgcagctg gcacgacagg tttcccgact ggaaagcggg   5640
cagtgagcgc aacgcaatta atgtgagtta gctcactcat taggcacccc aggctttaca   5700
ctttatgctt ccggctcgta tgttgtgtgg aattgtgagc ggataacaat ttcacacagg   5760
aaacagctat gaccatgatt acgccaagcg cgcaattaac cctcactaaa gggaacaaaa   5820
gctggagctg caagcttaat gtagtcttat gcaatactct tgtagtcttg caacatggta   5880
acgatgagtt agcaacatgc cttacaagga gagaaaaagc accgtgcatg ccgattggtg   5940
gaagtaaggt ggtacgatcg tgccttatta ggaaggcaac agacgggtct gacatggatt   6000
ggacgaacca ctgaattgcc gcattgcaga gatattgtat ttaagtgcct agctcgatac   6060
```

```
ataaacgggt ctctctggtt agaccagatc tgagcctggg agctctctgg ctaactaggg    6120
aacccactgc ttaagcctca ataaagcttg ccttgagtgc ttcaagtagt gtgtgcccgt    6180
ctgttgtgtg actctggtaa ctagagatcc ctcagaccct tttagtcagt gtggaaaatc    6240
tctagcagtg gcgcccgaac agggacttga aagcgaaagg gaaaccagag gagctctctc    6300
gacgcaggac tcggcttgct gaagcgcgca cggcaagagg cgaggggcgg cgactggtga    6360
gtacgccaaa aattttgact agcggaggct agaaggagag agatgggtgc gagagcgtca    6420
gtattaagcg ggggagaatt agatcgcgat gggaaaaaat tcggttaagg ccaggggaa     6480 agaaaaaata taaattaaaa catatagtat gggcaagcag ggagctagaa cgattcgcag    6540
ttaatcctgg cctgttagaa acatcagaag gctgtagaca aatactggga cagctacaac    6600
catcccttca gacaggatca gaagaactta gatcattata taatacagta gcaaccctct    6660
attgtgtgca tcaaaggata gagataaaag acaccaagga agctttagac aagatagagg    6720
aagagcaaaa caaaagtaag accaccgcac agcaagcggc cgctgatctt cagacctgga    6780
ggaggagata tgagggacaa ttggagaagt gaattatata aatataaagt agtaaaaatt    6840
gaaccattag gagtagcacc caccaaggca agagaagag tggtgcagag agaaaaaaga     6900
gcagtgggaa taggagcttt gttccttggg ttcttgggag cagcaggaag cactatgggc    6960
gcagcgtcaa tgacgctgac ggtacaggcc agacaattat tgtctggtat agtgcagcag    7020
cagaacaatt tgctgagggc tattgaggcg caacagcatc tgttgcaact cacagtctgg    7080
ggcatcaagc agctccaggc aagaatcctg gctgtggaaa gatacctaaa ggatcaacag    7140
ctcctgggga tttggggttg ctctggaaaa ctcatttgca ccactgctgt gccttggaat    7200
gctagttgga gtaataaatc tctggaacag atttggaatc acacgacctg gatggagtgg    7260
gacagagaaa ttaacaatta cacaagctta atacactcct taattgaaga tcgcaaaac    7320 cagcaagaaa agaatgaaca agaattattg gaattagata aatgggcaag tttgtggaat    7380
tggtttaaca taacaaattg gctgtggtat ataaaattat tcataatgat agtaggaggc    7440
ttggtaggtt taagaatagt ttttgctgta ctttctatag tgaatagagt taggcaggga    7500
tattcaccat tatcgtttca gacccacctc ccaaccccga ggggacccga caggcccgaa    7560
ggaatagaag aagaaggtgg agagagagac agagacagat ccattcgatt agtgaacgga    7620
tctcgacggt atcgatcacg agactagcct cgacacaaat ggcagtattc atccacaatt    7680
ttaaaagaaa agggggggatt ggggggtaca gtgcagggga agaatagta gacataatag    7740 caacagacat acaaactaaa gaattacaaa aacaaattac aaaaattcaa aattttcggg    7800
tttattacag ggacagcaga gatccagttt atcgacttaa cttgtttatt gcagcttata    7860
atggttacaa ataaggcaat agcatcacaa atttcacaaa taaggcattt ttttcactgc    7920
attctagttt tggtttgtcc aaactcatca atgtatctta tcatgtctgg atctcaaatc    7980
cctcggaagc tgcgcctgtc ttaggttgga gtgatacatt tttatcactt ttacccgtct    8040
ttggattagg cagtagctct gacggccctc ctgtcttagg ttagtgaaaa atgtcactct    8100
cttacccgtc attggctgtc cagcttagct cgcaggggag gtggtcttca ttactggcta    8160
gctcttctgc ctctaaacag catctggctc ctcttcctct tgccggtttt agcagcgggg    8220
ctcagttcgg ccatcacttg gatcagctcg tggatggcct ttctctggac gttcagatcg    8280
gtcacggagt agttggtgag cttctcgaag tcgtccctct tcttcttgtt gctgttgaag    8340
aatttcacgt tcatatcctc cttgatggtc tcgacgctct tctggatgct ctggtcgtcc    8400
ttgaagttct tgaagagctt gaagtagaag ctcacgatct gggactgcat gatctttcta    8460
```

```
tcggactcct ccttccagtt cttcagaatg ccgagaaaca gtgtgccgtt atcggccacg    8520
tcggagtggc cggcattgaa gtacttcttg aggttctcgg cctccttcac gtagggtct     8580 tggcagtagc agcccagaga gcccagcacg atgcacagct ggaaggccag aatgtagctg    8640
gtgtacttca tggggccggg gttctcctcg acatctccgg cttgcttcag cagagagaaa    8700
ttggtggcgc cgctgcccat ttgccgaaga gccctcaggc tggactgcag gaactcctta    8760
aagctgcgca gaatgagatg agttgtcatg tcctgcagcc actggttctg tgcctgcagc    8820
ttcgtcagca ggctggcatt tgtggttggg tcaggggtgg ttattgcatc tagattcttt    8880 gccttttct gcaggaactg gatcaggact tttgtactca tctgcacagc tctggcttgt     8940
tcctcactac tctcaaatct gttctggagg tactctaggt atacctcaaa ctccaaaaga   9000
ccagtgatga ttttcaccag gcaagtctcc tcattgaatc cagattggaa gcatccatct    9060
ttttcagcca tctttggaag gttcaggttg ttttctgcca gtgcctcttt gctgctttca    9120
cacatgttac tcttgttaca tgtctccttt ctcagggctg agatgccgtc gaggatgtac    9180
cgaatttgtt tgtcaattcg ttctgaagag gtgagtggct gtctgtgtgg ggcggctaca    9240
tctttggaat cttctcctgg gggtactggg gcagggaagg cagcaggcaa caccaggagc    9300
agccccaggg agaaggcaac tggaccgaag gcgcttgtgg agaaggagtt catggtggcc    9360
aggagttgag gttactgtga gtagtgatta aagagagtga tagggaactc ttgaacaaga    9420
gatgcaattt atactgttaa ttctggaaaa atattatggg ggtgtcaaaa tgtcccggga    9480
ccaattgacg ccttctgtat gaaacagttt ttcctcctaa ttgacgcctt ctgtatgaaa    9540 cagttttcc tcctaattga cgccttctgt atgaaacagt ttttcctcct aattcgatgg     9600
gaccaattga cgccttctgt atgaaacagt ttttcctcct aattgacgcc ttctgtatga    9660
aacagttttt cctcctaatt gacgccttct gtatgaaaca gttttttcctc ctaattcgat    9720 atcaagctta tcgataccgt cgacctcgat gaattcgcta gcaaatccac tttggctcga    9780
```

<210> SEQ ID NO 19
<211> LENGTH: 390
<212> TYPE: DNA
<213> ORGANISM: Artificial Sequence
<220> FEATURE:
<223> OTHER INFORMATION: Synthesized

<400> SEQUENCE: 19

```
tcgaggtcga cggtatcgat aagcttgata tcgaattagg aggaaaaact gtttcataca      60
gaaggcgtca attaggagga aaaactgttt catacagaag gcgtcaatta ggaggaaaaa    120
ctgtttcata cagaaggcgt caattggtcc atcgaatta ggaggaaaaa ctgtttcata     180
cagaaggcgt caattaggag gaaaaactgt ttcatacaga aggcgtcaat taggaggaaa    240
aactgtttca tacagaaggc gtcaattggt cccgggacat tttgacaccc cataatatt     300 tttccagaat taacagtata aattgcatct cttgttcaag agttccctat cactctcttt    360
aatcactact cacagtaacc tcaactcctg                                      390
```

<210> SEQ ID NO 20
<211> LENGTH: 212
<212> TYPE: PRT
<213> ORGANISM: Homo sapiens

<400> SEQUENCE: 20

```
Met Asn Ser Phe Ser Thr Ser Ala Phe Gly Pro Val Ala Phe Ser Leu
1               5                   10                  15
```

Gly Leu Leu Leu Val Leu Pro Ala Ala Phe Pro Ala Pro Val Pro Pro
              20                  25                  30

Gly Glu Asp Ser Lys Asp Val Ala Ala Pro His Arg Gln Pro Leu Thr
              35                  40                  45

Ser Ser Glu Arg Ile Asp Lys Gln Ile Arg Tyr Ile Leu Asp Gly Ile
 50                  55                  60

Ser Ala Leu Arg Lys Glu Thr Cys Asn Lys Ser Asn Met Cys Glu Ser
 65                  70                  75                  80

Ser Lys Glu Ala Leu Ala Glu Asn Asn Leu Asn Leu Pro Lys Met Ala
                  85                  90                  95

Glu Lys Asp Gly Cys Phe Gln Ser Gly Phe Asn Glu Glu Thr Cys Leu
             100                 105                 110

Val Lys Ile Ile Thr Gly Leu Leu Glu Phe Glu Val Tyr Leu Glu Tyr
             115                 120                 125

Leu Gln Asn Arg Phe Glu Ser Ser Glu Glu Gln Ala Arg Ala Val Gln
130                 135                 140

Met Ser Thr Lys Val Leu Ile Gln Phe Leu Gln Lys Lys Ala Lys Asn
145                 150                 155                 160

Leu Asp Ala Ile Thr Thr Pro Asp Pro Thr Thr Asn Ala Ser Leu Leu
                 165                 170                 175

Thr Lys Leu Gln Ala Gln Asn Gln Trp Leu Gln Asp Met Thr Thr His
                 180                 185                 190

Leu Ile Leu Arg Ser Phe Lys Glu Phe Leu Gln Ser Ser Leu Arg Ala
                 195                 200                 205

Leu Arg Gln Met
         210

<210> SEQ ID NO 21
<211> LENGTH: 57
<212> TYPE: DNA
<213> ORGANISM: Artificial Sequence
<220> FEATURE:
<223> OTHER INFORMATION: Synthesized

<400> SEQUENCE: 21
gccacgaact tctctctgtt aaagcaagca ggagacgtgg aagaaaaccc cggtcct         57

<210> SEQ ID NO 22
<211> LENGTH: 326
<212> TYPE: PRT
<213> ORGANISM: Homo sapiens

<400> SEQUENCE: 22

Glu Glu Thr Arg Glu Leu Gln Ser Leu Ala Ala Ala Val Val Pro Ser
1               5                  10                  15

Ala Gln Thr Leu Lys Ile Thr Asp Phe Ser Phe Ser Asp Phe Glu Leu
              20                  25                  30

Ser Asp Leu Glu Thr Ala Leu Cys Thr Ile Arg Met Phe Thr Asp Leu
           35                  40                  45

Asn Leu Val Gln Asn Phe Gln Met Lys His Glu Val Leu Cys Arg Trp
 50                  55                  60

Ile Leu Ser Val Lys Lys Asn Tyr Arg Lys Asn Val Ala Tyr His Asn
 65                  70                  75                  80

Trp Arg His Ala Phe Asn Thr Ala Gln Cys Met Phe Ala Ala Leu Lys
                  85                  90                  95

Ala Gly Lys Ile Gln Asn Lys Leu Thr Asp Leu Glu Ile Leu Ala Leu

```
            100             105                 110
Leu Ile Ala Ala Leu Ser His Asp Leu Asp His Arg Gly Val Asn Asn
            115                 120                 125

Ser Tyr Ile Gln Arg Ser Glu His Pro Leu Ala Gln Leu Tyr Cys His
130                 135                 140

Ser Ile Met Glu His His Phe Asp Gln Cys Leu Met Ile Leu Asn
145                 150                 155                 160

Ser Pro Gly Asn Gln Ile Leu Ser Gly Leu Ser Ile Glu Glu Tyr Lys
                165                 170                 175

Thr Thr Leu Lys Ile Ile Lys Gln Ala Ile Leu Ala Thr Asp Leu Ala
                    180                 185                 190

Leu Tyr Ile Lys Arg Arg Gly Glu Phe Phe Glu Leu Ile Arg Lys Asn
                195                 200                 205

Gln Phe Asn Leu Glu Asp Pro His Gln Lys Glu Leu Phe Leu Ala Met
            210                 215                 220

Leu Met Thr Ala Cys Asp Leu Ser Ala Ile Thr Lys Pro Trp Pro Ile
225                 230                 235                 240

Gln Gln Arg Ile Ala Glu Leu Val Ala Thr Glu Phe Phe Asp Gln Gly
                245                 250                 255

Asp Arg Glu Arg Lys Glu Leu Asn Ile Glu Pro Thr Asp Leu Met Asn
                260                 265                 270

Arg Glu Lys Lys Asn Lys Ile Pro Ser Met Gln Val Gly Phe Ile Asp
                275                 280                 285

Ala Ile Cys Leu Gln Leu Tyr Glu Ala Leu Thr His Val Ser Glu Asp
            290                 295                 300

Cys Phe Pro Leu Leu Asp Gly Cys Arg Lys Asn Arg Gln Lys Trp Gln
305                 310                 315                 320

Ala Leu Ala Glu Gln Gln
                325

<210> SEQ ID NO 23
<211> LENGTH: 10436
<212> TYPE: DNA
<213> ORGANISM: Artificial Sequence
<220> FEATURE:
<223> OTHER INFORMATION: Synthesized

<400> SEQUENCE: 23
cggctccggt gcccgtcagt gggcagagcg cacatcgccc acagtccccg agaagttggg      60
gggaggggtc ggcaattgaa ccggtgccta gagaaggtgg cgcggggtaa actgggaaag    120
tgatgtcgtg tactggctcc gccttttttcc cgagggtggg ggagaaccgt atataagtgc    180
agtagtcgcc gtgaacgttc tttttcgcaa cgggtttgcc gccagaacac aggatccgcc    240
accatggcct accagtgac cgccttgctc ctgccgctgg ccttgctgct ccacgccgcc    300
aggccggata tccagatgac ccagagcccg agcagcctga gcgcgagcgt gggtgatcgc    360
gtgaccatta cctgcagggc aagtcaggac attagtaaat atttaaattg gtatcagcag    420
aaaccgggta agcgccgaaa actgttaatt tatcatacat caagattaca ctcaggcgtg    480
ccgtcgcgtt ttagcggctc gggttcgggc accgattta ccctgaccat ctcgagcttg    540
cagccggagg acttcgccac ctactattgc aacagggta atacgcttcc gtacacgttc    600
ggtcagggca ccaaagtgga gatcaaaggt ggcggtggct cgggcggtgg tgggtcgggt    660
ggcggcggat ctgaggtgca gctggtggag tctgggggag gcttggtaca gcctgggggg    720
tccctgagac tctcctgtgc agcctctgga gtgtccctgc tgattatgg cgtgtcctgg    780
```

```
gtccgccagg ctccagggaa ggggctggag tgggtttcag tgatctgggg cagcgagaca    840
acctactaca acagcgccct gaagtccgga ttcaccatct ccagagacaa tgccaagaac    900
tcactgtatc tgcaaatgaa cagcctgaga gccgaggaca cggctgtgta ttactgtgcg    960
aagcactact actacggcgg cagctacgct atggactact ggggccaagg aaccctggtc   1020
accgtgtcct caaccacgac gccagcgccg cgaccaccaa caccggcgcc caccatcgcg   1080
tcgcagcccc tgtccctgcg cccagaggcg tgccggccag cggcgggggg cgcagtgcac   1140 acgaggggc tggacttcgc ctgtgatatc tacatctggg cgcccttggc cgggacttgt    1200
ggggtccttc tcctgtcact ggttatcacc ctttactgca acggggcag aaagaaactc    1260 ctgtatatat tcaaacaacc atttatgaga ccagtacaaa ctactcaaga ggaagatggc   1320
tgtagctgcc gatttccaga agaagaagaa ggaggatgtg aactgagagt gaagttcagc   1380
aggagcgcag acgccccgc gtaccagcag ggccagaacc agctctataa cgagctcaat    1440
ctaggacgaa gagaggagta cgatgttttg gacaagaggc gtggccggga ccctgagatg   1500 ggggaaagc cgagaaggaa gaaccctcag gaaggcctgt acaatgaact gcagaaagat    1560 aagatgcgg aggcctacag tgagattggg atgaaaggcg agcgccggag gggcaagggg    1620
cacgatggcc tttaccaggg tctcagtaca gccaccaagg acacctacga cgcccttcac   1680
atgcaggccc tgcccctcg ctaagtcgac tctagaacta gtaatcaacc tctggattac    1740
aaaatttgtg aaagattgac tggtattctt aactatgttg ctccttttac gctatgtgga   1800
tacgctgctt taatgccttt gtatcatgct attgcttccc gtatggcttt cattttctcc   1860
tccttgtata atcctggtt gctgtctctt tatgaggagt tgtggcccgt tgtcaggcaa    1920
cgtggcgtgg tgtgcactgt gtttgctgac gcaaccccca ctggttgggg cattgccacc   1980
acctgtcagc tccttccgg actttcgct ttcccctcc ctattgccac ggcggaactc     2040
atcgccgcct gccttgcccg ctgctggaca ggggctcggc tgttgggcac tgacaattcc   2100
gtggtgttgt cggggaaatc atcgtccttt ccttggctgc tcgcctgtgt tgccacctgg   2160
attctgcgcg gacgtccttc tgctacgtc ccttcggccc tcaatccagc ggaccttcct    2220
tcccgcggcc tgctgccggc tctgcggcct cttccgcgtc ttcgccttcg ccctcagacg   2280
agtcggatct ccctttgggc cgcctccccg cctccgcgg aattcgagct cggtaccttt    2340
aagaccaatg acttacaagg cagctgtaga tcttagccac tttttaaaag aaaagggggg   2400
actggaaggg ctaattcact cccaacgaag acaagatctg cttttgctt gtactgggtc    2460 tctctggtta gaccagatct gagcctggga gctctctggc taactaggga acccactgct   2520
taagcctcaa taaagcttgc cttgagtgct tcaagtagtg tgtgcccgtc tgttgtgtga   2580
ctctggtaac tagagatccc tcagacccct ttagtcagtg tggaaaatct ctagcagtag   2640
tagttcatgt catcttatta ttcagtattt ataacttgca aagaaatgaa tatcagagag   2700
tgagaggaac ttgtttattg cagcttataa tggttacaaa taaagcaata gcatcacaaa   2760
tttcacaaat aaagcatttt tttcactgca ttctagttgt ggtttgtcca aactcatcaa   2820
tgtatcttat catgtctggc tctagctatc ccgcccctaa ctccgcccat cccgccccta   2880
actccgccca gttccgccca ttctccgccc catggctgac taattttttt tatttatgca   2940
gaggccgagg ccgcctcggc ctctgagcta ttccagaagt agtgaggagg cttttttgga   3000
ggcctaggga cgtacccaat tcgccctata gtgagtcgta ttacgcgcgc tcactggccg   3060
tcgttttaca acgtcgtgac tgggaaaacc ctggcgttac ccaacttaat cgccttgcag   3120
```

```
cacatccccc tttcgccagc tggcgtaata gcgaagaggc ccgcaccgat cgcccttccc    3180
aacagttgcg cagcctgaat ggcgaatggg acgcgccctg tagcggcgca ttaagcgcgg    3240
cgggtgtggt ggttacgcgc agcgtgaccg ctacacttgc cagcgccta gcgcccgctc     3300 ctttcgcttt cttcccttcc tttctcgcca cgttcgccgg ctttccccgt caagctctaa    3360
atcgggggct cccttaggg ttccgattta gtgctttacg gcacctcgac cccaaaaaac    3420
ttgattaggg tgatggttca cgtagtgggc catcgccctg atagacggtt tttcgccctt    3480
tgacgttgga gtccacgttc tttaatagtg gactcttgtt ccaaactgga caacactca    3540 accctatctc ggtctattct tttgatttat aagggatttt gccgatttcg gcctattggt    3600 taaaaatga gctgatttaa caaaaattta acgcgaattt taacaaaata ttaacgctta    3660
caatttaggt ggcacttttc ggggaaatgt gcgcggaacc cctatttgtt tattttctta   3720
aatacattca aatatgtatc cgctcatgag acaataaccc tgataaatgc ttcaataata   3780 ttgaaaagg aagagtatga gccatattca acgggaaacg tcttgctcta ggccgcgatt    3840
aaattccaac atggatgctg atttatatgg gtataaatgg ctcgcgata atgtcgggca    3900 atcaggtgcg acaatctatc gattgtatgg gaagcccgat gcgccagagt tgtttctgaa   3960
acatggcaaa ggtagcgttg ccaatgatgt tacagatgag atggtcagac taaactggct   4020
gacggaattt atgcctcttc cgaccatcaa gcatttttatc cgtactcctg atgatgcatg   4080
gttactcacc actgcgatcc ccgggaaaac agcattccag gtattagaag aatatcctga   4140
ttcaggtgaa atattgttg atgcgctggc agtgttcctg cgccggttgc attcgattcc    4200
tgtttgtaat tgtccttta acagcgatcg cgtatttcgt ctggctcagg cgcaatcacg    4260
aatgaataac ggtttggttg atgcgagtga ttttgatgac gagcgtaatg gctggcctgt    4320
tgaacaagtc tggaaagaaa tgcataaact tttgccattc tcaccggatt cagtcgtcac    4380
tcatggtgat ttctcacttg ataaccttat ttttgacgag gggaaattaa taggttgtat    4440
tgatgttgga cgagtcggaa tcgcagaccg ataccaggat cttgccatcc tatggaactg    4500
cctcggtgag ttttctcctt cattacagaa acggcttttt caaaaatatg gtattgataa    4560
tcctgatatg aataaattgc agtttcattt gatgctcgat gagttttct aactgtcaga    4620 ccaagtttac tcatatatac tttagattga tttaaaactt cattttaat ttaaaaggat    4680 ctaggtgaag atccttttg ataatctcat gaccaaaatc ccttaacgtg agttttcgtt    4740
ccactgagcg tcagaccccg tagaaaagat caaaggatct tcttgagatc cttttttct    4800 gcgcgtaatc tgctgcttgc aaacaaaaaa accaccgcta ccagcggtgg tttgtttgcc    4860
ggatcaagag ctaccaactc ttttccgaa ggtaactggc ttcagcagag cgcagatacc    4920
aaatactgtt cttctagtgt agccgtagtt aggccaccac ttcaagaact ctgtagcacc    4980
gcctacatac ctcgctctgc taatcctgtt accagtggct gctgccagtg gcgataagtc    5040
gtgtcttacc gggttggact caagacgata gttaccggat aaggcgcagc ggtcgggctg    5100
aacggggggt tcgtgcacac agcccagctt ggagcgaacg acctacaccg aactgagata    5160
cctacagcgt gagctatgag aaagcgccac gcttcccgaa gggagaaagg cggacaggta    5220
tccggtaagc ggcagggtcg gaacaggaga gcgcacgagg gagcttccag ggggaaacgc    5280
ctggtatctt tatagtcctg tcgggtttcg ccacctctga cttgagcgtc gatttttgtg    5340
atgctcgtca gggggggcgga gcctatggaa aaacgccagc aacgcggcct tttacggtt    5400 cctggccttt tgctggcctt ttgctcacat gttcttcct gcgttatccc ctgattctgt    5460
ggataaccgt attaccgcct ttgagtgagc tgataccgct cgccgcagcc gaacgaccga    5520
```

```
gcgcagcgag tcagtgagcg aggaagcgga agagcgccca atacgcaaac cgcctctccc    5580
cgcgcgttgg ccgattcatt aatgcagctg gcacgacagg tttcccgact ggaaagcggg    5640
cagtgagcgc aacgcaatta atgtgagtta gctcactcat taggcacccc aggctttaca    5700
ctttatgctt ccggctcgta tgttgtgtgg aattgtgagc ggataacaat ttcacacagg    5760
aaacagctat gaccatgatt acgccaagcg cgcaattaac cctcactaaa gggaacaaaa    5820
gctggagctg caagcttaat gtagtcttat gcaatactct tgtagtcttg caacatggta    5880
acgatgagtt agcaacatgc cttacaagga gagaaaagc accgtgcatg ccgattggtg     5940
gaagtaaggt ggtacgatcg tgccttatta ggaaggcaac agacgggtct gacatggatt    6000
ggacgaacca ctgaattgcc gcattgcaga gatattgtat ttaagtgcct agctcgatac    6060
ataaacgggt ctctctggtt agaccagatc tgagcctggg agctctctgg ctaactaggg    6120
aacccactgc ttaagcctca ataaagcttg ccttgagtgc ttcaagtagt gtgtgcccgt    6180
ctgttgtgtg actctggtaa ctagagatcc ctcagaccct tttagtcagt gtggaaaatc    6240
tctagcagtg gcgcccgaac agggacttga agcgaaagg gaaaccagag gagctctctc     6300
gacgcaggac tcggcttgct gaagcgcgca cggcaagagg cgaggggcgg cgactggtga    6360
gtacgccaaa attttgact agcggaggct agaaggagag agatgggtgc gagagcgtca     6420
gtattaagcg ggggagaatt agatcgcgat gggaaaaaat tcggttaagg ccaggggaa     6480 agaaaaaata taaattaaaa catatagtat gggcaagcag ggagctagaa cgattcgcag    6540
ttaatcctgg cctgttagaa acatcagaag gctgtagaca atactggga cagctacaac     6600 catcccttca gacaggatca aagaactta gatcattata taatacagta gcaaccctct      6660
attgtgtgca tcaaaggata gagataaaag acaccaagga agctttagac aagatagagg    6720
aagagcaaaa caaaagtaag accaccgcac agcaagcggc cgctgatctt cagacctgga    6780
ggaggagata tgagggacaa ttggagaagt gaattatata atataaagt agtaaaatt       6840 gaaccattag gagtagcacc caccaaggca agagaagag tggtgcagag agaaaaaaga    6900
gcagtgggaa taggagcttt gttccttggg ttcttgggag cagcaggaag cactatgggc    6960
gcagcgtcaa tgacgctgac ggtacaggcc agacaattat tgtctggtat agtgcagcag    7020
cagaacaatt tgctgagggc tattgaggcg caacagcatc tgttgcaact cacagtctgg    7080
ggcatcaagc agctccaggc aagaatcctg gctgtggaaa gatacctaaa ggatcaacag    7140
ctcctgggga tttggggttg ctctggaaaa ctcatttgca ccactgctgt gccttggaat    7200
gctagttgga gtaataaatc tctggaacag atttggaatc acacgacctg gatggagtgg    7260
gacagagaaa ttaacaatta cacaagctta atacactcct taattgaaga atcgcaaaac    7320
cagcaagaaa agaatgaaca agaattattg gaattagata atgggcaag tttgtggaat     7380 tggtttaaca taacaaattg gctgtggtat ataaaattat tcataatgat agtaggaggc    7440
ttggtaggtt taagaatagt ttttgctgta ctttctatag tgaatagagt taggcaggga    7500
tattcaccat tatcgtttca gacccacctc ccaaccccga ggggacccga caggcccgaa    7560
ggaatagaag aagaaggtgg agagagagac agagacagat ccattcgatt agtgaacgga    7620
tctcgacggt atcgatcacg agactagcct cgacacaaat ggcagtattc atccacaatt    7680
ttaaaagaaa agggggggatt gggggtaca gtgcaggga aagaatagta gacataatag     7740
caacagacat acaaactaaa gaattacaaa aacaaattac aaaaattcaa atttcggg       7800 tttattacag ggacagcaga gatccagttt atcgacttaa cttgtttatt gcagcttata    7860
```

```
atggttacaa ataaggcaat agcatcacaa atttcacaaa taaggcattt ttttcactgc   7920
attctagttt tggtttgtcc aaactcatca atgtatctta tcatgtctgg atctcaaatc   7980
cctcggaagc tgcgcctgtc ttaggttgga gtgatacatt tttatcactt ttacccgtct   8040
ttggattagg cagtagctct gacggccctc ctgtcttagg ttagtgaaaa atgtcactct   8100
cttacccgtc attggctgtc cagcttagct cgcaggggag gtggtctcag tcgttggagc   8160
cgaagtccag agagatgatg gtgtctccag cggcgggggc cagcagtgtc agagcatcgg   8220
gctccttctt cagcttgtca acagagagc tggtgtcctc gctctccacc ttggtgaaga    8280
gctgggtcat cttcatgtcg ctgctctcca cgggcttcag cacgcactcg gtctgctgca   8340
gagagaagat cagatcgtgc tggatgattc ctctggcagc ggcctctcta gcagcggctt   8400
cgctggcgtt caggtagctc atcacccggt cgatggtcac ggcccggatc cggaaggcat   8460
gcaggaggat gcacagcttg atcttggtct tgtagaagtc gggctcttcc aggctggact   8520
tctggggcac tgtctcgctg ttgaagttca gggcctgcat cagctcgtcg atcacggcca   8580
gcatgttctg atccaggaag atctgccgct gggggtccat cagcagcttg gcgttcatgg   8640
tcttgaactc cacctggtac atcttcaggt cctcgtagat gctgctcagg cacagggcca   8700
tcatgaagct ggtcttctg ctggccaggc aagagccgtt ggtgatgaag cttgtctccc    8760
gagagttcag acagctctcg ttcttggtca gttccagggg caggcaggcc tccacggtgc   8820
tggtcttatc cttggtgatg tcctcgtggt cgatttcctc gctggtgcag gggtagaatt   8880
ccagggtctg ccgggccttc tgcagcatgt tgctcacggc ccgcagcagg ttctggctgt   8940
ggtgcaggca ggggaacatg ccgggtcgg ggtagccac gggcaggttc cggcttcctc     9000
cgcccctcc gccgctgcag ggcacgctgg cccactcgga ccaggagctg ctgtagtacc    9060
ggtcctgggc ccgcacgctg atgctggcgt tcttccggca gatcacggtg gcgctggtct   9120
tgtcggtgaa cacccggtct ttcttctccc gcttgctctt gccctgcacc tgcacacaga   9180
aggtcaggct gaagtagctg tggggggtgg accaggtgtc agggtactcc caggacacct   9240
ccacctgccg gctgttcttc aggggcttca gctgcaggtt cttgggggg tcgggcttga    9300
tgatgtcccg gatgaaaaag ctggaggtgt agttctcgta cttcagcttg tgcacggcgt   9360
ccaccatcac ctcgatgggc aggctttcct cggcggcagg gcaggcgcta tcttcctggc   9420
actcgacgct gtactcgtac tctttgttgt cgccccgcac tctctcggcg ctcagggtgg   9480
cggctccgca ggtcacgccc tgagggtcgc tgctgccccg gctgctcttc acgctgaagg   9540
tcaggtcggt gctgatggtg gtcagccacc aacaggtgaa ccggccgctg tagttcttgg   9600
cctcgcaccg caggaaggtc ttgttcttgg gctctttctg gtccttcagg atgtcggtgg   9660
accagatgcc atcctctttc ttgtgcagca gcagcaggct gtgggacagc acttcgccgc   9720
ccttgtggca ggtgtactgg ccggcgtcgc cgaactcttt gacctggatg gtcagggtct   9780
tgccgctgcc cagcacctcg ctgctctggt ccagggtcca ggtgatgccg tcctcttcgg   9840
gggtgtcgca ggtcagcacc accatctcgc cagggcgtc gggataccag tccagctcca    9900
ccacgtacac gtcttcttc agctcccaga tggccaccag ggggctggcc aggaacacca   9960
ggctgaacca gctgatgacc agctgctgat gacacatggt ggccaggagt tgaggttact   10020
gtgagtagtg attaaagaga gtgataggga actcttgaac aagagatgca atttatactg   10080
ttaattctgg aaaatatta tggggtgtc aaaatgtccc gggaccaatt gacgccttct     10140
gtatgaaaca gttttcctc ctaattgacg ccttctgtat gaaacagttt ttcctcctaa    10200
ttgacgcctt ctgtatgaaa cagttttcc tcctaattcg atgggaccaa ttgacgcctt    10260
```

```
ctgtatgaaa cagttttcc tcctaattga cgccttctgt atgaaacagt ttttcctcct    10320
aattgacgcc ttctgtatga aacagttttt cctcctaatt cgatatcaag cttatcgata    10380
ccgtcgacct cgatgaattc gctagcaaat ccactttggc tcgagaagct tgatat       10436
```

<210> SEQ ID NO 24
<211> LENGTH: 219
<212> TYPE: PRT
<213> ORGANISM: Homo sapiens

<400> SEQUENCE: 24

Met Cys Pro Ala Arg Ser Leu Leu Val Ala Thr Leu Val Leu Leu
1               5                   10                  15

Asp His Leu Ser Leu Ala Arg Asn Leu Pro Val Ala Thr Pro Asp Pro
            20                  25                  30

Gly Met Phe Pro Cys Leu His His Ser Gln Asn Leu Leu Arg Ala Val
        35                  40                  45

Ser Asn Met Leu Gln Lys Ala Arg Gln Thr Leu Glu Phe Tyr Pro Cys
    50                  55                  60

Thr Ser Glu Glu Ile Asp His Glu Asp Ile Thr Lys Asp Lys Thr Ser
65                  70                  75                  80

Thr Val Glu Ala Cys Leu Pro Leu Glu Leu Thr Lys Asn Glu Ser Cys
                85                  90                  95

Leu Asn Ser Arg Glu Thr Ser Phe Ile Thr Asn Gly Ser Cys Leu Ala
            100                 105                 110

Ser Arg Lys Thr Ser Phe Met Met Ala Leu Cys Leu Ser Ser Ile Tyr
        115                 120                 125

Glu Asp Leu Lys Met Tyr Gln Val Glu Phe Lys Thr Met Asn Ala Lys
    130                 135                 140

Leu Leu Met Asp Pro Lys Arg Gln Ile Phe Leu Asp Gln Asn Met Leu
145                 150                 155                 160

Ala Val Ile Asp Glu Leu Met Gln Ala Leu Asn Phe Asn Ser Glu Thr
                165                 170                 175

Val Pro Gln Lys Ser Ser Leu Glu Glu Pro Asp Phe Tyr Lys Thr Lys
            180                 185                 190

Ile Lys Leu Cys Ile Leu Leu His Ala Phe Arg Ile Arg Ala Val Thr
        195                 200                 205

Ile Asp Arg Val Met Ser Tyr Leu Asn Ala Ser
    210                 215

<210> SEQ ID NO 25
<211> LENGTH: 74
<212> TYPE: PRT
<213> ORGANISM: Artificial Sequence
<220> FEATURE:
<223> OTHER INFORMATION: Synthesized

<400> SEQUENCE: 25

Gly Ile Ile Gln His Asp Leu Ile Phe Ser Leu Gln Gln Thr Glu Cys
1               5                   10                  15

Val Leu Lys Pro Val Glu Ser Ser Asp Met Lys Met Thr Gln Leu Phe
            20                  25                  30

Thr Lys Val Glu Ser Glu Asp Thr Ser Ser Leu Phe Asp Lys Leu Lys
        35                  40                  45

Lys Glu Pro Asp Ala Leu Thr Leu Leu Ala Pro Ala Ala Gly Asp Thr
    50                  55                  60

Ile Ile Ser Leu Asp Phe Gly Ser Asn Asp
65                  70

<210> SEQ ID NO 26
<211> LENGTH: 485
<212> TYPE: PRT
<213> ORGANISM: Artificial Sequence
<220> FEATURE:
<223> OTHER INFORMATION: Synthesized

<400> SEQUENCE: 26

Met Ala Leu Pro Val Thr Ala Leu Leu Leu Pro Leu Ala Leu Leu Leu
1               5                   10                  15

His Ala Ala Arg Pro Glu Ile Val Met Thr Gln Ser Pro Ala Thr Leu
            20                  25                  30

Ser Val Ser Pro Gly Glu Arg Ala Thr Leu Ser Cys Arg Ala Ser Gln
        35                  40                  45

Ser Val Ser Arg Asn Leu Ala Trp Tyr Gln Gln Lys Pro Gly Gln Ala
    50                  55                  60

Pro Arg Leu Leu Ile Tyr Gly Ala Ser Thr Arg Ala Thr Gly Ile Pro
65                  70                  75                  80

Ala Arg Phe Ser Gly Ser Gly Ser Gly Thr Glu Phe Thr Leu Thr Ile
                85                  90                  95

Gly Ser Leu Gln Ser Glu Asp Phe Ala Val Tyr Tyr Cys Gln Gln Tyr
            100                 105                 110

Lys Thr Trp Pro Arg Thr Phe Gly Gln Gly Thr Asn Val Glu Ile Lys
        115                 120                 125

Gly Gly Gly Gly Ser Gly Gly Gly Ser Gly Gly Gly Gly Ser Gln
    130                 135                 140

Val Gln Leu Gln Gln Trp Gly Ala Gly Leu Leu Lys Pro Ser Glu Thr
145                 150                 155                 160

Leu Ser Leu Thr Cys Ala Val Phe Gly Gly Ser Phe Ser Gly Tyr Tyr
                165                 170                 175

Trp Ser Trp Ile Arg Gln Pro Pro Gly Lys Gly Leu Glu Trp Ile Gly
            180                 185                 190

Glu Ile Asn His Arg Gly Asn Thr Asn Asp Asn Pro Ser Leu Lys Ser
        195                 200                 205

Arg Val Thr Ile Ser Val Asp Thr Ser Lys Asn Gln Phe Ala Leu Lys
    210                 215                 220

Leu Ser Ser Val Thr Ala Ala Asp Thr Ala Val Tyr Tyr Cys Ala Arg
225                 230                 235                 240

Glu Arg Gly Tyr Thr Tyr Gly Asn Phe Asp His Trp Gly Gln Gly Thr
                245                 250                 255

Leu Val Thr Val Ser Ser Ala Lys Pro Thr Thr Thr Pro Ala Pro Arg
            260                 265                 270

Pro Pro Thr Pro Ala Pro Thr Ile Ala Ser Gln Pro Leu Ser Leu Arg
        275                 280                 285

Pro Glu Ala Cys Arg Pro Ala Ala Gly Gly Ala Val His Thr Arg Gly
    290                 295                 300

Leu Asp Phe Ala Cys Asp Ile Tyr Ile Trp Ala Pro Leu Ala Gly Thr
305                 310                 315                 320

Cys Gly Val Leu Leu Leu Ser Leu Val Ile Thr Lys Arg Gly Arg Lys
                325                 330                 335

Lys Leu Leu Tyr Ile Phe Lys Gln Pro Phe Met Arg Pro Val Gln Thr
            340                 345                 350

```
Thr Gln Glu Glu Asp Gly Cys Ser Cys Arg Phe Pro Glu Glu Glu
            355                 360                 365

Gly Gly Cys Glu Leu Arg Val Lys Phe Ser Arg Ser Ala Asp Ala Pro
    370                 375                 380

Ala Tyr Lys Gln Gly Gln Asn Gln Leu Tyr Asn Glu Leu Asn Leu Gly
385                 390                 395                 400

Arg Arg Glu Glu Tyr Asp Val Leu Asp Lys Arg Arg Gly Arg Asp Pro
                405                 410                 415

Glu Met Gly Gly Lys Pro Arg Arg Lys Asn Pro Gln Glu Gly Leu Tyr
            420                 425                 430

Asn Glu Leu Gln Lys Asp Lys Met Ala Glu Ala Tyr Ser Glu Ile Gly
        435                 440                 445

Met Lys Gly Glu Arg Arg Arg Gly Lys Gly His Asp Gly Leu Tyr Gln
    450                 455                 460

Gly Leu Ser Thr Ala Thr Lys Asp Thr Tyr Asp Ala Leu His Met Gln
465                 470                 475                 480

Ala Leu Pro Pro Arg
            485

<210> SEQ ID NO 27
<211> LENGTH: 119
<212> TYPE: PRT
<213> ORGANISM: Artificial Sequence
<220> FEATURE:
<223> OTHER INFORMATION: Synthesized

<400> SEQUENCE: 27

Gln Val Gln Leu Gln Gln Trp Gly Ala Gly Leu Leu Lys Pro Ser Glu
1               5                   10                  15

Thr Leu Ser Leu Thr Cys Ala Val Phe Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Arg Gly Asn Ile Asn Asp Asn Pro Ser Leu Lys
    50                  55                  60

Ser Arg Val Thr Ile Ser Val Asp Thr Ser Lys Asn Gln Phe Ala Leu
65                  70                  75                  80

Lys Leu Ser Ser Val Thr Ala Ala Asp Thr Ala Val Tyr Tyr Cys Ala
                85                  90                  95

Arg Glu Arg Gly Tyr Thr Tyr Gly Asn Tyr Glu His Trp Gly Gln Gly
            100                 105                 110

Thr Leu Val Thr Val Ser Ser
        115

<210> SEQ ID NO 28
<211> LENGTH: 107
<212> TYPE: PRT
<213> ORGANISM: Artificial Sequence
<220> FEATURE:
<223> OTHER INFORMATION: Synthesized

<400> SEQUENCE: 28

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Thr Val Asn Arg Asn
            20                  25                  30

Leu Ala Trp Tyr Gln Gln Lys Pro Gly Gln Ala Pro Arg Leu Leu Ile
        35                  40                  45
```

```
Tyr Gly Ala Ser Thr Arg Ala Thr Gly Ile Pro Ala Arg Phe Ser Gly
         50                  55                  60

Ser Gly Ser Gly Thr Glu Phe Thr Leu Thr Ile Gly Ser Leu Gln Ser
 65              70                  75                  80

Glu Asp Phe Ala Val Tyr Tyr Cys Gln Gln Tyr Lys Thr Trp Pro Arg
                 85                  90                  95

Thr Phe Gly Gln Gly Thr Asn Val Glu Ile Lys
                100                 105

<210> SEQ ID NO 29
<211> LENGTH: 485
<212> TYPE: PRT
<213> ORGANISM: Artificial Sequence
<220> FEATURE:
<223> OTHER INFORMATION: Synthesized

<400> SEQUENCE: 29

Met Ala Leu Pro Val Thr Ala Leu Leu Leu Pro Leu Ala Leu Leu Leu
 1               5                  10                  15

His Ala Ala Arg Pro Glu Ile Val Met Thr Gln Ser Pro Ala Thr Leu
                20                  25                  30

Ser Val Ser Pro Gly Glu Arg Ala Thr Leu Ser Cys Arg Ala Ser Gln
             35                  40                  45

Thr Val Asn Arg Asn Leu Ala Trp Tyr Gln Gln Lys Pro Gly Gln Ala
     50                  55                  60

Pro Arg Leu Leu Ile Tyr Gly Ala Ser Thr Arg Ala Thr Gly Ile Pro
 65                  70                  75                  80

Ala Arg Phe Ser Gly Ser Gly Ser Gly Thr Glu Phe Thr Leu Thr Ile
                 85                  90                  95

Gly Ser Leu Gln Ser Glu Asp Phe Ala Val Tyr Tyr Cys Gln Gln Tyr
                100                 105                 110

Lys Thr Trp Pro Arg Thr Phe Gly Gln Gly Thr Asn Val Glu Ile Lys
            115                 120                 125

Gly Gly Gly Gly Ser Gly Gly Gly Ser Gly Gly Gly Gly Ser Gln
130                 135                 140

Val Gln Leu Gln Gln Trp Gly Ala Gly Leu Leu Lys Pro Ser Glu Thr
145                 150                 155                 160

Leu Ser Leu Thr Cys Ala Val Phe Gly Gly Ser Phe Ser Gly Tyr Tyr
                165                 170                 175

Trp Ser Trp Ile Arg Gln Pro Pro Gly Lys Gly Leu Glu Trp Ile Gly
                180                 185                 190

Glu Ile Asn His Arg Gly Asn Ile Asn Asp Asn Pro Ser Leu Lys Ser
            195                 200                 205

Arg Val Thr Ile Ser Val Asp Thr Ser Lys Asn Gln Phe Ala Leu Lys
        210                 215                 220

Leu Ser Ser Val Thr Ala Ala Asp Thr Ala Val Tyr Tyr Cys Ala Arg
225                 230                 235                 240

Glu Arg Gly Tyr Thr Tyr Gly Asn Tyr Glu His Trp Gly Gln Gly Thr
                245                 250                 255

Leu Val Thr Val Ser Ser Thr Thr Pro Ala Pro Arg Pro Pro Thr
                260                 265                 270

Pro Ala Pro Thr Ile Ala Ser Gln Pro Leu Ser Leu Arg Pro Glu Ala
            275                 280                 285

Cys Arg Pro Ala Ala Gly Gly Ala Val His Thr Arg Gly Leu Asp Phe
        290                 295                 300
```

```
Ala Cys Asp Ile Tyr Ile Trp Ala Pro Leu Ala Gly Thr Cys Gly Val
305                 310                 315                 320

Leu Leu Leu Ser Leu Val Ile Thr Leu Tyr Cys Lys Arg Gly Arg Lys
            325                 330                 335

Lys Leu Leu Tyr Ile Phe Lys Gln Pro Phe Met Arg Pro Val Gln Thr
        340                 345                 350

Thr Gln Glu Glu Asp Gly Cys Ser Cys Arg Phe Pro Glu Glu Glu Glu
    355                 360                 365

Gly Gly Cys Glu Leu Arg Val Lys Phe Ser Arg Ser Ala Asp Ala Pro
370                 375                 380

Ala Tyr Gln Gln Gly Gln Asn Gln Leu Tyr Asn Glu Leu Asn Leu Gly
385                 390                 395                 400

Arg Arg Glu Glu Tyr Asp Val Leu Asp Lys Arg Arg Gly Arg Asp Pro
                405                 410                 415

Glu Met Gly Gly Lys Pro Arg Arg Lys Asn Pro Gln Glu Gly Leu Tyr
            420                 425                 430

Asn Glu Leu Gln Lys Asp Lys Met Ala Glu Ala Tyr Ser Glu Ile Gly
            435                 440                 445

Met Lys Gly Glu Arg Arg Arg Gly Lys Gly His Asp Gly Leu Tyr Gln
450                 455                 460

Gly Leu Ser Thr Ala Thr Lys Asp Thr Tyr Asp Ala Leu His Met Gln
465                 470                 475                 480

Ala Leu Pro Pro Arg
                485

<210> SEQ ID NO 30
<211> LENGTH: 482
<212> TYPE: PRT
<213> ORGANISM: Artificial Sequence
<220> FEATURE:
<223> OTHER INFORMATION: Synthesized

<400> SEQUENCE: 30

Met Ala Leu Pro Val Thr Ala Leu Leu Leu Pro Leu Ala Leu Leu Leu
1               5                   10                  15

His Ala Ala Arg Pro Glu Ile Val Met Thr Gln Ser Pro Ala Thr Leu
            20                  25                  30

Ser Val Ser Pro Gly Glu Arg Ala Thr Leu Ser Cys Arg Ala Ser Gln
        35                  40                  45

Thr Val Asn Arg Asn Leu Ala Trp Tyr Gln Gln Lys Pro Gly Gln Ala
    50                  55                  60

Pro Arg Leu Leu Ile Tyr Gly Ala Ser Thr Arg Ala Thr Gly Ile Pro
65                  70                  75                  80

Ala Arg Phe Ser Gly Ser Gly Ser Gly Thr Glu Phe Thr Leu Thr Ile
                85                  90                  95

Gly Ser Leu Gln Ser Glu Asp Phe Ala Val Tyr Tyr Cys Gln Gln Tyr
            100                 105                 110

Lys Thr Trp Pro Arg Thr Phe Gly Gln Gly Thr Asn Val Glu Ile Lys
        115                 120                 125

Gly Gly Gly Gly Ser Gly Gly Gly Gly Ser Gly Gly Gly Gly Ser Gln
    130                 135                 140

Val Gln Leu Gln Gln Trp Gly Ala Gly Leu Leu Lys Pro Ser Glu Thr
145                 150                 155                 160

Leu Ser Leu Thr Cys Ala Val Phe Gly Gly Ser Phe Ser Gly Tyr Tyr
                165                 170                 175
```

Trp Ser Trp Ile Arg Gln Pro Pro Gly Lys Gly Leu Glu Trp Ile Gly
            180                 185                 190

Glu Ile Asn His Arg Gly Asn Ile Asn Asp Asn Pro Ser Leu Lys Ser
        195                 200                 205

Arg Val Thr Ile Ser Val Asp Thr Ser Lys Asn Gln Phe Ala Leu Lys
    210                 215                 220

Leu Ser Ser Val Thr Ala Ala Asp Thr Ala Val Tyr Tyr Cys Ala Arg
225                 230                 235                 240

Glu Arg Gly Tyr Thr Tyr Gly Asn Tyr Glu His Trp Gly Gln Gly Thr
                245                 250                 255

Leu Val Thr Val Ser Ser Lys Ile Glu Val Met Tyr Pro Pro Pro Tyr
            260                 265                 270

Leu Asp Asn Glu Lys Ser Asn Gly Thr Ile Ile His Val Lys Gly Lys
        275                 280                 285

His Leu Cys Pro Ser Pro Leu Phe Pro Gly Pro Ser Lys Pro Phe Trp
    290                 295                 300

Val Leu Val Val Val Gly Gly Val Leu Ala Cys Tyr Ser Leu Leu Val
305                 310                 315                 320

Thr Val Ala Phe Ile Ile Phe Trp Val Arg Ser Lys Arg Ser Arg Leu
                325                 330                 335

Leu His Ser Asp Tyr Met Asn Met Thr Pro Arg Arg Pro Gly Pro Thr
            340                 345                 350

Arg Lys His Tyr Gln Pro Tyr Ala Pro Pro Arg Asp Phe Ala Ala Tyr
        355                 360                 365

Arg Ser Arg Val Lys Phe Ser Arg Ser Ala Asp Ala Pro Ala Tyr Gln
    370                 375                 380

Gln Gly Gln Asn Gln Leu Tyr Asn Glu Leu Asn Leu Gly Arg Arg Glu
385                 390                 395                 400

Glu Tyr Asp Val Leu Asp Lys Arg Arg Gly Arg Asp Pro Glu Met Gly
                405                 410                 415

Gly Lys Pro Arg Arg Lys Asn Pro Gln Glu Gly Leu Tyr Asn Glu Leu
            420                 425                 430

Gln Lys Asp Lys Met Ala Glu Ala Tyr Ser Glu Ile Gly Met Lys Gly
        435                 440                 445

Glu Arg Arg Arg Gly Lys Gly His Asp Gly Leu Tyr Gln Gly Leu Ser
    450                 455                 460

Thr Ala Thr Lys Asp Thr Tyr Asp Ala Leu His Met Gln Ala Leu Pro
465                 470                 475                 480

Pro Arg

<210> SEQ ID NO 31
<211> LENGTH: 119
<212> TYPE: PRT
<213> ORGANISM: Artificial Sequence
<220> FEATURE:
<223> OTHER INFORMATION: Synthesized

<400> SEQUENCE: 31

Gln Val Gln Leu Gln Gln Trp Gly Ala Gly Leu Leu Lys Pro Ser Glu
1               5                   10                  15

Thr Leu Ser Leu Thr Cys Ala Val Phe Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Arg Gly Asn Ile Asn Asp Asn Pro Ser Leu Lys
                50                  55                  60

Ser Arg Val Thr Ile Ser Val Asp Thr Ser Lys Asn Gln Phe Ala Leu
 65                  70                  75                  80

Lys Leu Ser Ser Val Thr Ala Ala Asp Thr Ala Val Tyr Tyr Cys Ala
                    85                  90                  95

Arg Glu Arg Gly Tyr Ser Phe Gly Asn Tyr Asp His Trp Gly Gln Gly
                100                 105                 110

Thr Leu Val Thr Val Ser Ser
            115

<210> SEQ ID NO 32
<211> LENGTH: 107
<212> TYPE: PRT
<213> ORGANISM: Artificial Sequence
<220> FEATURE:
<223> OTHER INFORMATION: Synthesized

<400> SEQUENCE: 32

Glu Ile Val Met Thr Gln Ser Pro Ala Thr Leu Ser Val Ser Pro Gly
 1               5                  10                  15

Glu Arg Ala Thr Leu Ser Cys Arg Ala Ser Gln Thr Val Thr Arg Asn
                20                  25                  30

Leu Ala Trp Tyr Gln Gln Lys Pro Gly Gln Ala Pro Arg Leu Leu Ile
             35                  40                  45

Tyr Gly Ala Ser Thr Arg Ala Thr Gly Ile Pro Ala Arg Phe Ser Gly
         50                  55                  60

Ser Gly Ser Gly Thr Glu Phe Thr Leu Thr Ile Gly Ser Leu Gln Ser
 65                  70                  75                  80

Glu Asp Phe Ala Val Tyr Tyr Cys Gln Gln Tyr Lys Ser Trp Pro Arg
                    85                  90                  95

Thr Phe Gly Gln Gly Thr Asn Val Glu Ile Lys
                100                 105

<210> SEQ ID NO 33
<211> LENGTH: 485
<212> TYPE: PRT
<213> ORGANISM: Artificial Sequence
<220> FEATURE:
<223> OTHER INFORMATION: Synthesized

<400> SEQUENCE: 33

Met Ala Leu Pro Val Thr Ala Leu Leu Leu Pro Leu Ala Leu Leu Leu
 1               5                  10                  15

His Ala Ala Arg Pro Glu Ile Val Met Thr Gln Ser Pro Ala Thr Leu
                20                  25                  30

Ser Val Ser Pro Gly Glu Arg Ala Thr Leu Ser Cys Arg Ala Ser Gln
             35                  40                  45

Thr Val Thr Arg Asn Leu Ala Trp Tyr Gln Gln Lys Pro Gly Gln Ala
         50                  55                  60

Pro Arg Leu Leu Ile Tyr Gly Ala Ser Thr Arg Ala Thr Gly Ile Pro
 65                  70                  75                  80

Ala Arg Phe Ser Gly Ser Gly Ser Gly Thr Glu Phe Thr Leu Thr Ile
                    85                  90                  95

Gly Ser Leu Gln Ser Glu Asp Phe Ala Val Tyr Tyr Cys Gln Gln Tyr
                100                 105                 110

Lys Ser Trp Pro Arg Thr Phe Gly Gln Gly Thr Asn Val Glu Ile Lys
                115                 120                 125

Gly Gly Gly Gly Ser Gly Gly Gly Ser Gly Gly Gly Ser Gln
            130                 135                 140

Val Gln Leu Gln Gln Trp Gly Ala Gly Leu Leu Lys Pro Ser Glu Thr
145                 150                 155                 160

Leu Ser Leu Thr Cys Ala Val Phe Gly Gly Ser Phe Ser Gly Tyr Tyr
                165                 170                 175

Trp Ser Trp Ile Arg Gln Pro Pro Gly Lys Gly Leu Glu Trp Ile Gly
            180                 185                 190

Glu Ile Asn His Arg Gly Asn Ile Asn Asp Asn Pro Ser Leu Lys Ser
        195                 200                 205

Arg Val Thr Ile Ser Val Asp Thr Ser Lys Asn Gln Phe Ala Leu Lys
210                 215                 220

Leu Ser Ser Val Thr Ala Ala Asp Thr Ala Val Tyr Tyr Cys Ala Arg
225                 230                 235                 240

Glu Arg Gly Tyr Ser Phe Gly Asn Tyr Asp His Trp Gly Gln Gly Thr
                245                 250                 255

Leu Val Thr Val Ser Ser Thr Thr Thr Pro Ala Pro Arg Pro Pro Thr
            260                 265                 270

Pro Ala Pro Thr Ile Ala Ser Gln Pro Leu Ser Leu Arg Pro Glu Ala
        275                 280                 285

Cys Arg Pro Ala Ala Gly Gly Ala Val His Thr Arg Gly Leu Asp Phe
290                 295                 300

Ala Cys Asp Ile Tyr Ile Trp Ala Pro Leu Ala Gly Thr Cys Gly Val
305                 310                 315                 320

Leu Leu Leu Ser Leu Val Ile Thr Leu Tyr Cys Lys Arg Gly Arg Lys
                325                 330                 335

Lys Leu Leu Tyr Ile Phe Lys Gln Pro Phe Met Arg Pro Val Gln Thr
            340                 345                 350

Thr Gln Glu Glu Asp Gly Cys Ser Cys Arg Phe Pro Glu Glu Glu Glu
        355                 360                 365

Gly Gly Cys Glu Leu Arg Val Lys Phe Ser Arg Ser Ala Asp Ala Pro
370                 375                 380

Ala Tyr Gln Gln Gly Gln Asn Gln Leu Tyr Asn Glu Leu Asn Leu Gly
385                 390                 395                 400

Arg Arg Glu Glu Tyr Asp Val Leu Asp Lys Arg Arg Gly Arg Asp Pro
                405                 410                 415

Glu Met Gly Gly Lys Pro Arg Arg Lys Asn Pro Gln Glu Gly Leu Tyr
            420                 425                 430

Asn Glu Leu Gln Lys Asp Lys Met Ala Glu Ala Tyr Ser Glu Ile Gly
        435                 440                 445

Met Lys Gly Glu Arg Arg Arg Gly Lys Gly His Asp Gly Leu Tyr Gln
450                 455                 460

Gly Leu Ser Thr Ala Thr Lys Asp Thr Tyr Asp Ala Leu His Met Gln
465                 470                 475                 480

Ala Leu Pro Pro Arg
                485

<210> SEQ ID NO 34
<211> LENGTH: 482
<212> TYPE: PRT
<213> ORGANISM: Artificial Sequence
<220> FEATURE:
<223> OTHER INFORMATION: Synthesized

<400> SEQUENCE: 34

```
Met Ala Leu Pro Val Thr Ala Leu Leu Leu Pro Leu Ala Leu Leu Leu
1               5                   10                  15

His Ala Ala Arg Pro Glu Ile Val Met Thr Gln Ser Pro Ala Thr Leu
            20                  25                  30

Ser Val Ser Pro Gly Glu Arg Ala Thr Leu Ser Cys Arg Ala Ser Gln
        35                  40                  45

Thr Val Thr Arg Asn Leu Ala Trp Tyr Gln Lys Pro Gly Gln Ala
    50                  55                  60

Pro Arg Leu Leu Ile Tyr Gly Ala Ser Thr Arg Ala Thr Gly Ile Pro
65                  70                  75                  80

Ala Arg Phe Ser Gly Ser Gly Ser Gly Thr Glu Phe Thr Leu Thr Ile
                85                  90                  95

Gly Ser Leu Gln Ser Glu Asp Phe Ala Val Tyr Tyr Cys Gln Gln Tyr
            100                 105                 110

Lys Ser Trp Pro Arg Thr Phe Gly Gln Gly Thr Asn Val Glu Ile Lys
        115                 120                 125

Gly Gly Gly Gly Ser Gly Gly Gly Ser Gly Gly Gly Gly Ser Gln
    130                 135                 140

Val Gln Leu Gln Gln Trp Gly Ala Gly Leu Leu Lys Pro Ser Glu Thr
145                 150                 155                 160

Leu Ser Leu Thr Cys Ala Val Phe Gly Gly Ser Phe Ser Gly Tyr Tyr
                165                 170                 175

Trp Ser Trp Ile Arg Gln Pro Pro Gly Lys Gly Leu Glu Trp Ile Gly
            180                 185                 190

Glu Ile Asn His Arg Gly Asn Ile Asn Asp Asn Pro Ser Leu Lys Ser
        195                 200                 205

Arg Val Thr Ile Ser Val Asp Thr Ser Lys Asn Gln Phe Ala Leu Lys
    210                 215                 220

Leu Ser Ser Val Thr Ala Ala Asp Thr Ala Val Tyr Tyr Cys Ala Arg
225                 230                 235                 240

Glu Arg Gly Tyr Ser Phe Gly Asn Tyr Asp His Trp Gly Gln Gly Thr
                245                 250                 255

Leu Val Thr Val Ser Ser Lys Ile Glu Val Met Tyr Pro Pro Pro Tyr
            260                 265                 270

Leu Asp Asn Glu Lys Ser Asn Gly Thr Ile Ile His Val Lys Gly Lys
        275                 280                 285

His Leu Cys Pro Ser Pro Leu Phe Pro Gly Pro Ser Lys Pro Phe Trp
    290                 295                 300

Val Leu Val Val Val Gly Gly Val Leu Ala Cys Tyr Ser Leu Leu Val
305                 310                 315                 320

Thr Val Ala Phe Ile Ile Phe Trp Val Arg Ser Lys Arg Ser Arg Leu
                325                 330                 335

Leu His Ser Asp Tyr Met Asn Met Thr Pro Arg Arg Pro Gly Pro Thr
            340                 345                 350

Arg Lys His Tyr Gln Pro Tyr Ala Pro Pro Arg Asp Phe Ala Ala Tyr
        355                 360                 365

Arg Ser Arg Val Lys Phe Ser Arg Ser Ala Asp Ala Pro Ala Tyr Gln
    370                 375                 380

Gln Gly Gln Asn Gln Leu Tyr Asn Glu Leu Asn Leu Gly Arg Arg Glu
385                 390                 395                 400

Glu Tyr Asp Val Leu Asp Lys Arg Arg Gly Arg Asp Pro Glu Met Gly
                405                 410                 415
```

-continued

Gly Lys Pro Arg Arg Lys Asn Pro Gln Glu Gly Leu Tyr Asn Glu Leu
                420                 425                 430

Gln Lys Asp Lys Met Ala Glu Ala Tyr Ser Glu Ile Gly Met Lys Gly
            435                 440                 445

Glu Arg Arg Arg Gly Lys Gly His Asp Gly Leu Tyr Gln Gly Leu Ser
450                 455                 460

Thr Ala Thr Lys Asp Thr Tyr Asp Ala Leu His Met Gln Ala Leu Pro
465                 470                 475                 480

Pro Arg

<210> SEQ ID NO 35
<211> LENGTH: 107
<212> TYPE: PRT
<213> ORGANISM: Artificial Sequence
<220> FEATURE:
<223> OTHER INFORMATION: Synthesized

<400> SEQUENCE: 35

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Thr Val Asn Arg Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Gly Ser Leu Gln Ser
65                  70                  75                  80

Glu Asp Phe Ala Val Tyr Tyr Cys Gln Gln Tyr Lys Thr Trp Pro Arg
                85                  90                  95

Ser Phe Gly Gln Gly Thr Asn Val Glu Ile Lys
            100                 105

<210> SEQ ID NO 36
<211> LENGTH: 485
<212> TYPE: PRT
<213> ORGANISM: Artificial Sequence
<220> FEATURE:
<223> OTHER INFORMATION: Synthesized

<400> SEQUENCE: 36

Met Ala Leu Pro Val Thr Ala Leu Leu Leu Pro Leu Ala Leu Leu Leu
1               5                   10                  15

His Ala Ala Arg Pro Glu Ile Val Met Thr Gln Ser Pro Ala Thr Leu
            20                  25                  30

Ser Val Ser Pro Gly Glu Arg Ala Thr Leu Ser Cys Arg Ala Ser Gln
        35                  40                  45

Thr Val Asn Arg Asn Leu Ala Trp Tyr Gln Gln Lys Pro Gly Gln Ala
    50                  55                  60

Pro Arg Leu Leu Ile Tyr Gly Ala Ser Thr Arg Ala Thr Gly Ile Pro
65                  70                  75                  80

Ala Arg Phe Ser Gly Ser Gly Ser Gly Thr Glu Phe Thr Leu Thr Ile
                85                  90                  95

Gly Ser Leu Gln Ser Glu Asp Phe Ala Val Tyr Tyr Cys Gln Gln Tyr
            100                 105                 110

Lys Thr Trp Pro Arg Ser Phe Gly Gln Gly Thr Asn Val Glu Ile Lys
        115                 120                 125

Gly Gly Gly Ser Gly Gly Gly Ser Gly Gly Gly Ser Gln
    130             135             140

Val Gln Leu Gln Gln Trp Gly Ala Gly Leu Leu Lys Pro Ser Glu Thr
145                 150                 155                 160

Leu Ser Leu Thr Cys Ala Val Phe Gly Gly Ser Phe Ser Gly Tyr Tyr
                165                 170                 175

Trp Ser Trp Ile Arg Gln Pro Pro Gly Lys Gly Leu Glu Trp Ile Gly
            180                 185                 190

Glu Ile Asn His Arg Gly Asn Ile Asn Asp Asn Pro Ser Leu Lys Ser
            195                 200                 205

Arg Val Thr Ile Ser Val Asp Thr Ser Lys Asn Gln Phe Ala Leu Lys
        210                 215                 220

Leu Ser Ser Val Thr Ala Ala Asp Thr Ala Val Tyr Tyr Cys Ala Arg
225                 230                 235                 240

Glu Arg Gly Tyr Thr Tyr Gly Asn Tyr Glu His Trp Gly Gln Gly Thr
                245                 250                 255

Leu Val Thr Val Ser Ser Thr Thr Pro Ala Pro Arg Pro Pro Thr
            260                 265                 270

Pro Ala Pro Thr Ile Ala Ser Gln Pro Leu Ser Leu Arg Pro Glu Ala
        275                 280                 285

Cys Arg Pro Ala Ala Gly Gly Ala Val His Thr Arg Gly Leu Asp Phe
290                 295                 300

Ala Cys Asp Ile Tyr Ile Trp Ala Pro Leu Ala Gly Thr Cys Gly Val
305                 310                 315                 320

Leu Leu Leu Ser Leu Val Ile Thr Leu Tyr Cys Lys Arg Gly Arg Lys
                325                 330                 335

Lys Leu Leu Tyr Ile Phe Lys Gln Pro Phe Met Arg Pro Val Gln Thr
            340                 345                 350

Thr Gln Glu Glu Asp Gly Cys Ser Cys Arg Phe Pro Glu Glu Glu Glu
        355                 360                 365

Gly Gly Cys Glu Leu Arg Val Lys Phe Ser Arg Ser Ala Asp Ala Pro
370                 375                 380

Ala Tyr Gln Gln Gly Gln Asn Gln Leu Tyr Asn Glu Leu Asn Leu Gly
385                 390                 395                 400

Arg Arg Glu Glu Tyr Asp Val Leu Asp Lys Arg Arg Gly Arg Asp Pro
                405                 410                 415

Glu Met Gly Gly Lys Pro Arg Arg Lys Asn Pro Gln Glu Gly Leu Tyr
            420                 425                 430

Asn Glu Leu Gln Lys Asp Lys Met Ala Glu Ala Tyr Ser Glu Ile Gly
        435                 440                 445

Met Lys Gly Glu Arg Arg Arg Gly Lys Gly His Asp Gly Leu Tyr Gln
450                 455                 460

Gly Leu Ser Thr Ala Thr Lys Asp Thr Tyr Asp Ala Leu His Met Gln
465                 470                 475                 480

Ala Leu Pro Pro Arg
            485

<210> SEQ ID NO 37
<211> LENGTH: 482
<212> TYPE: PRT
<213> ORGANISM: Artificial Sequence
<220> FEATURE:
<223> OTHER INFORMATION: Synthesized

<400> SEQUENCE: 37

```
Met Ala Leu Pro Val Thr Ala Leu Leu Leu Pro Leu Ala Leu Leu Leu
1               5                   10                  15

His Ala Ala Arg Pro Glu Ile Val Met Thr Gln Ser Pro Ala Thr Leu
            20                  25                  30

Ser Val Ser Pro Gly Glu Arg Ala Thr Leu Ser Cys Arg Ala Ser Gln
        35                  40                  45

Thr Val Asn Arg Asn Leu Ala Trp Tyr Gln Gln Lys Pro Gly Gln Ala
    50                  55                  60

Pro Arg Leu Leu Ile Tyr Gly Ala Ser Thr Arg Ala Thr Gly Ile Pro
65                  70                  75                  80

Ala Arg Phe Ser Gly Ser Gly Ser Gly Thr Glu Phe Thr Leu Thr Ile
                85                  90                  95

Gly Ser Leu Gln Ser Glu Asp Phe Ala Val Tyr Tyr Cys Gln Gln Tyr
            100                 105                 110

Lys Thr Trp Pro Arg Ser Phe Gly Gln Gly Thr Asn Val Glu Ile Lys
        115                 120                 125

Gly Gly Gly Gly Ser Gly Gly Gly Ser Gly Gly Gly Gly Ser Gln
    130                 135                 140

Val Gln Leu Gln Gln Trp Gly Ala Gly Leu Leu Lys Pro Ser Glu Thr
145                 150                 155                 160

Leu Ser Leu Thr Cys Ala Val Phe Gly Gly Ser Phe Ser Gly Tyr Tyr
                165                 170                 175

Trp Ser Trp Ile Arg Gln Pro Pro Gly Lys Gly Leu Glu Trp Ile Gly
            180                 185                 190

Glu Ile Asn His Arg Gly Asn Ile Asn Asp Asn Pro Ser Leu Lys Ser
        195                 200                 205

Arg Val Thr Ile Ser Val Asp Thr Ser Lys Asn Gln Phe Ala Leu Lys
    210                 215                 220

Leu Ser Ser Val Thr Ala Ala Asp Thr Ala Val Tyr Tyr Cys Ala Arg
225                 230                 235                 240

Glu Arg Gly Tyr Thr Tyr Gly Asn Tyr Glu His Trp Gly Gln Gly Thr
                245                 250                 255

Leu Val Thr Val Ser Ser Lys Ile Glu Val Met Tyr Pro Pro Pro Tyr
            260                 265                 270

Leu Asp Asn Glu Lys Ser Asn Gly Thr Ile Ile His Val Lys Gly Lys
        275                 280                 285

His Leu Cys Pro Ser Pro Leu Phe Pro Gly Pro Ser Lys Pro Phe Trp
    290                 295                 300

Val Leu Val Val Val Gly Gly Val Leu Ala Cys Tyr Ser Leu Leu Val
305                 310                 315                 320

Thr Val Ala Phe Ile Ile Phe Trp Val Arg Ser Lys Arg Ser Arg Leu
                325                 330                 335

Leu His Ser Asp Tyr Met Asn Met Thr Pro Arg Arg Pro Gly Pro Thr
            340                 345                 350

Arg Lys His Tyr Gln Pro Tyr Ala Pro Pro Arg Asp Phe Ala Ala Tyr
        355                 360                 365

Arg Ser Arg Val Lys Phe Ser Arg Ser Ala Asp Ala Pro Ala Tyr Gln
    370                 375                 380

Gln Gly Gln Asn Gln Leu Tyr Asn Glu Leu Asn Leu Gly Arg Arg Glu
385                 390                 395                 400

Glu Tyr Asp Val Leu Asp Lys Arg Arg Gly Arg Asp Pro Glu Met Gly
                405                 410                 415

Gly Lys Pro Arg Arg Lys Asn Pro Gln Glu Gly Leu Tyr Asn Glu Leu
```

```
                   420                 425                 430
Gln Lys Asp Lys Met Ala Glu Ala Tyr Ser Glu Ile Gly Met Lys Gly
                435                 440                 445

Glu Arg Arg Gly Lys Gly His Asp Gly Leu Tyr Gln Gly Leu Ser
            450                 455                 460

Thr Ala Thr Lys Asp Thr Tyr Asp Ala Leu His Met Gln Ala Leu Pro
465                 470                 475                 480

Pro Arg

<210> SEQ ID NO 38
<211> LENGTH: 107
<212> TYPE: PRT
<213> ORGANISM: Artificial Sequence
<220> FEATURE:
<223> OTHER INFORMATION: Synthesized

<400> SEQUENCE: 38

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Thr Val Asn Arg Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Gly Ser Leu Gln Ser
65                  70                  75                  80

Glu Asp Phe Ala Val Tyr Tyr Cys Gln Gln Tyr Lys Asn Trp Pro Arg
                85                  90                  95

Ser Phe Gly Gln Gly Thr Asn Val Glu Ile Lys
            100                 105

<210> SEQ ID NO 39
<211> LENGTH: 485
<212> TYPE: PRT
<213> ORGANISM: Artificial Sequence
<220> FEATURE:
<223> OTHER INFORMATION: Synthesized

<400> SEQUENCE: 39

Met Ala Leu Pro Val Thr Ala Leu Leu Leu Pro Leu Ala Leu Leu Leu
1               5                   10                  15

His Ala Ala Arg Pro Glu Ile Val Met Thr Gln Ser Pro Ala Thr Leu
            20                  25                  30

Ser Val Ser Pro Gly Glu Arg Ala Thr Leu Ser Cys Arg Ala Ser Gln
        35                  40                  45

Thr Val Asn Arg Asn Leu Ala Trp Tyr Gln Gln Lys Pro Gly Gln Ala
    50                  55                  60

Pro Arg Leu Leu Ile Tyr Gly Ala Ser Thr Arg Ala Thr Gly Ile Pro
65                  70                  75                  80

Ala Arg Phe Ser Gly Ser Gly Ser Gly Thr Glu Phe Thr Leu Thr Ile
                85                  90                  95

Gly Ser Leu Gln Ser Glu Asp Phe Ala Val Tyr Tyr Cys Gln Gln Tyr
            100                 105                 110

Lys Asn Trp Pro Arg Ser Phe Gly Gln Gly Thr Asn Val Glu Ile Lys
        115                 120                 125

Gly Gly Gly Gly Ser Gly Gly Gly Gly Ser Gly Gly Gly Gly Ser Gln
```

```
            130                 135                 140
Val Gln Leu Gln Gln Trp Gly Ala Gly Leu Leu Lys Pro Ser Glu Thr
145                 150                 155                 160

Leu Ser Leu Thr Cys Ala Val Phe Gly Gly Ser Phe Ser Gly Tyr Tyr
                165                 170                 175

Trp Ser Trp Ile Arg Gln Pro Pro Gly Lys Gly Leu Glu Trp Ile Gly
            180                 185                 190

Glu Ile Asn His Arg Gly Asn Ile Asn Asp Asn Pro Ser Leu Lys Ser
        195                 200                 205

Arg Val Thr Ile Ser Val Asp Thr Ser Lys Asn Gln Phe Ala Leu Lys
    210                 215                 220

Leu Ser Ser Val Thr Ala Ala Asp Thr Ala Val Tyr Tyr Cys Ala Arg
225                 230                 235                 240

Glu Arg Gly Tyr Thr Tyr Gly Asn Tyr Glu His Trp Gly Gln Gly Thr
                245                 250                 255

Leu Val Thr Val Ser Ser Thr Thr Thr Pro Ala Pro Arg Pro Pro Thr
            260                 265                 270

Pro Ala Pro Thr Ile Ala Ser Gln Pro Leu Ser Leu Arg Pro Glu Ala
        275                 280                 285

Cys Arg Pro Ala Ala Gly Gly Ala Val His Thr Arg Gly Leu Asp Phe
    290                 295                 300

Ala Cys Asp Ile Tyr Ile Trp Ala Pro Leu Ala Gly Thr Cys Gly Val
305                 310                 315                 320

Leu Leu Leu Ser Leu Val Ile Thr Leu Tyr Cys Lys Arg Gly Arg Lys
                325                 330                 335

Lys Leu Leu Tyr Ile Phe Lys Gln Pro Phe Met Arg Pro Val Gln Thr
            340                 345                 350

Thr Gln Glu Glu Asp Gly Cys Ser Cys Arg Phe Pro Glu Glu Glu Glu
        355                 360                 365

Gly Gly Cys Glu Leu Arg Val Lys Phe Ser Arg Ser Ala Asp Ala Pro
    370                 375                 380

Ala Tyr Gln Gln Gly Gln Asn Gln Leu Tyr Asn Glu Leu Asn Leu Gly
385                 390                 395                 400

Arg Arg Glu Glu Tyr Asp Val Leu Asp Lys Arg Arg Gly Arg Asp Pro
                405                 410                 415

Glu Met Gly Gly Lys Pro Arg Arg Lys Asn Pro Gln Glu Gly Leu Tyr
            420                 425                 430

Asn Glu Leu Gln Lys Asp Lys Met Ala Glu Ala Tyr Ser Glu Ile Gly
        435                 440                 445

Met Lys Gly Glu Arg Arg Arg Gly Lys Gly His Asp Gly Leu Tyr Gln
    450                 455                 460

Gly Leu Ser Thr Ala Thr Lys Asp Thr Tyr Asp Ala Leu His Met Gln
465                 470                 475                 480

Ala Leu Pro Pro Arg
                485

<210> SEQ ID NO 40
<211> LENGTH: 482
<212> TYPE: PRT
<213> ORGANISM: Artificial Sequence
<220> FEATURE:
<223> OTHER INFORMATION: Synthesized

<400> SEQUENCE: 40

Met Ala Leu Pro Val Thr Ala Leu Leu Leu Pro Leu Ala Leu Leu Leu
```

```
  1               5                  10                   15
His Ala Ala Arg Pro Glu Ile Val Met Thr Gln Ser Pro Ala Thr Leu
             20                  25                  30

Ser Val Ser Pro Gly Glu Arg Ala Thr Leu Ser Cys Arg Ala Ser Gln
             35                  40                  45

Thr Val Asn Arg Asn Leu Ala Trp Tyr Gln Gln Lys Pro Gly Gln Ala
             50                  55                  60

Pro Arg Leu Leu Ile Tyr Gly Ala Ser Thr Arg Ala Thr Gly Ile Pro
 65                  70                  75                  80

Ala Arg Phe Ser Gly Ser Gly Ser Gly Thr Glu Phe Thr Leu Thr Ile
                 85                  90                  95

Gly Ser Leu Gln Ser Glu Asp Phe Ala Val Tyr Tyr Cys Gln Gln Tyr
            100                 105                 110

Lys Asn Trp Pro Arg Ser Phe Gly Gln Gly Thr Asn Val Glu Ile Lys
            115                 120                 125

Gly Gly Gly Gly Ser Gly Gly Gly Ser Gly Gly Gly Ser Gln
            130                 135                 140

Val Gln Leu Gln Gln Trp Gly Ala Gly Leu Leu Lys Pro Ser Glu Thr
145                 150                 155                 160

Leu Ser Leu Thr Cys Ala Val Phe Gly Gly Ser Phe Ser Gly Tyr Tyr
            165                 170                 175

Trp Ser Trp Ile Arg Gln Pro Pro Gly Lys Gly Leu Glu Trp Ile Gly
            180                 185                 190

Glu Ile Asn His Arg Gly Asn Ile Asn Asp Asn Pro Ser Leu Lys Ser
            195                 200                 205

Arg Val Thr Ile Ser Val Asp Thr Ser Lys Asn Gln Phe Ala Leu Lys
            210                 215                 220

Leu Ser Ser Val Thr Ala Ala Asp Thr Ala Val Tyr Tyr Cys Ala Arg
225                 230                 235                 240

Glu Arg Gly Tyr Thr Tyr Gly Asn Tyr Glu His Trp Gly Gln Gly Thr
            245                 250                 255

Leu Val Thr Val Ser Ser Lys Ile Glu Val Met Tyr Pro Pro Pro Tyr
            260                 265                 270

Leu Asp Asn Glu Lys Ser Asn Gly Thr Ile Ile His Val Lys Gly Lys
            275                 280                 285

His Leu Cys Pro Ser Pro Leu Phe Pro Gly Pro Ser Lys Pro Phe Trp
            290                 295                 300

Val Leu Val Val Val Gly Gly Val Leu Ala Cys Tyr Ser Leu Leu Val
305                 310                 315                 320

Thr Val Ala Phe Ile Ile Phe Trp Val Arg Ser Lys Arg Ser Arg Leu
            325                 330                 335

Leu His Ser Asp Tyr Met Asn Met Thr Pro Arg Arg Pro Gly Pro Thr
            340                 345                 350

Arg Lys His Tyr Gln Pro Tyr Ala Pro Pro Arg Asp Phe Ala Ala Tyr
            355                 360                 365

Arg Ser Arg Val Lys Phe Ser Arg Ser Ala Asp Ala Pro Ala Tyr Gln
            370                 375                 380

Gln Gly Gln Asn Gln Leu Tyr Asn Glu Leu Asn Leu Gly Arg Arg Glu
385                 390                 395                 400

Glu Tyr Asp Val Leu Asp Lys Arg Arg Gly Arg Asp Pro Glu Met Gly
            405                 410                 415

Gly Lys Pro Arg Arg Lys Asn Pro Gln Glu Gly Leu Tyr Asn Glu Leu
            420                 425                 430
```

```
Gln Lys Asp Lys Met Ala Glu Ala Tyr Ser Glu Ile Gly Met Lys Gly
        435                 440                 445

Glu Arg Arg Gly Lys Gly His Asp Gly Leu Tyr Gln Gly Leu Ser
450                 455                 460

Thr Ala Thr Lys Asp Thr Tyr Asp Ala Leu His Met Gln Ala Leu Pro
465                 470                 475                 480

Pro Arg

<210> SEQ ID NO 41
<211> LENGTH: 107
<212> TYPE: PRT
<213> ORGANISM: Artificial Sequence
<220> FEATURE:
<223> OTHER INFORMATION: Synthesized

<400> SEQUENCE: 41

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Thr Val Thr Arg Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
50                  55                  60

Ser Gly Ser Gly Thr Glu Phe Thr Leu Thr Ile Gly Ser Leu Gln Ser
65                  70                  75                  80

Glu Asp Phe Ala Val Tyr Tyr Cys Gln Gln Tyr Lys Ser Trp Pro Arg
                85                  90                  95

Ser Phe Gly Gln Gly Thr Asn Val Glu Ile Lys
            100                 105

<210> SEQ ID NO 42
<211> LENGTH: 485
<212> TYPE: PRT
<213> ORGANISM: Artificial Sequence
<220> FEATURE:
<223> OTHER INFORMATION: Synthesized

<400> SEQUENCE: 42

Met Ala Leu Pro Val Thr Ala Leu Leu Leu Pro Leu Ala Leu Leu Leu
1               5                   10                  15

His Ala Ala Arg Pro Glu Ile Val Met Thr Gln Ser Pro Ala Thr Leu
            20                  25                  30

Ser Val Ser Pro Gly Glu Arg Ala Thr Leu Ser Cys Arg Ala Ser Gln
        35                  40                  45

Thr Val Thr Arg Asn Leu Ala Trp Tyr Gln Gln Lys Pro Gly Gln Ala
    50                  55                  60

Pro Arg Leu Leu Ile Tyr Gly Ala Ser Thr Arg Ala Thr Gly Ile Pro
65                  70                  75                  80

Ala Arg Phe Ser Gly Ser Gly Ser Gly Thr Glu Phe Thr Leu Thr Ile
                85                  90                  95

Gly Ser Leu Gln Ser Glu Asp Phe Ala Val Tyr Tyr Cys Gln Gln Tyr
            100                 105                 110

Lys Ser Trp Pro Arg Ser Phe Gly Gln Gly Thr Asn Val Glu Ile Lys
        115                 120                 125

Gly Gly Gly Gly Ser Gly Gly Gly Ser Gly Gly Gly Gly Ser Gln
    130                 135                 140
```

Val Gln Leu Gln Gln Trp Gly Ala Gly Leu Leu Lys Pro Ser Glu Thr
145                 150                 155                 160

Leu Ser Leu Thr Cys Ala Val Phe Gly Gly Ser Phe Ser Gly Tyr Tyr
                165                 170                 175

Trp Ser Trp Ile Arg Gln Pro Pro Gly Lys Gly Leu Glu Trp Ile Gly
            180                 185                 190

Glu Ile Asn His Arg Gly Asn Ile Asn Asp Asn Pro Ser Leu Lys Ser
        195                 200                 205

Arg Val Thr Ile Ser Val Asp Thr Ser Lys Asn Gln Phe Ala Leu Lys
    210                 215                 220

Leu Ser Ser Val Thr Ala Ala Asp Thr Ala Val Tyr Tyr Cys Ala Arg
225                 230                 235                 240

Glu Arg Gly Tyr Ser Phe Gly Asn Tyr Asp His Trp Gly Gln Gly Thr
                245                 250                 255

Leu Val Thr Val Ser Ser Thr Thr Thr Pro Ala Pro Arg Pro Pro Thr
            260                 265                 270

Pro Ala Pro Thr Ile Ala Ser Gln Pro Leu Ser Leu Arg Pro Glu Ala
        275                 280                 285

Cys Arg Pro Ala Ala Gly Gly Ala Val His Thr Arg Gly Leu Asp Phe
290                 295                 300

Ala Cys Asp Ile Tyr Ile Trp Ala Pro Leu Ala Gly Thr Cys Gly Val
305                 310                 315                 320

Leu Leu Leu Ser Leu Val Ile Thr Leu Tyr Cys Lys Arg Gly Arg Lys
                325                 330                 335

Lys Leu Leu Tyr Ile Phe Lys Gln Pro Phe Met Arg Pro Val Gln Thr
            340                 345                 350

Thr Gln Glu Glu Asp Gly Cys Ser Cys Arg Phe Pro Glu Glu Glu Glu
        355                 360                 365

Gly Gly Cys Glu Leu Arg Val Lys Phe Ser Arg Ser Ala Asp Ala Pro
    370                 375                 380

Ala Tyr Gln Gln Gly Gln Asn Gln Leu Tyr Asn Glu Leu Asn Leu Gly
385                 390                 395                 400

Arg Arg Glu Glu Tyr Asp Val Leu Asp Lys Arg Arg Gly Arg Asp Pro
                405                 410                 415

Glu Met Gly Gly Lys Pro Arg Arg Lys Asn Pro Gln Glu Gly Leu Tyr
            420                 425                 430

Asn Glu Leu Gln Lys Asp Lys Met Ala Glu Ala Tyr Ser Glu Ile Gly
        435                 440                 445

Met Lys Gly Glu Arg Arg Arg Gly Lys Gly His Asp Gly Leu Tyr Gln
    450                 455                 460

Gly Leu Ser Thr Ala Thr Lys Asp Thr Tyr Asp Ala Leu His Met Gln
465                 470                 475                 480

Ala Leu Pro Pro Arg
                485

<210> SEQ ID NO 43
<211> LENGTH: 482
<212> TYPE: PRT
<213> ORGANISM: Artificial Sequence
<220> FEATURE:
<223> OTHER INFORMATION: Synthesized

<400> SEQUENCE: 43

Met Ala Leu Pro Val Thr Ala Leu Leu Leu Pro Leu Ala Leu Leu Leu
1               5                   10                  15

His Ala Ala Arg Pro Glu Ile Val Met Thr Gln Ser Pro Ala Thr Leu
            20                  25                  30

Ser Val Ser Pro Gly Glu Arg Ala Thr Leu Ser Cys Arg Ala Ser Gln
        35                  40                  45

Thr Val Thr Arg Asn Leu Ala Trp Tyr Gln Lys Pro Gly Gln Ala
    50                  55                  60

Pro Arg Leu Leu Ile Tyr Gly Ala Ser Thr Arg Ala Thr Gly Ile Pro
65                  70                  75                  80

Ala Arg Phe Ser Gly Ser Gly Ser Gly Thr Glu Phe Thr Leu Thr Ile
                85                  90                  95

Gly Ser Leu Gln Ser Glu Asp Phe Ala Val Tyr Tyr Cys Gln Gln Tyr
            100                 105                 110

Lys Ser Trp Pro Arg Ser Phe Gly Gln Gly Thr Asn Val Glu Ile Lys
        115                 120                 125

Gly Gly Gly Gly Ser Gly Gly Gly Ser Gly Gly Gly Ser Gln
    130                 135                 140

Val Gln Leu Gln Gln Trp Gly Ala Gly Leu Leu Lys Pro Ser Glu Thr
145                 150                 155                 160

Leu Ser Leu Thr Cys Ala Val Phe Gly Gly Ser Phe Ser Gly Tyr Tyr
                165                 170                 175

Trp Ser Trp Ile Arg Gln Pro Pro Gly Lys Gly Leu Glu Trp Ile Gly
            180                 185                 190

Glu Ile Asn His Arg Gly Asn Ile Asn Asp Asn Pro Ser Leu Lys Ser
        195                 200                 205

Arg Val Thr Ile Ser Val Asp Thr Ser Lys Asn Gln Phe Ala Leu Lys
    210                 215                 220

Leu Ser Ser Val Thr Ala Ala Asp Thr Ala Val Tyr Tyr Cys Ala Arg
225                 230                 235                 240

Glu Arg Gly Tyr Ser Phe Gly Asn Tyr Asp His Trp Gly Gln Gly Thr
                245                 250                 255

Leu Val Thr Val Ser Ser Lys Ile Glu Val Met Tyr Pro Pro Pro Tyr
            260                 265                 270

Leu Asp Asn Glu Lys Ser Asn Gly Thr Ile Ile His Val Lys Gly Lys
        275                 280                 285

His Leu Cys Pro Ser Pro Leu Phe Pro Gly Pro Ser Lys Pro Phe Trp
    290                 295                 300

Val Leu Val Val Val Gly Gly Val Leu Ala Cys Tyr Ser Leu Leu Val
305                 310                 315                 320

Thr Val Ala Phe Ile Ile Phe Trp Val Arg Ser Lys Arg Ser Arg Leu
                325                 330                 335

Leu His Ser Asp Tyr Met Asn Met Thr Pro Arg Arg Pro Gly Pro Thr
            340                 345                 350

Arg Lys His Tyr Gln Pro Tyr Ala Pro Pro Arg Asp Phe Ala Ala Tyr
        355                 360                 365

Arg Ser Arg Val Lys Phe Ser Arg Ser Ala Asp Ala Pro Ala Tyr Gln
    370                 375                 380

Gln Gly Gln Asn Gln Leu Tyr Asn Glu Leu Asn Leu Gly Arg Arg Glu
385                 390                 395                 400

Glu Tyr Asp Val Leu Asp Lys Arg Arg Gly Arg Asp Pro Glu Met Gly
                405                 410                 415

Gly Lys Pro Arg Arg Lys Asn Pro Gln Glu Gly Leu Tyr Asn Glu Leu
            420                 425                 430

```
Gln Lys Asp Lys Met Ala Glu Ala Tyr Ser Glu Ile Gly Met Lys Gly
            435                 440                 445

Glu Arg Arg Gly Lys Gly His Asp Gly Leu Tyr Gln Gly Leu Ser
    450                 455                 460

Thr Ala Thr Lys Asp Thr Tyr Asp Ala Leu His Met Gln Ala Leu Pro
465                 470                 475                 480

Pro Arg

<210> SEQ ID NO 44
<211> LENGTH: 1257
<212> TYPE: DNA
<213> ORGANISM: Artificial Sequence
<220> FEATURE:
<223> OTHER INFORMATION: Synthesized

<400> SEQUENCE: 44
```

| | | | | |
|---|---|---|---|---|
| tcccaggtga | gtcagaactg | ccacaatggc | agctatgaaa | tcagcgtcct gatgatgggc | 60 |
| aactcagcct | tgcagagcc | cctgaaaaac | ttggaagatg | cggtgaatga ggggctggaa | 120 |
| atagtgagag | gacgtctgca | aaatgctggc | ctaaatgtga | ctgtgaacgc tactttcatg | 180 |
| tattcggatg | gtctgattca | taactcaggc | gactgccgga | gtagcacctg tgaaggcctc | 240 |
| gacctactca | ggaaaatttc | aaatgcacaa | cggatgggct | gtgtcctcat agggccctca | 300 |
| tgtacatact | ccaccttcca | gatgtaccct | gacacagaat | tgagctaccc catgatctca | 360 |
| gctggaagtt | ttggattgtc | atgtgactat | aaagaaacct | aaccaggct gatgtctcca | 420 |
| gctagaaagt | tgatgtactt | cttggttaac | ttttggaaaa | ccaacgatct gcccttcaaa | 480 |
| acttattcct | ggagcacttc | gtatgtttac | aagaatggta | cagaaactga ggactgtttc | 540 |
| tggtacccta | atgctctgga | ggctagcgtt | tcctatttct | cccacgaact cggctttaag | 600 |
| gtggtgttaa | gacaagataa | ggagtttcag | gatatcttaa | tggaccacaa caggaaaagc | 660 |
| aatgtgatta | ttatgtgtgg | tggtccagag | ttcctctaca | agctgaaggg tgaccgagca | 720 |
| gtggctgaag | acattgtcat | tattctagtg | gatcttttca | tgaccagta ctttgaggac | 780 |
| aatgtcacag | cccctgacta | tatgaaaaat | gtccttgttc | tgacgctgtc tcctgggaat | 840 |
| tcccttctaa | atagctcttt | ctccaggaat | ctatcaccaa | caaaacgaga ctttgctctt | 900 |
| gcctatttga | atggaatcct | gctctttgga | catatgctga | agatatttct tgaaaatgga | 960 |
| gaaaatatta | ccacccccaa | atttgctcat | gctttcagga | atctcacttt tgaagggtat | 1020 |
| gacggtccag | tgaccttgga | tgactggggg | gatgttgaca | gtaccatggt gcttctgtat | 1080 |
| acctctgtgg | acaccaagaa | atacaaggtt | cttttgacct | atgataccca cgtaaataag | 1140 |
| acctatcctg | tggatatgag | ccccacattc | acttggaaga | actctaaact tcctaatgat | 1200 |
| attacaggcc | ggggccctca | ggctagcggt | gcagctcatc | accaccatca ccattag | 1257 |

```
<210> SEQ ID NO 45
<211> LENGTH: 357
<212> TYPE: DNA
<213> ORGANISM: Artificial Sequence
<220> FEATURE:
<223> OTHER INFORMATION: Synthesized

<400> SEQUENCE: 45
```

| | | | | |
|---|---|---|---|---|
| caggtgcagc | tgcagcagtg | gggagctggc | ctgctgaagc | caagcgagac actgtccctg | 60 |
| acatgtgccg | tgttcggcgg | aagcttttcc | ggttattatt | ggagctggat caggcagccc | 120 |
| cctggaaagg | gcctggagtg | gatcggagag | atcaaccaca | gaggtaacat taacgacaac | 180 |

```
cnctcnntga agtctcgcgt gaccatctct gtggatacaa gcaagaacca gttcgccctg    240
aagctgagct ccgtgaccgc tgctgacaca gccgtgtact actgtgctag ggaaagaggt    300
tatagttttg gtaattatga ccactgggga cagggcaccc tggtgacagt gtcctca       357
```

<210> SEQ ID NO 46
<211> LENGTH: 357
<212> TYPE: DNA
<213> ORGANISM: Artificial Sequence
<220> FEATURE:
<223> OTHER INFORMATION: Synthesized

<400> SEQUENCE: 46

```
caggtgcagc tgcagcagtg gggagctggc ctgctgaagc caagcgagac actgtccctg     60
acatgtgccg tgttcggcgg aagcttttcc ggttattatt ggagctggat caggcagccc    120
cctggaaagg gcctggagtg gatcggagag atcaaccaca gaggtaacat taacgacaac    180
ccctccctga agtctcgcgt gaccatctct gtggatacaa gcaagaacca gttcgccctg    240
aagctgagct ccgtgaccgc tgctgacaca gccgtgtact actgtgctag ggaaagaggt    300
tatacttatg gtaattatga acactgggga cagggcaccc tggtgacagt gtcctca       357
```

<210> SEQ ID NO 47
<211> LENGTH: 321
<212> TYPE: DNA
<213> ORGANISM: Artificial Sequence
<220> FEATURE:
<223> OTHER INFORMATION: Synthesized

<400> SEQUENCE: 47

```
gagatcgtga tgacccagtc ccctgccaca ctgtccgtgt ctccaggaga gagggccacc     60
ctgtcttgca gggctagcca gactgtcaat agaaacctgg cctggtacca gcagaagcca    120
ggccaggctc ccagactgct gatctacgga gcttccacca gggctacagg aatcccagct    180
agattcagcg gctccggatc tggcaccgag tttacccctg caatcggctc tctgcagagc    240
gaggacttcg ccgtgtacta ctgccagcag tacaaaactt ggcctagatc ttttggacag    300
ggcacaaacg tggagatcaa g                                              321
```

<210> SEQ ID NO 48
<211> LENGTH: 321
<212> TYPE: DNA
<213> ORGANISM: Artificial Sequence
<220> FEATURE:
<223> OTHER INFORMATION: Synthesized

<400> SEQUENCE: 48

```
gagatcgtga tgacccagtc ccctgccaca ctgtccgtgt ctccaggaga gagggccacc     60
ctgtcttgca gggctagcca gactgtcaat agaaacctgg cctggtacca gcagaagcca    120
ggacaggctc ccagactgct gatctacgga gcttccacca gggctacagg aatcccagct    180
agattcagcg gctccggatc tggcaccgag tttacccctg caatcggctc tctgcagagc    240
gaggacttcg ccgtgtacta ctgccagcag tacaaaaatt ggcctagatc ttttggacag    300
ggcacaaacg tggagatcaa g                                              321
```

<210> SEQ ID NO 49
<211> LENGTH: 321
<212> TYPE: DNA
<213> ORGANISM: Artificial Sequence
<220> FEATURE:
<223> OTHER INFORMATION: Synthesized

<400> SEQUENCE: 49

```
gagatcgtga tgacccagtc ccctgccaca ctgtccgtgt ctccaggaga gagggccacc      60
ctgtcttgca gggctagcca gactgtcaat agaaacctgg cctggtacca gcagaagcca     120
ggccaggctc ccagactgct gatctacgga gcttccacca gggctacagg aatcccagct    180
agattcagcg gctccggatc tggcaccgag tttaccctga caatcggctc tctgcagagc    240
gaggacttcg ccgtgtacta ctgccagcag tacaaaagtt ggcctagaac ttttggacag    300
ggcacaaacg tggagatcaa g                                                321
```

<210> SEQ ID NO 50
<211> LENGTH: 321
<212> TYPE: DNA
<213> ORGANISM: Artificial Sequence
<220> FEATURE:
<223> OTHER INFORMATION: Synthesized

<400> SEQUENCE: 50

```
gagatcgtga tgacccagtc ccctgccaca ctgtccgtgt ctccaggaga gagggccacc     60
ctgtcttgca gggctagcca gactgtcaat agaaacctgg cctggtacca gcagaagcca    120
ggccaagctc ccagactgct gatctacgga gcttccacca gggctacagg aatcccagct    180
agattcagcg gctccggatc tggcaccgag tttaccctga caatcggctc tctgcagagc    240
gaggacttcg ccgtgtacta ctgccagcag tacaaaagtt ggcctagatc ttttggacag    300
ggcacaaacg tggagatcaa g                                               321
```

<210> SEQ ID NO 51
<211> LENGTH: 321
<212> TYPE: DNA
<213> ORGANISM: Artificial Sequence
<220> FEATURE:
<223> OTHER INFORMATION: Synthesized

<400> SEQUENCE: 51

```
gagatcgtga tgacccagtc ccctgccaca ctgtccgtgt ctccaggaga gagggccacc     60
ctgtcttgca gggctagcca gactgtcaat agaaacctgg cctggtacca gcagaagcca    120
ggacaggctc ccagactgct gatctacgga gcttccacca gggctacagg aatcccagct    180
agattcagcg gctccggatc tggcaccgag tttaccctga caatcggctc tctgcagagc    240
gaggacttcg ccgtgtacta ctgccagcag tacaaaactt ggcctagaac ttttggacag    300
ggcacaaacg tggagatcaa g                                               321
```

<210> SEQ ID NO 52
<211> LENGTH: 241
<212> TYPE: PRT
<213> ORGANISM: Artificial Sequence
<220> FEATURE:
<223> OTHER INFORMATION: Synthesized

<400> SEQUENCE: 52

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Thr Val Thr Arg Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly

```
Ser Gly Ser Gly Thr Glu Phe Thr Leu Thr Ile Gly Ser Leu Gln Ser
 65                  70                  75                  80

Glu Asp Phe Ala Val Tyr Tyr Cys Gln Gln Tyr Lys Ser Trp Pro Arg
                 85                  90                  95

Thr Phe Gly Gln Gly Thr Asn Val Glu Ile Lys Gly Gly Gly Gly Ser
            100                 105                 110

Gly Gly Gly Gly Ser Gly Gly Gly Ser Gln Val Gln Leu Gln Gln
            115                 120                 125

Trp Gly Ala Gly Leu Leu Lys Pro Ser Glu Thr Leu Ser Leu Thr Cys
            130                 135                 140

Ala Val Phe Gly Gly Ser Phe Ser Gly Tyr Tyr Trp Ser Trp Ile Arg
145                 150                 155                 160

Gln Pro Pro Gly Lys Gly Leu Glu Trp Ile Gly Glu Ile Asn His Arg
            165                 170                 175

Gly Asn Ile Asn Asp Asn Pro Ser Leu Lys Ser Arg Val Thr Ile Ser
            180                 185                 190

Val Asp Thr Ser Lys Asn Gln Phe Ala Leu Lys Leu Ser Ser Val Thr
            195                 200                 205

Ala Ala Asp Thr Ala Val Tyr Tyr Cys Ala Arg Glu Arg Gly Tyr Ser
            210                 215                 220

Phe Gly Asn Tyr Asp His Trp Gly Gln Gly Thr Leu Val Thr Val Ser
225                 230                 235                 240

Ser

<210> SEQ ID NO 53
<211> LENGTH: 241
<212> TYPE: PRT
<213> ORGANISM: Artificial Sequence
<220> FEATURE:
<223> OTHER INFORMATION: Synthesized

<400> SEQUENCE: 53

Glu Ile Val Met Thr Gln Ser Pro Ala Thr Leu Ser Val Ser Pro Gly
 1               5                  10                  15

Glu Arg Ala Thr Leu Ser Cys Arg Ala Ser Gln Thr Val Thr Arg Asn
                 20                  25                  30

Leu Ala Trp Tyr Gln Gln Lys Pro Gly Gln Ala Pro Arg Leu Leu Ile
             35                  40                  45

Tyr Gly Ala Ser Thr Arg Ala Thr Gly Ile Pro Ala Arg Phe Ser Gly
     50                  55                  60

Ser Gly Ser Gly Thr Glu Phe Thr Leu Thr Ile Gly Ser Leu Gln Ser
 65                  70                  75                  80

Glu Asp Phe Ala Val Tyr Tyr Cys Gln Gln Tyr Lys Ser Trp Pro Arg
                 85                  90                  95

Ser Phe Gly Gln Gly Thr Asn Val Glu Ile Lys Gly Gly Gly Gly Ser
            100                 105                 110

Gly Gly Gly Gly Ser Gly Gly Gly Ser Gln Val Gln Leu Gln Gln
            115                 120                 125

Trp Gly Ala Gly Leu Leu Lys Pro Ser Glu Thr Leu Ser Leu Thr Cys
            130                 135                 140

Ala Val Phe Gly Gly Ser Phe Ser Gly Tyr Tyr Trp Ser Trp Ile Arg
145                 150                 155                 160

Gln Pro Pro Gly Lys Gly Leu Glu Trp Ile Gly Glu Ile Asn His Arg
            165                 170                 175
```

Gly Asn Ile Asn Asp Asn Pro Ser Leu Lys Ser Arg Val Thr Ile Ser
            180                 185                 190

Val Asp Thr Ser Lys Asn Gln Phe Ala Leu Lys Leu Ser Ser Val Thr
        195                 200                 205

Ala Ala Asp Thr Ala Val Tyr Tyr Cys Ala Arg Glu Arg Gly Tyr Ser
    210                 215                 220

Phe Gly Asn Tyr Asp His Trp Gly Gln Gly Thr Leu Val Thr Val Ser
225                 230                 235                 240

Ser

<210> SEQ ID NO 54
<211> LENGTH: 241
<212> TYPE: PRT
<213> ORGANISM: Artificial Sequence
<220> FEATURE:
<223> OTHER INFORMATION: Synthesized

<400> SEQUENCE: 54

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Thr Val Asn Arg Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Gly Ser Leu Gln Ser
65                  70                  75                  80

Glu Asp Phe Ala Val Tyr Tyr Cys Gln Gln Tyr Lys Thr Trp Pro Arg
                85                  90                  95

Thr Phe Gly Gln Gly Thr Asn Val Glu Ile Lys Gly Gly Gly Gly Ser
            100                 105                 110

Gly Gly Gly Gly Ser Gly Gly Gly Ser Gln Val Gln Leu Gln Gln
        115                 120                 125

Trp Gly Ala Gly Leu Leu Lys Pro Ser Glu Thr Leu Ser Leu Thr Cys
    130                 135                 140

Ala Val Phe Gly Gly Ser Phe Ser Gly Tyr Tyr Trp Ser Trp Ile Arg
145                 150                 155                 160

Gln Pro Pro Gly Lys Gly Leu Glu Trp Ile Gly Glu Ile Asn His Arg
                165                 170                 175

Gly Asn Ile Asn Asp Asn Pro Ser Leu Lys Ser Arg Val Thr Ile Ser
            180                 185                 190

Val Asp Thr Ser Lys Asn Gln Phe Ala Leu Lys Leu Ser Ser Val Thr
        195                 200                 205

Ala Ala Asp Thr Ala Val Tyr Tyr Cys Ala Arg Glu Arg Gly Tyr Thr
    210                 215                 220

Tyr Gly Asn Tyr Glu His Trp Gly Gln Gly Thr Leu Val Thr Val Ser
225                 230                 235                 240

Ser

<210> SEQ ID NO 55
<211> LENGTH: 241
<212> TYPE: PRT
<213> ORGANISM: Artificial Sequence
<220> FEATURE:
<223> OTHER INFORMATION: Synthesized

<400> SEQUENCE: 55

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Thr Val Asn Arg Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Gly Ser Leu Gln Ser
65                  70                  75                  80

Glu Asp Phe Ala Val Tyr Tyr Cys Gln Gln Tyr Lys Thr Trp Pro Arg
                85                  90                  95

Ser Phe Gly Gln Gly Thr Asn Val Glu Ile Lys Gly Gly Gly Gly Ser
            100                 105                 110

Gly Gly Gly Gly Ser Gly Gly Gly Ser Gln Val Gln Leu Gln Gln
        115                 120                 125

Trp Gly Ala Gly Leu Leu Lys Pro Ser Glu Thr Leu Ser Leu Thr Cys
    130                 135                 140

Ala Val Phe Gly Gly Ser Phe Ser Gly Tyr Tyr Trp Ser Trp Ile Arg
145                 150                 155                 160

Gln Pro Pro Gly Lys Gly Leu Glu Trp Ile Gly Glu Ile Asn His Arg
                165                 170                 175

Gly Asn Ile Asn Asp Asn Pro Ser Leu Lys Ser Arg Val Thr Ile Ser
            180                 185                 190

Val Asp Thr Ser Lys Asn Gln Phe Ala Leu Lys Leu Ser Ser Val Thr
        195                 200                 205

Ala Ala Asp Thr Ala Val Tyr Tyr Cys Ala Arg Glu Arg Gly Tyr Thr
    210                 215                 220

Tyr Gly Asn Tyr Glu His Trp Gly Gln Gly Thr Leu Val Thr Val Ser
225                 230                 235                 240

Ser

<210> SEQ ID NO 56
<211> LENGTH: 241
<212> TYPE: PRT
<213> ORGANISM: Artificial Sequence
<220> FEATURE:
<223> OTHER INFORMATION: Synthesized

<400> SEQUENCE: 56

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Thr Val Asn Arg Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Gly Ser Leu Gln Ser
65                  70                  75                  80

Glu Asp Phe Ala Val Tyr Tyr Cys Gln Gln Tyr Lys Asn Trp Pro Arg
                85                  90                  95

Ser Phe Gly Gln Gly Thr Asn Val Glu Ile Lys Gly Gly Gly Gly Ser

```
            100                 105                 110
Gly Gly Gly Gly Ser Gly Gly Gly Ser Gln Val Gln Leu Gln Gln
            115                 120                 125

Trp Gly Ala Gly Leu Leu Lys Pro Ser Glu Thr Leu Ser Leu Thr Cys
            130                 135                 140

Ala Val Phe Gly Gly Ser Phe Ser Gly Tyr Tyr Trp Ser Trp Ile Arg
145                 150                 155                 160

Gln Pro Pro Gly Lys Gly Leu Glu Trp Ile Gly Glu Ile Asn His Arg
                165                 170                 175

Gly Asn Ile Asn Asp Asn Pro Ser Leu Lys Ser Arg Val Thr Ile Ser
                180                 185                 190

Val Asp Thr Ser Lys Asn Gln Phe Ala Leu Lys Leu Ser Ser Val Thr
                195                 200                 205

Ala Ala Asp Thr Ala Val Tyr Tyr Cys Ala Arg Glu Arg Gly Tyr Thr
                210                 215                 220

Tyr Gly Asn Tyr Glu His Trp Gly Gln Gly Thr Leu Val Thr Val Ser
225                 230                 235                 240

Ser

<210> SEQ ID NO 57
<211> LENGTH: 121
<212> TYPE: PRT
<213> ORGANISM: Artificial Sequence
<220> FEATURE:
<223> OTHER INFORMATION: Synthesized

<400> SEQUENCE: 57

Glu Val Gln Leu Val Glu Ser Gly Gly Gly Leu Val Gln Pro Lys Gly
1               5                   10                  15

Ser Leu Lys Leu Ser Cys Ala Ala Ser Gly Phe Thr Phe Ser Asp Ala
                20                  25                  30

Trp Met Asp Trp Val Arg Gln Ser Pro Glu Lys Gly Leu Glu Trp Val
            35                  40                  45

Ala Glu Ile Arg Ser Lys Ala Asn Ile His Ala Thr Tyr Tyr Ala Glu
        50                  55                  60

Ser Val Lys Gly Arg Phe Thr Ile Ser Arg Asp Asp Ser Lys Ser Ser
65                  70                  75                  80

Val Tyr Leu Gln Met Asn Asn Leu Arg Thr Glu Asp Thr Gly Ile Tyr
                85                  90                  95

Tyr Cys Thr Pro Tyr Tyr Thr Tyr Ala Pro Arg Phe Ala Tyr Trp Gly
                100                 105                 110

Arg Gly Thr Leu Val Thr Val Ser Ser
            115                 120

<210> SEQ ID NO 58
<211> LENGTH: 112
<212> TYPE: PRT
<213> ORGANISM: Artificial Sequence
<220> FEATURE:
<223> OTHER INFORMATION: Synthesized

<400> SEQUENCE: 58

Ser Ile Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
                20                  25                  30

Asn Gly Asn Thr Tyr Leu His Trp Tyr Leu Gln Lys Pro Gly Gln Ser
```

```
                35                  40                  45
Pro Lys Leu Leu Ile Tyr Lys Val Ser Asn Arg Phe Ser Gly Val Pro
 50                  55                  60
Asp Arg Phe Ser Gly Ser Gly Ser Gly Thr Asp Phe Thr Leu Lys Ile
 65                  70                  75                  80
Ser Arg Val Glu Ala Glu Asp Leu Gly Val Tyr Phe Cys Ser Gln Ser
                 85                  90                  95
Thr His Val Pro Phe Thr Phe Gly Ser Gly Thr Lys Leu Glu Met Lys
                100                 105                 110
```

<210> SEQ ID NO 59
<211> LENGTH: 492
<212> TYPE: PRT
<213> ORGANISM: Artificial Sequence
<220> FEATURE:
<223> OTHER INFORMATION: Synthesized

<400> SEQUENCE: 59

```
Met Ala Leu Pro Val Thr Ala Leu Leu Leu Pro Leu Ala Leu Leu Leu
 1               5                  10                  15
His Ala Ala Arg Pro Ser Ile Val Met Thr Gln Thr Pro Leu Ser Leu
                20                  25                  30
Pro Val Ser Leu Gly Asp Gln Ala Ser Ile Ser Cys Arg Ser Ser Gln
                35                  40                  45
Ser Leu Val His Ser Asn Gly Asn Thr Tyr Leu His Trp Tyr Leu Gln
 50                  55                  60
Lys Pro Gly Gln Ser Pro Lys Leu Leu Ile Tyr Lys Val Ser Asn Arg
 65                  70                  75                  80
Phe Ser Gly Val Pro Asp Arg Phe Ser Gly Ser Gly Ser Gly Thr Asp
                 85                  90                  95
Phe Thr Leu Lys Ile Ser Arg Val Glu Ala Glu Asp Leu Gly Val Tyr
                100                 105                 110
Phe Cys Ser Gln Ser Thr His Val Pro Phe Thr Phe Gly Ser Gly Thr
                115                 120                 125
Lys Leu Glu Met Lys Gly Gly Gly Gly Ser Gly Gly Gly Ser Gly
            130                 135                 140
Gly Gly Gly Ser Glu Val Gln Leu Val Glu Ser Gly Gly Gly Leu Val
145                 150                 155                 160
Gln Pro Lys Gly Ser Leu Lys Leu Ser Cys Ala Ala Ser Gly Phe Thr
                165                 170                 175
Phe Ser Asp Ala Trp Met Asp Trp Val Arg Gln Ser Pro Glu Lys Gly
                180                 185                 190
Leu Glu Trp Val Ala Glu Ile Arg Ser Lys Ala Asn Ile His Ala Thr
                195                 200                 205
Tyr Tyr Ala Glu Ser Val Lys Gly Arg Phe Thr Ile Ser Arg Asp Asp
            210                 215                 220
Ser Lys Ser Ser Val Tyr Leu Gln Met Asn Asn Leu Arg Thr Glu Asp
225                 230                 235                 240
Thr Gly Ile Tyr Tyr Cys Thr Pro Tyr Tyr Thr Tyr Ala Pro Arg Phe
                245                 250                 255
Ala Tyr Trp Gly Arg Gly Thr Leu Val Thr Val Ser Ser Thr Thr Thr
                260                 265                 270
Pro Ala Pro Arg Pro Pro Thr Pro Ala Pro Thr Ile Ala Ser Gln Pro
                275                 280                 285
Leu Ser Leu Arg Pro Glu Ala Cys Arg Pro Ala Ala Gly Gly Ala Val
```

```
                290                 295                 300
His Thr Arg Gly Leu Asp Phe Ala Cys Asp Ile Tyr Ile Trp Ala Pro
305                 310                 315                 320

Leu Ala Gly Thr Cys Gly Val Leu Leu Ser Leu Val Ile Thr Leu
                325                 330                 335

Tyr Cys Lys Arg Gly Arg Lys Lys Leu Leu Tyr Ile Phe Lys Gln Pro
                340                 345                 350

Phe Met Arg Pro Val Gln Thr Thr Gln Glu Glu Asp Gly Cys Ser Cys
                355                 360                 365

Arg Phe Pro Glu Glu Glu Glu Gly Gly Cys Glu Leu Arg Val Lys Phe
370                 375                 380

Ser Arg Ser Ala Asp Ala Pro Ala Tyr Gln Gln Gly Gln Asn Gln Leu
385                 390                 395                 400

Tyr Asn Glu Leu Asn Leu Gly Arg Arg Glu Glu Tyr Asp Val Leu Asp
                405                 410                 415

Lys Arg Arg Gly Arg Asp Pro Glu Met Gly Gly Lys Pro Arg Arg Lys
                420                 425                 430

Asn Pro Gln Glu Gly Leu Tyr Asn Glu Leu Gln Lys Asp Lys Met Ala
                435                 440                 445

Glu Ala Tyr Ser Glu Ile Gly Met Lys Gly Glu Arg Arg Arg Gly Lys
450                 455                 460

Gly His Asp Gly Leu Tyr Gln Gly Leu Ser Thr Ala Thr Lys Asp Thr
465                 470                 475                 480

Tyr Asp Ala Leu His Met Gln Ala Leu Pro Pro Arg
                485                 490

<210> SEQ ID NO 60
<211> LENGTH: 491
<212> TYPE: PRT
<213> ORGANISM: Artificial Sequence
<220> FEATURE:
<223> OTHER INFORMATION: Synthesized

<400> SEQUENCE: 60

Met Ala Leu Pro Val Thr Ala Leu Leu Leu Pro Leu Ala Leu Leu Leu
1               5                   10                  15

His Ala Ala Arg Pro Ser Ile Val Met Thr Gln Thr Pro Leu Ser Leu
                20                  25                  30

Pro Val Ser Leu Gly Asp Gln Ala Ser Ile Ser Cys Arg Ser Ser Gln
                35                  40                  45

Ser Leu Val His Ser Asn Gly Asn Thr Tyr Leu His Trp Tyr Leu Gln
50                  55                  60

Lys Pro Gly Gln Ser Pro Lys Leu Leu Ile Tyr Lys Val Ser Asn Arg
65                  70                  75                  80

Phe Ser Gly Val Pro Asp Arg Phe Ser Gly Ser Gly Ser Gly Thr Asp
                85                  90                  95

Phe Thr Leu Lys Ile Ser Arg Val Glu Ala Glu Asp Leu Gly Val Tyr
                100                 105                 110

Phe Cys Ser Gln Ser Thr His Val Pro Phe Thr Phe Gly Ser Gly Thr
                115                 120                 125

Lys Leu Glu Met Lys Gly Gly Gly Gly Ser Gly Gly Gly Gly Ser Gly
                130                 135                 140

Gly Gly Gly Ser Glu Val Gln Leu Val Glu Ser Gly Gly Gly Leu Val
145                 150                 155                 160

Gln Pro Lys Gly Ser Leu Lys Leu Ser Cys Ala Ala Ser Gly Phe Thr
```

```
                    165                 170                 175
Phe Ser Asp Ala Trp Met Asp Trp Val Arg Gln Ser Pro Glu Lys Gly
                180                 185                 190

Leu Glu Trp Val Ala Glu Ile Arg Ser Lys Ala Asn Ile His Ala Thr
            195                 200                 205

Tyr Tyr Ala Glu Ser Val Lys Gly Arg Phe Thr Ile Ser Arg Asp Asp
        210                 215                 220

Ser Lys Ser Ser Val Tyr Leu Gln Met Asn Asn Leu Arg Thr Glu Asp
225                 230                 235                 240

Thr Gly Ile Tyr Tyr Cys Thr Pro Tyr Tyr Thr Tyr Ala Pro Arg Phe
                245                 250                 255

Ala Tyr Trp Gly Arg Gly Thr Leu Val Thr Val Ser Ser Ala Ala Ala
                260                 265                 270

Ile Glu Val Met Tyr Pro Pro Pro Tyr Leu Asp Asn Glu Lys Ser Asn
                275                 280                 285

Gly Thr Ile Ile His Val Lys Gly Lys His Leu Cys Pro Ser Pro Leu
                290                 295                 300

Phe Pro Gly Pro Ser Lys Pro Phe Trp Val Leu Val Val Val Gly Gly
305                 310                 315                 320

Val Leu Ala Cys Tyr Ser Leu Leu Val Thr Val Ala Phe Ile Ile Phe
                325                 330                 335

Trp Val Arg Ser Lys Arg Ser Arg Leu Leu His Ser Asp Tyr Met Asn
                340                 345                 350

Met Thr Pro Arg Arg Pro Gly Pro Thr Arg Lys His Tyr Gln Pro Tyr
                355                 360                 365

Ala Pro Pro Arg Asp Phe Ala Ala Tyr Arg Ser Arg Val Lys Phe Ser
                370                 375                 380

Arg Ser Ala Asp Ala Pro Ala Tyr Gln Gln Gly Gln Asn Gln Leu Tyr
385                 390                 395                 400

Asn Glu Leu Asn Leu Gly Arg Arg Glu Glu Tyr Asp Val Leu Asp Lys
                405                 410                 415

Arg Arg Gly Arg Asp Pro Glu Met Gly Gly Lys Pro Arg Arg Lys Asn
                420                 425                 430

Pro Gln Glu Gly Leu Tyr Asn Glu Leu Gln Lys Asp Lys Met Ala Glu
                435                 440                 445

Ala Tyr Ser Glu Ile Gly Met Lys Gly Glu Arg Arg Arg Gly Lys Gly
                450                 455                 460

His Asp Gly Leu Tyr Gln Gly Leu Ser Thr Ala Thr Lys Asp Thr Tyr
465                 470                 475                 480

Asp Ala Leu His Met Gln Ala Leu Pro Pro Arg
                485                 490

<210> SEQ ID NO 61
<211> LENGTH: 118
<212> TYPE: PRT
<213> ORGANISM: Artificial Sequence
<220> FEATURE:
<223> OTHER INFORMATION: Synthesized

<400> SEQUENCE: 61

Gln Val Gln Leu Gln Gln Ser Gly Ala Glu Leu Ala Arg Pro Gly Ala
1               5                   10                  15

Ser Val Lys Met Ser Cys Lys Ala Ser Gly Asn Thr Phe Thr Ser Tyr
            20                  25                  30

Thr Met Arg Trp Val Lys Gln Gly Pro Gly Gln Gly Leu Glu Trp Ile
```

```
            35                  40                  45
Gly Tyr Ile Asn Pro Ser Ser Gly Tyr Thr Asn Tyr Asn Lys Lys Phe
 50                  55                  60

Lys Asp Lys Ala Thr Leu Thr Ala Asp Lys Ser Ser Thr Ala Tyr
 65                  70                  75                  80

Met Gln Leu Ser Ser Leu Thr Ser Asp Asp Ser Ala Val Tyr Tyr Cys
                 85                  90                  95

Val Phe Gly Asn Pro Arg Tyr Ala Met Asp Tyr Trp Gly Gln Gly Thr
                100                 105                 110

Ser Val Thr Val Ser Ser
            115
```

<210> SEQ ID NO 62
<211> LENGTH: 112
<212> TYPE: PRT
<213> ORGANISM: Artificial Sequence
<220> FEATURE:
<223> OTHER INFORMATION: Synthesized

<400> SEQUENCE: 62

```
Asp Ile Val Met Thr Gln Ser Pro Leu Thr Leu Ser Val Thr Ile Gly
 1               5                  10                  15

Gln Pro Ala Ser Ile Ser Cys Lys Ser Ser Gln Ser Leu Leu Asp Ser
            20                  25                  30

Asp Gly Lys Thr Tyr Leu Asn Trp Leu Leu Gln Arg Pro Gly Gln Ser
        35                  40                  45

Pro Lys Arg Leu Ile Tyr Leu Val Ser Lys Leu Asp Ser Gly Val Pro
 50                  55                  60

Asp Arg Phe Thr Gly Ser Gly Ser Gly Thr Asp Phe Thr Leu Lys Ile
 65                  70                  75                  80

Ser Arg Val Glu Ala Glu Asp Leu Gly Val Tyr Tyr Cys Trp Gln Gly
                 85                  90                  95

Thr His Phe Pro Trp Thr Phe Gly Gly Gly Thr Lys Leu Glu Met Lys
                100                 105                 110
```

<210> SEQ ID NO 63
<211> LENGTH: 489
<212> TYPE: PRT
<213> ORGANISM: Artificial Sequence
<220> FEATURE:
<223> OTHER INFORMATION: Synthesized

<400> SEQUENCE: 63

```
Met Ala Leu Pro Val Thr Ala Leu Leu Leu Pro Leu Ala Leu Leu Leu
 1               5                  10                  15

His Ala Ala Arg Pro Asp Ile Val Met Thr Gln Ser Pro Leu Thr Leu
            20                  25                  30

Ser Val Thr Ile Gly Gln Pro Ala Ser Ile Ser Cys Lys Ser Ser Gln
        35                  40                  45

Ser Leu Leu Asp Ser Asp Gly Lys Thr Tyr Leu Asn Trp Leu Leu Gln
 50                  55                  60

Arg Pro Gly Gln Ser Pro Lys Arg Leu Ile Tyr Leu Val Ser Lys Leu
 65                  70                  75                  80

Asp Ser Gly Val Pro Asp Arg Phe Thr Gly Ser Gly Ser Gly Thr Asp
                 85                  90                  95

Phe Thr Leu Lys Ile Ser Arg Val Glu Ala Glu Asp Leu Gly Val Tyr
                100                 105                 110
```

```
Tyr Cys Trp Gln Gly Thr His Phe Pro Trp Thr Phe Gly Gly Gly Thr
            115                 120                 125
Lys Leu Glu Met Lys Gly Gly Gly Ser Gly Gly Gly Gly Ser Gly
130                 135                 140
Gly Gly Gly Ser Gln Val Gln Leu Gln Gln Ser Gly Ala Glu Leu Ala
145                 150                 155                 160
Arg Pro Gly Ala Ser Val Lys Met Ser Cys Lys Ala Ser Gly Asn Thr
                165                 170                 175
Phe Thr Ser Tyr Thr Met Arg Trp Val Lys Gln Gly Pro Gly Gln Gly
            180                 185                 190
Leu Glu Trp Ile Gly Tyr Ile Asn Pro Ser Ser Gly Tyr Thr Asn Tyr
        195                 200                 205
Asn Lys Lys Phe Lys Asp Lys Ala Thr Leu Thr Ala Asp Lys Ser Ser
    210                 215                 220
Ser Thr Ala Tyr Met Gln Leu Ser Ser Leu Thr Ser Asp Asp Ser Ala
225                 230                 235                 240
Val Tyr Tyr Cys Val Phe Gly Asn Pro Arg Tyr Ala Met Asp Tyr Trp
                245                 250                 255
Gly Gln Gly Thr Ser Val Thr Val Ser Ser Thr Thr Thr Pro Ala Pro
            260                 265                 270
Arg Pro Pro Thr Pro Ala Pro Thr Ile Ala Ser Gln Pro Leu Ser Leu
        275                 280                 285
Arg Pro Glu Ala Cys Arg Pro Ala Ala Gly Gly Ala Val His Thr Arg
    290                 295                 300
Gly Leu Asp Phe Ala Cys Asp Ile Tyr Ile Trp Ala Pro Leu Ala Gly
305                 310                 315                 320
Thr Cys Gly Val Leu Leu Leu Ser Leu Val Ile Thr Leu Tyr Cys Lys
                325                 330                 335
Arg Gly Arg Lys Lys Leu Leu Tyr Ile Phe Lys Gln Pro Phe Met Arg
            340                 345                 350
Pro Val Gln Thr Thr Gln Glu Glu Asp Gly Cys Ser Cys Arg Phe Pro
        355                 360                 365
Glu Glu Glu Glu Gly Gly Cys Glu Leu Arg Val Lys Phe Ser Arg Ser
    370                 375                 380
Ala Asp Ala Pro Ala Tyr Gln Gln Gly Gln Asn Gln Leu Tyr Asn Glu
385                 390                 395                 400
Leu Asn Leu Gly Arg Arg Glu Glu Tyr Asp Val Leu Asp Lys Arg Arg
                405                 410                 415
Gly Arg Asp Pro Glu Met Gly Gly Lys Pro Arg Arg Lys Asn Pro Gln
            420                 425                 430
Glu Gly Leu Tyr Asn Glu Leu Gln Lys Asp Lys Met Ala Glu Ala Tyr
        435                 440                 445
Ser Glu Ile Gly Met Lys Gly Glu Arg Arg Arg Gly Lys Gly His Asp
    450                 455                 460
Gly Leu Tyr Gln Gly Leu Ser Thr Ala Thr Lys Asp Thr Tyr Asp Ala
465                 470                 475                 480
Leu His Met Gln Ala Leu Pro Pro Arg
                485

<210> SEQ ID NO 64
<211> LENGTH: 488
<212> TYPE: PRT
<213> ORGANISM: Artificial Sequence
<220> FEATURE:
<223> OTHER INFORMATION: Synthesized
```

<400> SEQUENCE: 64

```
Met Ala Leu Pro Val Thr Ala Leu Leu Pro Leu Ala Leu Leu Leu
1               5                   10                  15

His Ala Ala Arg Pro Asp Ile Val Met Thr Gln Ser Pro Leu Thr Leu
                20                  25                  30

Ser Val Thr Ile Gly Gln Pro Ala Ser Ile Ser Cys Lys Ser Ser Gln
         35                  40                  45

Ser Leu Leu Asp Ser Asp Gly Lys Thr Tyr Leu Asn Trp Leu Leu Gln
 50                  55                      60

Arg Pro Gly Gln Ser Pro Lys Arg Leu Ile Tyr Leu Val Ser Lys Leu
 65                  70                  75                  80

Asp Ser Gly Val Pro Asp Arg Phe Thr Gly Ser Gly Ser Gly Thr Asp
                 85                  90                  95

Phe Thr Leu Lys Ile Ser Arg Val Glu Ala Glu Asp Leu Gly Val Tyr
             100                 105                 110

Tyr Cys Trp Gln Gly Thr His Phe Pro Trp Thr Phe Gly Gly Gly Thr
         115                 120                 125

Lys Leu Glu Met Lys Gly Gly Gly Ser Gly Gly Gly Ser Gly
130                 135                 140

Gly Gly Gly Ser Gln Val Gln Leu Gln Gln Ser Gly Ala Glu Leu Ala
145                 150                 155                 160

Arg Pro Gly Ala Ser Val Lys Met Ser Cys Lys Ala Ser Gly Asn Thr
                 165                 170                 175

Phe Thr Ser Tyr Thr Met Arg Trp Val Lys Gln Gly Pro Gly Gln Gly
             180                 185                 190

Leu Glu Trp Ile Gly Tyr Ile Asn Pro Ser Ser Gly Tyr Thr Asn Tyr
         195                 200                 205

Asn Lys Lys Phe Lys Asp Lys Ala Thr Leu Thr Ala Asp Lys Ser Ser
210                 215                 220

Ser Thr Ala Tyr Met Gln Leu Ser Ser Leu Thr Ser Asp Asp Ser Ala
225                 230                 235                 240

Val Tyr Tyr Cys Val Phe Gly Asn Pro Arg Tyr Ala Met Asp Tyr Trp
                 245                 250                 255

Gly Gln Gly Thr Ser Val Thr Val Ser Ser Ala Ala Ile Glu Val
             260                 265                 270

Met Tyr Pro Pro Pro Tyr Leu Asp Asn Glu Lys Ser Asn Gly Thr Ile
         275                 280                 285

Ile His Val Lys Gly Lys His Leu Cys Pro Ser Pro Leu Phe Pro Gly
290                 295                 300

Pro Ser Lys Pro Phe Trp Val Leu Val Val Val Gly Gly Val Leu Ala
305                 310                 315                 320

Cys Tyr Ser Leu Leu Val Thr Val Ala Phe Ile Ile Phe Trp Val Arg
                 325                 330                 335

Ser Lys Arg Ser Arg Leu Leu His Ser Asp Tyr Met Asn Met Thr Pro
             340                 345                 350

Arg Arg Pro Gly Pro Thr Arg Lys His Tyr Gln Pro Tyr Ala Pro Pro
         355                 360                 365

Arg Asp Phe Ala Ala Tyr Arg Ser Arg Val Lys Phe Ser Arg Ser Ala
370                 375                 380

Asp Ala Pro Ala Tyr Gln Gln Gly Gln Asn Gln Leu Tyr Asn Glu Leu
385                 390                 395                 400

Asn Leu Gly Arg Arg Glu Glu Tyr Asp Val Leu Asp Lys Arg Arg Gly
```

```
                405                 410                 415
Arg Asp Pro Glu Met Gly Gly Lys Pro Arg Arg Lys Asn Pro Gln Glu
            420                 425             430

Gly Leu Tyr Asn Glu Leu Gln Lys Asp Lys Met Ala Glu Ala Tyr Ser
        435                 440             445

Glu Ile Gly Met Lys Gly Glu Arg Arg Arg Gly Lys Gly His Asp Gly
        450                 455             460

Leu Tyr Gln Gly Leu Ser Thr Ala Thr Lys Asp Thr Tyr Asp Ala Leu
465                 470             475                 480

His Met Gln Ala Leu Pro Pro Arg
                485
```

ANTI-GCC ANTIBODY AND CAR THEREOF FOR TREATING DIGESTIVE SYSTEM CANCER

CROSS REFERENCE TO RELATED APPLICATIONS

This application claims the benefit of U.S. Provisional Application No. 63/033,611, filed Jun. 2, 2020; U.S. application Ser. No. 16/999,357, filed Aug. 21, 2020; and U.S. Provisional Application No. 63/142,181, filed Jan. 27, 2021; all of which are incorporated herein by reference in their entirety.

SEQUENCE LISTING INFORMATION

A computer readable textfile, entitled "Sequence Listing.txt," created on or about May 12, 2021, with a file size of about 156 KB, contains the sequence listing for this application and is hereby incorporated by reference in its entirety.

TECHNICAL FIELD

The present disclosure relates to compositions and methods for expanding and maintaining modified cells, including genetically modified cells and uses thereof, to treat diseases, including cancer.

BACKGROUND

Cancer immunotherapy by chimeric antigen receptor (CAR) T cells has shown good clinical efficacy for liquid tumor treatment. However, CAR T cells have not been proven to be effective for treating solid tumors. There is still a need to improve immunotherapy so that it is effective in treating solid tumors. For example, colorectal cancer is the third diagnosed cancer in the U.S., and the second cause of cancer related death in men and women. Many digestive tract cancers are only found in later stages, but colorectal cancer can be found and treated at earlier stages or can even be prevented by screening tests. As another example, pancreatic cancer is the second cause of cancer-related death in 2020. Moreover, the CDC reports that liver cancer is increasing approximately 2.3% per year, and the death rate is growing rapidly at 3% per year.

SUMMARY

The present disclosure describes compositions and methods of treating the subject having digestive system cancer, the method comprising: administering an effective amount of a composition to the subject, the composition comprising a first population of cells comprising a first CAR binding a first antigen, and a second population of cells comprising a second CAR binding GCC, wherein the first antigen comprises a cell surface molecule of a white blood cell (WBC). Embodiments also relate to a method of enhancing anti-tumor efficacy of immunotherapy on the subject having digestive system cancer, the method comprising: administering an effective amount of a composition to the subject, the composition comprising a first population of cells comprising a first CAR binding a first antigen, and a second population of cells comprising a second CAR binding GCC, wherein the first antigen comprises a cell surface molecule of a white blood cell (WBC), and the anti-tumor efficacy of the composition is enhanced as compared to a subject that is administered an effective amount of the composition that does not have the first population of cells.

This Summary is not intended to identify key features or essential features of the claimed subject matter, nor is it intended to be used to limit the scope of the claimed subject matter.

BRIEF DESCRIPTION OF THE DRAWINGS

The Detailed Description is described with reference to the accompanying figures. The use of the same reference numbers in different figures indicates similar or identical items.

FIGS. 10A1, 10A2, 10A3, 10A4, 10B, and 10C show GCC expression patterns (FIGS. 10A1-10A4 and 10C) and components of the CoupledCAR® system (FIG. 10B).

DETAILED DESCRIPTION

Figure 1:
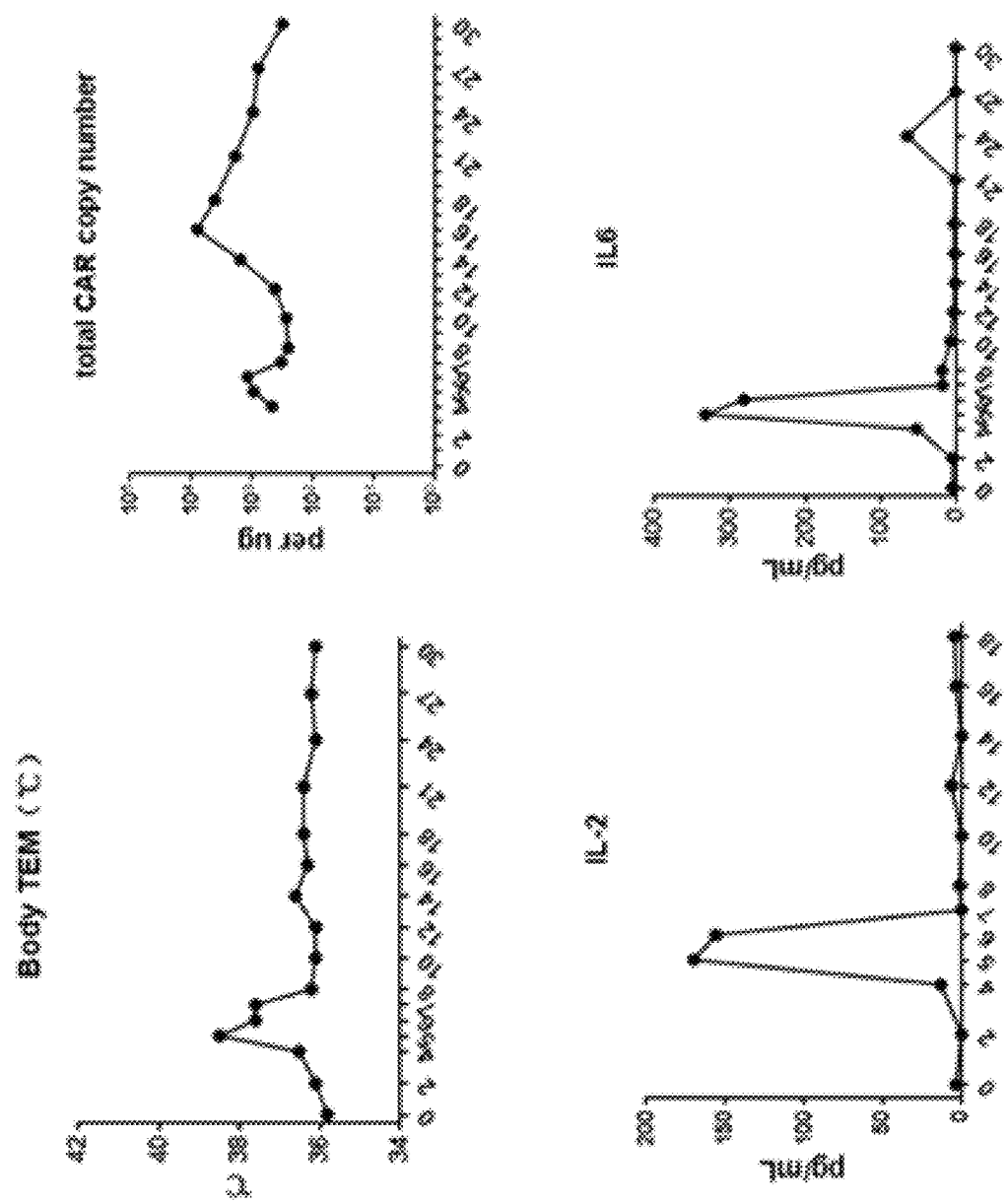
FIG. 1 shows the response of Patient 1 to infusion of mixed CAR T cells.
Figure 2:
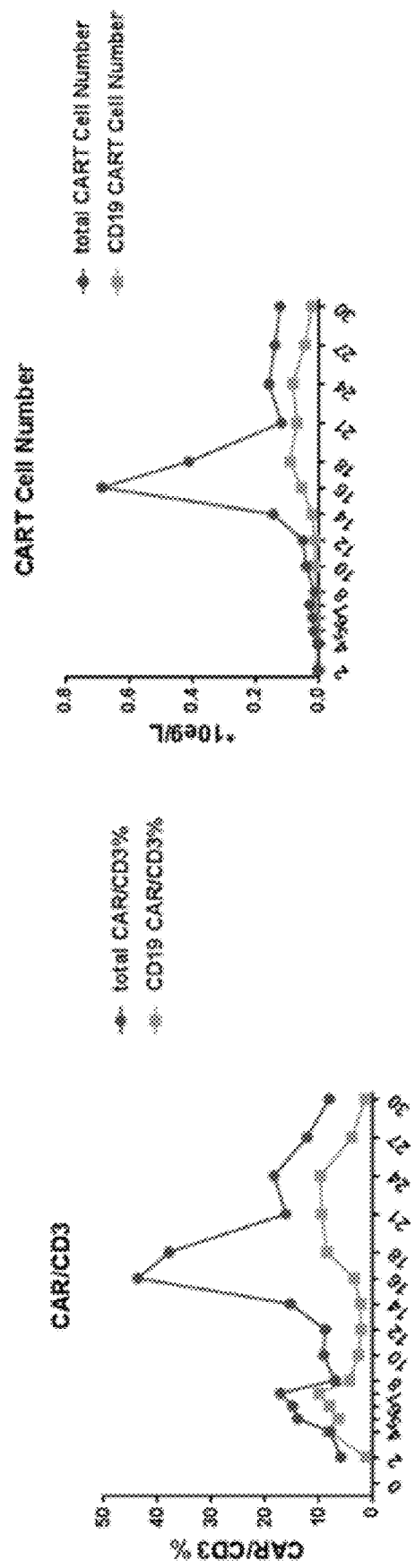
FIG. 2 shows the response of Patient 1 to infusion of mixed CAR T cells.
Figure 2:
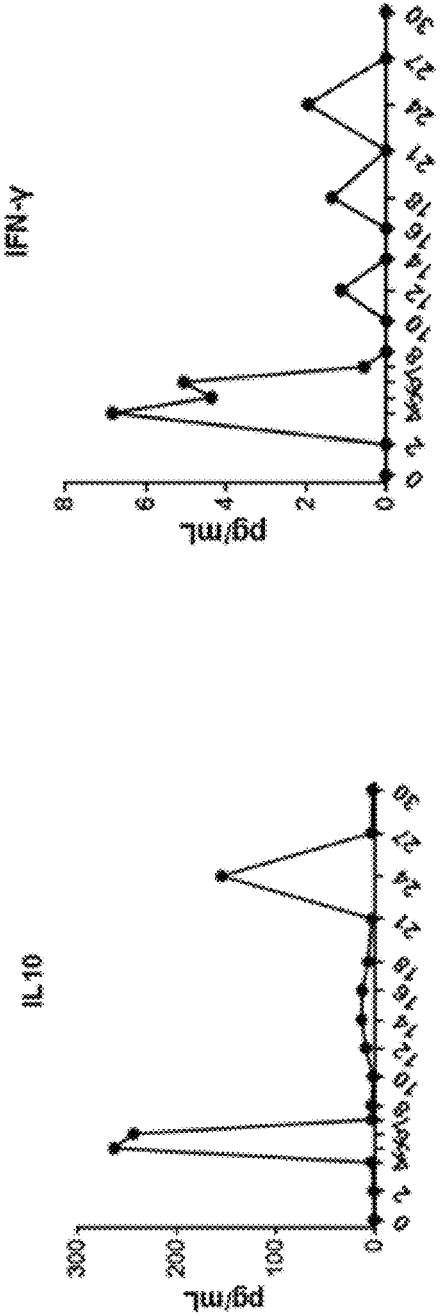

Unless defined otherwise, all technical and scientific terms used herein have the same meaning as commonly understood by those of ordinary skill in the art to which the disclosure belongs. Although any method and material similar or equivalent to those described herein can be used in the practice or testing of the present disclosure, preferred methods and materials are described. For the purposes of the present disclosure, the following terms are defined below.

The articles "a" and "an" are used herein to refer to one or to more than one (i.e., to at least one) of the grammatical object of the article. By way of example, "an element" means one element or more than one element.

By "about" is meant a quantity, level, value, number, frequency, percentage, dimension, size, amount, weight, or length that varies by as much as 20, 15, 10, 9, 8, 7, 6, 5, 4, 3, 2 or 1% to a reference quantity, level, value, number, frequency, percentage, dimension, size, amount, weight or length.

The term "activation," as used herein, refers to the state of a cell that has been sufficiently stimulated to induce detectable cellular proliferation. Activation can also be associated with induced cytokine production and detectable effector functions. The term "activated T cells" refers to, among other things, T cells that are undergoing cell division.

The term "antibody" is used in the broadest sense and refers to monoclonal antibodies (including full length monoclonal antibodies), polyclonal antibodies, multispecific antibodies (e.g., bispecific antibodies), and antibody fragments so long as they exhibit the desired biological activity or function. The antibodies in the present disclosure may exist in a variety of forms including, for example, polyclonal antibodies; monoclonal antibodies; Fv, Fab, Fab', and F(ab')$_2$ fragments; as well as single chain antibodies and humanized antibodies (Harlow et al., 1999, In: Using Antibodies: A Laboratory Manual, Cold Spring Harbor Laboratory Press, NY; Harlow et al., 1989, In: Antibodies: A Laboratory Manual, Cold Spring Harbor, New York; Houston et al., 1988, Proc. Natl. Acad. Sci. USA 85:5879-5883; Bird et al., 1988, Science 242:423-426).

The term "antibody fragments" refers to a portion of a full-length antibody, for example, the antigen binding or variable region of the antibody. Other examples of antibody fragments include Fab, Fab', F(ab')$_2$, and Fv fragments; diabodies; linear antibodies; single-chain antibody molecules; and multispecific antibodies formed from antibody fragments.

The term "Fv" refers to the minimum antibody fragment which contains a complete antigen-recognition and -binding site. This fragment consists of a dimer of one heavy- and one light-chain variable region domain in a tight, non-covalent association. From the folding of these two domains emanates six hypervariable loops (3 loops each from the H and L chain) that contribute amino acid residues for antigen binding and confer antigen binding specificity to the antibody. However, even a single variable domain (or half of an Fv including only three complementarity determining regions (CDRs) specific for an antigen) has the ability to recognize and bind antigen, although at a lower affinity than the entire binding site (the dimer).

An "antibody heavy chain," as used herein, refers to the larger of the two types of polypeptide chains present in all antibody molecules in their naturally occurring conformations. An "antibody light chain," as used herein, refers to the smaller of the two types of polypeptide chains present in all antibody molecules in their naturally occurring conformations. K and λ light chains refer to the two major antibody light chain isotypes.

The term "synthetic antibody" refers to an antibody that is generated using recombinant DNA technology, such as, for example, an antibody expressed by a bacteriophage. The term also includes an antibody that has been generated by the synthesis of a DNA molecule encoding the antibody and the expression of the DNA molecule to obtain the antibody or to obtain an amino acid encoding the antibody. The synthetic DNA is obtained using technology that is available and well known in the art.

The term "antigen" refers to a molecule that provokes an immune response, which may involve either antibody production, or the activation of specific immunologically competent cells, or both. Antigens include any macromolecule, including all proteins or peptides or molecules derived from recombinant or genomic DNA. For example, DNA including a nucleotide sequence or a partial nucleotide sequence encoding a protein or peptide that elicits or stimulates an immune response, and therefore, encodes an "antigen," as the term is used herein. An antigen need not be encoded solely by a full-length nucleotide sequence of a gene. An antigen can be generated, synthesized, or derived from a biological sample including a tissue sample, a tumor sample, a cell, or a biological fluid.

The term "anti-tumor effect," as used herein, refers to a biological effect associated with a decrease in tumor volume, a decrease in the number of tumor cells, a decrease in the number of metastases, decrease in tumor cell proliferation, decrease in tumor cell survival, an increase in life expectancy of a subject having tumor cells, or amelioration of various physiological symptoms associated with the cancerous condition. An "anti-tumor effect" can also be manifested by the ability of the peptides, polynucleotides, cells, and antibodies in the prevention of the occurrence of tumor in the first place.

The term "auto-antigen" refers to an endogenous antigen mistakenly recognized by the immune system as being foreign. Auto-antigens include cellular proteins, phosphoproteins, cellular surface proteins, cellular lipids, nucleic acids, glycoproteins, including cell surface receptors.

The term "autologous" is used to describe a material derived from a subject that is subsequently re-introduced into the same subject.

The term "allogeneic" is used to describe a graft derived from a different subject of the same species. As an example, a donor subject may be related or unrelated to the recipient subject, but the donor subject has immune system markers which are similar to the recipient subject.

The term "xenogeneic" is used to describe a graft derived from a subject of a different species. As an example, the donor subject is from a different species than a recipient subject, and the donor subject and the recipient subject can be genetically and immunologically incompatible.

The term "cancer" is used to refer to a disease characterized by the rapid and uncontrolled growth of aberrant cells. Cancer cells can spread locally or through the bloodstream and lymphatic system to other parts of the body. Examples of various cancers include breast cancer, prostate cancer, ovarian cancer, cervical cancer, skin cancer, pancreatic cancer, colorectal cancer, renal cancer, liver cancer, brain cancer, lymphoma, leukemia, lung cancer, and the like.

Throughout this specification, unless the context requires otherwise, the words "comprise," "includes," and "including" will be understood to imply the inclusion of a stated step or element or group of steps or elements but not the exclusion of any other step or element or group of steps or elements.

The phrase "consisting of" is meant to include, and is limited to, whatever follows the phrase "consisting of." Thus, the phrase "consisting of" indicates that the listed elements are required or mandatory and that no other elements may be present.

The phrase "consisting essentially of" is meant to include any element listed after the phrase and can include other elements that do not interfere with or contribute to the activity or action specified in the disclosure for the listed elements. Thus, the phrase "consisting essentially of" indicates that the listed elements are required or mandatory, but those other elements are optional and may or may not be present depending upon whether or not they affect the activity or action of the listed elements.

The terms "complementary" and "complementarity" refer to polynucleotides (i.e., a sequence of nucleotides) related to the base-pairing rules. For example, the sequence "A-G-T" is complementary to the sequence "T-C-A." Complementarity may be "partial," in which only some of the nucleic acids' bases are matched according to the base pairing rules, or there may be "complete" or "total" complementarity between the nucleic acids. The degree of complementarity between nucleic acid strands has significant effects on the efficiency and strength of hybridization between nucleic acid strands.

The term "corresponds to" or "corresponding to" refers to (a) a polynucleotide having a nucleotide sequence that is substantially identical or complementary to all or a portion of a reference polynucleotide sequence or encoding an amino acid sequence identical to an amino acid sequence in a peptide or protein, or (b) a peptide or polypeptide having an amino acid sequence that is substantially identical to a sequence of amino acids in a reference peptide or protein.

The term "co-stimulatory ligand" refers to a molecule on an antigen-presenting cell (e.g., an APC, dendritic cell, B cell, and the like) that specifically binds a cognate co-stimulatory molecule on a T cell, thereby providing a signal which, in addition to the primary signal provided by, for instance, binding of a TCR/CD3 complex with an MHC molecule loaded with peptide, mediates a T cell response, including at least one of proliferation, activation, differentiation, and other cellular responses. A co-stimulatory ligand can include B7-1 (CD80), B7-2 (CD86), PD-L1, PD-L2, 4-1BBL, OX40L, inducible co-stimulatory ligand (ICOS-L), intercellular adhesion molecule (ICAM), CD30L, CD40, CD70, CD83, HLA-G, MICA, MICB, HVEM, lymphotoxin beta receptor, 3/TR6, ILT3, ILT4, HVEM, a ligand for CD7, an agonist or antibody that binds the Toll ligand receptor, and a ligand that specifically binds with B7-H3. A co-stimulatory ligand also includes, inter alia, an agonist or an antibody that specifically binds with a co-stimulatory molecule present on a T cell, such as CD27, CD28, 4-1BB, OX40, CD30, CD40, PD-1, ICOS, lymphocyte function-associated antigen-1 (LFA-1), CD2, CD7, LIGHT, NKG2C, B7-H3, and a ligand that specifically binds CD83.

The term "co-stimulatory molecule" refers to the cognate binding partner on a T cell that specifically binds with a co-stimulatory ligand, thereby mediating a co-stimulatory response by the T cell, such as proliferation. Co-stimulatory molecules include an MHC class I molecule, BTLA, and a Toll-like receptor.

The term "co-stimulatory signal" refers to a signal, which in combination with a primary signal, such as TCR/CD3 ligation, leads to T cell proliferation and/or upregulation or downregulation of key molecules.

The terms "disease" and "condition" may be used interchangeably or may be different in that the particular malady or condition may not have a known causative agent (so that etiology has not yet been worked out), and it is therefore not yet recognized as a disease but only as an undesirable condition or syndrome, wherein a more or less specific set of symptoms have been identified by clinicians. The term "disease" is a state of health of a subject wherein the subject cannot maintain homeostasis, and wherein if the disease is not ameliorated, then the subject's health continues to deteriorate. In contrast, a "disorder" in a subject is a state of health in which the animal is able to maintain homeostasis, but in which the animal's state of health is less favorable than it would be in the absence of the disorder. Left untreated, a disorder does not necessarily cause a further decrease in the animal's state of health.

The term "effective" refers to adequate to accomplish a desired, expected, or intended result. For example, an "effective amount" in the context of treatment may be an amount of a compound sufficient to produce a therapeutic or prophylactic benefit.

The term "encoding" refers to the inherent property of specific sequences of nucleotides in a polynucleotide, such as a gene, a cDNA, or an mRNA, to serve as a template for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence (except that a "T" is replaced by a "U") and is usually provided in sequence listings, and the non-coding strand, used as the template for transcription of a gene or cDNA, can be referred to as encoding the protein or other product of that gene or cDNA.

The term "exogenous" refers to a molecule that does not naturally occur in a wild-type cell or organism but is typically introduced into the cell by molecular biological techniques. Examples of exogenous polynucleotides include vectors, plasmids, and/or man-made nucleic acid constructs encoding the desired protein. With regard to polynucleotides and proteins, the term "endogenous" or "native" refers to a naturally-occurring polynucleotide or amino acid sequences that may be found in a given wild-type cell or organism. Also, a particular polynucleotide sequence that is isolated from a first organism and transferred to a second organism by molecular biological techniques is typically considered an "exogenous" polynucleotide or amino acid sequence with respect to the second organism. In specific embodiments, polynucleotide sequences can be "introduced" by molecular biological techniques into a microorganism that already contains such a polynucleotide sequence, for instance, to create one or more additional copies of an otherwise naturally-occurring polynucleotide sequence, and thereby facilitate overexpression of the encoded polypeptide.

The term "expression or overexpression" refers to the transcription and/or translation of a particular nucleotide sequence into a precursor or mature protein, for example, driven by its promoter. "Overexpression" refers to the production of a gene product in transgenic organisms or cells that exceeds levels of production in normal or non-transformed organisms or cells. As defined herein, the term "expression" refers to expression or overexpression.

The term "expression vector" refers to a vector including a recombinant polynucleotide including expression control (regulatory) sequences operably linked to a nucleotide sequence to be expressed. An expression vector includes sufficient cis-acting elements for expression; other elements for expression can be supplied by the host cell or in an in vitro expression system. Expression vectors include all those known in the art, such as cosmids, plasmids (e.g., naked or contained in liposomes), and viruses (e.g., lentiviruses, retroviruses, adenoviruses, and adeno-associated viruses) that incorporate the recombinant polynucleotide.

Viruses can be used to deliver nucleic acids into a cell in vitro and in vivo (in a subject). Examples of viruses useful for delivery of nucleic acids into cells include retrovirus, adenovirus, herpes simplex virus, vaccinia virus, and adeno-associated virus.

There also exist non-viral methods for delivering nucleic acids into a cell, for example, electroporation, gene gun, sonoporation, magnetofection, and the use of oligonucleotides, lipoplexes, dendrimers, and inorganic nanoparticles.

The term "homologous" refers to sequence similarity or sequence identity between two polypeptides or between two polynucleotides when a position in both of the two compared sequences is occupied by the same base or amino acid monomer subunit, e.g., if a position in each of two DNA molecules is occupied by adenine, then the molecules are homologous at that position. The percent of homology between two sequences is a function of the number of matching or homologous positions shared by the two sequences divided by the number of positions compared ×100. For example, if 6 of 10 of the positions in two sequences are matched or homologous, then the two sequences are 60% homologous. By way of example, the DNA sequences ATTGCC and TATGGC share 50% homology. A comparison is made when two sequences are aligned to give maximum homology.

The term "immunoglobulin" or "Ig" refers to a class of proteins, which function as antibodies. The five members included in this class of proteins are IgA, IgG, IgM, IgD, and IgE. IgA is the primary antibody that is present in body secretions, such as saliva, tears, breast milk, gastrointestinal secretions, and mucus secretions of the respiratory and genitourinary tracts. IgG is the most common circulating antibody. IgM is the main immunoglobulin produced in the primary immune response in most subjects. It is the most efficient immunoglobulin in agglutination, complement fixation, and other antibody responses and is important in defense against bacteria and viruses. IgD is the immunoglobulin that has no known antibody function but may serve as an antigen receptor. IgE is the immunoglobulin that mediates immediate hypersensitivity by causing the release of mediators from mast cells and basophils upon exposure to the allergen.

The term "isolated" refers to a material that is substantially or essentially free from components that normally accompany it in its native state. The material can be a cell or a macromolecule such as a protein or nucleic acid. For example, an "isolated polynucleotide," as used herein, refers to a polynucleotide, which has been purified from the sequences which flank it in a naturally-occurring state, e.g., a DNA fragment that has been removed from the sequences that are normally adjacent to the fragment. Alternatively, an "isolated peptide" or an "isolated polypeptide" and the like, as used herein, refer to in vitro isolation and/or purification of a peptide or polypeptide molecule from its natural cellular environment and from association with other components of the cell.

The term "substantially purified" refers to a material that is substantially free from components that are normally associated with it in its native state. For example, a substantially purified cell refers to a cell that has been separated from other cell types with which it is normally associated in its naturally occurring or native state. In some instances, a population of substantially purified cells refers to a homogenous population of cells. In other instances, this term refers simply to a cell that has been separated from the cells with which they are naturally associated in their natural state. In embodiments, the cells are cultured in vitro. In embodiments, the cells are not cultured in vitro.

In the context of the present disclosure, the following abbreviations for the commonly occurring nucleic acid bases are used. "A" refers to adenosine, "C" refers to cytosine, "G" refers to guanosine, "T" refers to thymidine, and "U" refers to uridine.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may, in some version, contain an intron(s).

The term "lentivirus" refers to a genus of the Retroviridae family. Lentiviruses are unique among the retroviruses in being able to infect non-dividing cells; they can deliver a significant amount of genetic information into the DNA of the host cell, so they are one of the most efficient methods of a gene delivery vector. Moreover, the use of lentiviruses enables the integration of the genetic information into the host chromosome, resulting in stably transduced genetic information. HIV, SIV, and FIV are all examples of lentiviruses. Vectors derived from lentiviruses offer the means to achieve significant levels of gene transfer in vivo.

The term "modulating" refers to mediating a detectable increase or decrease in the level of a response in a subject compared with the level of a response in the subject in the absence of a treatment or compound and/or compared with the level of a response in an otherwise identical but untreated subject. The term encompasses perturbing and/or affecting a native signal or response, thereby mediating a beneficial therapeutic response in a subject, preferably a human.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence, or a ribosome binding site is operably linked to a coding sequence if it is positioned so as to facilitate translation.

The term "under transcriptional control" refers to a promoter being operably linked to and in the correct location and orientation in relation to a polynucleotide to control (regulate) the initiation of transcription by RNA polymerase and expression of the polynucleotide.

The term "overexpressed" tumor antigen or "overexpression" of the tumor antigen is intended to indicate an abnormal level of expression of the tumor antigen in a cell from a disease area such as a solid tumor within a specific tissue or organ of the patient relative to the level of expression in a normal cell from that tissue or organ. Patients having a solid tumor or a hematological malignancy characterized by overexpression of the tumor antigen can be determined by standard assays known in the art.

Solid tumors are abnormal masses of tissue that usually do not contain cysts or liquid areas. Solid tumors can be benign or malignant. Different types of solid tumors are named for the type of cells that form them (such as sarcomas, carcinomas, and lymphomas). Examples of solid tumors, such as sarcomas and carcinomas, include fibrosarcoma, myxosarcoma, liposarcoma, chondrosarcoma, osteosarcoma, synovioma, mesothelioma, Ewing's tumor, leiomyosarcoma, rhabdomyosarcoma, colon carcinoma, lymphoid malignancy, pancreatic cancer, breast cancer, lung cancers, ovarian cancer, prostate cancer, hepatocellular carcinoma, squamous cell carcinoma, basal cell carcinoma, adenocarcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, seminoma, bladder carcinoma, melanoma, and CNS tumors (such as a glioma (such as brainstem glioma and mixed gliomas), glioblastoma (also known as glioblastoma multiforme), astrocytoma, CNS lymphoma, germinoma, medulloblastoma, Schwannoma craniopharyogioma, ependymoma, pinealoma, hemangioblastoma, acoustic neuroma, oligodendroglioma, menangioma, neuroblastoma, retinoblastoma, and brain metastases).

A solid tumor antigen is an antigen expressed on a solid tumor. In embodiments, solid tumor antigens are also expressed at low levels on healthy tissue. Examples of solid tumor antigens and their related disease tumors are provided in Table 1.

TABLE 1

| Solid Tumor antigen | Disease tumor |
|---|---|
| PRLR | Breast Cancer |
| CLCA1 | colorectal Cancer |
| MUC12 | colorectal Cancer |
| GCC | Digestive System Cancer such as colorectal Cancer, Esophagus Cancer, Gastric Cancer, Pancreatic Cancer, Liver Cancer |
| GPR35 | colorectal Cancer |
| CR1L | Gastric Cancer |
| MUC 17 | Gastric Cancer |
| TMPRSS11B | esophageal Cancer |
| MUC21 | esophageal Cancer |
| TMPRSS11E | esophageal Cancer |
| CD207 | bladder Cancer |
| SLC30A8 | pancreatic Cancer |
| CFC1 | pancreatic Cancer |
| SLC12A3 | Cervical Cancer |
| SSTR1 | Cervical tumor |
| GPR27 | Ovary tumor |
| FZD10 | Ovary tumor |
| TSHR | Thyroid Tumor |
| SIGLEC15 | Urothelial cancer |
| SLC6A3 | Renal cancer |
| KISS1R | Renal cancer |
| QRFPR | Renal cancer: |
| GPR119 | Pancreatic cancer |
| CLDN6 | Endometrial cancer/Urothelial cancer |
| UPK2 | Urothelial cancer (including bladder cancer) |
| ADAM12 | Breast cancer, pancreatic cancer, and the like |
| SLC45A3 | Prostate cancer |
| ACPP | Prostate cancer |
| MUC21 | Esophageal cancer |
| MUC16 | Ovarian cancer |
| MS4Al2 | Colorectal cancer |
| ALPP | Endometrial cancer |
| CEA | Colorectal carcinoma |
| EphA2 | Glioma |
| FAP | Mesothelioma |
| GPC3 | Lung squamous cell carcinoma |
| IL13-Rα2 | Glioma |
| Mesothelin | Metastatic cancer |
| PSMA | Prostate cancer |
| ROR1 | Breast lung carcinoma |
| VEGFR-II | Metastatic cancer |
| GD2 | Neuroblastoma |
| FR-α | Ovarian carcinoma |
| ErbB2 | Carcinomas |
| EpCAM | Carcinoma |

TABLE 1-continued

| Solid Tumor antigen | Disease tumor |
|---|---|
| EGFRvIII | Glioma-Glioblastoma |
| EGFR | Glioma-NSCL cancer |
| tMUC1 | Cholangiocarcinoma, Pancreatic cancer, Breast |
| PSCA | pancreas, stomach, or prostate cancer |
| FCER2, GPR18, FCRLA, CXCR5, FCRL3, FCRL2, HTR3A, and CLEC17A | breast cancer |
| TRPMI, SLC45A2, and SLC24A5 | lymphoma |
| DPEP3 | melanoma |
| KCNK16 | ovarian, testis |
| LIM2 or KCNV2 | pancreatic |
| SLC26A4 | thyroid cancer |
| CD171 | Neuroblastoma |
| Glypican-3 | Sarcoma |
| IL-13 | Glioma |
| CD79a/b | Lymphoma |

The term "parenteral administration" of a composition includes, e.g., subcutaneous (s.c.), intravenous (i.v.), intramuscular (i.m.), intrasternal injection, or infusion techniques.

The terms "patient," "subject," and "individual," and the like are used interchangeably herein and refer to any human or animal, amenable to the methods described herein. In embodiments, the patient, subject, or individual is a human or animal. In embodiments, the term "subject" is intended to include living organisms in which an immune response can be elicited (e.g., mammals). Examples of subjects include humans, and animals, such as dogs, cats, mice, rats, and transgenic species thereof.

A subject in need of treatment or in need thereof includes a subject having a disease, condition, or disorder that needs to be treated. A subject in need thereof also includes a subject that needs treatment for the prevention of a disease, condition, or disorder.

The term "polynucleotide" or "nucleic acid" refers to mRNA, RNA, cRNA, rRNA, cDNA, or DNA. The term typically refers to a polymeric form of nucleotides of at least 10 bases in length, either ribonucleotides or deoxynucleotides, or a modified form of either type of nucleotide. The term includes all forms of nucleic acids, including single and double-stranded forms of nucleic acids.

The terms "polynucleotide variant" and "variant," and the like refer to polynucleotides displaying substantial sequence identity with a reference polynucleotide sequence or polynucleotides that hybridize with a reference sequence under stringent conditions that are defined hereinafter. These terms also encompass polynucleotides that are distinguished from a reference polynucleotide by the addition, deletion, or substitution of at least one nucleotide. Accordingly, the terms "polynucleotide variant" and "variant" include polynucleotides in which one or more nucleotides have been added or deleted, or replaced with different nucleotides. In this regard, it is well understood in the art that certain alterations inclusive of mutations, additions, deletions, and substitutions can be made to a reference polynucleotide whereby the altered polynucleotide retains the biological function or activity of the reference polynucleotide or has increased activity in relation to the reference polynucleotide (i.e., optimized). Polynucleotide variants include, for example, polynucleotides having at least 50% (and at least 51% to at least 99% and all integer percentages in between, e.g., 90%, 95%, or 98%) sequence identity with a reference polynucleotide sequence described herein. The terms "polynucleotide variant" and "variant" also include naturally-occurring allelic variants and orthologs.

The terms "polypeptide," "polypeptide fragment," "peptide," and "protein" are used interchangeably herein to refer to a polymer of amino acid residues and to variants and synthetic analogues of the same. Thus, these terms apply to amino acid polymers in which one or more amino acid residues are synthetic non-naturally occurring amino acids, such as a chemical analogue of a corresponding naturally occurring amino acid, as well as to naturally-occurring amino acid polymers. In embodiments, polypeptides may include enzymatic polypeptides, or "enzymes," which typically catalyze (i.e., increase the rate of) various chemical reactions.

The term "polypeptide variant" refers to polypeptides that are distinguished from a reference polypeptide sequence by the addition, deletion, or substitution of at least one amino acid residue. In embodiments, a polypeptide variant is distinguished from a reference polypeptide by one or more substitutions, which may be conservative or non-conservative. In embodiments, the polypeptide variant comprises conservative substitutions, and, in this regard, it is well understood in the art that some amino acids may be changed to others with broadly similar properties without changing the nature of the activity of the polypeptide. Polypeptide variants also encompass polypeptides in which one or more amino acids have been added or deleted, or replaced with different amino acid residues.

The term "promoter" refers to a DNA sequence recognized by the synthetic machinery of the cell or introduced synthetic machinery required to initiate the specific transcription of a polynucleotide sequence. The term "expression control (regulatory) sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

The term "bind," "binds," or "interacts with" refers to a molecule recognizing and adhering to a second molecule in a sample or organism but does not substantially recognize or adhere to other structurally unrelated molecules in the sample. The term "specifically binds," as used herein with respect to an antibody, refers to an antibody that recognizes a specific antigen but does not substantially recognize or bind other molecules in a sample. For example, an antibody that specifically binds an antigen from one species may also bind that antigen from one or more species. But, such cross-species reactivity does not itself alter the classification of an antibody as specific. In another example, an antibody that specifically binds an antigen may also bind different allelic forms of the antigen. However, such cross reactivity does not itself alter the classification of an antibody as specific. In some instances, the terms "specific binding" or "specifically binding" can be used in reference to the interaction of an antibody, a protein, or a peptide with a second chemical species, to mean that the interaction is dependent upon the presence of a particular structure (e.g., an antigenic determinant or epitope) on the chemical species; for example, an antibody recognizes and binds a specific protein structure rather than to any protein. If an antibody is specific for epitope "A," the presence of a molecule containing epitope A (or free, unlabeled A) in a reaction containing labeled "A" and the antibody will reduce the amount of labeled A bound to the antibody.

By "statistically significant," it is meant that the result was unlikely to have occurred by chance. Statistical significance can be determined by any method known in the art. Commonly used measures of significance include the p-value, which is the frequency or probability with which the observed event would occur if the null hypothesis were true. If the obtained p-value is smaller than the significance level, then the null hypothesis is rejected. In simple cases, the significance level is defined at a p-value of 0.05 or less. A "decreased" or "reduced" or "lesser" amount is typically a "statistically significant" or a physiologically significant amount and may include a decrease that is about 1.1, 1.2, 1.3, 1.4, 1.5, 1.6 1.7, 1.8, 1.9, 2, 2.5, 3, 3.5, 4, 4.5, 5, 6, 7, 8, 9, 10, 15, 20, 30, 40, or 50 or more times (e.g., 100, 500, 1000 times) (including all integers and decimal points in between and above 1, e.g., 1.5, 1.6, 1.7. 1.8, etc.) an amount or level described herein.

The term "stimulation" refers to a primary response induced by binding of a stimulatory molecule (e.g., a TCR/CD3 complex) with its cognate ligand, thereby mediating a signal transduction event, such as signal transduction via the TCR/CD3 complex. Stimulation can mediate altered expression of certain molecules, such as downregulation of TGF-$\beta$ and/or reorganization of cytoskeletal structures.

The term "stimulatory molecule" refers to a molecule on a T cell that specifically binds a cognate stimulatory ligand present on an antigen-presenting cell. For example, a functional signaling domain derived from a stimulatory molecule is the zeta chain associated with the T cell receptor complex. The stimulatory molecule includes a domain responsible for signal transduction.

The term "stimulatory ligand" refers to a ligand that when present on an antigen-presenting cell (e.g., an APC, a dendritic cell, a B-cell, and the like.) can specifically bind with a cognate binding partner (referred to herein as a "stimulatory molecule") on a cell, for example, a T cell, thereby mediating a primary response by the T cell, including activation, initiation, or stimulation of an immune response, proliferation, and similar processes. Stimulatory ligands are well-known in the art and encompass, inter alia, an MHC Class I molecule loaded with a peptide, an anti-CD3 antibody, a superagonist anti-CD28 antibody, and a superagonist anti-CD2 antibody.

The term "therapeutic" refers to treatment and/or prophylaxis. A therapeutic effect is obtained by suppression, remission, or eradication of a disease state or alleviating the symptoms of a disease state.

The term "therapeutically effective amount" refers to the amount of the subject compound that will elicit the biological or medical response of a tissue, system, or subject that is being sought by the researcher, veterinarian, medical doctor or another clinician. The term "therapeutically effective amount" includes that amount of a compound that, when administered, is sufficient to prevent the development of, or alleviate to some extent, one or more of the signs or symptoms of the disorder or disease being treated. The therapeutically effective amount will vary depending on the compound, the disease, and its severity, and the age, weight, etc., of the subject to be treated.

The term "treat a disease" refers to the reduction of the frequency or severity of at least one sign or symptom of a disease or disorder experienced by a subject.

The term "transfected" or "transformed" or "transduced" refers to a process by which an exogenous nucleic acid is transferred or introduced into the host cell. A "transfected" or "transformed" or "transduced" cell is one that has been transfected, transformed, or transduced with an exogenous nucleic acid. The cell includes the primary subject cell and its progeny.

The term "vector" refers to a polynucleotide that comprises an isolated nucleic acid and which can be used to deliver the isolated nucleic acid to the interior of a cell. Numerous vectors are known in the art including linear polynucleotides, polynucleotides associated with ionic or amphiphilic compounds, plasmids, and viruses. Thus, the term "vector" includes an autonomously replicating plasmid or a virus. The term also includes non-plasmid and non-viral compounds which facilitate the transfer of nucleic acid into cells, such as, for example, polylysine compounds, liposomes, and the like. Examples of viral vectors include adenoviral vectors, adeno-associated virus vectors, retroviral vectors, and others. For example, lentiviruses are complex retroviruses, which, in addition to the common retroviral genes gag, pol, and env, contain other genes with regulatory or structural function. Lentiviral vectors are well known in the art. Some examples of lentivirus include the Human Immunodeficiency Viruses: HIV-1, HIV-2, and the Simian Immunodeficiency Virus: SIV. Lentiviral vectors have been generated by multiply attenuating the HIV virulence genes, for example, the genes env, vif, vpr, vpu, and nef are deleted, making the vector biologically safe.

Ranges: throughout this disclosure, various aspects of the disclosure can be presented in a range format. It should be understood that the description in range format is merely for convenience and brevity and should not be construed as an inflexible limitation on the scope of the disclosure. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6, etc., as well as individual numbers within that range, for example, 1, 2, 2.7, 3, 4, 5, 5.3, and 6. This applies regardless of the breadth of the range.

A "chimeric antigen receptor" (CAR) molecule is a recombinant polypeptide including at least an extracellular domain, a transmembrane domain, and a cytoplasmic domain or intracellular domain. In embodiments, the domains of the CAR are on the same polypeptide chain, for example, a chimeric fusion protein. In embodiments, the domains are on different polypeptide chains, for example, the domains are not contiguous.

The extracellular domain of a CAR molecule includes an antigen binding domain. The antigen binding domain is for expanding and/or maintaining the modified cells, such as a CAR T cell, or for killing a tumor cell, such as a solid tumor. In embodiments, the antigen binding domain for expanding and/or maintaining modified cells binds an antigen, for example, a cell surface molecule or marker, on the surface of a WBC. In embodiments, the WBC is at least one of GMP (granulocyte macrophage precursor), MDP (monocyte-macrophage/dendritic cell precursors), cMoP (common monocyte precursor), basophil, eosinophil, neutrophil, SatM (Segerate-nucleus-containing atypical monocyte), macrophage, monocyte, CDP (common dendritic cell precursor), cDC (conventional DC), pDC (plasmacytoid DC), CLP (common lymphocyte precursor), B cell, ILC (Innate Lymphocyte), NK cell, megakaryocyte, myeloblast, pro-myelocyte, myelocyte, meta-myelocyte, band cells, lymphoblast, prolymphocyte, monoblast, megakaryoblast, promegakaryocyte, megakaryocyte, platelets, or MSDC (Myeloid-derived suppressor cell). In embodiments, the WBC is a granulocyte, monocyte, and/or lymphocyte. In embodiments, the WBC is a lymphocyte, for example, a B cell. In embodiments, the WBC is a B cell. In embodiments, the cell surface molecule of a B cell includes CD19, CD22, CD20, BCMA, CD5, CD7, CD2, CD16, CD56, CD30, CD14, CD68, CD11b, CD18, CD169, CD1c, CD33, CD38, CD138, or CD13. In embodiments, the cell surface molecule of the B cell is CD19, CD20, CD22, or BCMA. In embodiments, the cell surface molecule of the B cell is CD19.

The cells described herein, including modified cells such as CAR cells and modified T cells, can be derived from stem cells. Stem cells may be adult stem cells, embryonic stem cells, more particularly non-human stem cells, cord blood stem cells, progenitor cells, bone marrow stem cells, induced pluripotent stem cells, totipotent stem cells, or hematopoietic stem cells. A modified cell may also be a dendritic cell, an NK-cell, a B-cell, or a T cell selected from the group consisting of inflammatory T lymphocytes, cytotoxic T lymphocytes, regulatory T lymphocytes, or helper T lymphocytes. In embodiments, Modified cells may be derived from the group consisting of CD4+ T lymphocytes and CD8+ T lymphocytes. Prior to the expansion and genetic modification of the cells of the invention, a source of cells may be obtained from a subject through a variety of non-limiting methods. T cells may be obtained from a number of non-limiting sources, including peripheral blood mononuclear cells, bone marrow, lymph node tissue, cord blood, thymus tissue, tissue from a site of infection, ascites, pleural effusion, spleen tissue, and tumors. In embodiments of the present invention, any number of T cell lines available and known to those skilled in the art may be used. In embodiments, modified cells may be derived from a healthy donor, from a patient diagnosed with cancer, or from a patient diagnosed with an infection. In embodiments, a modified cell is part of a mixed population of cells that present different phenotypic characteristics.

A population of cells refers to a group of two or more cells. The cells of the population could be the same, such that the population is a homogenous population of cells. The cells of the population could be different, such that the population is a mixed population or a heterogeneous population of cells. For example, a mixed population of cells could include modified cells comprising a first CAR and cells comprising a second CAR, wherein the first CAR and the second CAR bind different antigens.

The term "stem cell" refers to any of certain types of cell which have the capacity for self-renewal and the ability to differentiate into other kind(s) of a cell. For example, a stem cell gives rise either to two daughter stem cells (as occurs in vitro with embryonic stem cells in culture) or to one stem cell and a cell that undergoes differentiation (as occurs, e.g., in hematopoietic stem cells, which give rise to blood cells). Different categories of stem cells may be distinguished on the basis of their origin and/or on the extent of their capacity for differentiation into other types of cells. For example, stem cells may include embryonic stem (ES) cells (i.e., pluripotent stem cells), somatic stem cells, induced pluripotent stem cells, and any other types of stem cells.

The pluripotent embryonic stem cells are found in the inner cell mass of a blastocyst and have an innate capacity for differentiation. For example, pluripotent embryonic stem cells have the potential to form any type of cell in the body. When grown in vitro for long periods of time, ES cells maintain pluripotency as progeny cells retain the potential for multilineage differentiation.

Somatic stem cells can include fetal stem cells (from the fetus) and adult stem cells (found in various tissues, such as bone marrow). These cells have been regarded as having a capacity for differentiation that is lower than that of the pluripotent ES cells—with the capacity of fetal stem cells being greater than that of adult stem cells. Somatic stem cells apparently differentiate into only a limited number of types of cells and have been described as multipotent. The "tissue-specific" stem cells normally give rise to only one type of cell. For example, embryonic stem cells may be differentiated into blood stem cells (e.g., Hematopoietic stem cells (HSCs)), which may be further differentiated into various blood cells (e.g., red blood cells, platelets, white blood cells, etc.).

Induced pluripotent stem cells (i.e., iPS cells or iPSCs) may include a type of pluripotent stem cell artificially derived from a non-pluripotent cell (e.g., an adult somatic cell) by inducing an expression of specific genes. Induced pluripotent stem cells are similar to natural pluripotent stem cells, such as embryonic stem (ES) cells, in many aspects, such as the expression of certain stem cell genes and proteins, chromatin methylation patterns, doubling time, embryoid body formation, teratoma formation, viable chimera formation, and potency and differentiability. Induced pluripotent cells can be obtained from adult stomach, liver, skin, and blood cells.

In embodiments, the antigen binding domain for killing a tumor binds an antigen on the surface of a tumor, for example, a tumor antigen or tumor marker. Tumor antigens are proteins that are produced by tumor cells that elicit or stimulate an immune response, particularly T cell mediated immune responses. Tumor antigens are well known in the art and include, for example, tumor associated MUC1 (tMUC1), a glioma-associated antigen, carcinoembryonic antigen (CEA), β-human chorionic gonadotropin, alphafetoprotein (AFP), lectin-reactive AFP, thyroglobulin, RAGE-1, MN-CA IX, human telomerase reverse transcriptase, RU1, RU2 (AS), intestinal carboxyl esterase, mut hsp70-2, M-CSF, prostase, prostate-specific antigen (PSA), PAP, NY-ESO-1, LAGE-1a, p53, prostein, PSMA, Her2/neu, surviving, telomerase, prostate-carcinoma tumor antigen-1 (PCTA-1), MAGE, ELF2M, neutrophil elastase, ephrinB2, CD22, insulin growth factor (IGF)-I, IGF-II, IGF-I receptor, CD19, and mesothelin. For example, when the tumor antigen is CD19, the CAR thereof can be referred to as CD19 CAR or 19CAR, which is a CAR molecule that includes an antigen binding domain that binds CD19.

In embodiments, the extracellular antigen binding domain of a CAR includes at least one scFv or at least a single domain antibody. As an example, there can be two scFvs on a CAR. The scFv includes a light chain variable (VL) region and a heavy chain variable (VH) region of a target antigen-specific monoclonal antibody joined by a flexible linker. Single chain variable region fragments can be made by linking light and/or heavy chain variable regions by using a short linking peptide (Bird et al., Science 242:423-426, 1988). An example of a linking peptide is the GS linker having the amino acid sequence (GGGGS)$_3$ (SEQ ID NO: 13), which bridges approximately 3.5 nm between the carboxy terminus of one variable region and the amino terminus of the other variable region. Linkers of other sequences have been designed and used (Bird et al., 1988, supra). In general, linkers can be short, flexible polypeptides and preferably comprised of about 20 or fewer amino acid residues. The single chain variants can be produced either recombinantly or synthetically. For the synthetic production of scFv, an automated synthesizer can be used. For recombinant production of scFv, a suitable plasmid containing a polynucleotide that encodes the scFv can be introduced into a suitable host cell, either eukaryotic, such as yeast, plant, insect, or mammalian cells, or prokaryotic, such as E. coli. Polynucleotides encoding the scFv of interest can be made by routine manipulations such as ligation of polynucleotides. The resultant scFv can be isolated using standard protein purification techniques known in the art.

The cytoplasmic domain of the CAR molecules described herein includes one or more co-stimulatory domains and one or more signaling domains. The co-stimulatory and signaling domains function to transmit the signal and activate molecules, such as T cells, in response to antigen binding. The one or more co-stimulatory domains are derived from stimulatory molecules and/or co-stimulatory molecules, and the signaling domain is derived from a primary signaling domain, such as the CD3 zeta domain. In embodiments, the signaling domain further includes one or more functional signaling domains derived from a co-stimulatory molecule. In embodiments, the co-stimulatory molecules are cell surface molecules (other than antigens receptors or their ligands) that are required for activating a cellular response to an antigen.

In embodiments, the co-stimulatory domain includes the intracellular domain of CD27, CD28, 4-1BB, OX40, CD30, CD40, PD-1, ICOS, lymphocyte function-associated antigen-1 (LFA-1), CD2, CD7, LIGHT, NKG2C, B7-H3, a ligand that specifically binds with CD83, or any combination thereof. In embodiments, the signaling domain includes a CD3 zeta domain derived from a T cell receptor.

The CAR molecules described herein also include a transmembrane domain. The incorporation of a transmembrane domain in the CAR molecules stabilizes the molecule. In embodiments, the transmembrane domain of the CAR molecules is the transmembrane domain of a CD28 or 4-1BB molecule.

Between the extracellular domain and the transmembrane domain of the CAR, there may be incorporated a spacer domain. As used herein, the term "spacer domain" generally means any oligo- or polypeptide that functions to link the transmembrane domain to the extracellular domain and/or the cytoplasmic domain on the polypeptide chain. A spacer domain may include up to 300 amino acids, preferably 10 to 100 amino acids, and most preferably 25 to 50 amino acids.

The present disclosure also describes a method for treating a subject having digestive system cancer, the method comprising: obtaining cells from the subject or a healthy donor; contacting the cells with (1) a first vector comprising a polynucleotide encoding a first antigen binding molecule that binds a first antigen and (2) a second vector comprising a polynucleotide encoding a second antigen binding molecule that binds GCC to obtain a population of modified cells; and administering an effective amount of modified cells to the subject, wherein: the first antigen is different from the second antigen; and the level of T cell response (e.g., cell expansion) in the subject is higher than the level in a subject administered with an effective amount of cells that have been contacted with the second vector but not the first vector, wherein: the first antigen is different from the second antigen.

The present disclosure also describes a method for treating a subject having digestive system cancer, the method comprising: obtaining cells from the subject or a healthy donor; contacting the cells with (1) a first vector comprising a polynucleotide encoding a first antigen binding molecule that binds a first antigen and (2) a second vector comprising a polynucleotide encoding a second antigen binding molecule that binds GCC to obtain a population of modified cells; and administering an effective amount of modified cells to the subject, wherein: the first antigen is different from the second antigen The present disclosure also describes a method for enhancing treatment of a subject having digestive system cancer, the method comprising: obtaining cells from the subject or a healthy donor; contacting the cells with (1) a first vector comprising a polynucleotide encoding a first antigen binding molecule that binds a first antigen and (2) a second vector comprising a polynucleotide encoding a second antigen binding molecule that binds GCC to obtain a population of modified cells; and administering an effective amount of modified cells to the subject, wherein: the first antigen is different from the second antigen, and the level of inhibition of tumor growth by the effective amount of modified cells is higher than the level of inhibition of tumor growth by the effective amount of cells that have been contacted with the second vector but not the first vector.

The present disclosure also describes a method for in vitro cell preparation, the method comprising: introducing a first vector comprising a polynucleotide encoding a first antigen binding molecule that binds a first antigen into a first population of cells; introducing a second vector comprising a polynucleotide encoding a second antigen binding molecule that binds GCC into a second population of cells; and culturing the first and second population of cells, wherein the first antigen is different from the second antigen.

The present disclosure also describes a method for treating a subject having digestive cancer, the method comprising: introducing a first vector comprising a polynucleotide encoding a first antigen binding molecule that binds a first antigen into a first population of cells to obtain a first population of modified cells; introducing a second vector comprising a polynucleotide encoding a second antigen binding molecule that binds GCC into a second population of cells to obtain a second population of modified cells; and administering an effective amount of the first and second population of modified cells to the subject, wherein: the first antigen is different from the second antigen; and the level of T cell response (e.g., cell expansion) in the subject is higher than the level in a subject administered an effective amount of the second population of modified cells but not the first population of modified cells.

The present disclosure also describes a method for treating a subject having digestive cancer, the method comprising: introducing a first vector comprising a polynucleotide encoding a first antigen binding molecule that binds a first antigen into a first population of cells to obtain a first population of modified cells; introducing a second vector comprising a polynucleotide encoding a second antigen binding molecule that binds GCC into a second population of cells to obtain a second population of modified cells; and administering an effective amount of the first and second population of modified cells to the subject, wherein: the first antigen is different from the second antigen.

The present disclosure also describes a method for enhancing treatment of a subject having digestive cancer, the method comprising: introducing a first vector comprising a polynucleotide encoding a first antigen binding molecule that binds a first antigen into a first population of cells to obtain a first population of modified cells; introducing a second vector comprising a polynucleotide encoding a second antigen binding molecule that binds GCC into a second population of cells to obtain a second population of modified cells; and administering an effective amount of the first and second population of modified cells to the subject, wherein: the first antigen is different from the second antigen; and the level of inhibition of tumor growth in the subject by the effective amount of first population of modified cells is higher than the level of inhibition of tumor growth in the subject by the effective amount of the second population of modified cells that is not administered the first population of modified cells.

The cells include macrophages, dendritic cells, or lymphocytes such as T cells or NK cells. In embodiments, the cells are T cells. In embodiments, the first antigen binding molecule binds a cell surface molecule of a WBC. In embodiments, the WBC is a granulocyte, a monocyte, or lymphocyte. In embodiments, the WBC is a B cell. In embodiments, the cell surface molecule of the WBC is CD19, CD22, CD20, BCMA, CD5, CD7, CD2, CD16, CD56, CD30, CD14, CD68, CD11b, CD18, CD169, CD1c, CD33, CD38, CD138, or CD13. In embodiments, the cell surface molecule of the WBC is CD19, CD20, CD22, or BCMA. In embodiments, the cell surface molecule of the WBC is CD19.

In embodiments, the first and second binding molecules are CARs. In embodiments, the CAR comprises an extracellular domain, a transmembrane domain, and an intracellular domain, and the extracellular domain binds a tumor antigen. In embodiments, the intracellular domain comprising a co-stimulatory domain comprises an intracellular domain of a co-stimulatory molecule selected from the group consisting of CD27, CD28, 4-1BB, OX40, CD30, CD40, PD-1, ICOS, lymphocyte function-associated antigen-1 (LFA-1), CD2, CD7, LIGHT, NKG2C, B7-H3, and any combination thereof. In embodiments, the intracellular domain comprises a CD3 zeta signaling domain.

In embodiments, the population of modified cells comprises cells comprising the first binding molecule and cells comprising the second binding molecules. In embodiments, the population of modified cells comprises cells comprising the first binding molecule, cells comprising the second binding molecules, and cells comprising both the first binding molecule and the second binding molecule.

In embodiments, the increase in T cell response is based on the increase in the number of copies of CAR(s) and/or the amount of cytokine released (e.g., IL-6 and IFN-γ. In embodiments, the T cell response comprises cytokine releases, cell expansion, and/or activation levels. In embodiments, the first vector further comprises a polynucleotide encoding IL-6 or IFNγ, or a combination thereof. In embodiments, the first vector further comprises a polynucleotide encoding IL-12. In embodiments, the polynucleotide comprises a polynucleotide encoding NFAT and/or VHL. In embodiments, the population of modified cells comprises cells expressing the first binding molecule and IL-6 or IFNγ, or a combination thereof, cells expressing the second binding molecules, cells expressing the first and second molecules, and/or cells expressing the first binding molecule and IL-12. In embodiments, the population of modified cells comprises cells expressing the second binding molecule and IL-6 or IFNγ, or a combination thereof, cells expressing the second binding molecules, cells expressing the first and second molecules, and/or cells expressing the first binding molecule and IL-12. In embodiments, the population of modified cells comprises cells expressing the second binding molecule and IL-6 or IFNγ, or a combination thereof, cells expressing the second binding molecules, cells expressing the first and second molecules, and/or cells expressing the second binding molecule and IL-12. In embodiments, the population of modified cells comprises cells expressing a dominant negative form of PD-1.

The present disclosure describes nucleic acids encoding at least two different antigen binding domains. In embodiments, there is a first antigen binding domain that binds an antigen on the surface of a WBC, and there is a second antigen binding domain that binds an antigen on a tumor that is different from the antigen on the surface of a WBC. The first antigen binding domain functions to expand the cells that it is introduced into, while the second antigen binding domain functions to inhibit the growth of or kill tumor cells containing GCC upon binding to GCC. In embodiments, a nucleic acid described herein encodes both the first and second antigen binding domains on the same nucleic acid molecule. In embodiments, the two antigen binding domains are encoded by two separate nucleic acid molecules. For example, a first nucleic acid encodes a first antigen binding domain and a second nucleic acid encodes a second antigen binding domain.

In embodiments, the present disclosure describes nucleic acids encoding a first antigen binding domain of a binding molecule and a second antigen binding domain of a binding molecule, wherein the first antigen binding domain binds a cell surface molecule of a WBC, and the second antigen binding domain binds an antigen different from the cell surface molecule of the WBC. In embodiments, the first antigen binding domain binds a cell surface antigen of a B cell or a B cell marker. In embodiments, the second binding domain does not bind a B cell marker. For example, the second antigen binding domain is on a CAR having one of the amino acid sequences of SEQ ID NO: 8.

In embodiments, the first and second antigen binding domains are on two different binding molecules (first and second binding molecules), such as a first CAR and a second CAR. As an example, a first CAR includes an extracellular binding domain that binds a marker on the surface of a B cell, and a second CAR includes an extracellular binding domain that binds a target antigen of a tumor cell. In embodiments, the first CAR and second CAR are encoded by different nucleic acids. In embodiments, the first CAR and second CAR are two different binding molecules but are encoded by a single nucleic acid.

In embodiments, the two different antigen binding domains can be on the same binding molecule, for example, on a bispecific CAR, and encoded by a single nucleic acid. In embodiments, the bispecific CAR can have two different scFv molecules joined together by linkers.

Further, the present disclosure describes compositions including a mixed population of the modified cells described herein. In embodiments, the modified cells include modified lymphocytes, modified dendritic cells, and modified macrophages. In embodiments, the modified lymphocytes are modified T cells or modified NK cells. In embodiments, the modified T cells are CAR T cells.

The present disclosure describes a mixed population of modified cells effective for expanding and/or maintaining the modified cells in a patient. In embodiments, examples of a mixed population of modified cells include the following: (1) a first modified cell expressing an antigen binding domain for expanding and/or maintaining the modified cells and a second modified cell expressing an antigen binding domain for killing a target cell, such as a tumor cell; (2) the modified cells of (1) and a further modified cell expressing at least two different antigen binding domains, a first antigen binding domain for expanding and/or maintaining the modified cells and a second antigen binding domain for killing a target cell (wherein the two different antigen binding domains are expressed on the same cell); (3) a modified cell expressing at least two different antigen binding domains, a first antigen binding domain for expanding and/or maintaining the modified cells and a second antigen binding domain for killing a target cell (wherein the two different antigen binding domains are expressed on the same cell); (4) a modified cell expressing an antigen binding domain for killing a target cell and a modified cell expressing at least two antigen binding domains, a first antigen binding domain for expanding and/or maintaining the modified cells and a second antigen binding domain for killing a target cell (wherein the two different antigen binding domains are expressed on the same modified cell); or (5) a modified cell expressing an antigen binding domain for expanding and/or maintaining the modified cells and a modified cell expressing at least two antigen binding domains, a first antigen binding domain for expanding and/or maintaining the modified cells and a second antigen binding domain for killing a target cell (wherein the two different antigen binding domains are expressed on the same modified cell). In embodiments, the two antigen binding domains are different molecules. In embodiments, the antigen binding domain for expanding the modified cells (the first antigen binding domain) is an antigen binding domain that binds a WBC, such as a B cell, and the antigen binding domain for killing a target cell, such as tumor cell, (the second antigen binding domain) is an antigen binding domain that binds a tumor. In embodiments, the antigen binding domain binding a B cell binds the surface antigen of the B cell, for example, CD19, and the antigen binding domain binding a tumor binds an antigen of a tumor, for example, GCC. In embodiments, the tumor cell is a solid tumor cell.

In embodiments, the mixed population of modified cells may include at least one of the following modified cells: a first modified cell expressing an antigen binding domain for expanding and/or maintaining the modified cells, a second modified cell expressing an antigen binding domain for killing a target cell, such as a tumor cell, and a third modified cell expressing both the antigen binding domain for expanding and/or maintaining the modified cells and the antigen binding domain for killing a target cell. For example, the mixed population of modified cells includes the first and second modified cells, the first and third modified cells, or the second and third modified cells. In embodiments, the first modified cell expresses a CAR binding an antigen of WBC (e.g., CD19); the second modified cell expresses a CAR or TCR binding a solid tumor antigen, and the third modified cell expresses the CAR binding the antigen of WBC and the CAR/TCR binding the solid tumor antigen. It has been reported that persistent antigen exposure can cause T cell exhaustion. Thus, a population of modified cells, including the third modified cell, can exhaust at a higher rate than the mixed population of modified cells. For example, the population of modified cells, including the third modified cell alone, can exhaust at a higher rate than the mixed population of modified cells, including the first and the second modified cells, in the presence of the antigen of WBC. Examples of the solid tumor antigens of TCR comprise TPO, TGM3, TDGF1, TROP2, LY6K, TNFSF13B, HEG1, LY75, HLA-G, CEACAM8, CEACAM6, EPHA2, GPRCSD, PLXDC2, HAVCR1, CLEC12A, CD79B, OR51E2, CDH17, IFITM1, MELTF, DR5, SLC6A3, ITGAM, SLC44A1, RHOC, CD109, ABCG2, ABCA10, ABCG8, 5t4, HHLA2, PRAME, CDH6, ESR1, SLC2A1, GJAS, ALPP, FGD2, PMEL, CYP19A1, MLANA, STEAP1, SSX2, PLAC1, ANKRD30A, CPA2, TTN, ZDHHC23, ARPP21, RBPMS, PAX5, MIA, CIZ1, AMACR, BAP31, IDO1, PGR, RAD51, USP17L2, OLAH, IGF2BP3, STS, IGF2, ACTA1, or CTAG1.

The mixed population of modified cells described herein includes about 1% to 10% modified cells expressing the first antigen binding domain, 50% to 60% modified cells expressing a second antigen binding domain, and about 10% modified cells expressing both the first antigen binding domain and the second antigen binding domain (wherein the first and second antigen binding domains are expressed in a single cell).

The present disclosure also describes methods of culturing cells described herein. The methods described herein include obtaining a cell comprising a first antigen binding domain and/or a second antigen binding domain, wherein the first antigen binding domain binds a cell surface molecule of a WBC, and the second antigen binding domain binds an antigen different from the cell surface molecule of the WBC; and culturing the cell in the presence of an agent derived from a cell surface molecule of the WBC or from an antigen to which the second antigen binding domain binds. In embodiments, the agent is an extracellular domain of a cell surface molecule of a WBC.

The present disclosure also describes methods of culturing a mixed population of cells described herein. The methods described herein include obtaining a mixed population of cells comprising a first antigen binding domain and/or a second antigen binding domain, wherein the first antigen binding domain binds a cell surface molecule of a WBC, and the second antigen binding domain binds an antigen different from the cell surface molecule of the WBC; and culturing the cells in the presence of an agent derived from a cell surface molecule of the WBC or from an antigen to which the second antigen binding domain binds. In embodiments, the agent is an extracellular domain of a cell surface molecule of a WBC.

The present disclosure describes methods for in vitro cell preparation, and wherein the method includes providing cells; introducing one or more nucleic acids described herein encoding a first antigen binding domain and/or a second antigen binding domain into the cells, wherein the first antigen binding domain binds a cell surface molecule of a WBC, and the second antigen binding domain binds an antigen different from the cell surface molecule of the WBC; and culturing the cells in the presence of an agent derived from the cell surface molecule of the WBC or from an antigen to which the second antigen binding domain binds. The methods provide genetically modified cells including a first antigen binding domain, cells including a second binding domain, and cells including both the first and second antigen binding domain. The methods provide cells with single binding domains and cells expressing both antigen binding domains. The methods also provide a mixed population of cells, including a single binding domain and cells expressing both antigen binding domains. Additionally, the methods provide compositions, including a mixed population of cells described herein.

The present disclosure describes using the prepared cell preparation, the mixed population of cells, or the compositions of a mixed population of cells to enhance and maintain the T cell expansion in a subject having cancer in order to be effective in killing the tumorigenic cells in the subject. In embodiments, the method comprises introducing a plurality of nucleic acids described herein into T cells to obtain a mixed population of modified T cells, the plurality of nucleic acids encoding a chimeric antigen receptor (CAR) or TCR binding a solid tumor antigen and/or encoding a CAR binding an antigen of a WBC; and administering an effective amount of a mixed population of modified cells to the subject, wherein examples of a mixed population of modified cells include the following: (1) T cells containing a CAR or TCR binding a solid tumor antigen and T cells containing a CAR binding an antigen of a WBC; (2) the T cells of (1) and further T cells containing both (i) a CAR or TCR binding a solid tumor antigen, and (ii) a CAR binding an antigen of a WBC (both (i) and (ii) are in a single modified T cell); (3) T cells containing both (i) the CAR or TCR binding a solid tumor antigen, and (ii) a CAR binding an antigen of a WBC (both (i) and (ii) are in a single modified T cell); (4) T cells containing a CAR or TCR binding a solid tumor antigen and T cells containing both (i) a CAR or TCR binding a solid tumor antigen and (ii) a CAR binding an antigen of a WBC (both (i) and (ii) are in a single modified T cell); or (5) T cells containing a CAR binding an antigen of a WBC and T cells containing both (i) a CAR or TCR binding a solid tumor antigen and (ii) a CAR binding an antigen of a WBC (both (i) and (ii) are in a single modified T cell). In embodiments, the WBC is a B cell. Additionally, the present disclosure describes methods for introducing and/or enhancing lymphocyte (T cell) response in a subject wherein the response is to a therapeutic agent (e.g., cytokines) or therapy for treating the subject. Embodiments described herein involve a mechanism that expands and/or maintains the lymphocytes and a mechanism that relates to the binding of a CAR to a tumor cell. In embodiments, the first mechanism involves a molecule involved in expanding and/or maintaining the lymphocytes in a subject, and an additional mechanism involves a molecule directed to inhibiting the growth of or the killing of a tumor cell in the subject. In embodiments, the mechanisms involve signal transduction, and molecules or domains of molecules responsible for signal transduction are involved in the mechanisms described herein. For example, the first mechanism includes a CAR binding an antigen associated with blood, such as blood cells and blood plasma, or non-essential tissues, and the additional mechanism includes a CAR or TCR targeting an antigen associated with the tumor cell. Examples of non-essential tissues include the mammary gland, colon, gastric gland, ovary, blood components (such as WBC), and thyroid. In embodiments, the first mechanism involves a first antigen binding domain of a molecule, and the additional mechanism involves a second antigen binding domain of a molecule. In embodiments, the first mechanism and the additional mechanism are performed by a mixed population of modified cells. In embodiments, the mechanism involves a cell expressing an antigen associated with a tumor cell, and the additional mechanism involves a lymphocyte, such as a B cell, expressing a cell surface antigen. In embodiments, the CAR binding a solid tumor antigen is a bispecific CAR. In embodiments, the CAR binding an antigen of WBC is a bispecific CAR.

The methods described herein involve lymphocytes expressing an expansion molecule and a functional molecule. In embodiments, the expansion molecule expands and/or maintains the lymphocytes in a subject, and the function molecule inhibits the growth of or kills a tumor cell in the subject. In embodiments, the expansion molecule and the function molecule are on a single CAR molecule, for example, a bispecific CAR molecule. In embodiments, the expansion molecule and the function molecule are on separate molecules, for example, CAR and TCR or two different CARs. The expansion molecule can include a CAR binding to an antigen associated with blood (e.g., blood cells and blood plasma) or non-essential tissues, and the function molecule can include a CAR or TCR targeting an antigen associated with a tumor cell.

Lymphocyte or T cell response in a subject refers to cell-mediated immunity associated with a helper, killer, regulatory, and other types of T cells. For example, T cell response may include activities such as assisting other WBCs in immunologic processes and identifying and destroying virus-infected cells and tumor cells. T cell response in the subject can be measured via various indicators such as the number of virus-infected cells and/or tumor cells that T cells kill, the amount of cytokines (e.g., IL-6 and IFN-γ) that T cells release in vivo and/or in co-culturing with virus-infected cells and/or tumor cells, indicates a level of proliferation of T cells in the subject, a phenotype change of T cells, for example, changes to memory T cells, and level longevity or lifetime of T cells in the subject.

In embodiments, the method of enhancing T cell response described herein can effectively treat a subject in need thereof, for example, a subject diagnosed with a tumor. The term tumor refers to a mass, which can be a collection of fluid, such as blood, or a solid mass. A tumor can be malignant (cancerous) or benign. Examples of blood cancers include chronic lymphocytic leukemia, acute myeloid leukemia, acute lymphoblastic leukemia, and multiple myeloma.

The methods described herein can be used to treat a subject diagnosed with cancer. Cancer can be a blood cancer or can be a solid tumor, such as a sarcoma or carcinoma. The method of treating includes administering an effective amount of a mixed population of T cells described herein comprising a first antigen binding domain and/or a second antigen binding domain to the subject to provide a T-cell response, wherein the first antigen binding domain binds a cell surface molecule of a WBC, and the second antigen binding domain binds an antigen different from the cell surface molecule of the WBC. In embodiments, enhancing the T cell response in the subject includes selectively enhancing the proliferation of T cells expressing the first antigen binding domain and the second antigen binding domain in vivo.

The methods for enhancing T cell response in a subject include administering to the subject T cells comprising a CAR or a bispecific CAR including two different antigen binding domains and T cells comprising the first CAR and a second CAR, wherein the first CAR and the second CAR, and each includes a different antigen binding domain.

In embodiments, methods for enhancing T cell response in a subject described herein include administering to the subject T cells, including a CAR molecule and a TCR molecule. The CAR molecule targets or binds a surface marker of a white blood cell, and the TCR molecule binds a marker or an antigen of the tumor that is expressed on the surface or inside the tumor cell.

In embodiments, the methods for enhancing T cell response in a subject in need thereof include administering to the subject a mixed population of modified cells or a composition comprising a mixed population of modified cells. Examples of a mixed population of modified T cells include the following: (1) T cells containing a CAR binding an antigen of a WBC and T cells containing a CAR or TCR binding a tumor antigen; (2) the T cells of (1) and further T cells containing both (i) the CAR or TCR binding a tumor antigen, and (ii) a CAR binding an antigen of a WBC (both (i) and (ii) are in a single modified T cell); (3) T cells containing both (i) a CAR or TCR binding a tumor antigen, and (ii) a CAR binding an antigen of a WBC (both (i) and (ii) are in a single modified T cell); (4) T cells containing a CAR or TCR binding a tumor antigen and T cells containing both (i) a CAR or TCR binding a solid tumor antigen and (ii) a CAR binding an antigen of a WBC; or (5) T cells containing a CAR binding an antigen of a WBC and T cells containing both (i) a CAR or TCR binding a solid tumor antigen and (ii) the CAR binding the antigen of a WBC (both (i) and (ii) are in a single modified T cell). In embodiments, the subject is diagnosed with a solid tumor. In embodiments, the tumor antigen is a solid tumor antigen, for example, tMUC1. In embodiments, the WBC is a B cell, and the antigen is a B cell antigen. In embodiments, the B cell antigen is CD19. In embodiments, the tumor antigen is tMUC1, and the antigen of a WBC is CD19.

The present disclosure describes methods of expanding and/or maintaining cells expressing an antigen binding domain in vivo. The method includes administering an effective amount of a mixed population of modified cells or a composition including a mixed population of modified cells described herein to a subject. These methods described herein are useful for expanding T cells, NK cells, macrophages, and/or dendritic cells.

The mixed population of modified T cells described herein includes a first CAR and/or a second CAR or TCR. In embodiments, the first CAR contains a first antigen binding domain, and the second CAR or TCR contains a second antigen binding domain. For example, the first CAR and the second CAR or TCR include an extracellular antigen binding domain, a transmembrane domain, and a cytoplasmic domain. The cytoplasmic domain of the first CAR and second CAR includes a co-stimulatory domain and a CD3 zeta domain for transmitting signals for activation of cellular responses. In embodiments, the first CAR and second CAR or TCR are expressed on different modified T cells. In embodiments, the first CAR and second CAR or TCR are expressed on the same modified T cell.

In embodiments, in the mixed population of modified T cells described herein, the cytoplasmic domain of the first CAR, which contains an antigen binding domain for expanding and/or maintaining modified T cells, includes one or more co-stimulatory domains in the absence of a CD3 zeta domain such that activation or stimulation of the first CAR expands WBCs, such as lymphocytes, without introducing and/or activating the killing function of the modified T cells targeting the WBCs. In embodiments, the lymphocytes are T cells. In embodiments, when the cytoplasmic domain of the first CAR includes one or more co-stimulatory domains in the absence of a CD3 zeta domain, the second CAR includes a CD3 zeta domain.

In embodiments, the first and second antigen binding domains are on the same CAR (the first CAR), for example, a bispecific CAR with an extracellular antigen binding domain, a transmembrane domain, and a cytoplasmic domain. The extracellular antigen binding domain includes at least two scFvs and at least one of the scFvs functions as a first antigen binding domain for binding a cell surface molecule of a WBC. In embodiments, the bispecific CAR is expressed on a modified T cell.

In embodiments, in the mixed population of modified cells described herein, the first CAR, which includes an antigen binding domain for expanding and/or maintaining modified cells, may include a co-stimulatory domain without a signaling domain of CD3 zeta domain, and the CAR (second CAR) may comprise the MUC1 binding domain, a transmembrane domain, a co-stimulatory, and a CD3 zeta domain.

In embodiments, the antigen is a stomach or colon antigen. For example, the colon antigen is Guanylate cyclase 2C (GCC), having SEQ ID NO: 8. As used herein, "a colon antigen" refers to an antigen expressed on or by a colon cell.

Examples of colon cells include goblet cells and enterocytes. Guanylyl cyclase 2C (GCC) is principally expressed in intestinal epithelial cells. GCC is the receptor for diarrheagenic bacterial enterotoxins (STs) and the gut paracrine hormones guanylin and uroguanylin. These ligands regulate water and electrolyte transport in the intestinal and renal epithelia and are ultimately responsible for acute secretory diarrhea. As used herein, "GCC" refers to human Guanylyl cyclase 2C. The term should be construed to include not only human Guanylyl cyclase 2C but also variants, homologs, fragments, and portions thereof to the extent that such variants, homologs, fragments and portions thereof retain the ability of Guanylyl cyclase 2C to bind antibodies or ligands of human Guanylyl cyclase 2C as disclosed herein. In embodiments, the amino acid sequence of at least a portion of GCC comprises SEQ ID NO: 8. In embodiments, the cancer is stomach cancer, and the solid tumor antigen is GCC. The digestive or gastrointestinal (G.I.) system is made up of the esophagus, stomach, small and large intestines, liver, pancreas, and gallbladder. These organs work together to break down the food you eat into nutrients that are absorbed by the bloodstream and carried to all of the cells in your body. This is what gives your body the vital fuel it needs to function. GCC expression in primary tumors of the esophagus is 59%, stomach cancer is 68%, colorectal cancer is 98%, and pancreatic cancer is 64%. Also, 96.5% matched liver metastatic tumor specimens showed GCC staining. Thus, GCC can be used as a solid antigen for treating a subject having digestive system cancer using the treatment described in this Application. As defined herein, digestive system cancer includes cancer associated with the esophagus, stomach, small and large intestines (colorectal cancer), liver, and pancreas. More information about GCC expression associated with digestive system cancer can be found at Danaee H, Kalebic T, Wyant T, Fassan M, Mescoli C, Gao F, et al. (2017) Consistent expression of guanylyl cyclase-C in primary and metastatic gastrointestinal cancers. PLoS ONE 12(12): e0189953. https://doi.org/10.1371/journal.pone.0189953 and Birbe R, Palazzo J P, Walters R, Weinberg D, Schulz S, Waldman S A. Guanylyl cyclase C is a marker of intestinal metaplasia, dysplasia, and adenocarcinoma of the gastrointestinal tract. Hum Pathol. 2005; 36(2): 170-179. doi:10.1016/j.humpath.2004.12.002, which are incorporated by its reference.

In embodiments, the cytoplasmic domain or the transmembrane domain of the second CAR is modified such that the second CAR is capable of activating the modified T cell via cells expressing CD19 without damaging the cells expressing CD19.

Embodiments described herein relate to a bispecific chimeric antigen receptor, comprising: a first antigen binding domain, a second antigen binding domain, a cytoplasmic domain, and transmembrane domain, wherein the first antigen binding domain recognizes a first antigen, and the second antigen binding domain recognizes GCC, the first antigen is different from the second antigen.

In embodiments, the first antigen and the second antigen do not express on the same cell. In embodiments, the first antigen is an antigen of a blood component, and the second antigen is an antigen of a solid tumor.

Blood cells refer to red blood cells (RBCs), white blood cells (WBCs), platelets, or other blood cells. For example, RBCs are blood cells delivering oxygen ($O_2$) to the body tissues via the blood flow through the circulatory system. Platelets are cells that are involved in hemostasis, leading to the formation of blood clots. WBCs are cells of the immune system involved in defending the body against both infectious disease and foreign materials. There are a number of different types and sub-types of WBCs, and each has a different role to play. For example, granulocytes, monocytes, and lymphocytes are 3 major types of a white blood cells. There are three different forms of granulocytes: Neutrophils, Eosinophils, Basophils.

A cell surface molecule of a WBC refers to a molecule expressed on the surface of the WBC. For example, the cell surface molecule of a lymphocyte may include CD19, CD22, CD20, BCMA, CD5, CD7, CD2, CD16, CD56, and CD30. The cell surface molecule of a B cell may include CD19, CD20, CD22, BCMA. The cell surface molecule of a monocyte may include CD14, CD68, CD11b, CD18, CD169, and CD1c. The cell surface molecule of granulocyte may include CD33, CD38, CD138, and CD13.

In embodiments, the present disclosure describes a method of enhancing T cell response in a subject in need thereof or treating a tumor of a subject, the method comprising: administering an effective amount of a mixed population of modified T cells or a composition of a mixed population of modified T cells, described herein, to the subject to provide a T cell response such that the CAR T cell is expanded in the blood of the subject via cells expressing CD19. In embodiments, the method may further comprise infusing B cells into the subject to continue to activate and/or expand the CAR T cells. For example, the B cells of the subject or genetically modified B cells from a healthy donor may be obtained and stored before CAR T cell infusion. In embodiments, the method may further comprise administering a cell expressing CD19 or a polypeptide comprising at least an extracellular domain of CD19 or the antigen that the CAR T cells recognize. For example, the cell expressing CD19 may include cell lines such as K562 and NK92 that are transduced with nucleic acid sequences encoding CD19. In embodiments, the method may further comprise identifying CAR T cells expressing both first and second CAR, as well as administering the identifier CAR T cells to the subject. For example, GCC may be associated as a sorting marker such that CAR T cells expressing MUC1 may be identified timely.

In embodiments, the present disclosure describes a method of in vivo cell expansion and maintenance. In embodiments, the method may include administering an effective amount of a mixed population of modified T cells described herein to the subject in need thereof to provide a T cell response; and administering an effective amount of presenting cells (e.g., T cells) expressing a soluble agent that an extracellular domain of the CAR recognizes. In embodiments, the method may be implemented to enhance T cell response in a subject in need thereof. The method may include administering an effective amount of a mixed population of modified T cells comprising a CAR to the subject to provide a T cell response and administering an effective amount of presenting cells expressing a soluble agent that an extracellular domain of the CAR recognizes to enhance the T cell response in the subject. In embodiments, the presenting cells are T cells, dendritic cells, and/or antigen presenting cells. In embodiments, the enhancing T cell response in the subject may include selectively enhancing the proliferation of T cells comprising the CAR. In embodiments, the method may be used to enhance the treatment of a condition of a subject using modified T cells. The method may include administering a population of cells that express an agent or administering an agent that is formulated as a vaccine. In these instances, the modified T cells include a nucleic acid that encodes a CAR, and an extracellular domain of the CAR recognizes the agent. In embodiments, the method may be implemented to enhance the proliferation of the modified T cells in a subject having a disease. The method may include preparing the modified T cells comprising a CAR; administering an effective amount of the modified T cells to the subject; introducing, into cells, a nucleic acid encoding an agent that an extracellular domain of the CAR recognizes, and administering an effective amount of the cells (introduced with the nucleic acid encoding the agent) to the subject. In embodiments, the T cell expansion may be measured based on an increase in copy number of CAR molecules in genomic DNA of the T cells. In embodiments, the T cell expansion may be measured based on flow cytometry analysis on molecules expressed on the T cells.

Embodiments described herein relate to a mixed population of modified T cells comprising a first CAR and a second CAR or TCR in separate T cells and/or in the same T cells, wherein an antigen binding domain of the first CAR binds an antigen such as CD19, CD33, CD14, and BCMA, and an antigen binding domain of the second CAR binds a tumor-associated MUC. In embodiments, the tumor-associated MUC is MUC1 (for example, tMUC1) or MUC2. Embodiments described herein relate to a composition comprising a mixed population of the modified T cells and to a method of enhancing T cell response in a subject in need thereof or treating a tumor of a subject, the method comprising: administering an effective amount of the mixed population of modified T cells.

In embodiments, the cytoplasmic domain of the CAR molecules described herein comprises a co-stimulatory domain and a CD3 zeta domain. In embodiments, the CAR molecules described herein may include a co-stimulatory domain without a corresponding component of the CD3 zeta domain. In embodiments, the CAR molecules described herein may include a CD3 zeta domain without a co-stimulatory domain.

In embodiments, the modified cell comprises a dominant negative variant of a receptor of programmed death 1 (PD-1), cytotoxic T lymphocyte antigen-4 (CTLA-4), B- and T lymphocyte attenuator (BTLA), T cell immunoglobulin mucin-3 (TIM-3), lymphocyte-activation protein 3 (LAG-3), T cell immunoreceptor with Ig and ITIM domains (TIGIT), leukocyte-associated immunoglobulin-like receptor 1 (LAIRD, natural killer cell receptor 2B4 (2B4), or CD 160. In embodiments, the modified cell further comprises a nucleic acid sequence encoding a suicide gene, and/or the suicide gene comprises an HSV-TK suicide gene system. In embodiments, the isolated T cell comprises a reduced amount of TCR, as compared to the corresponding wide-type T cell.

Dominant-negative mutations have an altered gene product that acts antagonistically to the wild-type allele. These mutations usually result in an altered molecular function (often inactive) and are characterized by a dominant or semi-dominant phenotype. In embodiments, the modified cells described herein comprise the dominant negative (DN) form of the PD-1 receptor. In embodiments, the expression of the DN PD-1 receptor in the modified cells described herein is regulated by an inducible gene expression system. In embodiments, the inducible gene expression system is a lac system, a tetracycline system, or a galactose system.

The present disclosure describes pharmaceutical compositions. The pharmaceutical compositions include one or more of the following: CAR molecules, TCR molecules, modified CAR cells, modified cells comprising CAR or TCR, mix population of modified cells, nucleic acids, and vectors described herein. Pharmaceutical compositions are administered in a manner appropriate to the disease to be treated (or prevented). The quantity and frequency of administration will be determined by such factors as the condition of the patient, and the type and severity of the patient's disease, although appropriate dosages may be determined by clinical trials.

The term "pharmaceutically acceptable" means approved by a regulatory agency of the U.S. Federal or a state government or the EMA (European Medicines Agency) or listed in the U.S. Pharmacopeia (United States Pharmacopeia-33/National Formulary-28 Reissue, published by the United States Pharmacopeia Convention, Inc., Rockville Md., publication date: April 2010) or other generally recognized pharmacopeia for use in animals, and more particularly in humans.

The term "carrier" refers to a diluent, adjuvant {e.g., Freund's adjuvant (complete and incomplete)), excipient, or vehicle with which the therapeutic is administered. Pharmaceutical carriers can be sterile liquids, such as water and oils, including those of petroleum, animal, vegetable, or synthetic origins, such as peanut oil, soybean oil, mineral oil, sesame oil, and the like. Water is a preferred carrier when the pharmaceutical composition is administered intravenously. Saline solutions and aqueous dextrose and glycerol solutions can also be employed as liquid carriers, particularly for injectable solutions.

The present disclosure also describes a pharmaceutical composition comprising the first and the second population of cells described herein. The pharmaceutical composition described herein, comprising a first population of cells comprising a first antigen binding molecule and a second population of cells comprising a second antigen binding domain, are suitable for cancer therapy. For example, the binding of the first antigen binding molecule with an antigen enhances the expansion of the cells suitable for cancer therapy.

The present disclosure also describes a method for enhancing cancer therapy using the cells described herein that are suitable for cancer therapy. The method comprises administering an effective amount of a first composition to the subject having a form of cancer expressing a tumor antigen, the first composition comprising a first population of cells (e.g., T cells) comprising a first antigen binding molecule (e.g., CAR) binding a first antigen; and administering an effective amount of a second composition to the subject, the second composition comprising a population of the cells comprising a second antigen binding molecule. Administration of the first and second compositions can be performed simultaneously or separately, for example, sequentially. More information about the cells suitable for cancer therapy can be found at Eyileten et al., Immune Cells in Cancer Therapy and Drug Delivery, Mediators Inflamm. 2016; 2016: 5230219, which is incorporated herein for reference.

In embodiments, the method comprises administering an effective amount of a population of CAR T cells binding a WBC antigen; and administering an effective amount of a population of CAR T cells binding a solid tumor antigen. In embodiments, the method comprises administering an effective amount of a population of CAR T cells binding a WBC antigen; and administering an effective amount of a population of T cells binding a solid tumor antigen (T cells used in TCR and TIL therapies). In embodiments, the method comprises administering an effective amount of a population of CAR T cells binding a WBC antigen; and administering an effective amount of a population of NK cells or NK cells expressing CAR binding a solid tumor antigen. In embodiments, the method comprises administering an effective amount of a population of CAR T cells binding a WBC antigen; and administering an effective amount of a population of NK cells or NK cells expressing CAR binding a solid tumor antigen. In embodiments, the method comprises administering an effective amount of a population of CAR T cells binding a WBC antigen; and administering an effective amount of a population of DCs or DCs expressing CAR binding a solid tumor antigen. In embodiments, the method comprises administering an effective amount of a population of CAR T cells binding a WBC antigen; and administering an effective amount of a population of macrophages or macrophages expressing CAR binding a solid tumor antigen. In embodiments, the method comprises administering an effective amount of a population of CAR T cells binding a WBC antigen; and administering an effective amount of a population of neutrophils or neutrophils expressing CAR binding a solid tumor antigen. In embodiments, the method comprises administering an effective amount of a population of CAR T cells binding a WBC antigen; and administering an effective amount of a population of lymphocytes binding or targeting a solid tumor antigen. In embodiments, the solid tumor antigen can be located on the cell surface (e.g., GCC), on the extracellular matrix of the tumor microenvironment (e.g., $\alpha v \beta 5$ integrin), and/or inside of tumor cells (e.g., gp100).

When "an immunologically effective amount," "an antitumor effective amount," "a tumor-inhibiting effective amount," or "a therapeutically effective amount" is indicated, the precise amount of the compositions of the present disclosure to be administered can be determined by a physician with consideration of individual differences in age, weight, tumor size, the extent of infection or metastasis, and condition of the patient (subject). It can be stated that a pharmaceutical composition comprising the modified cells described herein may be administered at a dosage of $10^4$ to $10^9$ cells/kg body weight, preferably $10^5$ to $10^6$ cells/kg body weight, including all integer values within those ranges. Modified cell compositions may also be administered multiple times at these dosages. The cells can be administered by using infusion techniques that are commonly known in immunotherapy (see, e.g., Rosenberg et al., New Eng. J. of Med. 319:1676, 1988). The optimal dosage and treatment regime for a particular patient can readily be determined by one skilled in the art of medicine by monitoring the patient for signs of disease and adjusting the treatment accordingly. In embodiments, it may be desired to administer activated T cells to a subject and then subsequently redraw the blood (or have apheresis performed), collect the activated and expanded T cells, and reinfuse the patient with these activated and expanded T cells. This process can be carried out multiple times every few weeks. In embodiments, T cells can be activated from blood draws of from 10 cc to 400 cc. In embodiments, T cells are activated from blood draws of 20 cc, 30 cc, 40 cc, 50 cc, 60 cc, 70 cc, 80 cc, 90 cc, or 100 cc. Not to be bound by theory, using this multiple blood draw/multiple reinfusion protocols may select out certain populations of T cells.

In embodiments, a mixed population of a therapeutically effective amount of modified cells can be administered to the subject in need thereof sequentially or simultaneously. As an example, for a mixed population of two different modified cells, a therapeutically effective amount of the modified cells containing the antigen binding domain for expanding and/or maintaining the modified cells can be administered before, after, or at the same time a therapeutically effective amount of the modified cells containing the antigen binding domain for killing a target cell. As another example of a mixed population of two different modified cells, a therapeutically effective amount of the modified cells containing the antigen binding domain for killing a target cell can be administered before, after, or at the same time a therapeutically effective amount of the modified cells containing both the antigen binding domains of expanding and/or maintaining the modified cells and of killing a target cell (in a single modified cell). As an example, for a mixed population of three different modified cells including (1) modified cells containing an antigen binding domain for expanding and/or maintaining the modified cells, (2) modified cells containing an antigen binding domain for killing a target cell, and (3) modified cells containing both the antigen binding domains of expanding and/or maintaining the modified cells and of killing a target cell (in a single modified cell), a therapeutically effective amount of (1), (2) and (3) can be administered sequentially in any order (1, 2, 3; 2, 3, 1; 3, 1, 2; 1, 3, 2; 2, 1, 3; or 3, 2, 1) or simultaneously (1+2+3 at the same time). Moreover, two of the three modified cells can be combined and administered together, with the third one being administered before or after the combination. For example, the combination of (1) and (2) can be administered before or after (3); or the combination of (1) and (3) can be administered before or after (2); or the combination of (2) and (3) can be administered before or after (1).

The administration of the pharmaceutical compositions described herein may be carried out in any convenient manner, including by aerosol inhalation, injection, ingestion, transfusion, implantation, or transplantation. The compositions described herein may be administered to a patient subcutaneously, intradermally, intratumorally, intranodally, intramedullary, intramuscularly, by intravenous (i. v.) injection, or intraperitoneally. In embodiments, the modified cell compositions described herein are administered to subjects by intradermal or subcutaneous injection. In embodiments, the T cell compositions of the present disclosure are administered by i.v. injection. The compositions of modified cells may be injected directly into a tumor, lymph node, or site of infection. In embodiments, cells activated and expanded using the methods described herein, or other methods known in the art where T cells are expanded to therapeutic levels, are administered to patients in conjunction with (e.g., before, simultaneously, or following) any number of relevant treatment modalities, for example as a combination therapy, including but not limited to treatment with agents for antiviral therapy, cidofovir, and interleukin-2, Cytarabine (also known as ARA-C); or natalizumab treatment for MS patients; or efalizumab treatment for psoriasis patients or other treatments for PML patients. In further embodiments, the T cells described herein can be used in combination with chemotherapy, radiation, immunosuppressive agents, such as cyclosporin, azathioprine, methotrexate, mycophenolate, and FK506, antibodies, or other immunoablative agents such as CAM PATH, anti-CD3 antibodies, or other antibody therapies, cytoxin, fludaribine, cyclosporin, FK506, rapamycin, mycophenolic acid, steroids, FR901228, cytokines, and irradiation. These drugs inhibit either the calcium-dependent phosphatase calcineurin (cyclosporine and FK506) or inhibit the p70S6 kinase that is important for growth factor-induced signaling (rapamycin). (Liu et al., Cell 66:807-815, 1991; Henderson et al., Immun 73:316-321, 1991; Bierer et al., Curr. Opin. Immun 5:763-773, 1993; Isoniemi (supra)). In embodiments, the cell compositions described herein are administered to a subject in conjunction with (e.g., before, simultaneously, or following) bone marrow transplantation, T cell ablative therapy using either chemotherapy agents such as fludarabine, external-beam radiation therapy (XRT), cyclophosphamide, or antibodies such as OKT3 or CAM-PATH. In embodiments, the cell compositions described herein are administered following B-cell ablative therapy. For example, agents that react with CD20, e.g., Rituxan, may be administered to patients. In embodiments, subjects may undergo standard treatment with high dose chemotherapy followed by peripheral blood stem cell transplantation. In embodiments, following the transplant, subjects receive an infusion of the expanded immune cells of the present disclosure. In embodiments, expanded cells are administered before or following surgery. The dosage of the above treatments to be administered to a subject in need thereof will vary with the precise nature of the condition being treated and the recipient of the treatment. The scaling of dosages for human administration can be performed according to art-accepted practices by a physician, depending on various factors. Additional information on the methods of cancer treatment using modified cells is provided in U.S. Pat. No. 8,906,682, incorporated by reference in its entirety.

Embodiments described herein relate to an in vitro method for preparing modified cells. The method may include obtaining a sample of cells from a subject. For example, the sample may include T cells or T cell progenitors. The method may further include transfecting the sample of cells with a DNA encoding at least a CAR and culturing the sample of cells ex vivo in a medium that selectively enhances the proliferation of CAR-expressing T cells. The sample of cells can be a mixed population of modified cells described herein.

In embodiments, the sample is a cryopreserved sample. In embodiments, the sample of cells is from umbilical cord blood or a peripheral blood sample from the subject. In embodiments, the sample of cells is obtained by apheresis or venipuncture. In embodiments, the sample of cells is a subpopulation of T cells.

T cell response in a subject refers to cell-mediated immunity associated with helper, killer, regulatory, and other types of T cells. For example, T cell response may include activities such as assistance to other white blood cells in immunologic processes and identifying and destroying virus-infected cells and tumor cells. T cell response in the subject may be measured via various indicators such as a number of virus-infected cells and/or tumor cells that the T cells kill, a number of cytokines that the T cells release in co-culturing with virus-infected cells and/or tumor cells, a level of proliferation of the T cells in the subject, a phenotype change of the T cells (e.g., changes to memory T cells), and the longevity or the length of the lifetime of the T cells in the subject.

T cell response also includes the release of cytokines. Although cytokine release is often associated with systemic inflammation and complication of the disease, the release of cytokines appears to be also associated with the efficacy of a CAR T cell therapy. The release of cytokines may correlate with expansion and progressive immune activation of adoptively transferred cells, such as in CAR T cell therapy. The present disclosure describes the release of effector cytokines, such as IFN-γ, and pro- and anti-inflammatory cytokines, such as IL-6, in response to a mixed population of modified T cells described herein, especially in response to the presence of the first CAR including an antigen binding domain for expanding cells and a second CAR or TCR including an antigen binding domain for killing a target cell. In embodiments, the present disclosure describes the release of IL-6 and IFN-γ in a subject introduced with the first CAR and second CAR or TCR described herein. In embodiments, the subject is in need of cancer treatment, and the cancer treatment is pancreatic cancer treatment. In embodiments, the present disclosure describes determining the efficacy or monitoring the efficacy of a CAR T cell therapy by measuring the level of cytokine release. In embodiments, the release of cytokines (e.g., IL-6 and/or IFN-γ) in the subject in response to CAR T cell therapy using a mixed population of modified T cells described herein is more than that using T cells comprising the second CAR without the first CAR.

In embodiments, the modified cells described herein may further comprise a dominant negative variant of a receptor of programmed death 1 (PD-1), cytotoxic T lymphocyte antigen-4 (CTLA-4), B- and T lymphocyte attenuator (BTLA), T cell immunoglobulin mucin-3 (TIM-3), lymphocyte-activation protein 3 (LAG-3), T cell immunoreceptor with Ig and ITIM domains (TIGIT), leukocyte-associated immunoglobulin-like receptor 1 (LAIRD, natural killer cell receptor 2B4 (2B4), or CD 160 such that the T cell response induced by the mixed population of modified cells may be enhanced.

In embodiments, the modified cells described herein may further comprise a nucleic acid sequence encoding a suicide gene and/or a suicide gene comprising an HSV-TK suicide gene system such that the fate of the modified cell may be controlled. For example, the T cell can be induced to undergo apoptosis if the therapy imposes risks to the subject, and/or the subject encounters adverse effects, or if the therapy has been completed, a certain required condition has been met, and/or a predetermined time has passed.

The present disclosure describes a composition comprising a mixed population of modified cells described herein. In embodiments, there is the first population of modified cells comprising a first CAR binding a first antigen and a second population of modified cells comprising a second CAR or TCR binding GCC that is different from the first antigen. The first antigen can be an antigen of a WBC, such as a B cell, while the second antigen is a tumor antigen. The present disclosure describes a method of enhancing expansion and maintenance of the second population of modified cells for killing tumor cells. The method includes administering an effective amount of the composition comprising a mixed population of modified cells to a subject having a form of cancer associated with the tumor antigen, which the second CAR recognizes and binds. Embodiments also include a method of enhancing T cell response in a subject in need thereof or treating a subject having cancer. The method includes administering an effective amount of the composition described herein to the subject having a form of cancer associated with the tumor antigen, which the second CAR recognizes and binds. Further, the embodiments include a method of enhancing expansion and/or maintenance of modified cells in a subject, the method comprising: contacting T cells with a first vector comprising a first nucleic acid sequence encoding the first CAR and a second vector comprising a second nucleic acid sequence encoding the second CAR to obtain the composition described herein of a mixed population of modified cells; and administering an effective amount of the composition to the subject having a form of cancer associated with the tumor antigen which the second CAR recognizes and binds. Additional embodiments include a method of enhancing T cell response in a subject in need thereof or treating a subject having cancer, the method comprising: contacting T cells with a first vector comprising a first nucleic acid sequence encoding the first CAR and a second vector comprising a second nucleic acid sequence encoding the second CAR to obtain the composition described herein of a mixed population of modified cells; and administering an effective amount of the composition to the subject having a form of cancer associated with the tumor antigen, which the second CAR recognizes and binds. Embodiments include a method of enhancing expansion and maintenance of the modified cells in a subject, the method comprising: administering an effective amount of the composition described herein of a mixed population of modified cells.

In embodiments, at least the first population of modified cells are derived from a healthy donor. For example, the modified cells have a reduced expression of the endogenous TRAC gene. In these instances, the first population of modified cells may be generated in a large amount and used to infuse multiple subjects. Because the first population of modified cells is derived from a healthy donor, these cells may be removed by the immune system of a subject having the caner who is infused with the mixed cells. In embodiments, the mixed cells comprise the first population modified cells derived from the healthy donor and the second population of modified cells derived from the subject having cancer such that the first population of modified cells will be gradually removed from the subject after eliciting or causing cell expansion of the second population of modified cells in the subject, while the second population of the modified cell may continue to function and/or inhibit tumor cells since the second population of the modified cell are from the subject.

In embodiments, the composition comprises at least the first population and second population of modified cells. The first population of modified cells comprises a polynucleotide encoding the first CAR (e.g., CD19, CD22, and BCMA CARs) and a polynucleotide encoding one or more cytokines (e.g., IL-6, IL12, and IFNγ). The second population of modified cells comprises a polynucleotide encoding the second CAR binding a solid tumor antigen. For example, the composition comprises the first population, the second, the third, and the fourth populations of modified cells. The first population of modified cells comprises a polynucleotide encoding CAR binding a WBC antigen and IL-6. The second population of modified cells comprises a polynucleotide encoding CAR binding a solid tumor antigen. The third population of modified cells comprises a polynucleotide encoding CAR binding a WBC antigen and IL-12. The fourth population of modified cells comprises a polynucleotide encoding CAR binding a WBC antigen and IFNγ. These WBC antigens can be the same (e.g., CD19) or different (e.g., CD19 and BCMA). The first, the third, and the fourth populations of modified cells can be mixed based on a first predetermined ratio to obtain a group of modified cells, which can be then mixed based on a second predetermined ratio with the second population of modified cells to obtain a composition comprising a mixed population of modified cells. The predetermined ratio is used to control the amount of expression of one or more cytokines in the subject to achieve controllable, lasting, and efficient cytokine effects in the subject while having less cytotoxicity. In embodiments, the first predetermined ratio the first, the third, and the fourth populations of modified cells is set such that there are more modified cells comprising the polynucleotide encoding IFNγ than the modified cells comprising the polynucleotide encoding IL-12 or IL-6. For example, the first predetermined ratio is 1:1:10. In embodiments, the second predetermined ratio is determined such that there are more of the modified cells comprising the polynucleotide encoding the second CAR (e.g., the second population of modified cells) than the modified cells comprising the polynucleotide encoding the first CAR (e.g., the first, the second, and/or the third populations of modified cells). For example, the second predetermined ratio of the first population of modified cells and the second population of modified cells is less than 1:1 but more than 1:10,000. In embodiments, the second predetermined ratio is 1:1, 1:10, 1:100, 1:1000, and 1:10⁴, as well as individual numbers within that range, for example, 1:10, 1:100, or 1:1000. In embodiments, the second predetermined ratio is between 1:10 and 1:1000. In embodiments, the second predetermined ratio is between 1:10 and 1:100. In embodiments, the second predetermined ratio is between 1:1 and 1:100. In embodiments, the cells (e.g., NK cells, T cells, B cells, myeloid-derived cells, etc.) are obtained from a subject or a healthy donor and divided into at least two groups. These groups of cells may be transferred with two or more vectors, respectively. These cells can be further modified if obtained from a healthy donor. In embodiments, the second population of modified cells does not express one or more cytokines.

In embodiments, a polynucleotide encoding the first CAR is present in the modified cell in a recombinant DNA construct, in an mRNA, or in a viral vector. In embodiments, the polynucleotide is an mRNA, which is not integrated into the genome of the modified cell, such that the modified cell expresses the first CAR (e.g., CD19 CAR) for a finite period of time.

In embodiments, the mixed population of modified cells further includes a third population of modified cells expressing the third CAR and/or the fourth population of modified cells expressing a fourth CAR such that immune responses caused by the various population of modified cells can be coupled to boost CAR T treatment. In embodiments, CARs may be replaced by TCRs or a combination of CAR and TCR.

In embodiments, the mixed population of modified cells comprises a population of modified cells comprising at least two of a CAR binding a solid tumor antigen, a CAR binding a WBC antigen, a polynucleotide encoding IL-6, a polynucleotide encoding IFNγ, and a polynucleotide encoding IL-12. In these instances, the expression and/or activities of proteins encoded by these polynucleotides may be regulated by an NFAT and/or a HIF VHL binding domain.

Embodiments relate to a method of enhancing CAR T therapy by implementing multiple infusions of CAR T cells timely. The method includes obtaining PBMC from a subject or a healthy donor, preparing CAR T cells using the obtained PBMC, culturing the CAR T cells, for example, for a predetermined amount of time, administering a portion of the cultured CAR T cells to the subject, observing and/or measuring the CART cells in the blood of the subject, administering a second portion of the cultured CAR T cells when the level of the CAR T cells in the blood reaches a predetermined value or when the CAR T cells home to an organ (e.g., lymph node). For example, the first infused CAR T cells can be selectively activated and expanded in the organ and cause an immune response by the subject. Thus, infusion of the second portion of CAR T cells can be coupled with the immune response to enhance the activation and/or expansion of the second population of CAR T cells, thus enhancing the CAR T therapy.

The present disclosure describes a composition including a population of modified cells, including a first population of modified cells that comprises a first CAR without a second CAR and/or the second population of modified cells that comprise a second CAR without a first CAR. The present disclosure also describes a composition including a population of modified cells comprising the first CAR and second CAR (in a single modified cell). In embodiments, the composition includes a first and a second population of modified cells and a third population of modified cells comprising one or more nucleic acid sequences encoding the first CAR and the second CAR in the same modified cell. In embodiments, the composition comprises a second population of modified cells, in the absence of a first population of genetically modified cells, and a third population of modified cells comprising one or more nucleic acid sequences encoding the first CAR and the second CAR in the same modified cells.

In embodiments, the first population of modified cells comprises a polynucleotide encoding IL6 and/or IFNγ, and the second population of modified cells comprises a nucleic acid comprising a polynucleotide encoding IL-12 flanked by a polynucleotide encoding an NFAT promoter and a HIF VHL binding domain.

"NFAT promoter" refers to one or more NFAT responsive elements linked to a minimal promoter of any gene expressed by T-cells. In embodiments, the minimal promoter of a gene expressed by T-cells is a minimal human IL-2 promoter. The NFAT responsive elements may comprise, e.g., NFAT1, NFAT2, NFAT3, and/or NFAT4 responsive elements. The NFAT promoter (or a functional portion or functional variant thereof) may comprise any number of binding motifs, e.g., at least two, at least three, at least four, at least five, or at least six, at least seven, at least eight, at least nine, at least ten, at least eleven, or up to twelve binding motifs. In embodiments, the NFAT promoter comprises six NFAT binding motifs. In an especially preferred embodiment, the NFAT promoter nucleotide sequence comprises or consists of SEQ ID NO: 19 or a functional portion or functional variant thereof.

The NFAT promoter (or a functional portion or functional variant thereof) is operatively associated with the nucleotide sequence encoding IL-12 (or a functional portion or functional variant thereof). "Operatively associated with" means that the nucleotide sequence encoding IL-12 (or a functional portion or functional variant thereof) is transcribed into IL-12 mRNA when the NFAT protein binds to the NFAT promoter sequence (or a functional portion or functional variant thereof). Without being bound to a particular theory, it is believed that NFAT is regulated by a calcium signaling pathway. In particular, it is believed that TCR stimulation (by, e.g., an antigen) and/or stimulation of the calcium signaling pathway of the cell (by, e.g., PMA/lonomycin) increases intracellular calcium concentration and activates calcium channels. It is believed that the NFAT protein is then dephosporylated by calmoduin and translocates to the nucleus, where it binds with the NFAT promoter sequence (or a functional portion or functional variant thereof) and activates downstream gene expression. By providing an NFAT promoter (or a functional portion or functional variant thereof) that is operatively associated with the nucleotide sequence encoding IL-12 (or a functional portion or functional variant thereof), the nucleic acids of the invention advantageously make it possible to express IL-12 (or a functional portion or functional variant thereof) only when the host cell including the nucleic acid is stimulated by, e.g., PMA/lonomycin and/or an antigen. More information can be found at U.S. Pat. No. 8,556,882, which is incorporated by the reference.

Embodiments relate to a method of using or the use of polynucleotide encoding the antigen binding molecule and/or therapeutic agent(s) to enhance the expansion of the modified cells or to enhance the T cell response in a subject. The method or use includes: providing a viral particle (e.g., AAV, lentivirus or their variants) comprising a vector genome, the vector genome comprising the polynucleotide, wherein the polynucleotide is operably linked to an expression control element conferring transcription of the polynucleotide, and administering an amount of the viral particle to the subject such that the polynucleotide is expressed in the subject. In embodiments, the AAV preparation may include AAV vector particles, empty capsids, and host cell impurities, thereby providing an AAV product substantially free of AAV empty capsids. More information on the administration and preparation of the viral particle may be found at the U.S. Pat. No. 9,840,719 and Milani et al., Sci. Transl. Med. 11, eaav7325 (2019) 22 May 2019, which are incorporated herein by reference.

In embodiments, the polynucleotide may integrate into the genome of the modified cell, and the progeny of the modified cell will also express the polynucleotide, resulting in a stably transfected modified cell. In embodiments, the modified cell expresses the polynucleotide encoding the CAR, but the polynucleotide does not integrate into the genome of the modified cell such that the modified cell expresses the transiently transfected polynucleotide for a finite period of time (e.g., several days), after which the polynucleotide is lost through cell division or other factors. For example, the polynucleotide is present in the modified cell in a recombinant DNA construct, in an mRNA, or in a viral vector, and/or the polynucleotide is an mRNA, which is not integrated into the genome of the modified cell.

In embodiments, the first population of cells comprises the first CAR and the second CAR, and the second population of cells comprises the first CAR but does not comprise the second CAR. In embodiments, the first population of cells comprises the first CAR and the second CAR, and the second population of cells comprises the first CAR and the second CAR. In embodiments, the first population of cells comprises the first CAR but does not comprise the second CAR; the second population of cells comprises the first CAR and the second CAR. In embodiments, the first population of cells comprises the first CAR but does not contain the second CAR, and the second population of cells comprises the second CAR but does comprise the first CAR. In embodiments, the first population of cells comprises the second CAR but does not comprise the first CAR, and the second population of cells comprises the first CAR and the second CAR. In embodiments, the first population of cells comprises the first CAR but does not comprise the second CAR; the second population comprises a second CAR but does not comprise the first CAR, and a third population comprises the first CAR and the second CAR. As described herein, the first CAR includes an antigen binding domain for expanding and/or maintaining the modified cells, and the second CAR includes an antigen binding domain for killing target cells, such as tumors.

In embodiments, the antigen binding domain binds an antigen that is or that comprises a cell surface molecule of a white blood cell (WBC), a tumor antigen, or a solid tumor antigen. In embodiments, the WBCs are T cells, NK cells, or dendritic cells.

In embodiments, the WBC is a granulocyte, a monocyte, or lymphocyte. In embodiments, the WBC is a B cell. In embodiments, the cell surface molecule or antigen of the B cell is CD19, CD22, CD20, BCMA, CD5, CD7, CD2, CD16, CD56, CD30, CD14, CD68, CD11 b, CD18, CD169, CD1c, CD33, CD38, CD138, or CD13. In embodiments, the cell surface molecule or antigen of the B cell is CD19, CD20, CD22, or BCMA. In embodiments, the cell surface molecule or antigen of the B cell is CD19.

The present disclosure describes a composition for treating a solid tumor. The composition comprises first and second populations of modified cells. The first population of modified cells is engineered to express a first CAR (e.g., CD19, CD22, BCMA CARs). The second population of modified cells is engineered to express a second CAR (e.g., GCC, TSHR, PAP, and tMUC1). In embodiments, the first CAR binds a WBC antigen. In embodiments, the second CAR binds a solid tumor antigen. In embodiments, the first population of modified cells does not comprise the second CAR, and/or the second population of modified cells does not comprise the first CAR. The first population and the second population of modified cells can be mixed to obtain the mixed population of modified cells, which are infused in the subject. In embodiments, the first population and the second population of modified cells can be mixed based on a fifth predetermined ratio such that there are no more of the first population of modified cells than the second population of modified cells. For example, the fifth predetermined ratio of the first population and the second population of modified cells is less than 1:1 but more than 1:10,000. In embodiments, after infused to the subject, the first population of modified cells binds WBC (e.g., B cells) of the subject, kill the B cells, and cause one or more immune reactions of the Subject. In embodiments, the first population of modified cells may cause expansion of the second population of modified cells and may not directly bind and/or inhibit solid tumor cells, which may be later inhibited by the expanded second population of modified cells. In embodiments, the value of the fifth predetermined ratio may be less than 1:1 to reduce the cost of manufacture of the first population of modified cells, given that the first population of modified cells may not directly bind and/or inhibit solid tumor cells. Also, less amount of the first population of modified cells would take a longer time for the first population of modified cells to kill WBCs (e.g., B cells) and kill fewer WBCs during the therapy. Longer time for cells to kill WBCs may achieve better expansion of the second population of modified cells. Killing fewer WBCs during the therapy may cause less damage to the subject's immune systems and/or allow the immune system to recovery faster. Meanwhile, there should be a certain amount of the first population of modified cells to initiate and/or cause the expansion of the second population of modified cells in the subject. For example, the fifth predetermined ratio is 1:1, 1:10, 1:100, 1:1000, and 1:10$^4$, as well as individual numbers within that range, preferably 1:2, 1:3, 1:4, 1:5, 1:6, 1:7, 1:8, 1:9, 1:10, 1:100, or 1:1000. In embodiments, the fifth predetermined ratio is less than 1:1 and more than 1:100, as well as individual numbers within that range. In embodiments, the fifth predetermined ratio is less than 1:1 and more than 1:20, as well as individual numbers within that range. In embodiments, the fifth predetermined ratio is less than 1:1 and more than 1:17, as well as individual numbers within that range. In embodiments, the mixed cells infused in the subject may further comprise a third population of modified cells that are engineered to express the first CAR and the second CAR. In embodiments, for a reason similar to the fifth predetermined ratio, there is a sixth predetermined ratio of the third population of modified cells and the second population of modified cells is 1:1, 1:10, 1:100, 1:1000, and 1:10$^4$, as well as individual numbers within that range, preferably 1:2, 1:3, 1:4, 1:5, 1:6, 1:7, 1:8, 1:9, 1:10, 1:100, or 1:1000. In embodiments, the sixth predetermined ratio is less than 1:1 and more than 1:100, as well as individual numbers within that range. In embodiments, the composition may be used in the Innovative Cellular Therapeutics' CoupledCAR® system. More information on the CoupledCAR® system can be found at are provided in Innovative Cellular Therapeutics' PCT Patent Applications Nos: PCT/CN2016/075061, PCT/CN2018/08891, and PCT/US19/13068, and PCT/US20/13099, which are incorporated as a reference herein.

The present disclosure describes a method for generating a population of mixed cells, which may be used for treating a solid tumor. The method comprises contacting a population of cells with a first vector and a second vector to introducing the first vector and/or the second vector into the population of cells and to obtain the population of modified cells, which are then administered to a subject having cancer. The population of modified cells comprises at least the first and second populations of modified cells. The first population of modified cells is engineered to express a first CAR (e.g., CD19, CD22, BCMA CARs). The second population of modified cells is engineered to express a second CAR (e.g., GCC, TSHR, PAP, and tMUC1). In embodiments, the first CAR binds a WBC antigen. In embodiments, the second CAR binds a solid tumor antigen. In embodiments, the first population of modified cells does not comprise the second CAR, and/or the second population of modified cells does not comprise the first CAR. The first population and the second population of modified cells can be mixed to obtain the mixed population of modified cells, which are infused in the subject. In embodiments, the first population and the second population of modified cells can be mixed based on a fifth predetermined ratio such that there are no more of the first population of modified cells than the second population of modified cells. In embodiments, the population of modified cells may further comprise a third population of modified cells that are engineered to express the first CAR and the second CAR. In embodiments, multiplicity of infection (MOI) refers to the ratio of agents/vectors (e.g., phage or, more generally, virus, bacteria) to infection targets (e.g., cell). In embodiments, the population of cells is contacted with the first vector and the second vector at different MOIs. For example, the population of cells is contacted at a first predetermined MOI and contacted with the second vector at a second predetermined MOI. In embodiments, the first and second predetermined MOIs are designed to generate more or the same amount of the second population of modified cells than that of the first population of modified cells. For example, the ratio of the first predetermined MOI and the second predetermined MOI is 1:1, 1:10, 1:100, 1:1000, and 1:10$^4$, as well as individual numbers within that range, preferably 1:2, 1:3, 1:4, 1:5, 1:6, 1:7, 1:8, 1:9, 1:10, 1:100, or 1:1000. In embodiments, the ratio of the first predetermined MOI and the second predetermined MOI is less than 1:1 but more than 1:100, as well as individual numbers within that range. In embodiments, the ratio of the first predetermined MOI and the second predetermined MOI is less than 1:1 but more than 1:20, as well as individual numbers within that range. In embodiments, the ratio of the first predetermined MOI and the second predetermined MOI is less than 1:1 but more than 1:17, as well as individual numbers within that range.

Embodiments relate to a method of enhancing the expansion of a population of cells targeting a solid tumor and/or thereby enhancing treatment of the population of cells on the solid tumor, the method comprising administering an effective amount of a composition comprising the population of cells targeting the solid tumor and a population of cells targeting a WBC antigen. Embodiments relate to a method of generating a population of mixed cells, the method comprising: contacting a population of cells with a first vector at a first multiplicity of infection (MOI) and contacting the population of cells with a second vector at a second MOI to obtain a population of mixed cells comprising a population of cells targeting the solid tumor and a population of cells targeting a WBC antigen.

In embodiments, the population of cells is contacted with the first vector and the second vector simultaneously or sequentially. In embodiments, a ratio of the first MOI and the second MOI is determined such that there are more of the population of cells targeting the solid tumor than the population of cells targeting the WBC antigen in the mixed cells. In embodiments, a ratio of the first MOI and the second MOI is 1:1, 1:10, 1:100, 1:1000, and 1:104, as well as individual numbers within that range, preferably excluding 1.1 and 1:104. In embodiments, a ratio of the first MOI and the second MOI is 1:2, 1:3, 1:4, 1:5, 1:6, 1:7, 1:8, 1:9, 1:10, 1:100, or 1:1000, as well as individual numbers within that range. In embodiments, a ratio of the first MOI and the second MOI is less than 1:1 but more than 1:100, as well as individual numbers within that range. In embodiments, a ratio of the first population of cells and the second population of cells is 1:1, 1:10, 1:100, 1:1000, and 1:104, as well as individual numbers within that range. In embodiments, is 1:2, 1:3, 1:4, 1:5, 1:6, 1:7, 1:8, 1:9, 1:10, 1:100, or 1:1000, as well as individual numbers within that range. In embodiments, the ratio is less than 1:1 and more than 1:100, as well as individual numbers within that range.

Embodiments relate to a composition comprising the mixed cells generated using the methods above. Embodiments relate to a population of modified cells comprising the mixed cells generated using the methods above. Embodiments relate to a method of enhancing T cell response in a subject or treating a subject having cancer, the method comprising administering an effective amount of the composition above to the subject having a form of cancer associated with or expressing the tumor antigen.

In embodiments, the modified cells are introduced with a nucleic acid sequence encoding the one or more molecules and/or the binding molecule, which is present in the modified cell in a recombinant DNA construct, in an mRNA, or in a viral vector. In embodiments, the nucleic acid sequence is an mRNA, which is not integrated into the genome of the modified cell. In embodiments, the nucleic acid sequence is associated with an oxygen-sensitive polypeptide domain. In embodiments, the oxygen-sensitive polypeptide domain comprises HIF VHL binding domain. In embodiments, the nucleic acid sequence is regulated by a promoter comprising a binding site for a transcription modulator that modulates the expression and/or secretion of the therapeutic agent in the cell. In embodiments, the transcription modulator is or includes Hif1a, NFAT, FOXP3, and/or NFkB.

In embodiments, the modified cells comprise one or more molecules. In embodiments, the one or more molecules comprise at least one of a receptor of G-CSF or GM-CSF, or a combination thereof or comprise at least one of G-CSF or GM-CSF, or a combination thereof. In embodiments, the one or more molecules comprise at least one of IL-33, IL-1β, TNFα, MALP-2, IL1, and IL17.

In embodiments, there is more of the population of cells targeting the solid tumor than the population of cells targeting the WBC antigen.

In embodiments, the modified cells comprise the antigen binding molecule, the antigen binding molecule is CAR, which comprises an antigen-binding domain, a transmembrane domain, and an intracellular signaling domain. In embodiments, the antigen-binding domain binds to a tumor antigen is selected from a group consisting of: TSHR, CD19, CD123, CD22, CD30, CD171, CS-1, CLL-1, CD33, EGFRvIII, GD2, GD3, BCMA, Tn Ag, PSMA, ROR1, FLT3, FAP, TAG72, CD38, CD44v6, CEA, EPCAM, B7H3, KIT, IL-13Ra2, Mesothelin, IL-11Ra, PSCA, PRSS21, VEGFR2, LewisY, CD24, PDGFR-beta, SSEA-4, CD20, Folate receptor alpha, ERBB2 (Her2/neu), MUC1, EGFR, NCAM, Prostase, PAP, ELF2M, Ephrin B2, IGF-I receptor, CAIX, LMP2, gp100, bcr-abl, tyrosinase, EphA2, Fucosyl GM1, sLe, GM3, TGS5, HMWMAA, o-acetyl-GD2, Folate receptor beta, TEM1/CD248, TEM7R, CLDN6, GPRC5D, CXORF61, CD97, CD179a, ALK, Polysialic acid, PLAC1, GloboH, NY-BR-1, UPK2, HAVCR1, ADRB3, PANX3, GPR20, LY6K, OR51E2, TARP, WT1, NY-ESO-1, LAGE-1a, MAGE-A1, legumain, HPV E6, E7, MAGE A1, ETV6-AML, sperm protein 17, XAGE1, Tie 2, MAD-CT-1, MAD-CT-2, Fos-related antigen 1, p53, p53 mutant, prostein, survivin and telomerase, PCTA-1/Galectin 8, MelanA/MART1, Ras mutant, hTERT, sarcoma translocation breakpoints, ML-IAP, ERG (TMPRSS2 ETS fusion gene), NA17, PAX3, Androgen receptor, Cyclin B1, MYCN, RhoC, TRP-2, CYP1B1, BORIS, SART3, PAX5, OY-TES1, LCK, AKAP-4, SSX2, RAGE-1, human telomerase reverse transcriptase, RU1, RU2, intestinal carboxyl esterase, mut hsp70-2, CD79a, CD79b, CD72, LAIR1, FCAR, LILRA2, CD300LF, CLEC12A, BST2, EMR2, LY75, GPC3, FCRLS, and IGLL1.

In embodiments, the intracellular signaling domain comprises a co-stimulatory signaling domain, or a primary signaling domain and a co-stimulatory signaling domain, wherein the co-stimulatory signaling domain comprises a functional signaling domain of a protein selected from the group consisting of CD27, CD28, 4-1BB (CD137), OX40, CD30, CD40, PD-1, ICOS, lymphocyte function-associated antigen-1 (LFA-1), CD2, CD7, LIGHT, NKG2C, B7-H3, a ligand that specifically binds with CD83, CD5, ICAM-1, GITR, BAFFR, HVEM (LIGHTR), SLAMF7, NKp80 (KLRF1), CD160, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, NKp44, NKp30, NKp46, and NKG2D In embodiments, the modified cells comprise the antigen binding molecule, the antigen binding molecule is a modified TCR. In embodiments, the TCR is derived from spontaneously occurring tumor-specific T cells in patients. In embodiments, the TCR binds to a tumor antigen. In embodiments, the tumor antigen comprises CEA, gp100, MART-1, p53, MAGE-A3, or NY-ESO-1. In embodiments, the TCR comprises TCRγ and TCRδ Chains or TCRα and TCRβ chains, or a combination thereof.

In embodiments, the cells are an immune cell (e.g., a population of immune effector cells). For example, the immune cell is a T cell or an NK cell. In embodiments, the immune effector cell is a T cell. In embodiments, the T cell is a CD4+ T cell, a CD8+ T cell, or a combination thereof. In embodiments, the cells are human cells.

In embodiments, at least a portion of the modified cells comprises a nucleic acid sequence encoding a binding molecule and a dominant negative form of an inhibitory immune checkpoint molecule or a receptor thereof. In embodiments, the inhibitory immune checkpoint molecule is selected from the group consisting of programmed death 1 (PD-1), cytotoxic T lymphocyte antigen-4 (CTLA-4), B- and T lymphocyte attenuator (BTLA), T cell immunoglobulin mucin-3 (TIM-3), lymphocyte-activation protein 3 (LAG-3), T cell immunoreceptor with Ig and ITIM domains (TIGIT), leukocyte-associated immunoglobulin-like receptor 1 (LAIRD, natural killer cell receptor 2B4 (2B4), and CD 160. In embodiments, the inhibitory immune checkpoint molecule is modified PD-1. In embodiments, the modified PD-1 lacks a functional PD-1 intracellular domain for PD-1 signal transduction, interferes with a pathway between PD-1 of a human T cell of the human cells and PD-L1 of a certain cell, comprises or is a PD-1 extracellular domain or a PD-1 transmembrane domain, or a combination thereof, or a modified PD-1 intracellular domain comprising a substitution or deletion as compared to a wild-type PD-1 intracellular domain, or comprises or is a soluble receptor comprising a PD-1 extracellular domain that binds to PD-L1 of a certain cell.

In embodiments, the modified cells are engineered to express and secrete a therapeutic agent such as a cytokine. In embodiments, the therapeutic agent that is or comprises IL-6 or IFN-γ, or a combination thereof. In embodiments, the therapeutic agent that is or comprises IL-15 or IL-12, or a combination thereof. In embodiments, at least a portion of the modified cells comprises a small protein, or the therapeutic agent is or comprises a recombinant or native cytokine. In embodiments, the small protein is or comprises IL-12, IL-6, or IFN-γ.

In embodiments, the modified cells are derived from a healthy donor or the subject having cancer. In embodiments, the modified cells have a reduced expression of the endogenous TRAC gene.

In embodiments, the first population of cells comprises a first CAR binding the WBC antigen, and the second population of cells comprises a second CAR binding the solid tumor antigen. In embodiments, the first vector comprises a polynucleotide encoding a first CAR binding the WBC, and the second vector comprises a polynucleotide encoding a second CAR binding the solid tumor antigen. In embodiments, the WBC antigen is CD19, CD22, CD20, BCMA, CD5, CD7, CD2, CD16, CD56, CD30, CD14, CD68, CD11b, CD18, CD169, CD1c, CD33, CD38, CD138, or CD13. In embodiments, the WBC antigen is CD19, CD20, CD22, or BCMA. In embodiments, the solid tumor antigen is tMUC 1, PRLR, CLCA1, MUC12, GUCY2C, GPR35, CR1L, MUC 17, TMPRSS11B, MUC21, TMPRSS11E, CD207, SLC30A8, CFC1, SLC12A3, SSTR1, GPR27, FZD10, TSHR, SIGLEC15, SLC6A3, KISS1R, CLDN18.2, QRFPR, GPR119, CLDN6, UPK2, ADAM12, SLC45A3, ACPP, MUC21, MUC16, MS4A12, ALPP, CEA, EphA2, FAP, GPC3, IL13-Ra2, Mesothelin, PSMA, ROR1, VEGFR-II, GD2, FR-α, ErbB2, EpCAM, EGFRvIII, B7-H3, or EGFR. In embodiments, the solid tumor antigen is a tumor-associated MUC1, ACPP, TSHR, GUCY2C, UPK2, CLDN18.2, PSMA, DPEP3, CXCR5, B7-H3, MUC16, SIGLEC-15, CLDN6, Muc17, PRLR, and FZD10. In embodiments, the population of cells, the mixed cells, or the composition further comprise a third population of modified cells that are engineered to express the first CAR and the second CAR. In embodiments, a ratio of the third population of modified cells and the second population of modified cells is 1:1, 1:10, 1:100, 1:1000, and 1:104, as well as individual numbers within that range, preferably excluding 1.1 and 1:104. In embodiments, a ratio of the third population of cells and the second population of modified cells is 1:2, 1:3, 1:4, 1:5, 1:6, 1:7, 1:8, 1:9, 1:10, 1:100, or 1:1000, as well as individual numbers within that range. In embodiments, a ratio of the third population of modified cells and the second population of modified cells is less than 1:1 and more than:1:10, 1:17, 1:20, or 1:100, as well as individual numbers within that range.

In embodiments, the population of cells further comprises a nucleic acid sequence encoding hTERT, SV40LT, or a combination thereof. In embodiments, the population of cells is T cells that are more proliferable than T cells without nucleic acid. In embodiments, the proliferable T cell retains functions of normal T cells/CAR T cells, such as cell therapy functions. In embodiments, the T cell comprises a CAR and is cultured in the presence of an agent that is recognized by the extracellular domain of the CAR, thereby producing a modified CAR cell. In embodiments, integration of the nucleic acid sequence encoding hTERT, the nucleic acid encoding SV40LT, or a combination thereof includes genomic integration of the nucleic acid sequence encoding hTERT, a nucleic acid encoding SV40LT, or a combination thereof and constitutive expression of hTERT, SV40LT, or a combination thereof. In embodiments, expression of hTERT, SV40LT, or a combination thereof, is regulated by an inducible expression system such as a rtTA-TRE system. In embodiments, the modified T cell comprises a nucleic acid sequence encoding a suicide gene such as an HSV-TK system. In embodiments, the cell has a reduced graft-versus-host disease (GVHD) response in a bioincompatible human recipient as compared to the GVHD response of the primary human T cell. In embodiments, the cell has reduced expression of endogenous TRAC gene.

Embodiments relate to a pharmaceutical composition comprising a population of modified cells generated by the methods above and a population of additional modified cells, wherein the modified cells bind a first antigen, and the additional modified cells bind a second antigen, which is different from the first antigen. Embodiments relate to a method of eliciting or enhancing T cell response, treating a subject in need thereof or enhancing cancer treatment thereof, the method comprising administering an effective amount of the pharmaceutical composition above. Embodiments relate to a composition comprising a first population of cells comprising a first CAR binding a first antigen, and a second population of cells comprising a second CAR binding a second antigen, wherein the second antigen is a tumor antigen and is different from the first antigen. Embodiments relate to the use of the composition above or a method of enhancing expansion of cells in a subject in need thereof or treating a subject having cancer, the method comprising: administering an effective amount of the composition above to the subject, the subject having a form of cancer expressing a tumor antigen.

In embodiments, the expansion of the second population of cells in the subject is greater than the expansion of the second population of cells in a subject that is administered with the second population of cells but not the first population of cells.

In embodiments, the expansion is measured based on numbers of the second population of cells or copy numbers of DNA encoding the second CAR. In embodiments, the cells are T cells, NK cells, macrophages, or dendritic cells. In embodiments, the first antigen comprises a cell surface molecule of a white blood cell (WBC), a tumor antigen, or a solid tumor antigen. In embodiments, the WBC is a granulocyte, a monocyte, or a lymphocyte. In embodiments, the WBC is a B cell. In embodiments, the cell surface molecule of the WBC is CD19, CD22, CD20, BCMA, CD5, CD7, CD2, CD16, CD56, CD30, CD14, CD68, CD11 b, CD18, CD169, CD1c, CD33, CD38, CD138, or CD13. In embodiments, the cell surface molecule of the WBC is CD19, CD20, CD22, or BCMA. In embodiments, the cell surface molecule of the WBC is CD19 or BCMA. In embodiments, the tumor antigen is a solid tumor antigen. In embodiments, the solid tumor antigen is tumor associated MUC1 (tMUC1), PRLR, CLCA1, MUC12, GUCY2C, GPR35, CR1L, MUC 17, TMPRSS11B, MUC21, TMPRSS11E, CD207, SLC30A8, CFC1, SLC12A3, SSTR1, GPR27, FZD10, TSHR, SIGLEC15, SLC6A3, KISS1R, CLDN18.2, QRFPR, GPR119, CLDN6, UPK2, ADAM12, SLC45A3, ACPP, MUC21, MUC16, MS4A12, ALPP, CEA, EphA2, FAP, GPC3, IL13-Ra2, Mesothelin, PSMA, ROR1, VEGFR-II, GD2, FR-α, ErbB2, EpCAM, EGFRvIII, B7-H3, or EGFR. In embodiments, the solid tumor antigen comprises tMUC1, ACPP, TSHR, GUCY2C, UPK2, CLDN18.2, PSMA, DPEP3, CXCR5, B7-H3, MUC16, SIGLEC-15, CLDN6, Muc17, PRLR, or FZD10. In embodiments, the solid tumor antigen comprises tMUC1, ACPP, TSHR, GUCY2C, UPK2, or CLDN18.2.

In embodiments, the CAR comprises an antigen binding domain, a transmembrane domain, a co-stimulatory domain, and a CD3 zeta domain. In embodiments, the co-stimulatory domain comprises the intracellular domain of CD27, CD28, 4-1BB, OX40, CD30, CD40, PD-1, ICOS, lymphocyte function-associated antigen-1 (LFA-1), CD2, CD7, LIGHT, NKG2C, B7-H3, a ligand that binds CD83, or a combination thereof. In embodiments, the first CAR comprises an scFv binding CD19, an intracellular domain of 4-1BB or CD28, and CD3 zeta domain, and the second CAR comprises an scFv binding tMUC1, ACPP, TSHR, GUCY2C, or CLDN18.2, an intracellular domain of 4-1BB or CD28, and CD3 zeta domain.

In embodiments, an antigen binding domain of the first CAR comprises SEQ ID NO: 5, and an antigen binding domain of the second CAR comprises SEQ ID NO: 10. In embodiments, the second population of cells comprises a lentiviral vector encoding the second CAR and a dominant negative form of PD-1. In embodiments, the first population of cells comprises a lentiviral vector encoding the first CAR and a therapeutic agent. In embodiments, the therapeutic agent comprises a cytokine. In embodiments, the cytokine is IL6 and/or INFγ. In embodiments, the cytokine is at least one of IL6, IL12, IL-15, IL-7, TNF-α, or IFN-γ.

Embodiments relate to a method of enhancing anti-tumor efficacy of immunotherapy in a subject having cancer, the method comprising administering the subject an effective amount of a population of lymphocytes comprising an antigen binding molecule and one or more agents that enhance the expansion of lymphocytes comprising the antigen binding molecule in the subject.

In embodiments, the lymphocytes are T cells, DCs, macrophages, and/or NK cells. In embodiments, the antigen binding molecule is CAR or TCR, targeting an antigen associated with cancer described herein. In embodiments, the lymphocytes are T cells, and the antigen binding molecule is a CAR targeting a solid tumor antigen. In embodiments, the expansion of the lymphocytes is the antigen-dependent expansion of the lymphocytes such that the one or more agents expand the lymphocytes via the binding of an antigen and the antigen binding molecule. In embodiments, the one or more agents comprise a cell expressing an antigen that the antigen binding molecule binds. In embodiments, the cell is a T cell or APC. In embodiments, the one or more agents comprise an extracellular domain of an antigen that the antigen binding molecule binds. In embodiments, the expansion of the lymphocytes is the antigen-independent expansion of the lymphocytes such that: the one or more agents expand the lymphocytes not via the binding of an antigen and the antigen binding molecule, or the one or more agents expand the lymphocytes neither via the binding of the antigen and the antigen binding molecule nor via modification of the lymphocytes' genes downstream of MYD88 and CD40. In embodiments, the one or more agents comprising a CAR targeting a WBC antigen (e.g., CD19).

In embodiments, the one or more agents is a bispecific or trispecific antibody. More information on the bispecific antibody can be found at A Novel GUCY2C-CD3 T cell Engaging Bispecific construct (PF-07062119) for the Treatment of Gastrointestinal Cancers, Clin Cancer Res May 1, 2020 (26) (9) 2188-2202; DOI: 10.1158/1078-0432.CCR-19-3275, which is incorporated here by its reference. In embodiments, the antibody binds CD3 zeta and a WBC antigen (e.g., CD19). In embodiments, the one or more agents comprise a transcription factor or a modulator associated with the expansion of the lymphocytes. In embodiments, the one or more agents are secretable or a membrane protein. In embodiments, the expansion of the lymphocytes is measured based on a copy number of the antigen binding molecule in the genomic DNA of the lymphocytes and/or a number of the lymphocytes in the blood of the subject. In embodiments, the anti-tumor efficacy of immunotherapy in the subject is measured based on the reduction of a size of a tumor. In embodiments, the size of the tumor is determined using CT or PET CT scanning. In embodiments, the anti-tumor efficacy of immunotherapy in the subject is enhanced as compared to a subject that is administered with the effective amount of a population of lymphocytes comprising an antigen binding molecule but lacking the one or more agents.

Embodiments relate to a method of treating the subject having digestive system cancer, the method comprising: administering an effective amount of a composition to the subject, the composition comprising a first population of cells comprising a first CAR binding a first antigen, and a second population of cells comprising a second CAR binding GUCY2C, wherein the first antigen comprises a cell surface molecule of a white blood cell (WBC).

Embodiments relate to a method of enhancing anti-tumor efficacy of immunotherapy on the subject having digestive system cancer, the method comprising: administering an effective amount of a composition to the subject, the composition comprising a first population of cells comprising a first CAR binding a first antigen, and a second population of cells comprising a second CAR binding GUCY2C, wherein the first antigen comprises a cell surface molecule of a white blood cell (WBC), and the anti-tumor efficacy of the composition is enhanced as compared to a subject that is administered an effective amount of the composition that does not have the first population of cells.

In embodiments, the digestive system cancer comprises cancer associated with the esophagus, stomach, small and large intestines (colorectal cancer), liver, and/or pancreas. In embodiments, the digestive system cancer comprises primary cancer and metastatic cancer. In embodiments, the cells are T cells, NK cells, or dendritic cells. In embodiments, the WBC is a granulocyte, a monocyte, or lymphocyte. In embodiments, the WBC is a B cell. In embodiments, the cell surface molecule of the WBC is CD19, CD22, CD20, BCMA, CD5, CD7, CD2, CD16, CD56, CD30, CD14, CD68, CD11 b, CD18, CD169, CD1c, CD33, CD38, CD138, or CD13. In embodiments, the cell surface molecule of the WBC is CD19, CD20, CD22, or BCMA. In embodiments, the cell surface molecule of the WBC is CD19. In embodiments, the CAR comprises an antigen binding domain, a transmembrane domain, a co-stimulatory domain, and a CD3 zeta domain. In embodiments, the co-stimulatory domain comprises the intracellular domain of CD27, CD28, 4-1BB, OX40, CD30, CD40, PD-1, ICOS, lymphocyte function-associated antigen-1 (LFA-1), CD2, CD7, LIGHT, NKG2C, B7-H3, a ligand that binds CD83, or a combination thereof. In embodiments, the first CAR comprises an scFv binding CD19, an intracellular domain of 4-1BB or CD28, CD3 zeta domain, and the second CAR comprises an scFv binding GUCY2C or SEQ ID NO: 8, an intracellular domain of 4-1BB or CD28, CD3 zeta domain. In embodiments, an antigen binding domain of the first CAR comprises the SEQ ID NO: 5 or 6, and an antigen binding domain of the second CAR comprises SEQ ID NO: 26. In embodiments, the second population of cells comprises a lentiviral vector encoding the second CAR and a dominant negative form of PD-1. In embodiments, the first population of cells comprises a lentiviral vector encoding the first CAR and a therapeutic agent. In embodiments, the therapeutic agent comprises a cytokine. In embodiments, the cytokine is IL6 and/or INFγ. In embodiments, the cytokine is at least one of IL6, IL12, TNF-α, or IFN-γ.

Embodiments relate to a polynucleotide encoding the first CAR and the second CAR described herein. Embodiments relate to a vector comprising the polynucleotide. Embodiments relate to a cell comprising the vector. Embodiments relate to a composition comprising a population of cells. Embodiments relate to a method of causing T cell response, the method comprising administering an effective amount of the composition.

Embodiments relate to an antibody that binds GCC, wherein the antibody comprises a heavy chain variable region (HVR) comprising the amino acid sequence of SEQ ID NO: 31 and a light chain variable region (LVR) comprising the amino acid sequence of SEQ ID NO: 32 or 41.

In embodiments, the HVR comprises the amino acid sequence of SEQ ID NO: 31, and the LVR comprises the amino acid sequence of SEQ ID NO: 32.

In embodiments, the HVR comprises the amino acid sequence of SEQ ID NO: 31, and the LVR comprises the amino acid sequence of SEQ ID NO: 41.

In embodiments, the HVR is joined to a human IgG chain constant region, and the human IgG is IgG1 or IgG3.

In embodiments, the antibody or antibody fragment is conjugated to a cytotoxic agent, and the cytotoxic agent is a radioactive isotope or a toxin.

In embodiments, the antibody is an scFv, and the LVR is connected to HVR via a linker.

Embodiments relate to a CAR comprising an antigen binding domain comprising the antibody or fragment above.

Embodiments relate to a CAR comprising an antigen binding domain comprising the SEQ ID NO: 52 or 53, wherein the CAR binds GCC.

Embodiments relate to a CAR comprising an antigen binding domain comprising one of the SEQ ID NO: 52-56, wherein the CAR binds GCC.

Embodiments relate to a polynucleotide that encodes the antibody or antibody fragment or the CAR above. Embodiments relate to a modified cell comprising the polynucleotide.

In embodiments, the modified cell is a T cell.

In embodiments, the CAR comprises an extracellular domain, a transmembrane domain, and an intracellular domain, the extracellular domain comprising the binding domain that binds an antigen.

In embodiments, the intracellular domain comprises a co-stimulatory signaling region that comprises an intracellular domain of a co-stimulatory molecule selected from the group consisting of CD27, CD28, 4-1 BB, OX40, CD30, CD40, PD-1, ICOS, lymphocyte function-associated antigen-1 (LFA-1), CD2, CD7, LIGHT, NKG2C, B7-H3, and a combination thereof.

Embodiments relate to the use of the nucleic acid sequences, the CAR molecules, the antibodies, the vectors, the cells, the population of cells, the compositions, the pharmaceutical compositions, the kits, or the methods described herein for use in a method of treating a subject's body by therapy. In embodiments, the subject is a human or animal. In embodiments, the subject is suffering from cancer. In embodiments, the use elicits and/or enhances a T cell response in the subject.

Embodiments relate to the use of the nucleic acid sequences, the CAR molecules, the antibodies, the vectors, the cells, the population of cells, the compositions, the pharmaceutical compositions, the kit, or the methods described herein for use in a method of eliciting and/or enhancing a T cell response in a subject. In embodiments, the subject is a human or animal. In embodiments, the subject is suffering from cancer.

The present disclosure is further described by reference to the following exemplary embodiments and examples. These exemplary embodiments and examples are provided for purposes of illustration only and are not intended to be limiting unless otherwise specified. Thus, the present disclosure should in no way be construed as being limited to the following exemplary embodiments and examples but rather should be construed to encompass any and all variations which become evident as a result of the teaching provided herein.

Exemplary Embodiments

The following are exemplary embodiments:

1. A composition for use in a method of treating the subject having digestive system cancer, the method comprising: administering an effective amount of the composition to the subject, the composition comprising a first population of cells comprising a first CAR binding a first antigen, and a second population of cells comprising a second CAR binding GUCY2C, wherein the first antigen comprises a cell surface molecule of a white blood cell (WBC).

2. A composition for use in a method of enhancing anti-tumor efficacy of immunotherapy on the subject having digestive system cancer, the method comprising: administering an effective amount of the composition to the subject, the composition comprising a first population of cells comprising a first CAR binding a first antigen, and a second population of cells comprising a second CAR binding GUCY2C, wherein the first antigen comprises a cell surface molecule of a white blood cell (WBC), and the anti-tumor efficacy of the composition is enhanced as compared to a subject that is administered an effective amount of the composition that does not have the first population of cells.

3. The composition of embodiment 1 or 2, wherein the digestive system cancer comprises cancer associated with esophagus, stomach, small and large intestines (colorectal cancer), liver, and/or pancreas.

4. The composition of embodiment 3, wherein the digestive system cancer comprises primary cancer and metastatic cancer.

5. The composition of any of the preceding embodiments, wherein the cells are T cells, NK cells, or dendritic cells.

6. The composition of any of the preceding embodiments, wherein the WBC is a granulocyte, a monocyte, or lymphocyte.

7. The composition of any of the preceding embodiments, wherein the WBC is a B cell.

8. The composition of any of preceding embodiments, wherein the cell surface molecule of the WBC is CD19, CD22, CD20, BCMA, CD5, CD7, CD2, CD16, CD56, CD30, CD14, CD68, CD11 b, CD18, CD169, CD1c, CD33, CD38, CD138, or CD13.

9. The composition of any of the preceding embodiments, wherein the cell surface molecule of the WBC is CD19, CD20, CD22, or BCMA.

10. The composition of any of the preceding embodiments, wherein the cell surface molecule of the WBC is CD19.

11. The composition of any of the preceding embodiments, wherein the CAR comprises an antigen binding domain, a transmembrane domain, a co-stimulatory domain, and a CD3 zeta domain.

12. The composition of embodiment 11, wherein the co-stimulatory domain comprises the intracellular domain of CD27, CD28, 4-1BB, OX40, CD30, CD40, PD-1, ICOS, lymphocyte function-associated antigen-1 (LFA-1), CD2, CD7, LIGHT, NKG2C, B7-H3, a ligand that binds CD83, or a combination thereof.

13. The composition of any of the preceding embodiments, wherein the first CAR comprises an scFv binding CD19, an intracellular domain of 4-1BB or CD28, CD3 zeta domain, and the second CAR comprises an scFv binding GUCY2C or SEQ ID NO: 23, an intracellular domain of 4-1BB or CD28, CD3 zeta domain.

14. The composition of embodiment 13, wherein an antigen binding domain of the first CAR comprises the SEQ ID NO: 5 or 6, and an antigen binding domain of the second CAR comprises SEQ ID NO: 11.

15. The composition of any of the preceding embodiments, wherein the second population of cells comprises a lentiviral vector encoding the second CAR and a dominant negative form of PD-1.

16. The composition of any of the preceding embodiments, wherein the first population of cells comprises a lentiviral vector encoding the first CAR and a therapeutic agent.

17. The composition of embodiment 17, wherein the therapeutic agent comprises a cytokine.

18. The composition of embodiment 17, wherein the cytokine is IL6 and/or INFγ.

19. The composition of embodiment 17, wherein the cytokine is at least one of IL6, IL12, TNF-α, or IFN-γ.

20. A polynucleotide encoding the first CAR and the second CAR of any suitable preceding embodiments.

21. A vector comprising the polynucleotide of embodiment 20.

22. A cell comprising the vector of embodiment 21.

23. A composition comprising a population of cells of embodiment 137.

24. A composition of causing T cell response, the composition comprising administering an effective amount of the composition of embodiment 138.

25. An antibody that binds GCC, wherein the antibody comprises a heavy chain variable region (HVR) comprising the amino acid sequence of SEQ ID NO: 31 and a light chain variable region (LVR) comprising the amino acid sequence of SEQ ID NO: 32 or 41.

26. The antibody or antibody fragment of embodiment 25, wherein the HVR comprises the amino acid sequence of SEQ ID NO: 31 and the LVR comprise the amino acid sequence of SEQ ID NO: 32.

27. The antibody or antibody fragment of embodiment 25, wherein the HVR comprises the amino acid sequence of SEQ ID NO: 31, and the LVR comprises the amino acid sequence of SEQ ID NO: 41.

28. The antibody or antibody fragment of one of the embodiments 25-27, wherein the HVR is joined to a human IgG chain constant region, and the human IgG is IgG1 or IgG3.

29. The antibody or antibody fragment of one of the embodiments 25-27, wherein the antibody or antibody fragment is conjugated to a cytotoxic agent, and the cytotoxic agent is a radioactive isotope or a toxin.

30. The antibody or antibody fragment of one of the embodiments 25-27, wherein the antibody is an scFv, and the LVR is connected to HVR via a linker.

31. A chimeric antigen receptor (CAR) comprising an antigen binding domain comprising the antibody or fragment of one of the embodiments 25-30.

32. A CAR comprising an antigen binding domain comprising the SEQ ID NO: 52 or 53, wherein the CAR binds GCC.

33. A CAR comprising an antigen binding domain comprising one of the SEQ ID NO: 33 or 34, wherein the CAR binds GCC.

34. A polynucleotide that encodes the antibody or antibody fragment or the CAR of any one of embodiments 25-149.

35. A modified cell comprising the polynucleotide of embodiment 34.

36. The modified cell of embodiment 35, wherein the modified cell is a T cell.

37. The CAR, polynucleotide, or modified cell of one of the embodiments 31-36, wherein the CAR comprises an extracellular domain, a transmembrane domain, and an intracellular domain, the extracellular domain comprising the binding domain that binds an antigen.

38. The CAR, polynucleotide, or modified cell of one of embodiments 37, wherein the intracellular domain comprises a co-stimulatory signaling region that comprises an intracellular domain of a co-stimulatory molecule selected from the group consisting of CD27, CD28, 4-1BB, OX40, CD30, CD40, PD-1, ICOS, lymphocyte function-associated antigen-1 (LFA-1), CD2, CD7, LIGHT, NKG2C, B7-H3, and a combination thereof.

39. Use of the nucleic acid sequences, the CAR molecules, the antibodies, the vectors, the cells, the population of cells, the compositions, the pharmaceutical compositions, the kit, or the compositions of any one of embodiments 1-38 for use in a composition of treating a subject's body by therapy.

40. The use of embodiment 39, wherein the subject is a human or animal.

41. The use of embodiment 39 or 40, wherein the subject is suffering from cancer.

42. The use of any one of embodiments 39-41, wherein the use elicits and/or enhances a T cell response in the subject.

43. Use of the nucleic acid sequences, the CAR molecules, the antibodies, the vectors, the cells, the population of cells, the compositions, the pharmaceutical compositions, the kit, or the compositions of any one of embodiments 1-42 for use in a composition of eliciting and/or enhancing a T cell response in a subject.

44. The use of embodiment 43, wherein the subject is a human or animal.

45. The use of embodiment 42 or 43, wherein the subject is suffering from cancer.

Examples

CAR T Cell Expansion and Anti-tumor Activity in Patients

Clinical studies were designed to assess the safety and efficacy of infusing autologous T cells modified to express CARs binding several solid tumor markers. These CARs include 4-1BB/CD3-ζ. Patients received CART cells directed to CD19 and a solid tumor antigen (i.e., GCC). T cells of the patients were obtained, modified with the CART molecules, and infused back into the patients. T cell responses of the patients from the first and second arms were measured and compared using the following protocols, which were approved by the hospitals where the trials were conducted. All patients were provided with written informed consent. Information regarding these patients is provided below in Table 2 (SD: stable disease; PD: progressive disease; PR: partial remission; CR: complete remission; NR: no response).

TABLE 2

Clinical Trial Data

| Patient ID | Infusion of CAR T Cells/kg | Cytokine release syndrome (CRS) >2 | Efficacy | Infusion Methods |
|---|---|---|---|---|
| 1 | $3.78 \times 10^8$ | No | PR | Fresh cells |
| 2 | $2.72 \times 10^6$ | No | CR | Fresh cells |

TABLE 3

Cell Manufacture for Clinical Trials

| ID | Vectors and Multiplicity of Infection (MOI) | Pre-treatment |
|---|---|---|
| 1 | Vector 4: GCC CAR (CAR: SEQ ID NO: 26, scFv of the CAR: SEQ ID NO: 7): 50:1(MOI); and Vector 2: hCD19 CAR-NATF-IL6-2A-IFNy (Vector SEQ ID NO: 18, scFv of CD19 CAR: SEQ ID 5, 6xNFAT: SEQ ID: 19, aa of IL6: SEQ ID NO: 20, 2A is SEQ ID NO: 21, and aa of IFN-y: SEQ ID NO: 22): 10:1(MOI) | FC regimen at −2 days (cyclophosphamide 500 mg/m2, fludarabine 30 mg/m2) |
| 2 | Vector 4: GCC CAR (CAR: SEQ ID NO: 26, scFv of the CAR: SEQ ID NO: 7): 50:1(MOI); and Vector 2: hCD19 CAR-NATF-IL6-2A-IFNy (Vector SEQ ID NO: 18, scFv of CD19 CAR: SEQ ID 5, 6xNFAT: SEQ ID: 19, aa of IL6: SEQ ID NO: 20, 2A is SEQ ID NO: 21, and aa of IFN-y: SEQ ID NO: 22): 10:1(MOI), and Vector 3: hCD19 CAR-NATF-IL12-VHL (Vector SEQ ID NO: 23, scFv of CD19 CAR: SEQ ID 5, 6xNFAT: SEQ ID: 481, aa of IL12: SEQ ID NO: 24, VHL: SEQ ID NO: 25, 10:1(MOI) | FC regimen at −2 days (cyclophosphamide 500 mg/m2, fludarabine 30 mg/m2) |

Peripheral blood mononuclear cells (PBMCs) were collected from patients. T cells were obtained from the collected PBMCs. Various lentiviral vectors were generated and then transfected to the T cells, which were further cultured for several days before the co-cultivation assay. More information can be found in Tables 2, 3, and 5 below. Techniques related to cell cultures, construction of cytotoxic T lymphocyte assay can be found in "Control of large, established tumor xenografts with genetically retargeted human T cells containing CD28 and CD137 domains," PNAS, Mar. 3, 2009, vol. 106 no. 9, 3360-3365, which is incorporated herein by reference in its entirety. Detailed information about T cell manufactures, and protocols of the clinical trial can be found in Tables 6 and 7 as well as in PCT Publication WO 2020146743, which is incorporated herein by reference in its entirety.

Figure 3:
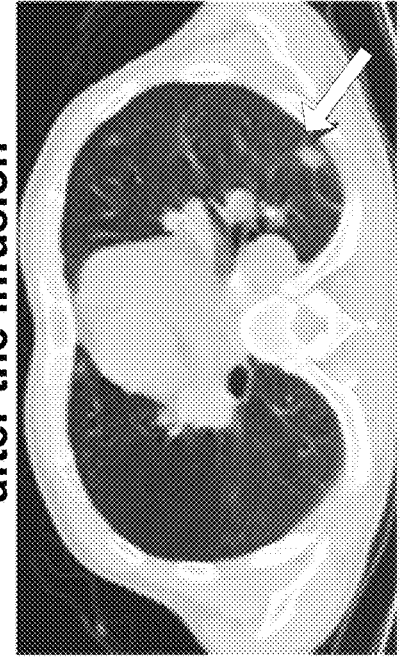
FIG. 3 shows CT and/or PET CT scanning images of Patient 1 before and after the infusion of mixed CAR T cells.
Figure 3:
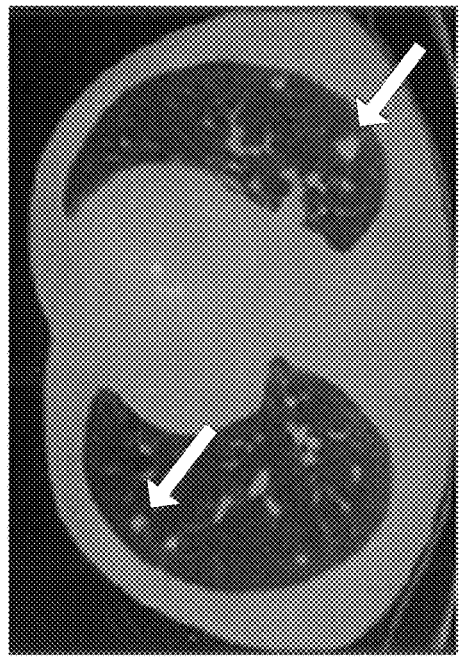
Figure 3:
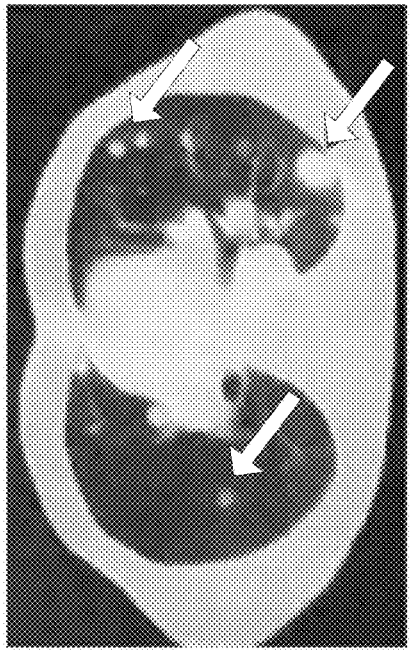
Figure 3:
Figure 4:
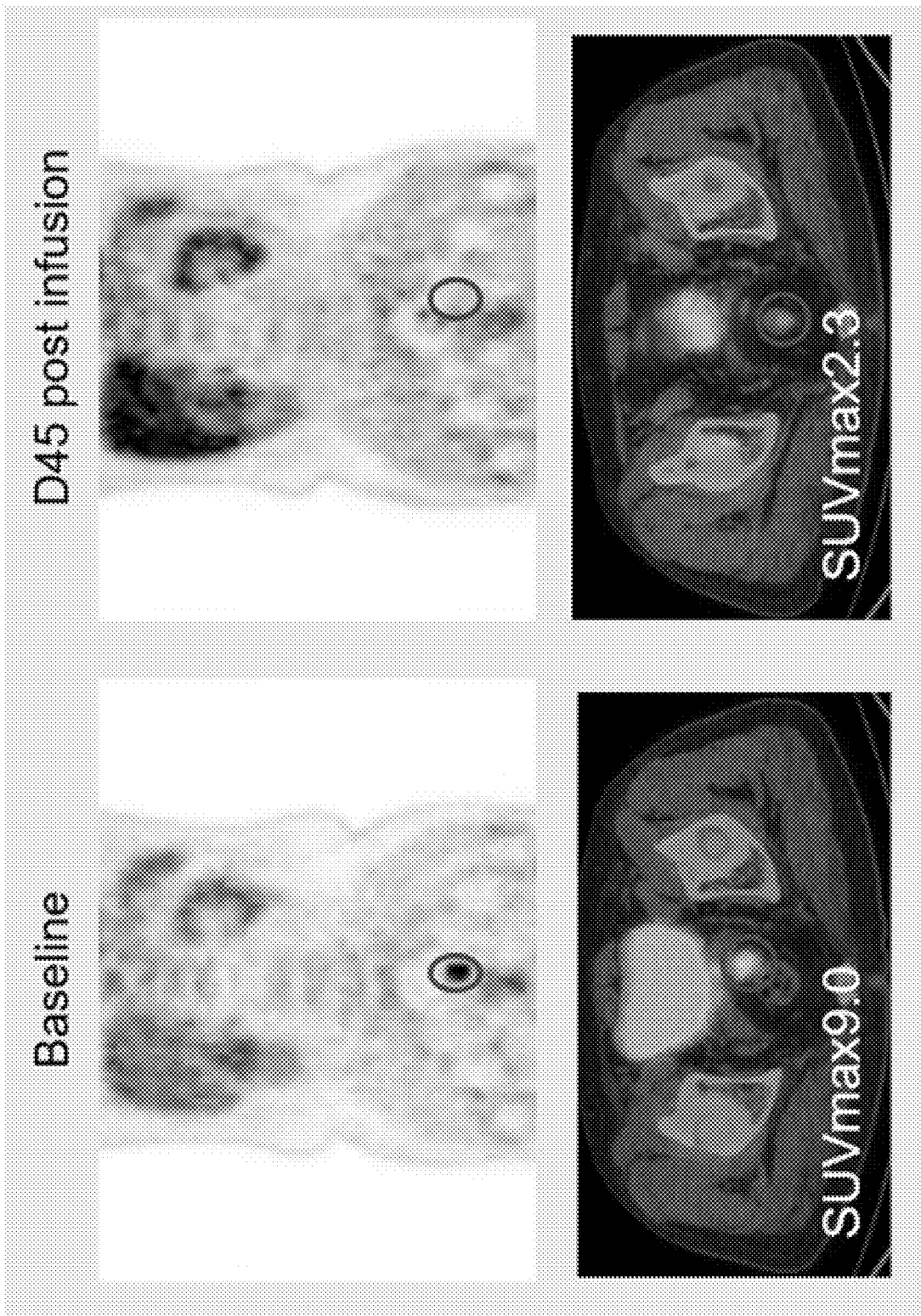
FIG. 4 shows CT and/or PET CT scanning images of Patient 2 before and after the infusion of mixed CAR T cells.
Figure 5:
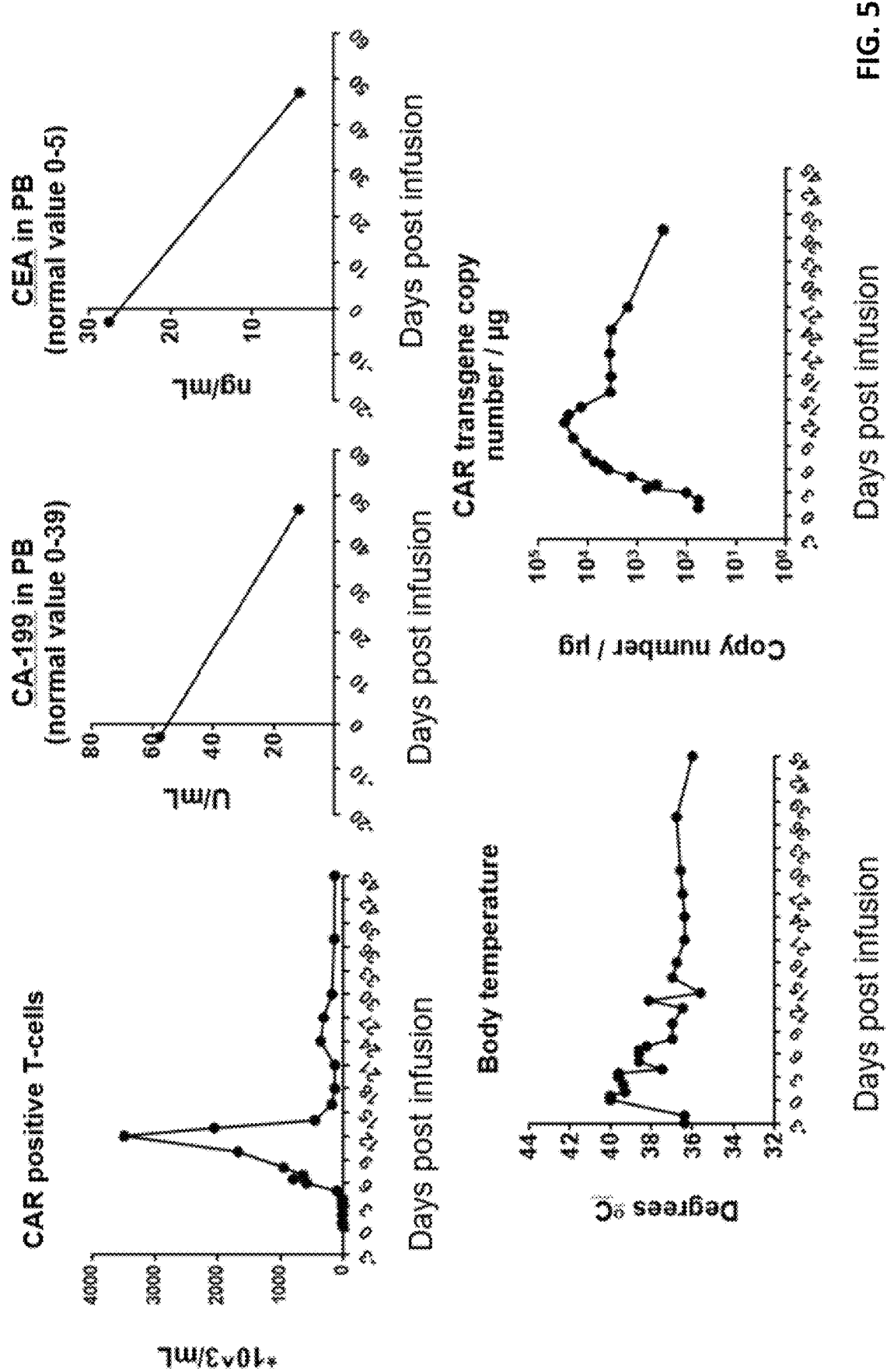
FIG. 5 shows response of Patient 2 to infusion of modified T cells.
Figure 6:
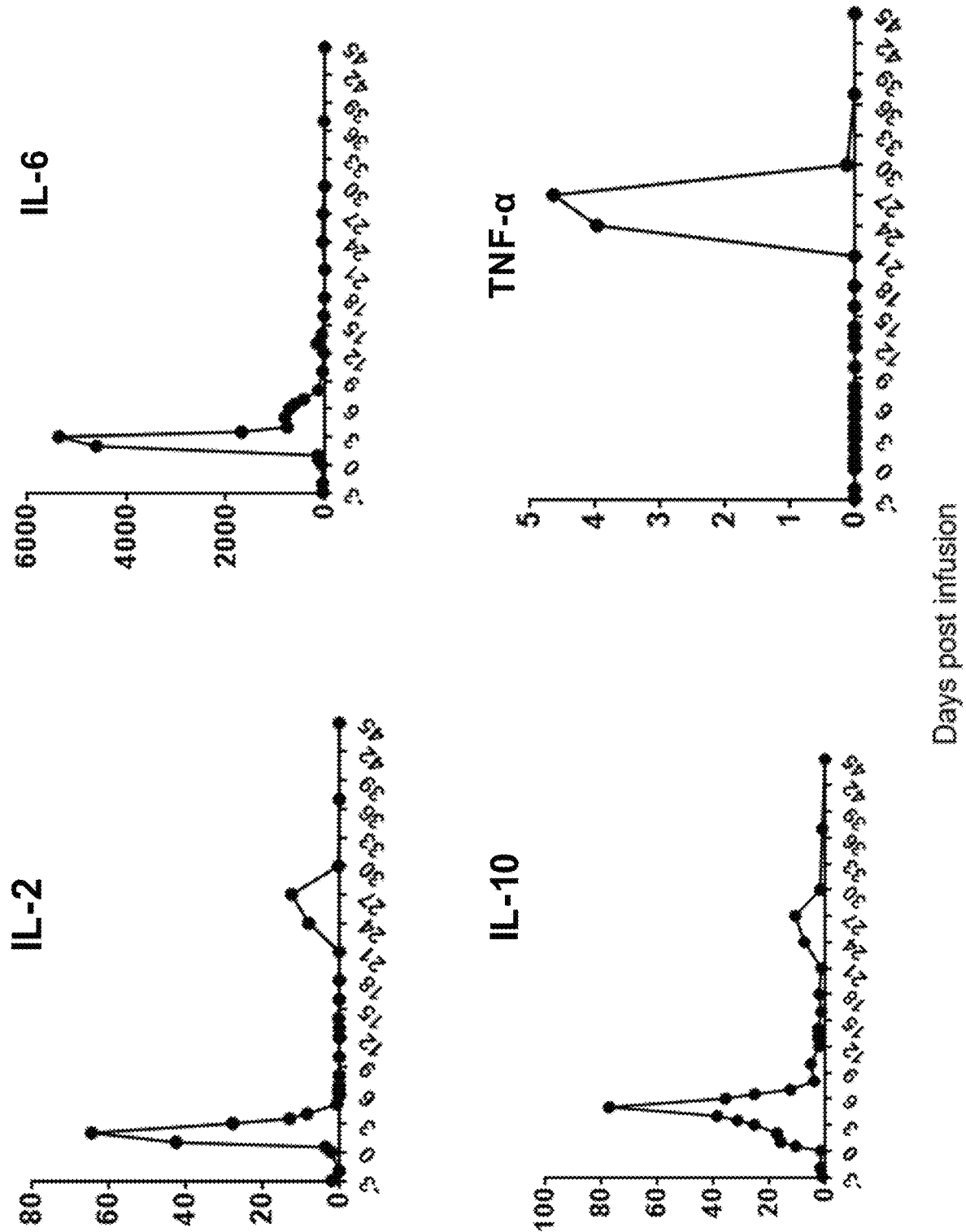
FIG. 6 shows response of Patient 2 to infusion of modified T cells.
Figure 7:
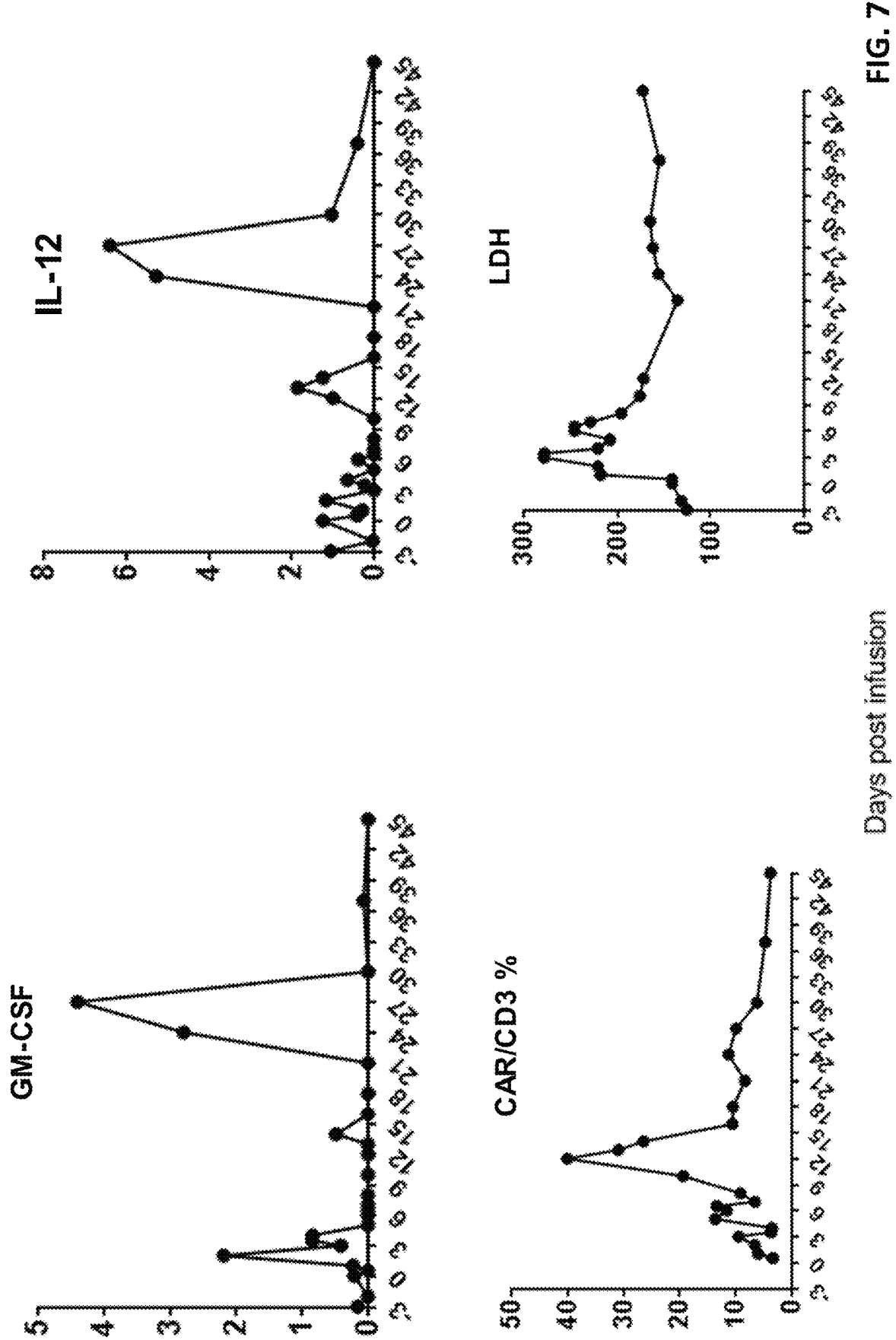
FIG. 7 shows response of Patient 2 to infusion of modified T cells.
Figure 8:
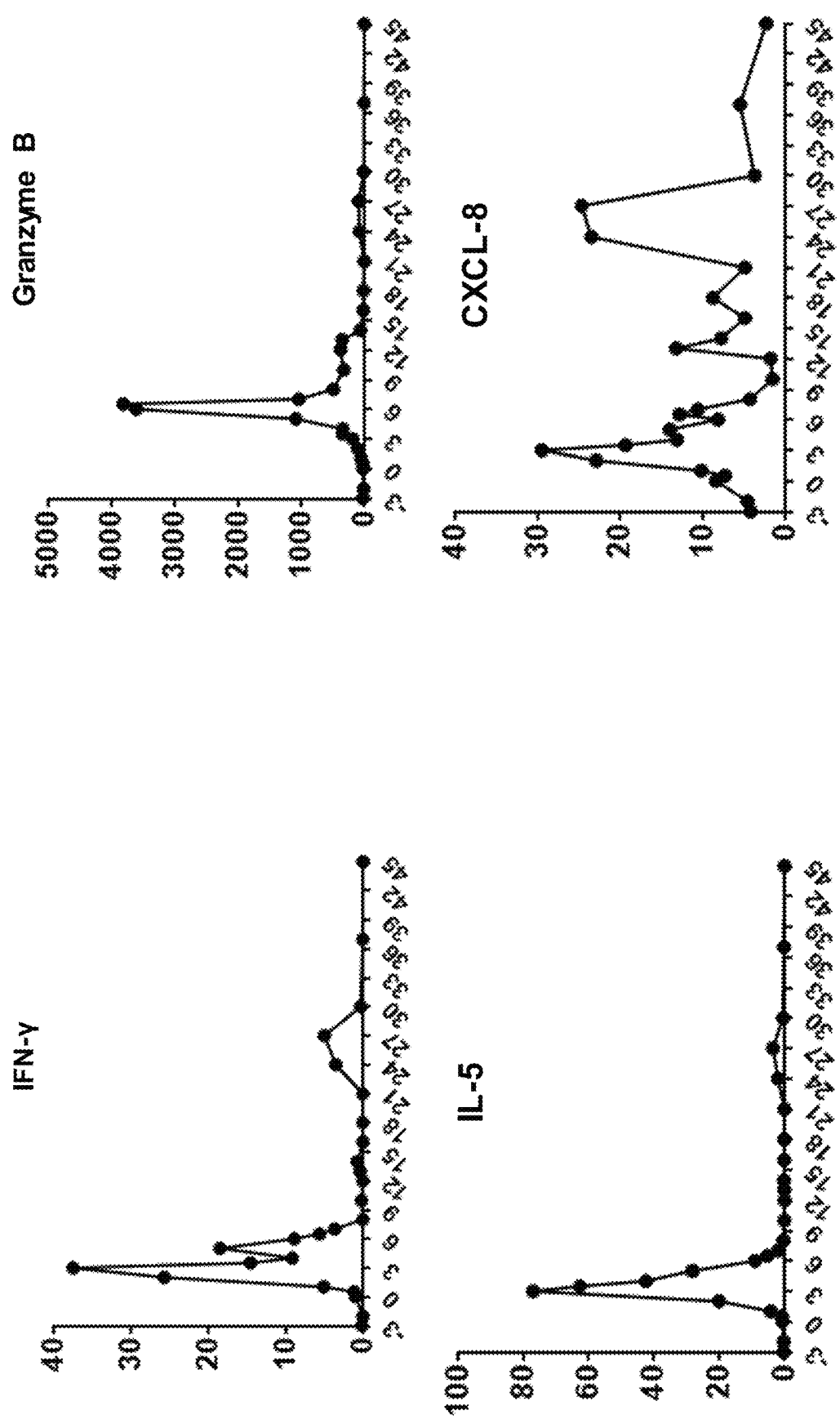
FIG. 8 shows response of Patient 2 to infusion of modified T cells.
Figure 9:
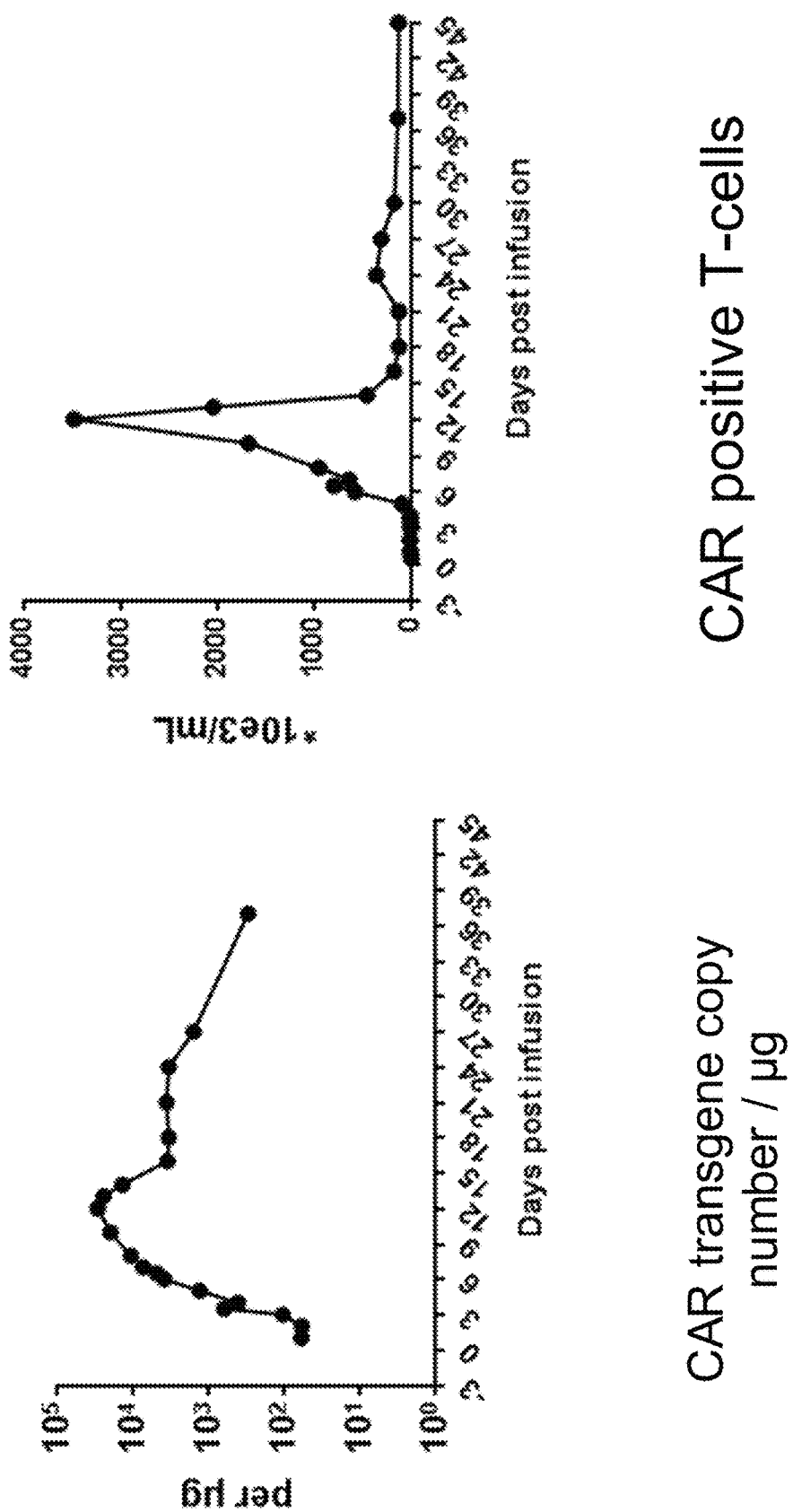
FIG. 9 shows response of Patient 2 to infusion of modified T cells.

Patient 1 was diagnosed with colorectal cancer and went through 8 cycles of chemotherapy as well as other treatments such as surgery before CAR T cell infusion. One month after infusion, PET-CT scanning results show most of the target lesions were significantly reduced (more than 50%), and the comprehensive calculation of tumor reduction was 44.7%. The patient was evaluated to have achieved PR (see arrows in FIG. 3). Patient 2 was diagnosed with colon cancer. He had a laparoscopic right hemicolectomy, 2 cycles of XELOX chemotherapy, 12 cycles of Erbitux+XELOX chemotherapy, 4 cycles of Erbitux+Tegio chemotherapy, a retroperitoneal lymph node radiotherapy with DT50Gy/25f, a left lobectomy of thyroid and partial isthmectomy, right thyroid tumor excision, left cervical lymph node dissection, anterior cervical partial resection, anterior cervical median lymph node dissection, and 5 cycles of Cetuximab and Irinotecan chemotherapy before entering the trial. Forty-five days after the infusion of the modified T cells, the patient achieved CR as shown in the CT/PET CT scanning images (FIG. 4).

CD19 CAR T Cells Promote the Expansion of GCC CAR T Cells

The non-transduced T cells were replaced with GCC CAR T cells targeting prostate cancer. In vitro experiments show that CD19 CAR T cells can, by killing B cells, promote GCC CAR T cells to expand and release cytokines.

FIG. 10 shows constructs and expression of CD19 CAR and GCC CAR in corresponding T cells. FIGS. 10A1-10A4 show by immunochemical staining that GCC is not expressed in normal gastric mucosa and esophageal epithelium but is expressed in colorectal cancer tissue (normal esophageal squamous epithelium (A1) and gastric mucosa (A2) showed no membrane staining; (A3) small intestine shows apical membrane staining of villi and crypt cells; (A4) cell membrane staining (immunohistochemistry, ×150) in colorectal cancer tissue, showing high expression in colorectal cancer tumors). FIG. 10B shows constructs of vector encoding GCC CAR and vector encoding CD19 CAR. FIG. 10C shows that the proportion of CD19 CAR expression is 59.65%, and the proportion of GCC CAR expression is 55.23%.

Figure 11:
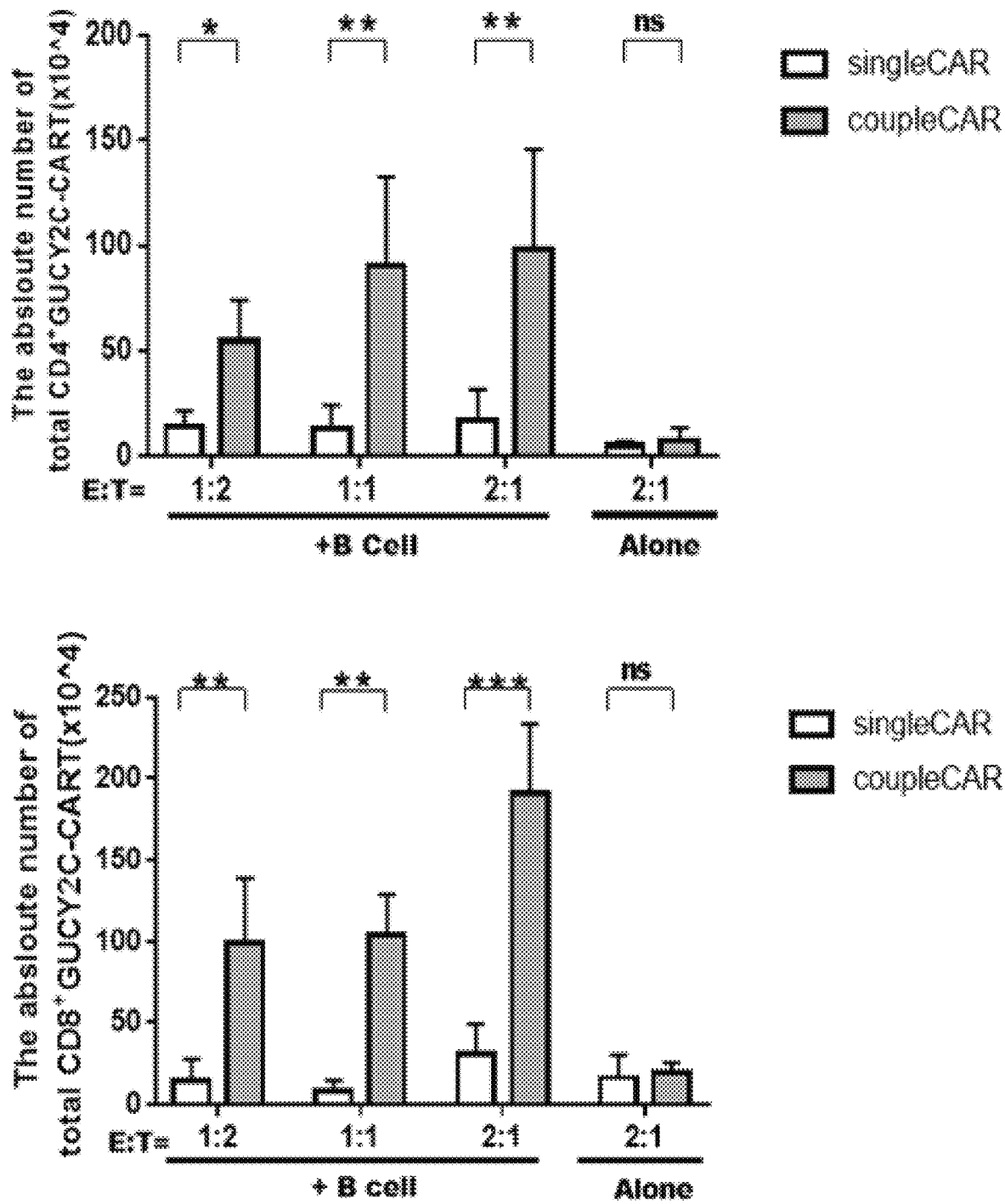
FIG. 11 shows GCC CAR T cell expansion in various culturing systems.

FIG. 11 shows expansion of GCC CAR T cells in various culturing systems (Ratio of GCC CAR:CD19 CAR:B cell is 2:0.5:1, 2:1:1, or 2:2:1). The expansion of the group of coupled CAR with B cells was significantly better than the group without the B cells. Statistics on total CD4/CD8 T cells show CD19 CAR T cells can significantly promote the expansion of GCC CAR T cells, and the expansion increases as the proportion of CD19 CAR increases. When E:T ratio is 2:1, the expansion of GCC CAR in the coupled CAR and B cells group was approximately 4 times that of the control group; the expansion effect of CD8 T cells was slightly higher; and the results were consistent in CD4 and CD8 T cells. After 96 hours, the expansion of GCC CAR T cells was determined. The vertical axis was the absolute number of CD4 and CD8 positive GCC CAR T in expansion.

Figure 12:
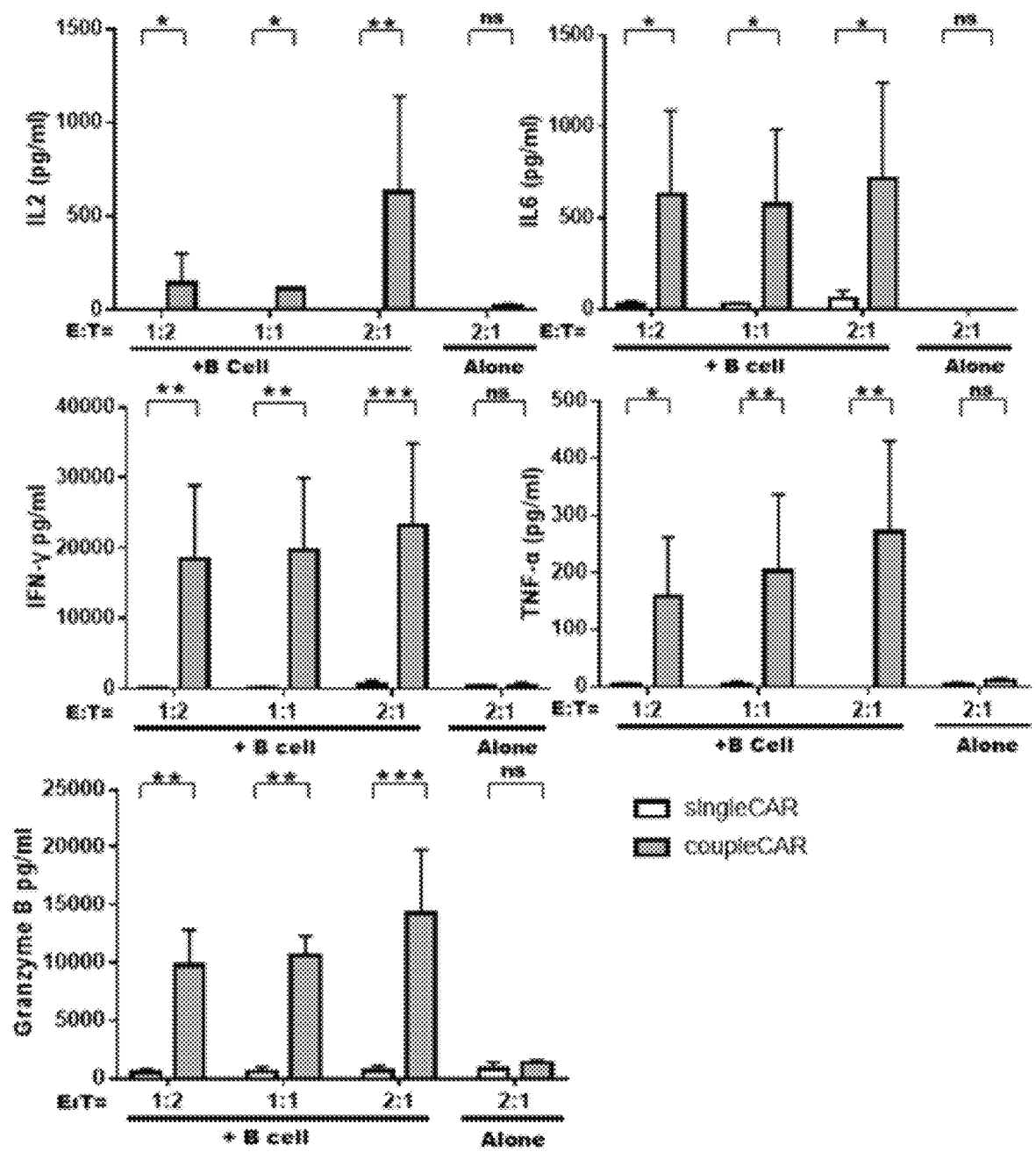
FIG. 12 shows results of cytokine release assay of CAR T cells co-cultured with substrate cells.
Figure 13:
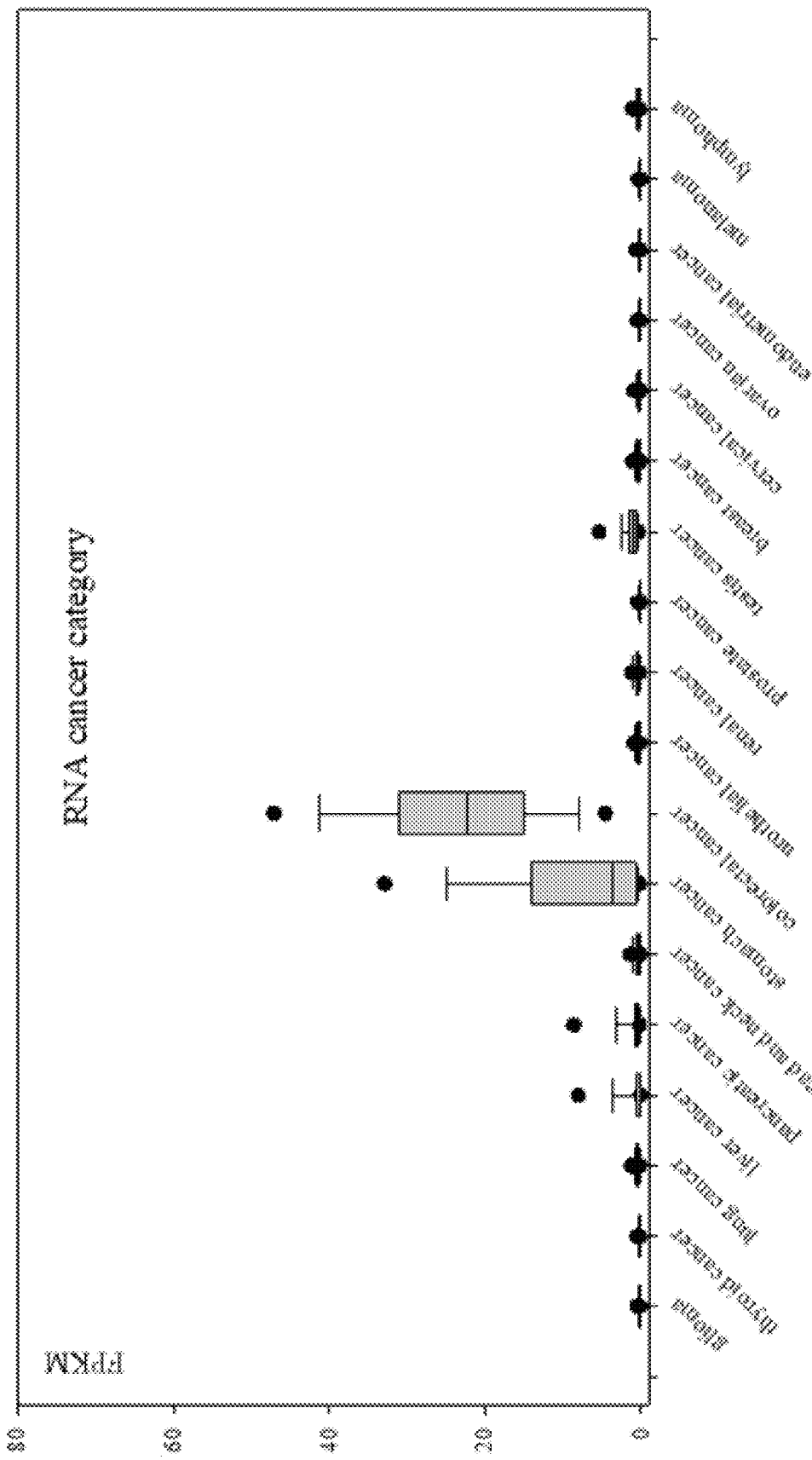
FIG. 13 shows expression patterns of GCC in colorectal and stomach cancer as compared with other cancers.
Figure 14:
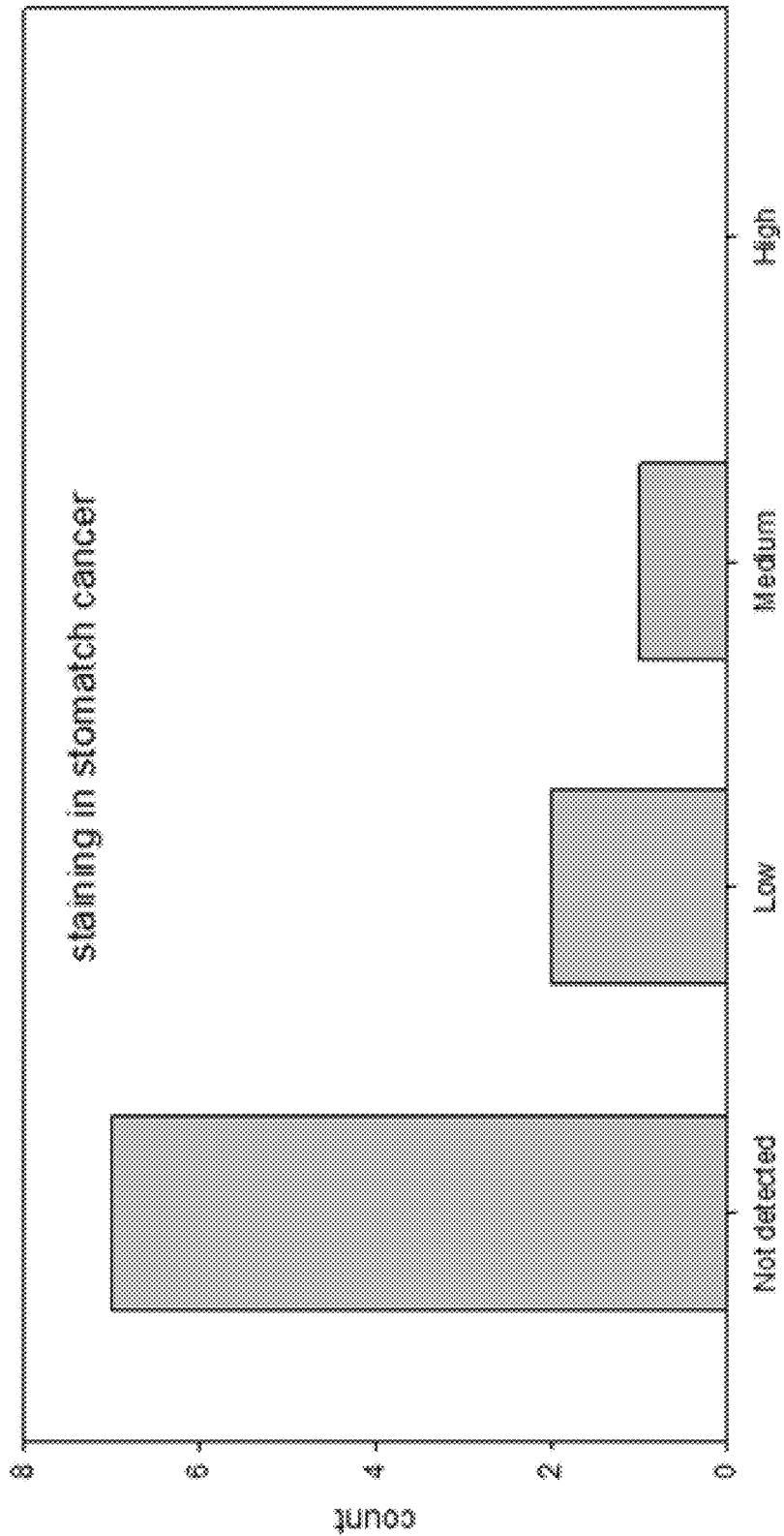
FIG. 14 shows expression patterns of GCC in stomach cancer.
Figure 15:
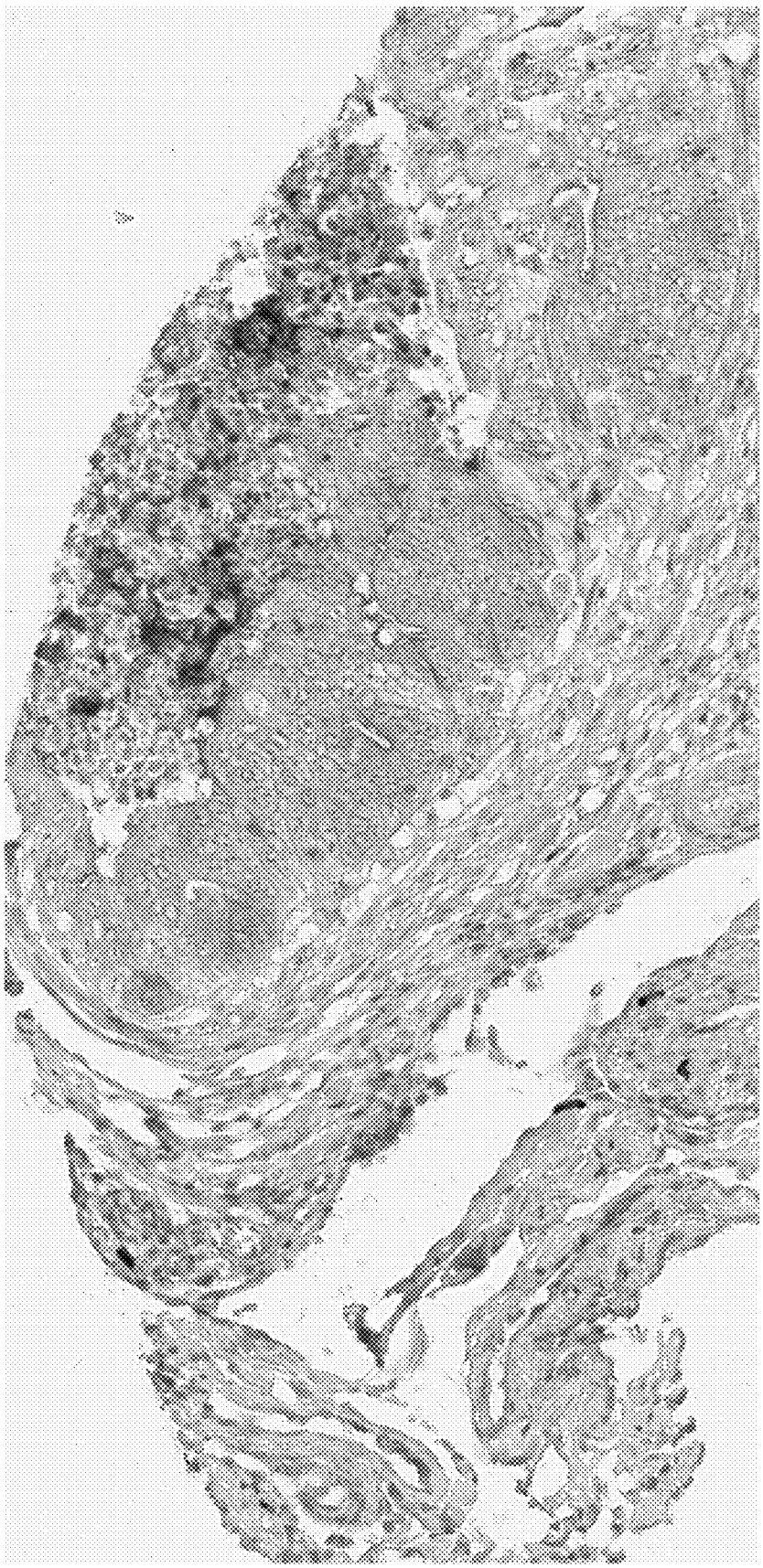
FIG. 15 shows expression patterns of GCC in stomach cancer.
Figure 16:
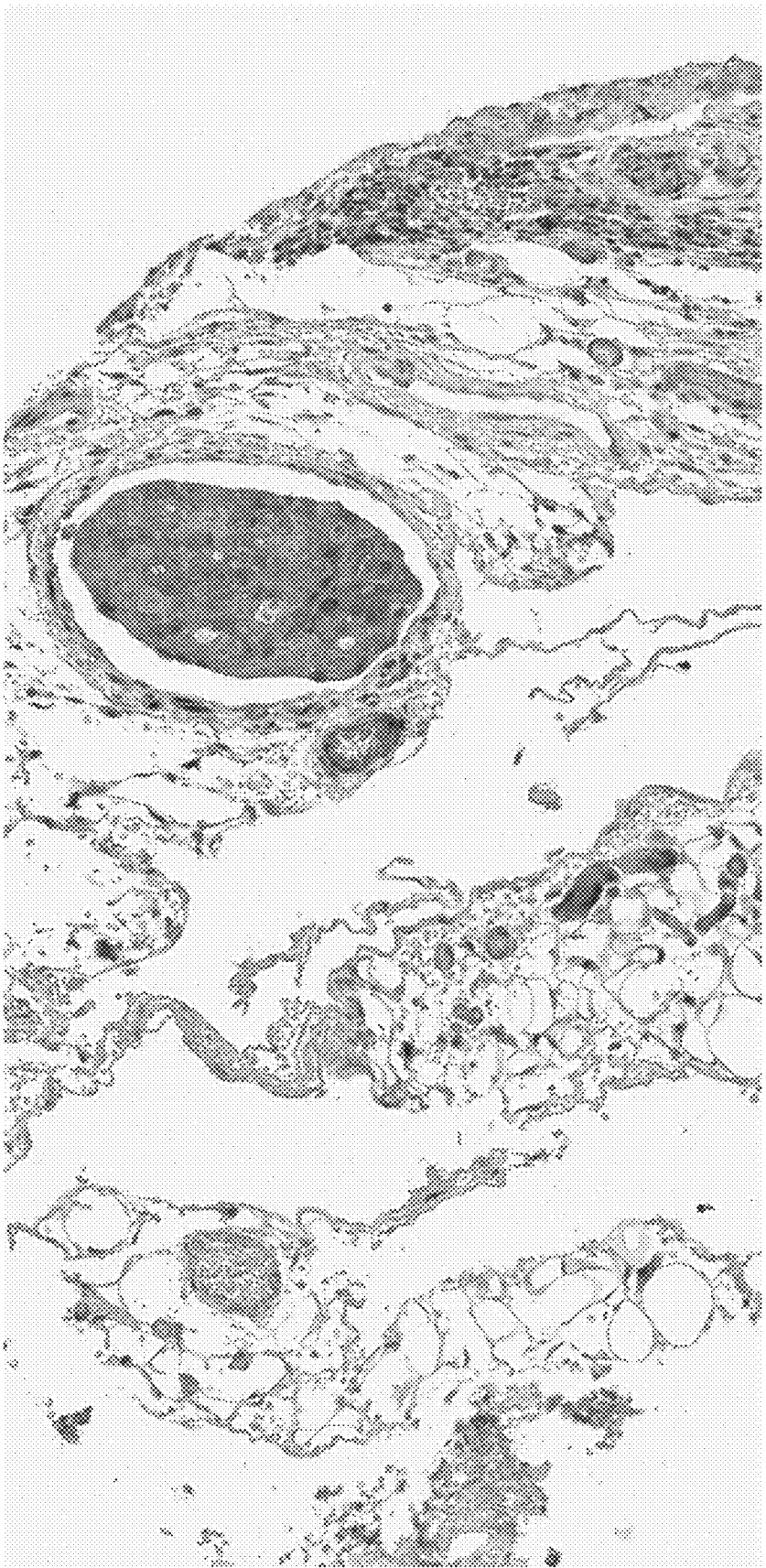
FIG. 16 shows expression patterns of GCC in stomach cancer.

FIG. 12 shows cytokine release analysis of co-cultured cells with respect to GCC CAR and CD19 CAR. CD19 CART cells mediate the release of various cytokines in the presence of B cells, and the higher the proportion of CD19 CAR, the more of the different cytokines are released, indicating that CD19 CAR promotes the expansion of GCC CART. Cells were co-cultured for 48 hours, and cell supernatant was collected to determine cytokines.

FIGS. 13-16 show expression of GCC in colorectal and stomach cancer. Further, it has been reported that in other types of cancer, the digestive tract showed higher expression of GCC than normal cells. For example, in normal esophagus and SCE (esophageal squamous cell carcinoma) specimens, the expression of GCC mRNA is low, while the expression of GCC mRNA in ACE (esophageal adenocarcinoma) and ACS (gastric adenocarcinoma) specimens is increased. Transformation associated with reflux at the gastroesophageal junction reflects activation by bile acid and acid of a transcriptional program involving NFkB and Cdx2, which mediate intestinal metaplasia and ectopic expression of GC-C. In addition, GCC expression has been found in primary tumors of the esophagus (59%), stomach (68%), CRC (98%), and pancreas (64%), and 96.5% matched liver metastatic tumor specimens showed GCC staining. Thus, the expression pattern of GCC in colorectal and stomach indicates that techniques of CoupledCAR® not only apply to treat colorectal cancer but also other cancer types associated with the digestive tract.

GCC Monoclonal Antibody

Figure 17:
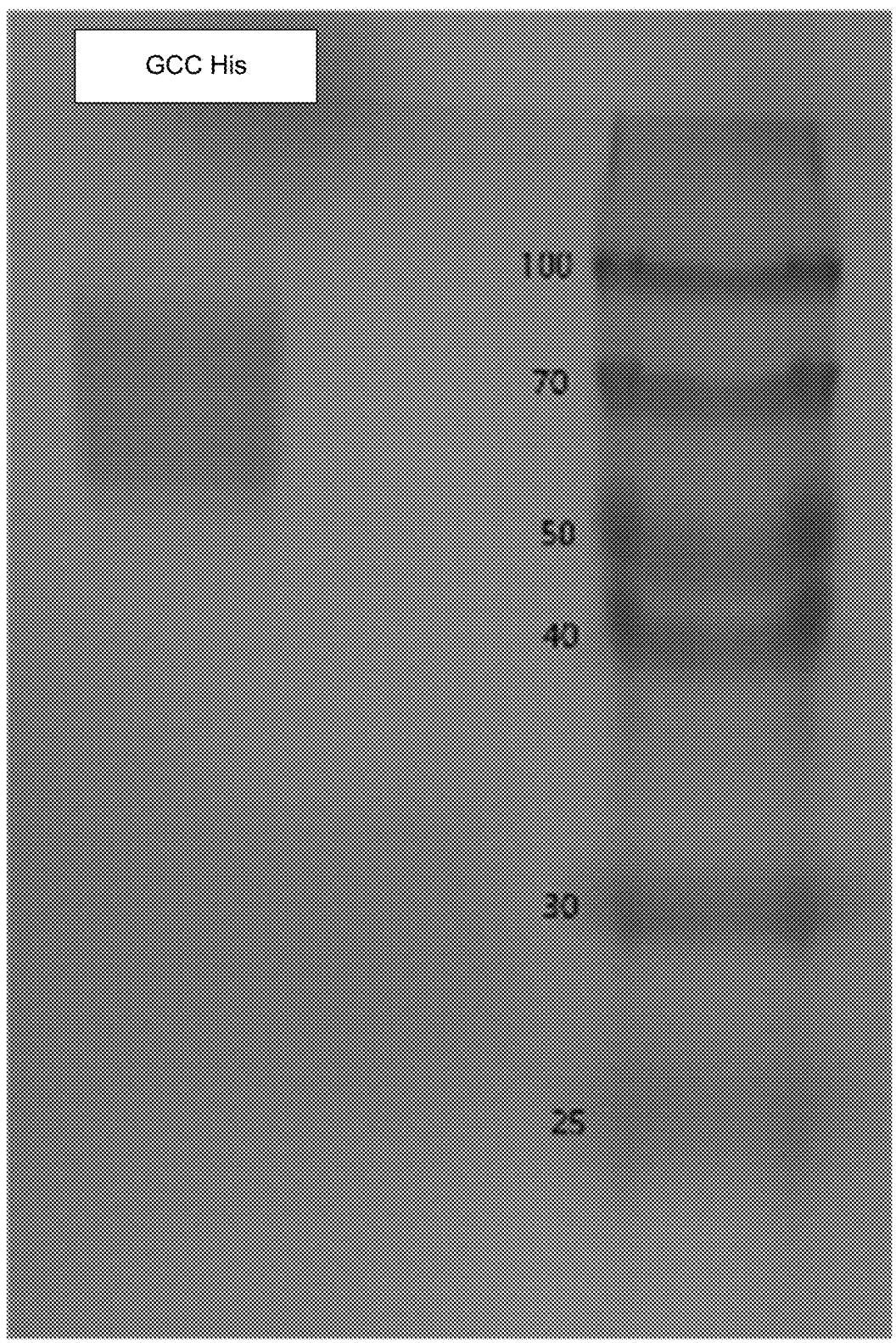
FIG. 17 shows SDS-PAGE analysis of purified recombinant GCC-His (GUC2C-His) fusion protein.
Figure 18:
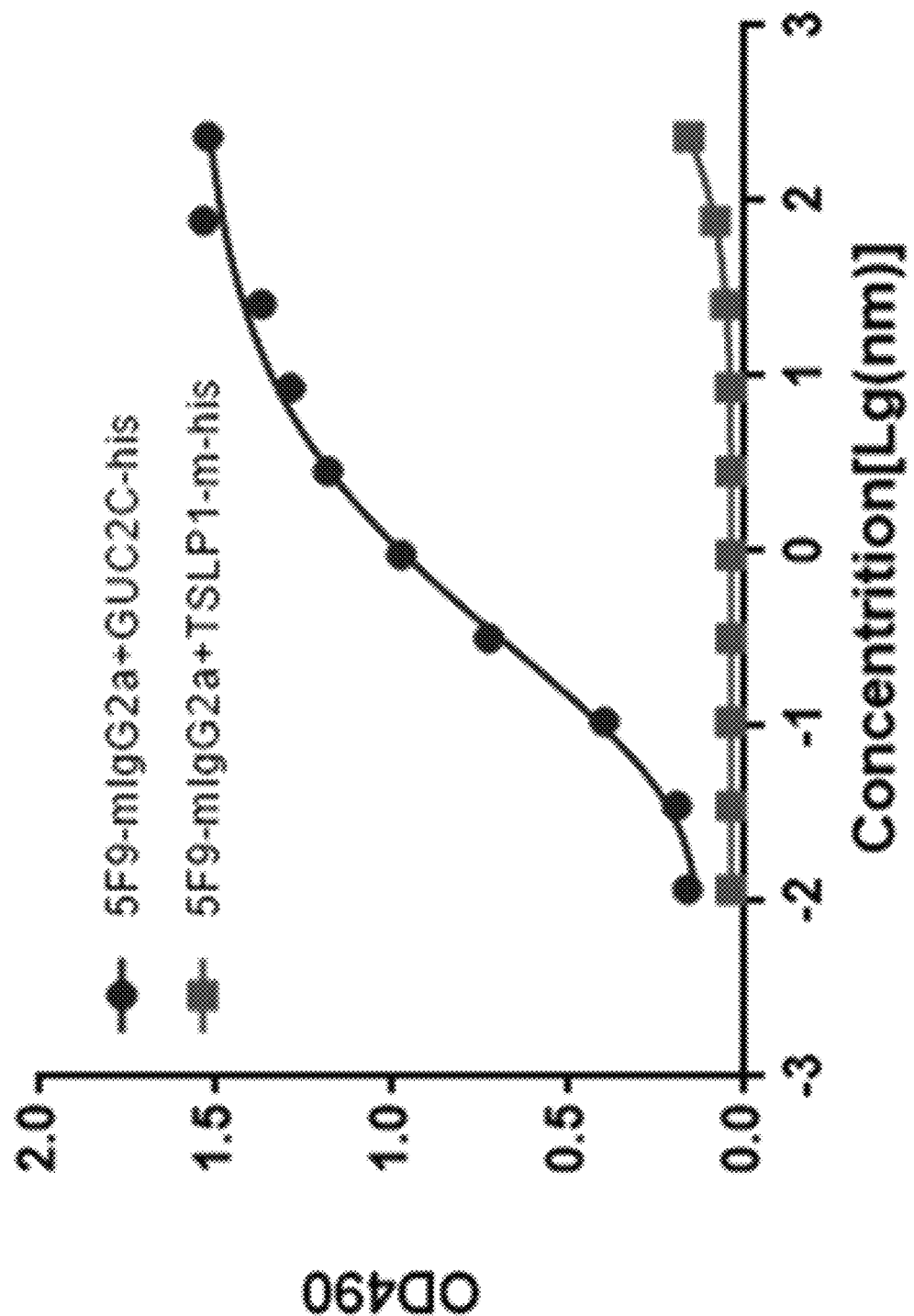
FIG. 18 shows ELISA analysis of purified recombinant GCC-His (GUC2C-His) fusion protein.

The sequence encoding the extracellular region of GCC was cloned into a recombinant protein expression vector PTSE-His system. The recombinant plasmid was transfected into HEK293 cells for expression of the fusion protein (GCC-His). The expressed fusion protein was purified using GE Histrap FF affinity chromatography column. SDS-PAGE analysis (FIG. 17) showed that GCC-His (the antigen) was expressed, and due to the heterogeneity of glycosylation, the molecular weight appeared to be about 60-80 KDa. GCC-His was analyzed by ELISA using the positive control antibody 5F9. The positive control antibody binds GCC-His. The extracellular region of the recombinant GCC is basically maintained. FIG. 18 shows ELISA analysis of purified recombinant GUC2C-His using the positive control antibody 5F9.

Based on Baxter's lambda recombinase system (λ-Int), the constructed fully human heavy chain antibody library (library capacity $2\times10^8$) and fully human light chain antibody library (library capacity $1.5\times10^7$) were recombined in bacteria, to obtain a recombinant human antibody library (Fab) with a library capacity exceeding $1.2\times10^{10}$. Using GCC-His as the antigen and following the solid-phase screening strategy of the classic phage antibody library, the above-mentioned large-capacity recombinant human Fab antibody library was displayed and screened. After several rounds of screening, about 1400 single clones were identified (phage-ELISA) and analyzed. Five positive monoclonals with different sequences that bind GCC were obtained. There are named R7C8+L1E2, R7C8+L1B9, R7C8+L1C9, R8C11+L3B4, R8C11+L4G6. Sequence analysis of all the clones showed that these clones have different CDRs from each other.

The light and heavy chains of the above 5 clones selected from the human recombinant antibody library were cloned into the mouse full antibody eukaryotic expression vectors pMABG2a and pMABK, and the 5 whole monoclonal antibodies (human variable region and mouse constant) were expressed using the HEK293 cell transient expression system. The 5 whole monoclonal antibodies were purified by Protein A affinity chromatography column. The anti-GCC monoclonal antibody 5F9 was prepared based on the amino acid sequence of the positive control 5F9. Among the 5 monoclonal antibodies, the expression level of antibody R7C8+L1E2 was low, so there was not enough antibody R7C8+L1E2 for further analysis.

Figure 19:
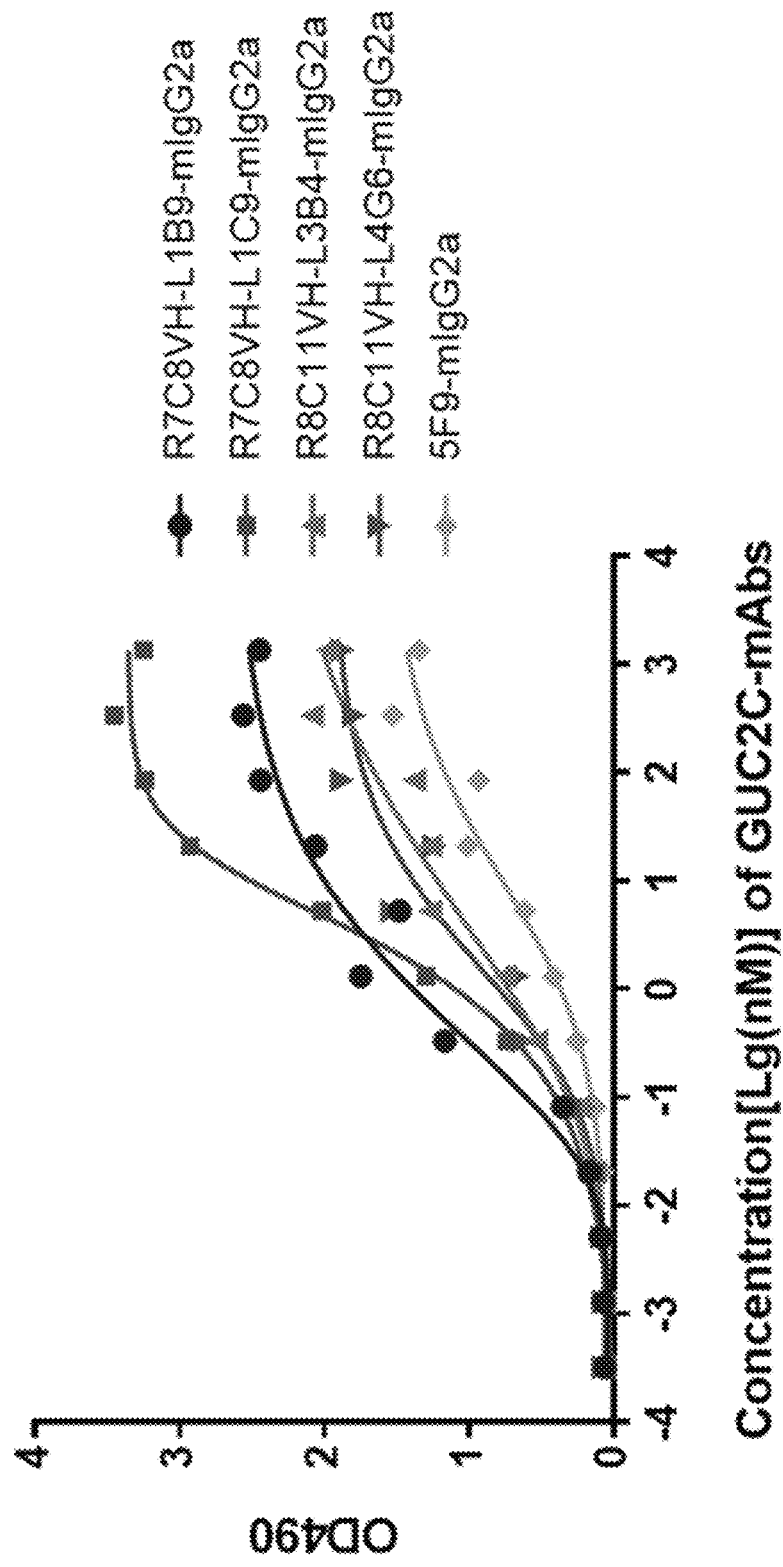
FIG. 19 shows ELISA analysis of GCC (GUC2C-His) binding to monoclonal antibodies (GUC2C mAbs).
Figure 20:
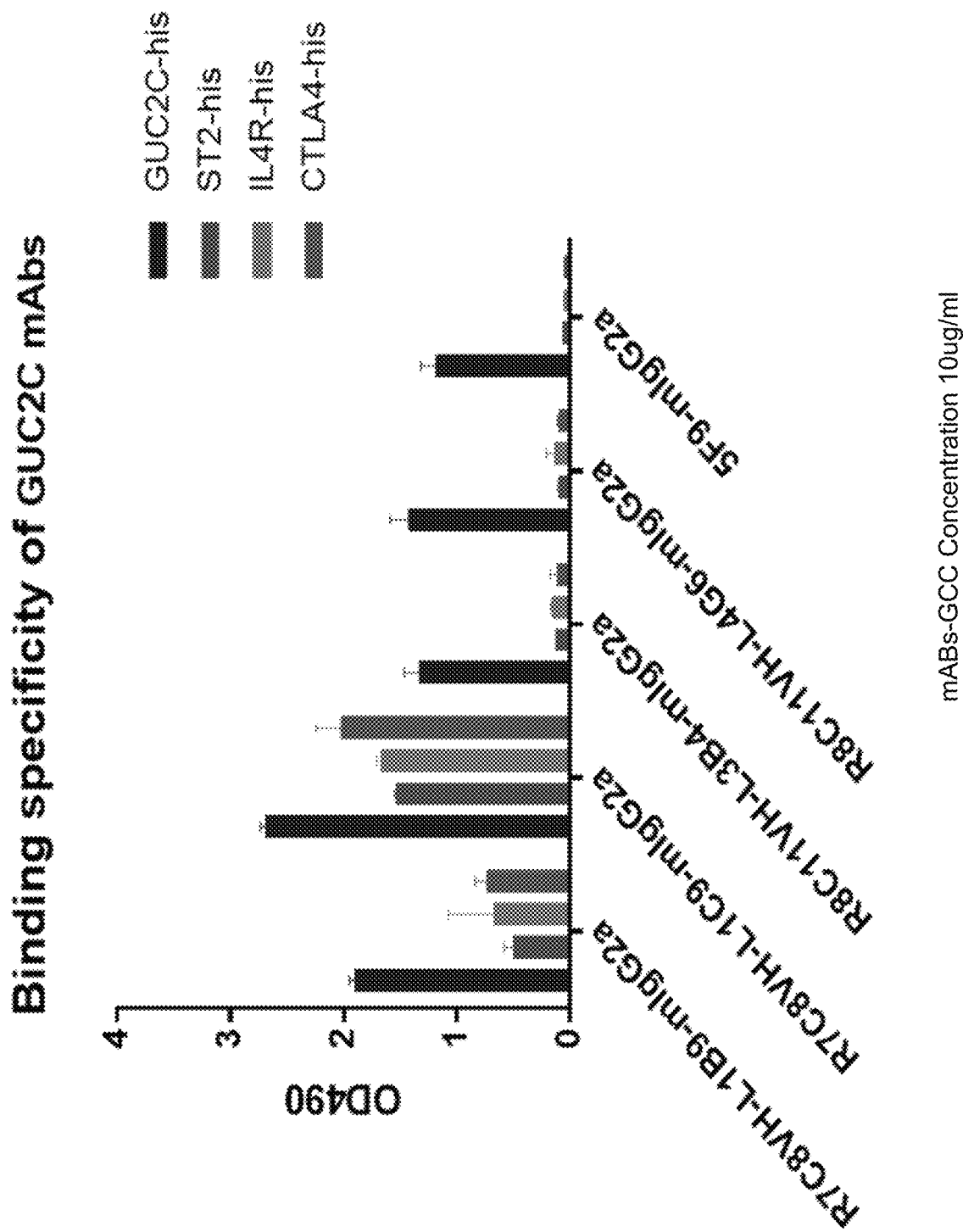
FIG. 20 shows ELISA analysis of the binding specificity of anti-GCC monoclonal antibodies (GUC2C mAbs).

The prepared 5 recombinant whole antibodies (including the 5F9 positive control antibody) were analyzed by ELISA. The affinity analysis based on BIAcore showed that the 5 monoclonal antibodies bind GCC-His (see Table 4 below). FIG. 19 shows GUC2C-His (GCC) binding these antibodies by ELISA analysis. The affinity of the 4 monoclonal antibodies (newly prepared anti-GCC monoclonal antibodies) for GUC2C-His is equal to or higher than that of the positive control 5F9 antibody. FIG. 20 shows ELISA analysis of the binding specificity of the 4 monoclonal antibodies as compared to the positive control 5F9. The binding specificity analysis based on ELISA showed that two of the monoclonal antibodies, R7C8+L1B9 and R7C8+L1C9, exhibited non-specific binding for irrelevant antigens, and the remaining three monoclonal antibodies (including the positive control 5F9 antibody) specifically bound GUC2C-His (antigen, GCC).

Figure 21:
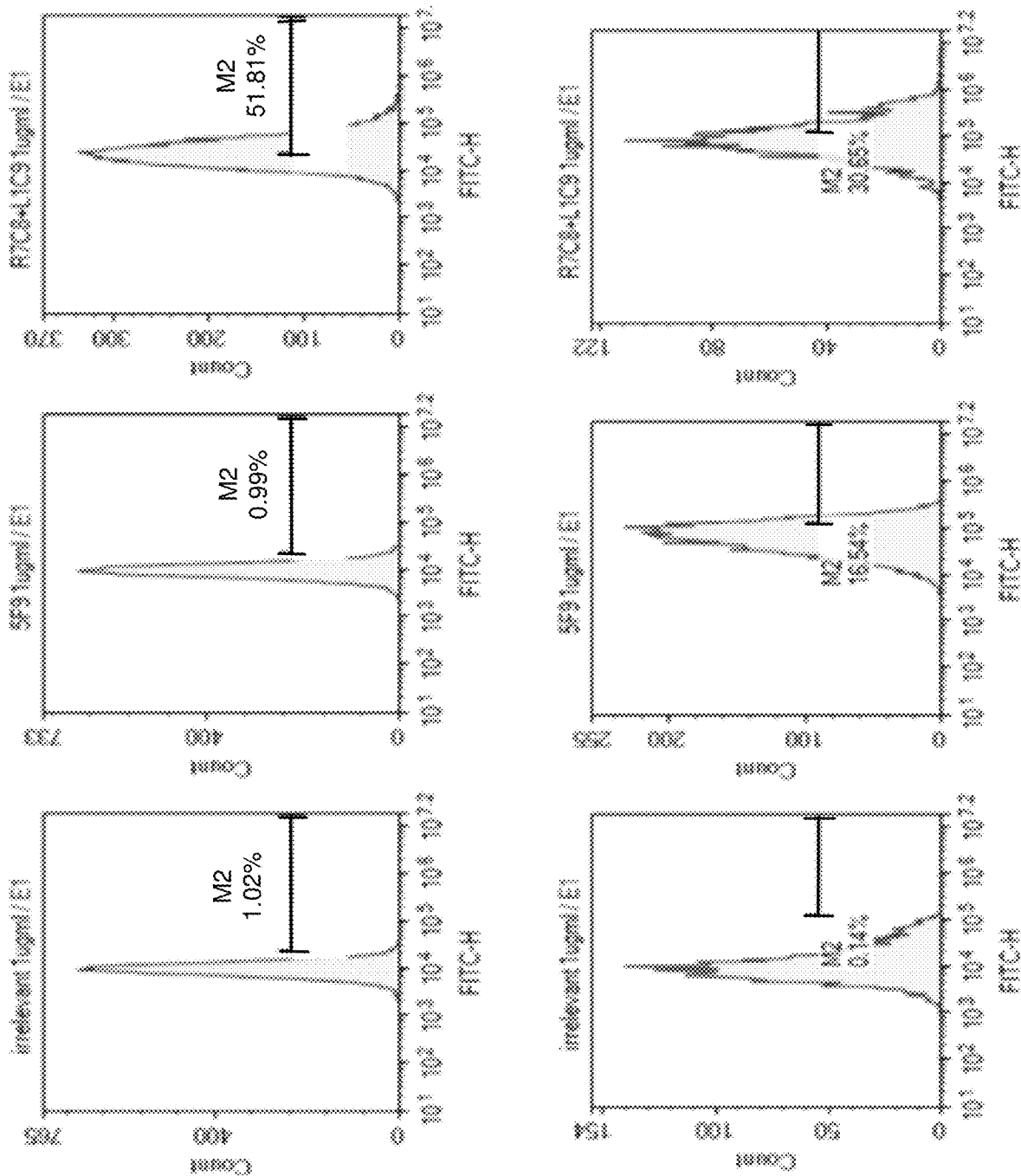
FIG. 21 shows flow cytometry (FCM) analysis of anti-GCC monoclonal antibodies binding to GCC on the cell surface.
Figure 22:
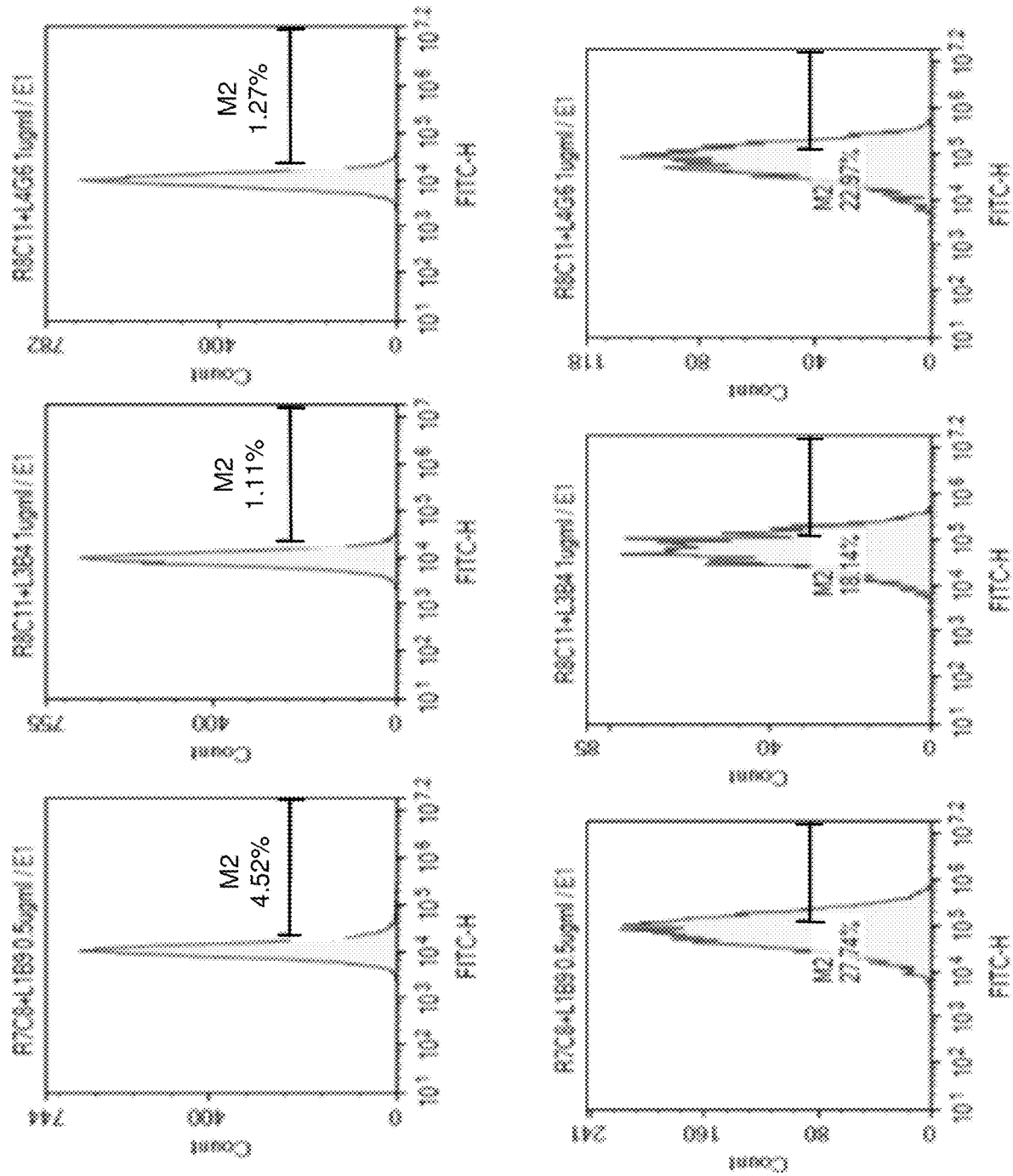
FIG. 22 shows additional FCM analysis of anti-GCC monoclonal antibodies binding to GCC on the cell surface.

Flow cytometry analysis was performed based on GCC positive cells T84 and negative cells HEK293T, and the results showed that R7C8+L1B9 and R7C8+L1C9 have non-specific binding to negative cells 293T, while monoclonal antibodies 5F9 and R8C11+L3B4 and R8C11+L4G6 can specifically bind to GCC-positive cells T84. FIG. 21 shows FCM analysis of anti-GCC monoclonal antibodies binding to GCC on the cell surface. The first line is the cell HEK293 T-test result, and the second line is the cell T84 test result. FIG. 22 shows additional FCM analysis of anti-GCC monoclonal antibodies binding to GCC on the cell surface. The first line is the cell HEK293 T-test result, and the second line is the cell T84 test result. This result is basically consistent with the above-mentioned protein ELISA specific analysis data.

TABLE 4

Anti-GCC Monoclonal Antibody Affinity
(BIAcore analysis, GCC-His as mobile phase)

|  | Ka | Kd | KD |
|---|---|---|---|
| 5F9-mIgG2a | 1.974E+4 | 3.445E−4 | 1.768E−8 |
| R7C8VH/L1B9VK-mIgG2a | 2.069E+4 | 9.111E−5 | 4.409E−9 |
| R7C8VH/L1C9VK-mIgG2a | 2.005E+4 | 8.720E−5 | 4.349E−9 |
| R8C11VH/L3B4VK-mIgG2a | 2.089E+4 | 2.346E−4 | 1.123E−8 |
| R8C11VH/L4G6VK-mIgG2a | 2.027E+4 | 2.402E−4 | 1.185E−8 |

In summary, the recombinant GCC extracellular domain (GCC-His) was used to complete the screening of the human recombinant antibody library. More than 1400 clones were analyzed, and only five clones were found to show specific binding to GCC. Among these five monoclonal antibodies, two monoclonal antibodies R8C11+L3B4 and R8C11+L4G6 showed specific binding to GCC-His and the naturally occurring GCC on the cell surface. Further study showed that the affinity of R8C11+L3B4 and R8C11+L4G6 for GCC-His is comparable to that of the positive control antibody 5F9.

TABLE 5

Sequence and identifiers

| Name | SEQ ID NO: |
|---|---|
| SP | 1 |
| Hinge & transmembrane domain | 2 |
| Co-stimulatory domain | 3 |
| CD3-zeta | 4 |
| scFv Humanized CD19 | 5 |
| scFv CD19 | 6 |
| scFv GUCY2C | 7 |
| GUCY2C antigen | 8 |
| CAR CD19 nucleic acid | 9 |
| Tumor associated MUC1 scFv 1 | 10 |
| Modified PD-1 intracellular domain-5 | 11 |
| WT CD3-zeta | 12 |
| GS linker | 13 |
| humanized-anti CD19-VH | 14 |
| humanized-anti CD19-VL | 15 |
| scfv GUCY2C LH | 16 |
| scfv GUCY2C HL | 17 |
| hCD19-CAR (4-1BB + CD3 zeta)-NATF-IL6-2A-IFNy | 18 |
| NFAT6x + minimal IL12 promoter | 19 |
| IL-6 aa Sequence | 20 |
| 2A | 21 |
| IFN-y aa | 22 |
| hCD19-CAR (4-1BB + CD3 zeta)-NATF-IL12-VHL | 23 |
| IL12 aa | 24 |
| Hif VHL-interaction domain Hif amino acid 344-417 | 25 |
| GUCY2C-CAR | 26 |
| GCC-VH R7C8 + L1E2 | 27 |
| GCC-VL R7C8 + L1E2 | 28 |
| 41BBCAR R7C8 + L1E2 | 29 |
| GCC-CD28CAR R7C8 + L1E2 | 30 |
| GCC-VH R8C11 + L3B4 | 31 |
| GCC-VL R8C11 + L3B4 | 32 |
| GCC-41BBCAR R8C11 + L3B4 | 33 |
| GCC-CD28CAR R8C11 + L3B4 | 34 |
| GCC-VL R7C8 + L1B9 | 35 |
| GCC-41BBCAR R7C8 + L1B9 | 36 |
| GCC-CD28CAR R7C8 + L1B9 | 37 |
| GCC-VL R7C8 + L1C9 | 38 |
| GCC-41BBCAR R7C8 + L1C9 | 39 |
| GCC-CD28CAR R7C8 + L1C9 | 40 |
| GCC-VL R8C11 + L4G6 | 41 |
| GCC-41BBCAR R8C11 + L4G6 | 42 |
| GCC-CD29CAR R8C11 + L4G6 | 43 |
| GCC-His | 44 |
| GCC-R8C11 (VH) | 45 |
| GCC-R7C8(VH) | 46 |
| GCC-L1B9(VK) | 47 |
| GCC-L1C9(VK) | 48 |
| GCC-L3B4(VK) | 49 |
| GCC-L4G6(VK) | 50 |
| GCC-L1E2(VK) | 51 |
| R8C11 + L3B4 scFv | 52 |
| R8C11 + L4G6 scFv | 53 |
| R7C8 + L1E2 scFv | 54 |
| R7C8 + L1B9 scFv | 55 |
| R7C8 + L1C9 scFv | 56 |
| GUC2C-R1G2VH-DNA | 57 |
| GUC2C-R1G2VK | 58 |
| GUC2C R1G2-41BBCAR | 59 |
| GUC2C R1G2-CD28CAR | 60 |
| GUC2C-R2G6VH | 61 |
| GUC2C-R2G6VK | 62 |
| GUC2C R2G6-41BBCAR | 63 |
| GUC2C R2G6-CD28CAR | 64 |

All publications, patents, and patent applications cited in this specification are incorporated herein by reference in their entirety as if each individual publication, patent, or patent application were specifically and individually indicated to be incorporated by reference. While the foregoing has been described in terms of various embodiments, the skilled artisan will appreciate that various modifications, substitutions, omissions, and changes may be made without departing from the spirit thereof.

The invention claimed is:

1. An antibody that binds GCC, wherein the antibody comprises a heavy chain variable region (HVR) comprising amino acid sequence SEQ ID NO: 31 and a light chain variable region (LVR) comprising amino acid sequence SEQ ID NO: 32 or 41.

2. The antibody of claim 1, wherein the HVR comprises amino acid sequence SEQ ID NO: 31, and the LVR comprises amino acid sequence SEQ ID NO: 32.

3. The antibody of claim 1, wherein the HVR comprises amino acid sequence SEQ ID NO: 31, and the LVR comprises amino acid sequence SEQ ID NO: 41.

4. The antibody of claim 1, wherein the HVR is joined to a human IgG constant region, and the human IgG is IgG1 or IgG3.

5. The antibody of claim 1, wherein the antibody is conjugated to a cytotoxic agent, and the cytotoxic agent is a radioactive isotope or a toxin.

6. The antibody of claim 1, wherein the antibody is an scFv, and the LVR is connected to HVR via a linker.

7. The antibody of claim 1, wherein the antibody comprises amino acid sequence SEQ ID NO: 52.

8. The antibody of claim 1, wherein the antibody comprises amino acid sequence SEQ ID NO: 53.

9. A polynucleotide that encodes the antibody of claim 1.

10. A chimeric antigen receptor (CAR) comprising an antigen binding domain comprising the antibody of claim 1 or an antigen-binding fragment thereof.

11. The CAR of claim 10, wherein the CAR comprises amino acid sequence SEQ ID NO: 52 or 53.

12. The CAR of claim 10, wherein the CAR comprises amino acid sequence SEQ ID NO: 33 or 34.

13. The CAR of claim 10, wherein the CAR comprises amino acid sequence SEQ ID NO: 42 or 43.

14. The CAR of claim 10, wherein the CAR comprises an extracellular domain, a transmembrane domain, and an intracellular domain, the extracellular domain comprising the antigen binding domain.

15. The CAR of claim 14, wherein the intracellular domain comprises a co-stimulatory signaling domain comprising one or more intracellular domains of CD27, CD28, 4-1BB, OX40, CD30, CD40, PD-1, ICOS, lymphocyte function-associated antigen-1 (LFA-1), CD2, CD7, LIGHT, NKG2C, and B7-H3.

16. The CAR of claim 14, wherein the intracellular domain of the CAR comprises a CD3 zeta domain.

17. A polynucleotide that encodes the CAR of claim 10.

18. A modified cell comprising the CAR of claim 10.

19. The modified cell of claim 18, wherein the modified cell is a T cell.

20. A method of stimulating an anti-tumor response of immunotherapy in a subject, the method comprising:
administering an effective amount of a composition comprising a population of the modified cells of claim 18 to the subject.

21. A method of stimulating an immune response, the method comprising: contacting a target cell comprising GCC with the modified cell of claim 18, thereby allowing the modified cell to release cytokines.

* * * * *